US011006975B1

(12) United States Patent
Cohen et al.

(10) Patent No.: US 11,006,975 B1
(45) Date of Patent: May 18, 2021

(54) STEERABLE EXTENDABLE DEVICES

(71) Applicant: Southern Methodist University, Dallas, TX (US)

(72) Inventors: Adam Cohen, Dallas, TX (US); Edmond Richer, Richardson, TX (US)

(73) Assignee: Southern Methodist University, Dallas, TX (US)

( * ) Notice: Subject to any disclaimer, the term of this patent is extended or adjusted under 35 U.S.C. 154(b) by 303 days.

(21) Appl. No.: 15/066,982

(22) Filed: Mar. 10, 2016

Related U.S. Application Data

(63) Continuation-in-part of application No. 14/213,193, filed on Mar. 14, 2014, now Pat. No. 9,282,993.

(Continued)

(51) Int. Cl.
*A61B 17/34* (2006.01)
*A61B 17/00* (2006.01)
*A61B 34/30* (2016.01)

(52) U.S. Cl.
CPC .... *A61B 17/3421* (2013.01); *A61B 17/00234* (2013.01); *A61B 34/30* (2016.02); *A61B 2017/00314* (2013.01); *A61B 2017/00477* (2013.01); *A61B 2017/00526* (2013.01); *A61B 2017/3443* (2013.01); *A61B 2034/301* (2016.02)

(58) Field of Classification Search
CPC .......... A61M 25/0119; A61M 25/0102; A61M 25/009; B29C 53/56; B29C 53/58; B29C 53/581; A61B 17/3421; A61B 34/30; A61B 17/00234; A61B 2017/00526; A61B 2017/00477; A61B 2034/301; A61B 2017/00314; A61B 2017/3443; B28C 53/582

See application file for complete search history.

(56) References Cited

U.S. PATENT DOCUMENTS 4,110,149 A * 8/1978 Poulsen ................. B29C 53/74
156/429
5,993,427 A * 11/1999 Rolland ............. A61M 25/0119
604/271

(Continued)

OTHER PUBLICATIONS

Chapman, M.P., et al., "A Highly Articulated Robotic System (CardioARM) is Safer than a Rigid System for Intrapericardial Intervention in a Porcine Model," IEEE ICRA Full Day Workshop, 2010.

(Continued)

*Primary Examiner* — Lauren P Farrar
*Assistant Examiner* — Hamza A Darb
(74) *Attorney, Agent, or Firm* — Edwin S. Flores; Chalker Flores, LLP

(57) ABSTRACT

The present invention is a Distally Assembled Steerable Cannula (DASC), a robotically-manipulated device that can be deployed and extended within a patient's body by growing from its distal end, or can be used in non-medical applications. In some embodiments, growth occurs by sequentially assembling segments that interlock to form a rigid tube with a complex 3-D shape. The segments are individually transported through the growing cannula, and then assembled at the distal end. A segment can be wedge-shaped in profile, allowing adjustment of the local radius and plane of curvature of the cannula to be controlled by relative segment orientation.

8 Claims, 118 Drawing Sheets

Related U.S. Application Data

(60) Provisional application No. 61/791,692, filed on Mar. 15, 2013, provisional application No. 61/884,123, filed on Sep. 29, 2013.

(56) References Cited

U.S. PATENT DOCUMENTS

| | | | |
|---|---|---|---|
| 6,858,005 | B2 | 2/2005 | Online et al. |
| 6,960,163 | B2 | 11/2005 | Ewers et al. |
| 2003/0135204 | A1 | 7/2003 | Lee et al. |
| 2004/0243143 | A1 | 12/2004 | Corcoran et al. |
| 2007/0066987 | A1 | 3/2007 | Scanlan, Jr. et al. |
| 2007/0123798 | A1* | 5/2007 | Rahamimov ...... A61B 1/00135 600/564 |
| 2008/0058596 | A1 | 3/2008 | Bob et al. |
| 2009/0260745 | A1* | 10/2009 | Iwai ...................... B29C 53/588 156/155 |
| 2010/0121312 | A1* | 5/2010 | Gielenz ............. A61M 25/0009 604/524 |
| 2011/0144590 | A1* | 6/2011 | Sakai, Jr. ........... A61B 17/3421 604/167.01 |
| 2013/0090598 | A1 | 4/2013 | Vargas |
| 2013/0098559 | A1* | 4/2013 | Lelarge ................... B29C 53/74 156/379 |
| 2013/0226151 | A1 | 8/2013 | Kaisha |
| 2014/0018626 | A1 | 1/2014 | Lee |

OTHER PUBLICATIONS

Degani, A., et al., "Percutaneous Intrapericardial Interventions Using a Highly Articulated Robotic Probe," Proceedings of the 2006 IEEE / RAS-EMBS iNternational Conference on Biomedical Robotics and Biomechatronics, Feb. 2006, pp. 7-12.

Dimaio, S., et al., "Needle Insertion Modeling and Simulation," IEEE Transactions on Robotics and Automation, vol. 19, No. 5, Oct. 2003.

Dupont, P. E., et al., "Design and Control of Concentric-Tube Robots," IEEE Trans Robot., 26(2)209-225, Apr. 1, 2010.

Dupont, P.E., et al., "Concentric Tube Robots for Minimally Invasive Surgery," The Hamlyn Symposium on Medical Robots, 2012.

Glozman, D., et al., "Image-guided robotic flexible needle steering," IEEE Trans. Robot., vol. 23, No. 3, Jun. 2007, pp. 459-467.

Goksel, O., et al., "Modeling and simulation of flexible needles," Medical Engineering & Physics, Jul. 7, 2009, 7:1153-1162.

Gosline, A., et al., "Percutaneous intracardiac beating-heart surgery using metal MEMS tissue approximation tools," Int. J. Rob. Res., 31(9):1081-1093, Aug. 1, 2012.

Majewicz, A., et al., "Behavoir of Tip-Steerable Needles in ex vivo and in vivo Tissue," IEEE Trans Biomed Eng., 59(10)2705-2715, Oct. 2012.

Mahvash, M., et al., "Toward a hybrid snake robot for single-port surgery," 33rd Annual International Conference of the IEEE EMBS, Boston, MA, Aug. 30-Sep. 3, 2011:5372-5375.

Okazawa, S., et al., "Hand-held steerable needle device," IEEE/ASME Trans. Mechatron., vol. 10, No. 3, Jun. 2005, pp. 285-296.

Sears, P., et al., "A Steerable Needle Technology Using Curved Concentric Tubes," IEEE/RSJ International Conference on Intelligent Robots and System, pp. 2850-2856, Oct. 9-15, 2006.

Webster, R., et al., "Nonholonomic modeling of needle steering," Int. J. Robot. Res., vol. 25, No. 5-6, pp. 509-525, May-Jun. 2006.

Webster, R. J., et al., "Mechanics of Precurved-Tube Continuum Robots," IEEE Transactions on Robotics, vol. 25, No. 1, Feb. 2009.

* cited by examiner

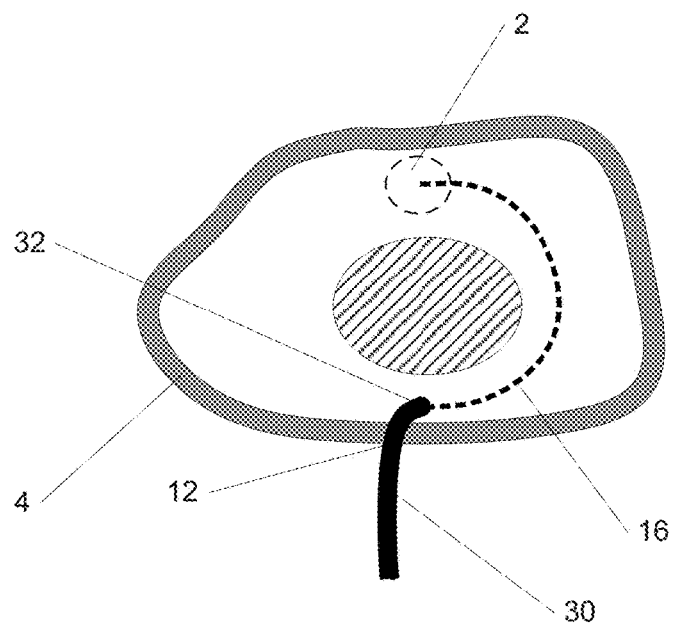
Fig. 4(a)
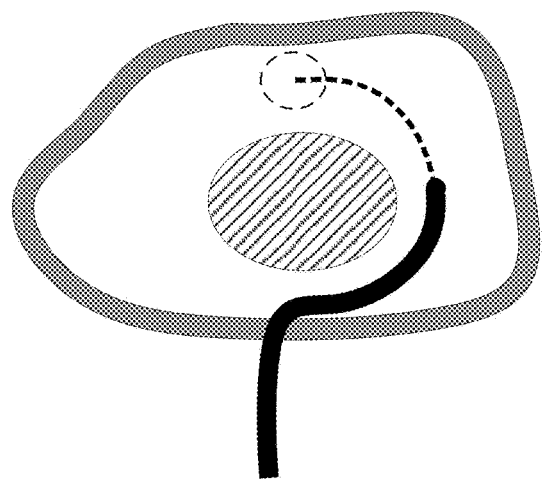 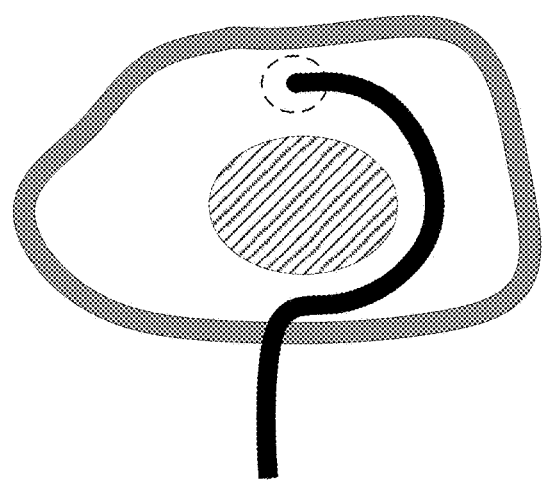
Fig. 4(b)                              Fig. 4(c)

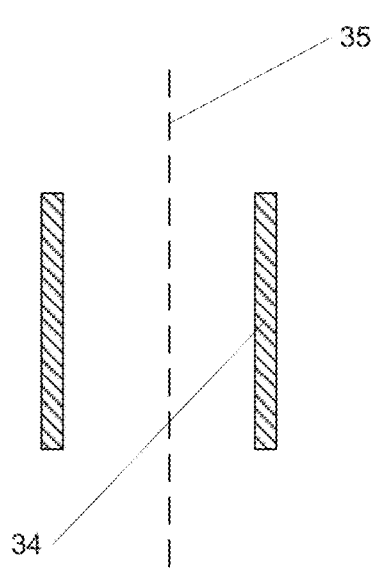
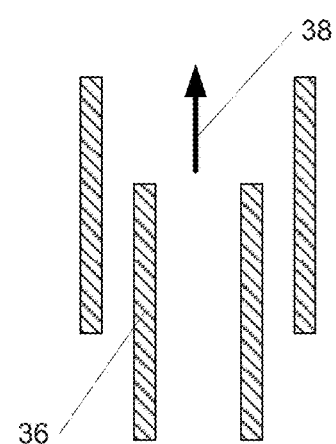
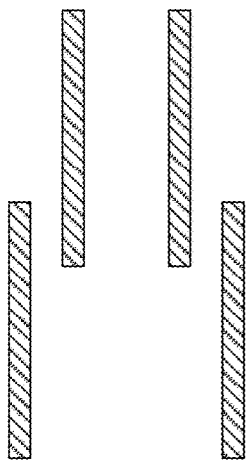
Fig. 5(a)  Fig. 5(b)  Fig. 5(c)
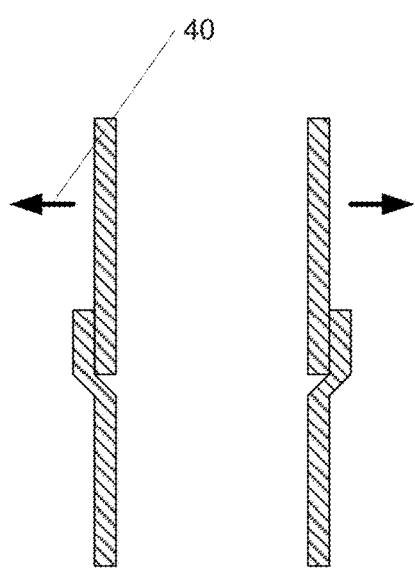
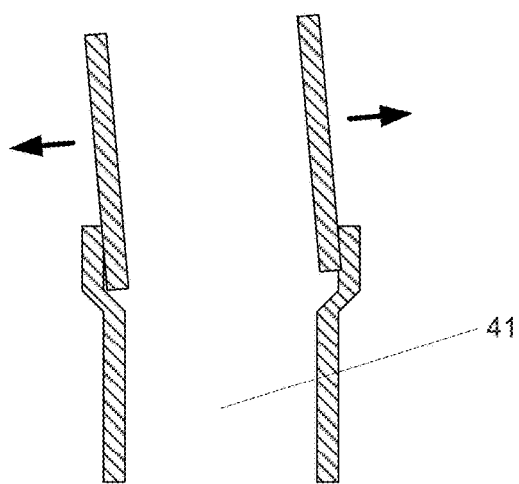
Fig. 5(d)  Fig. 5(d')

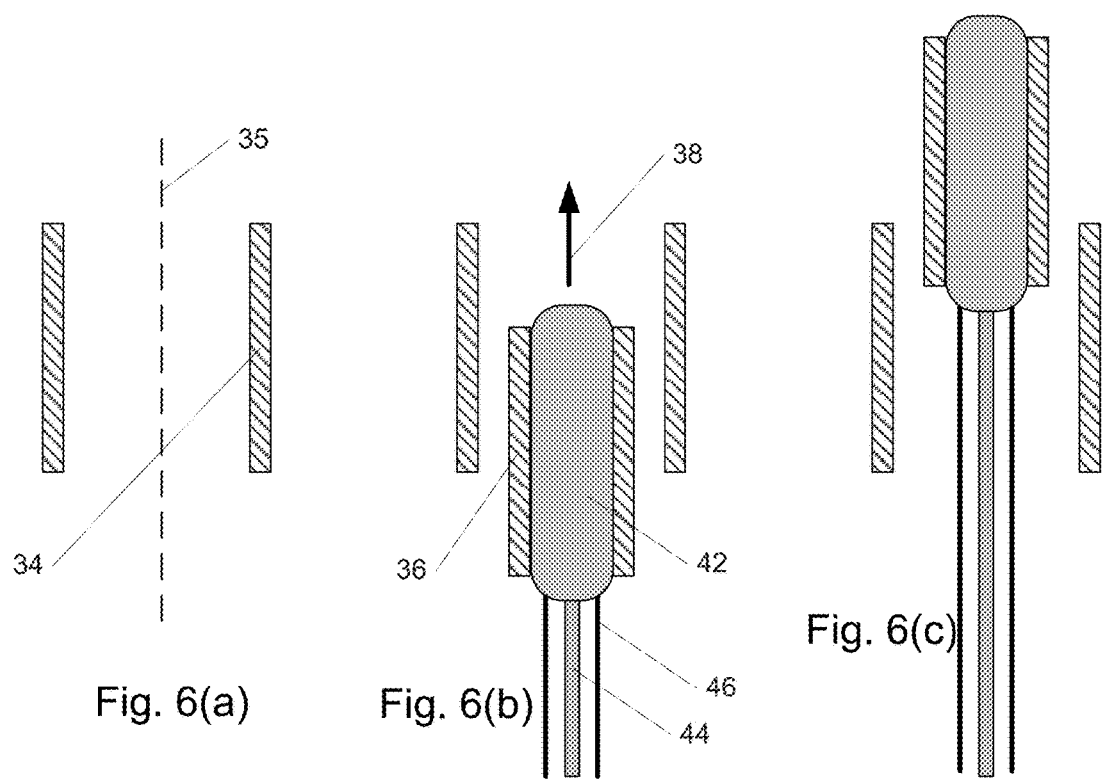
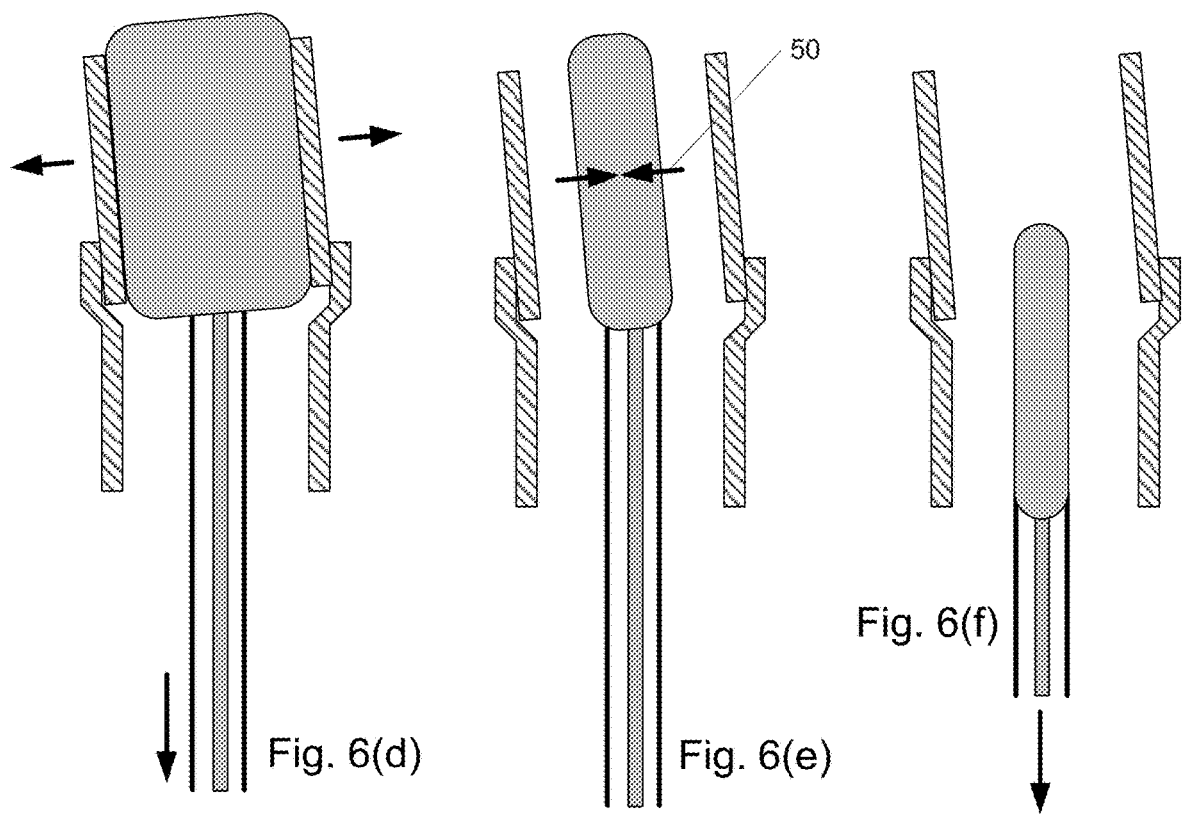

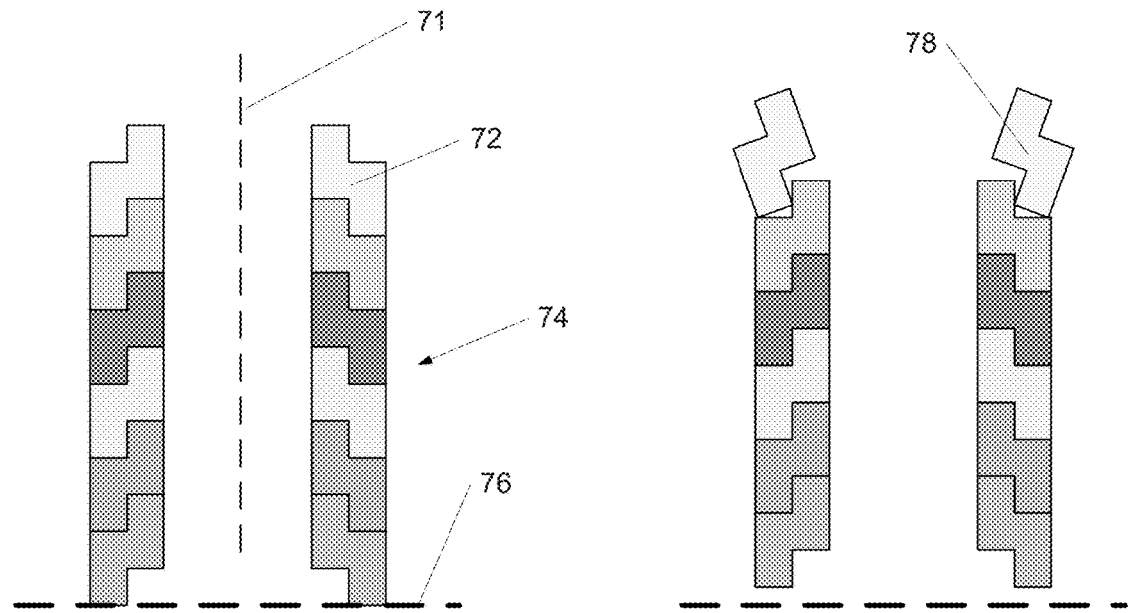
Fig. 8(a)
Fig. 8(b)
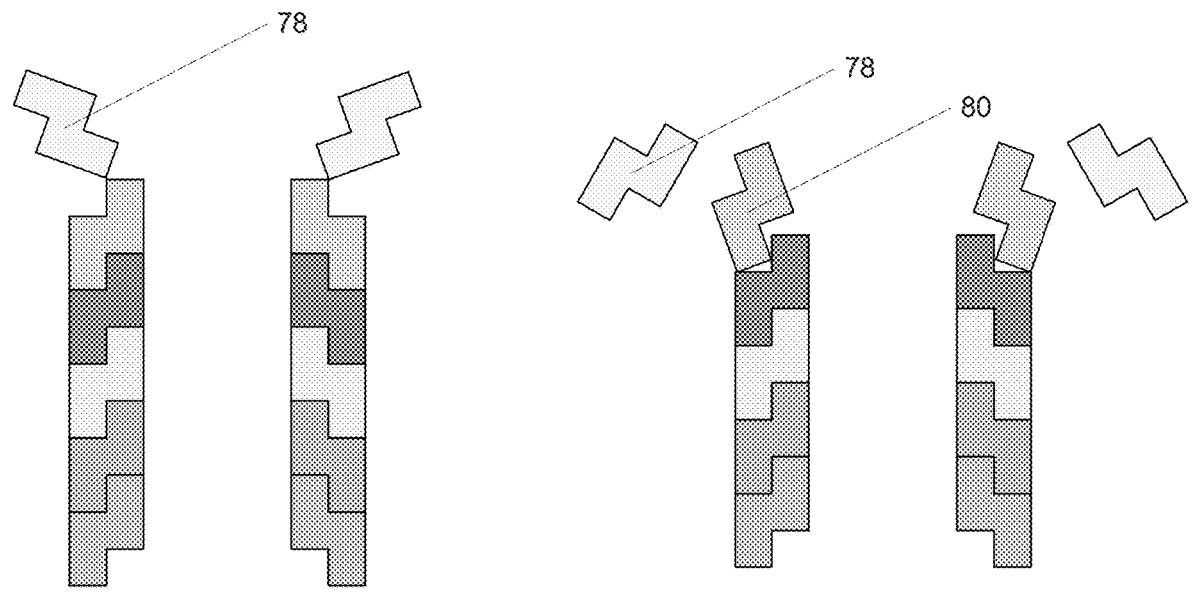
Fig. 8(c)
Fig. 8(d)

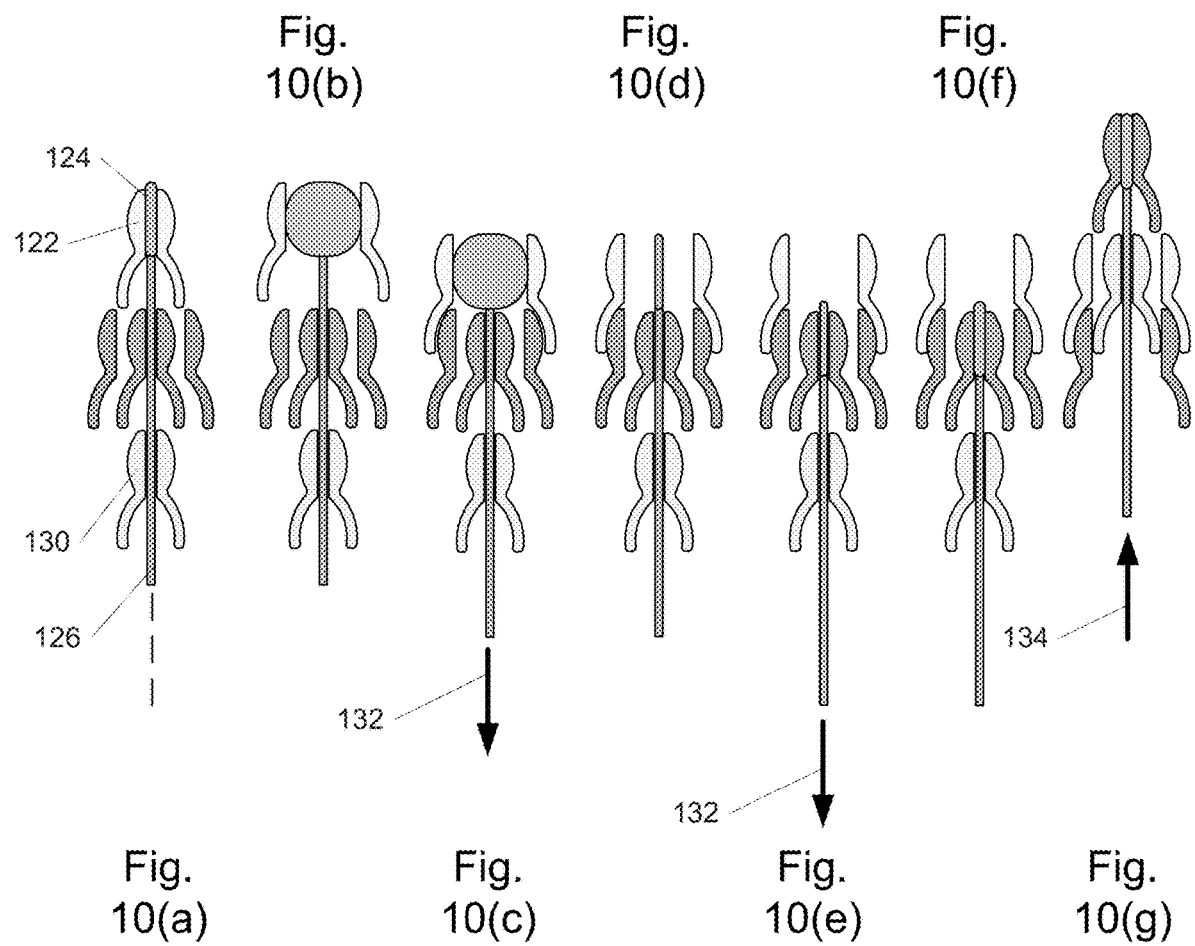

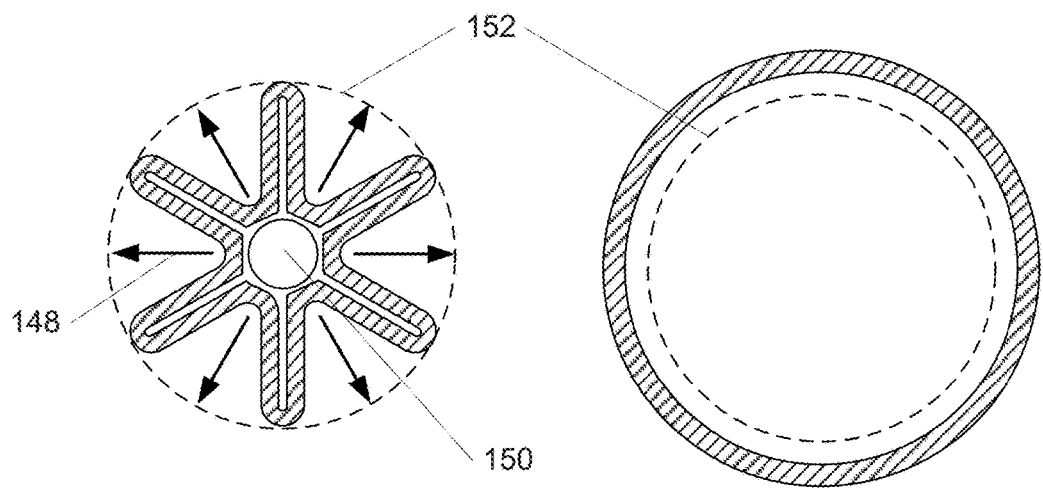
Fig. 12(a)  Fig. 12(b)
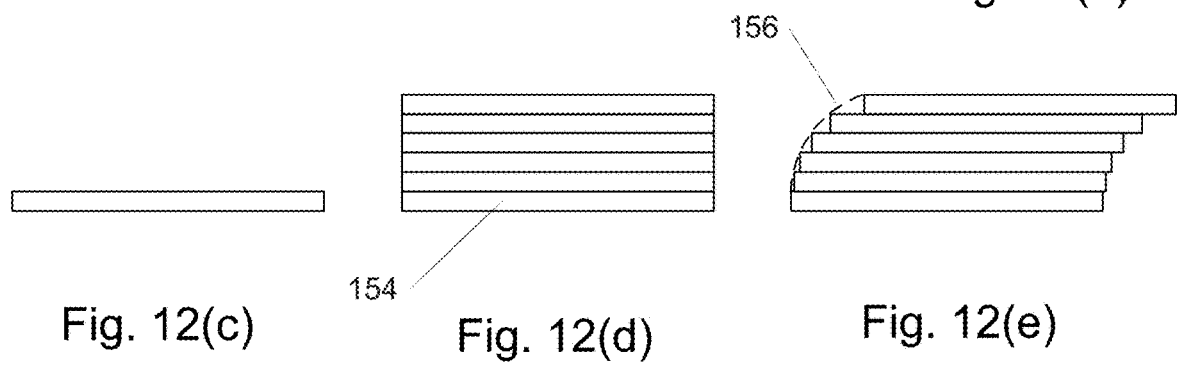
Fig. 12(c)  Fig. 12(d)  Fig. 12(e)
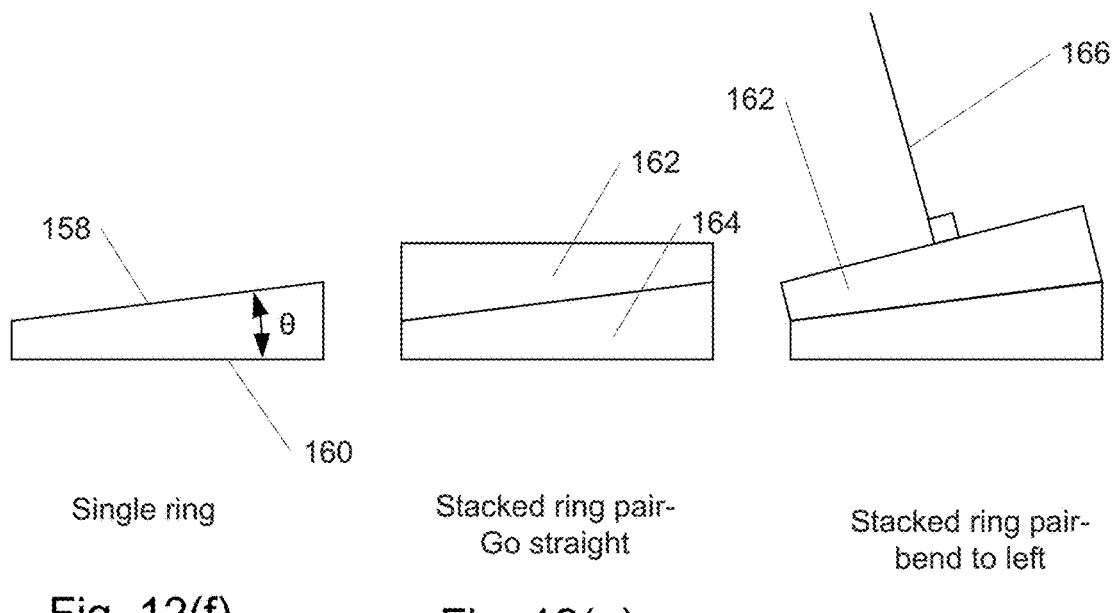
Single ring
Fig. 12(f)
Stacked ring pair-
Go straight
Fig. 12(g)
Stacked ring pair-
bend to left
Fig. 12(h)

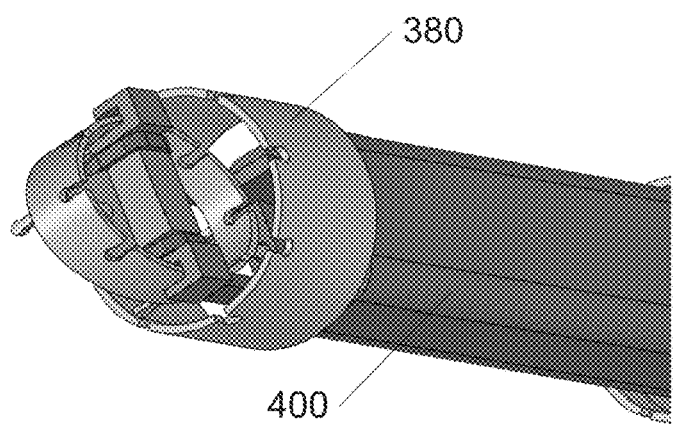
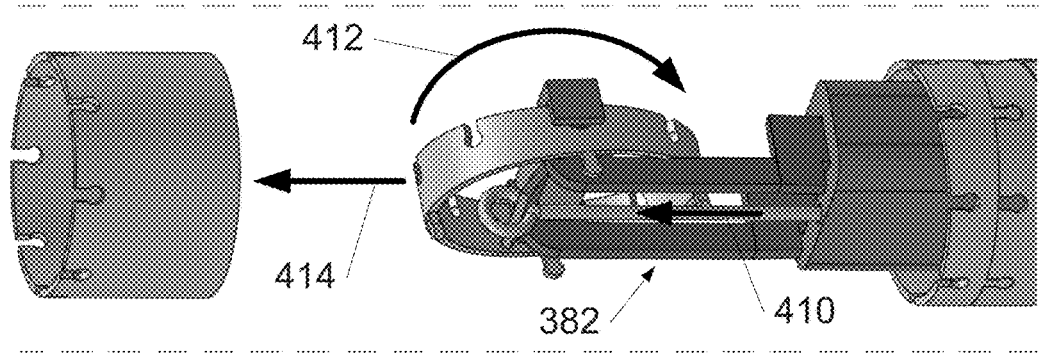
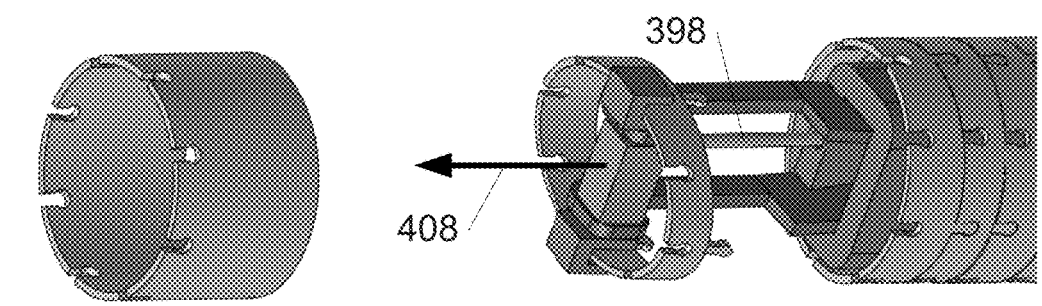
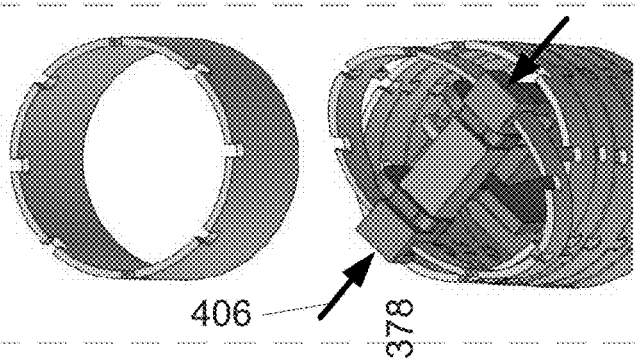
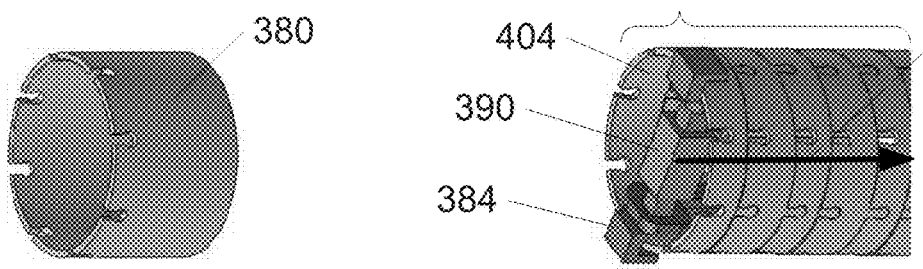

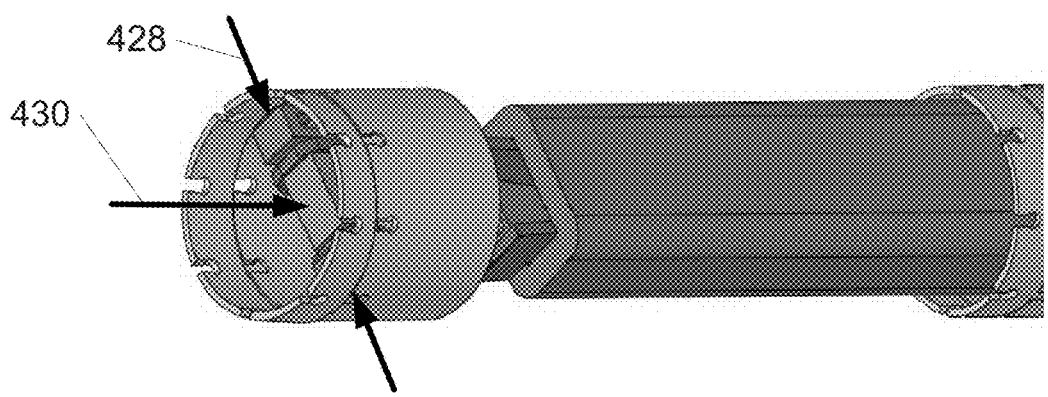
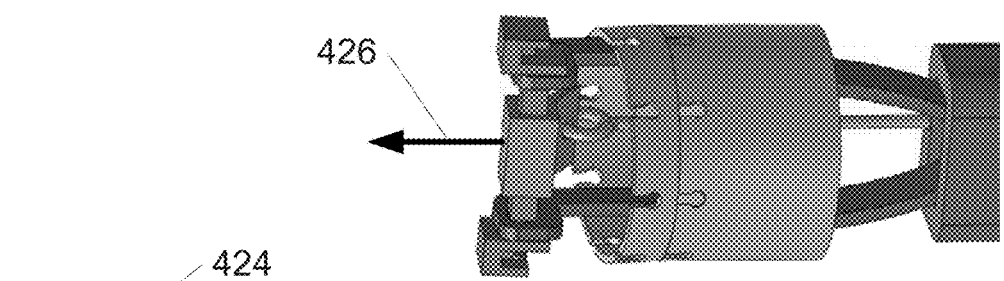
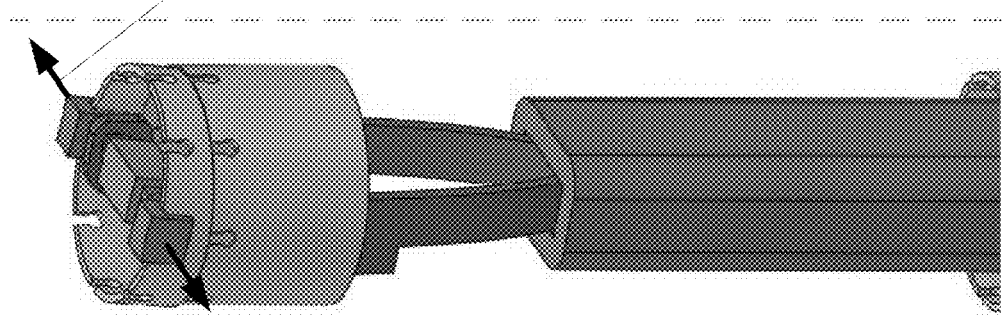
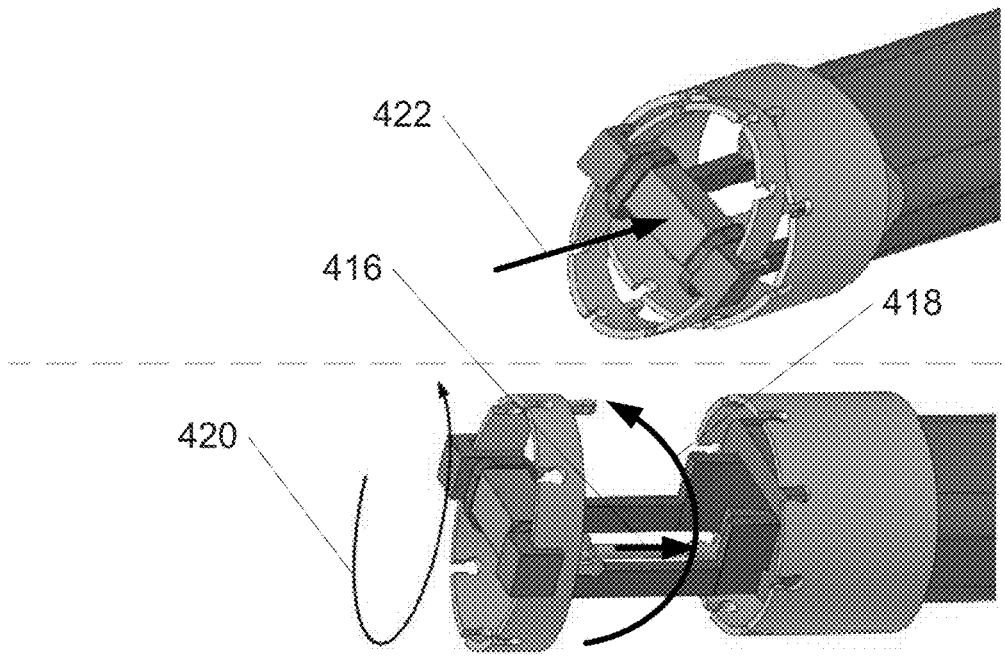

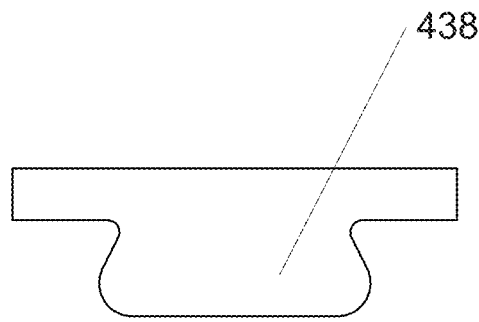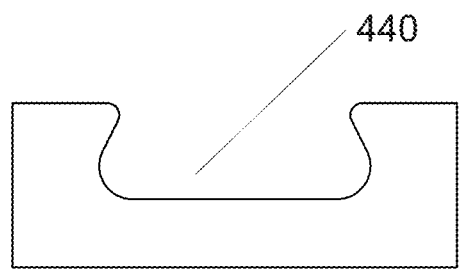
Fig. 36

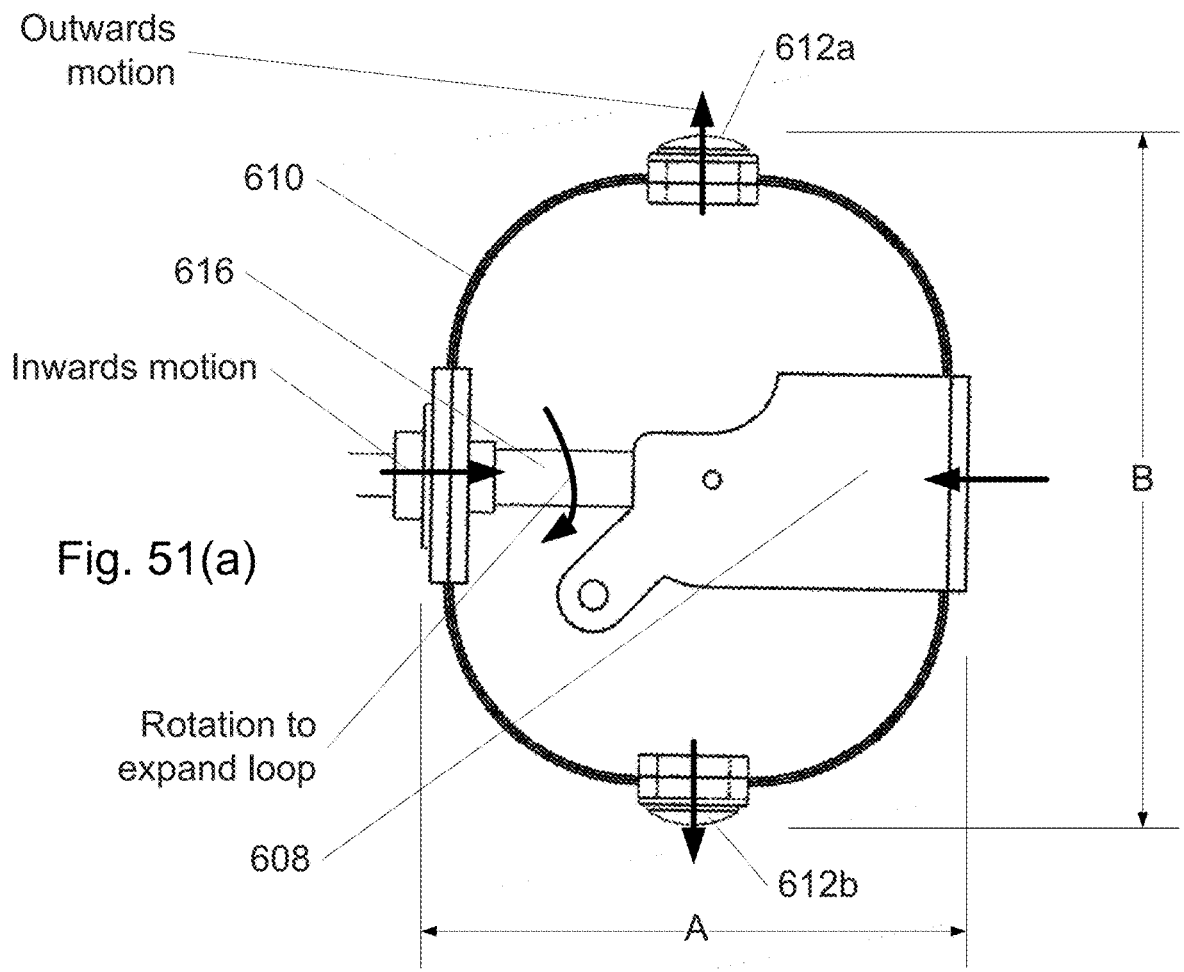

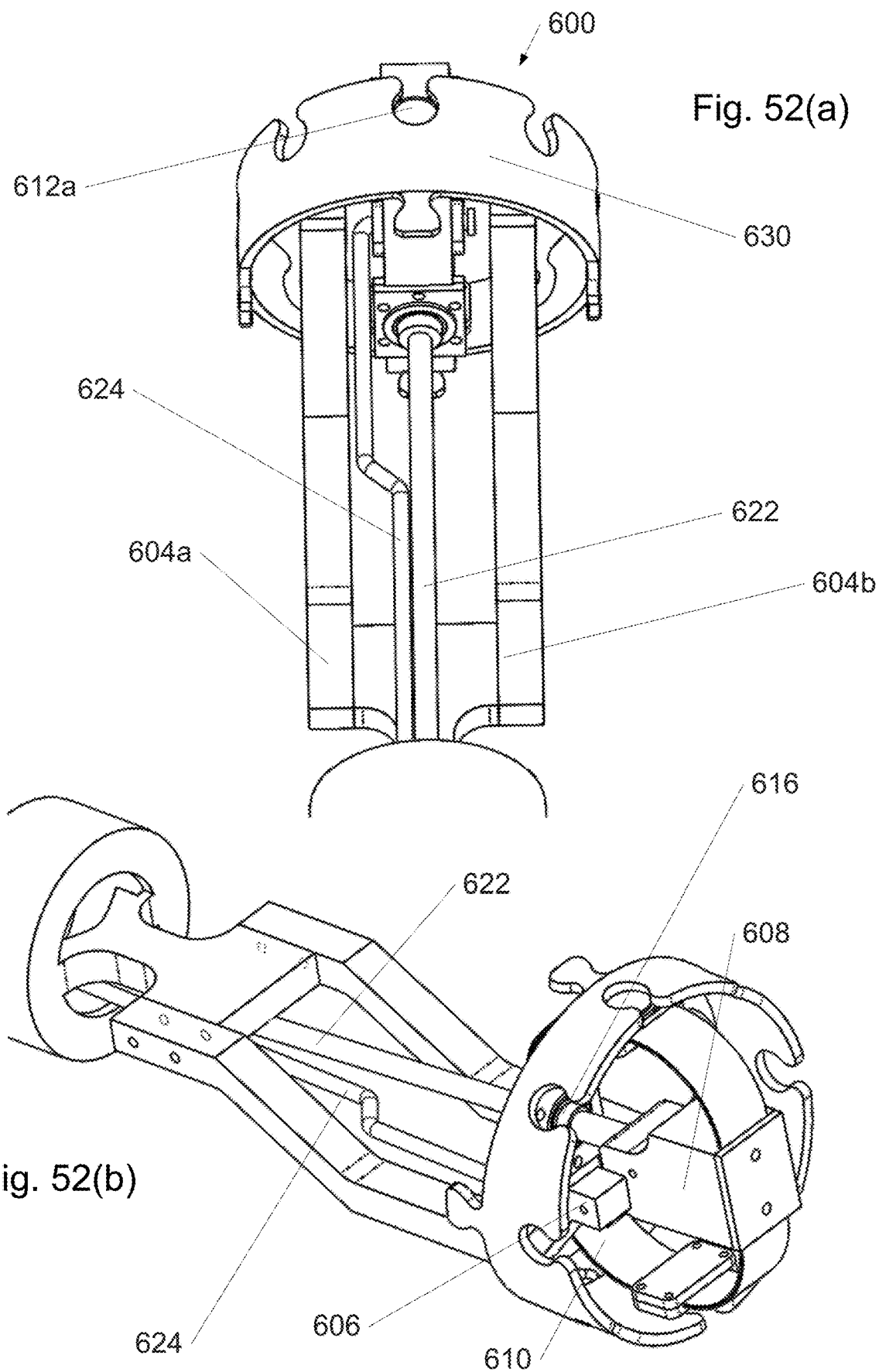

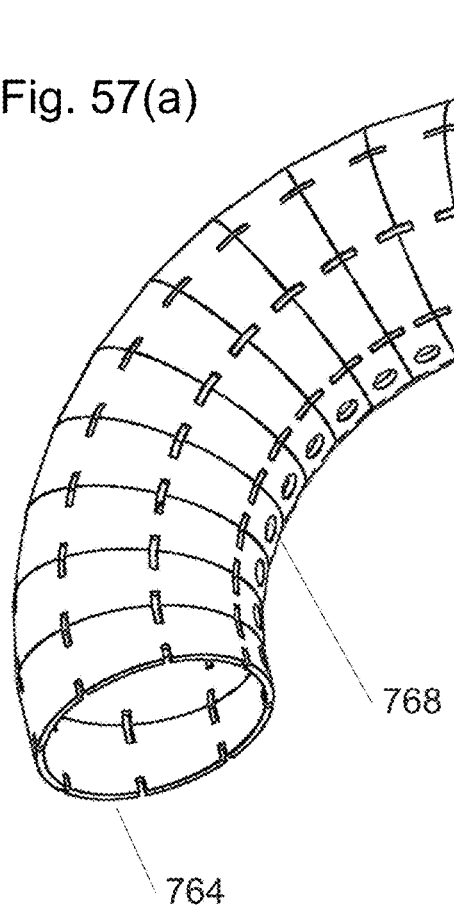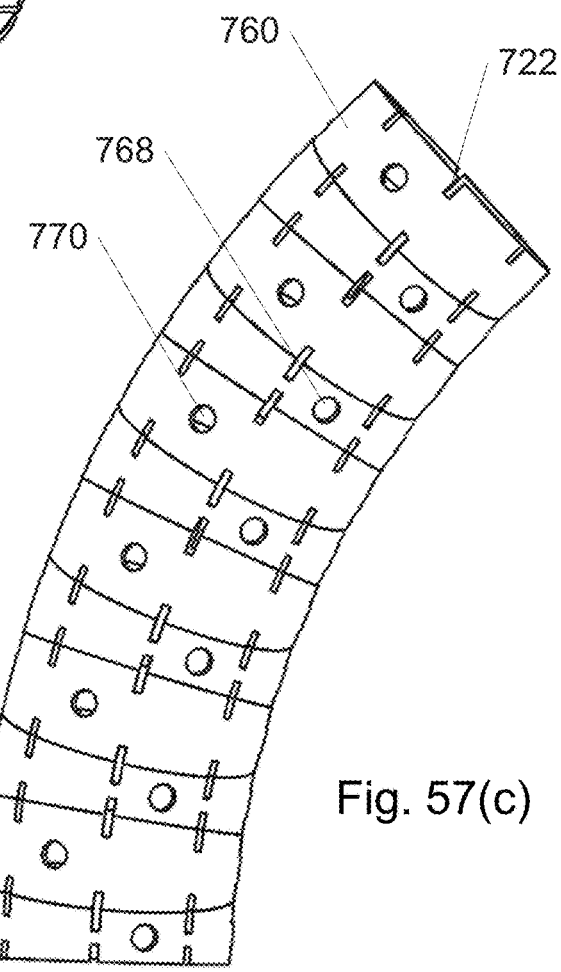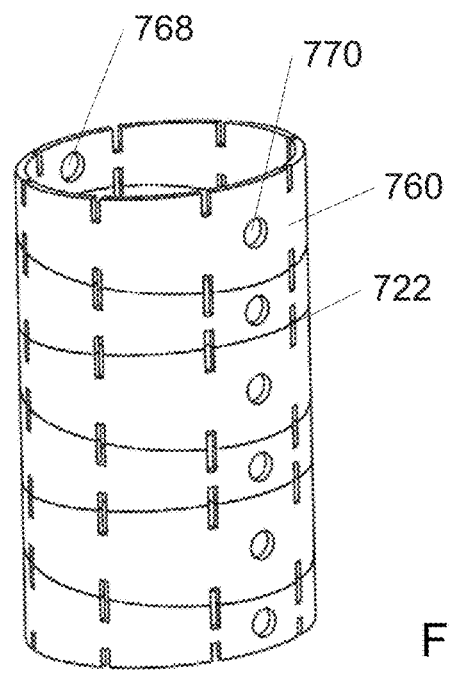
Fig. 57(a)
Fig. 57(b)
Fig. 57(c)

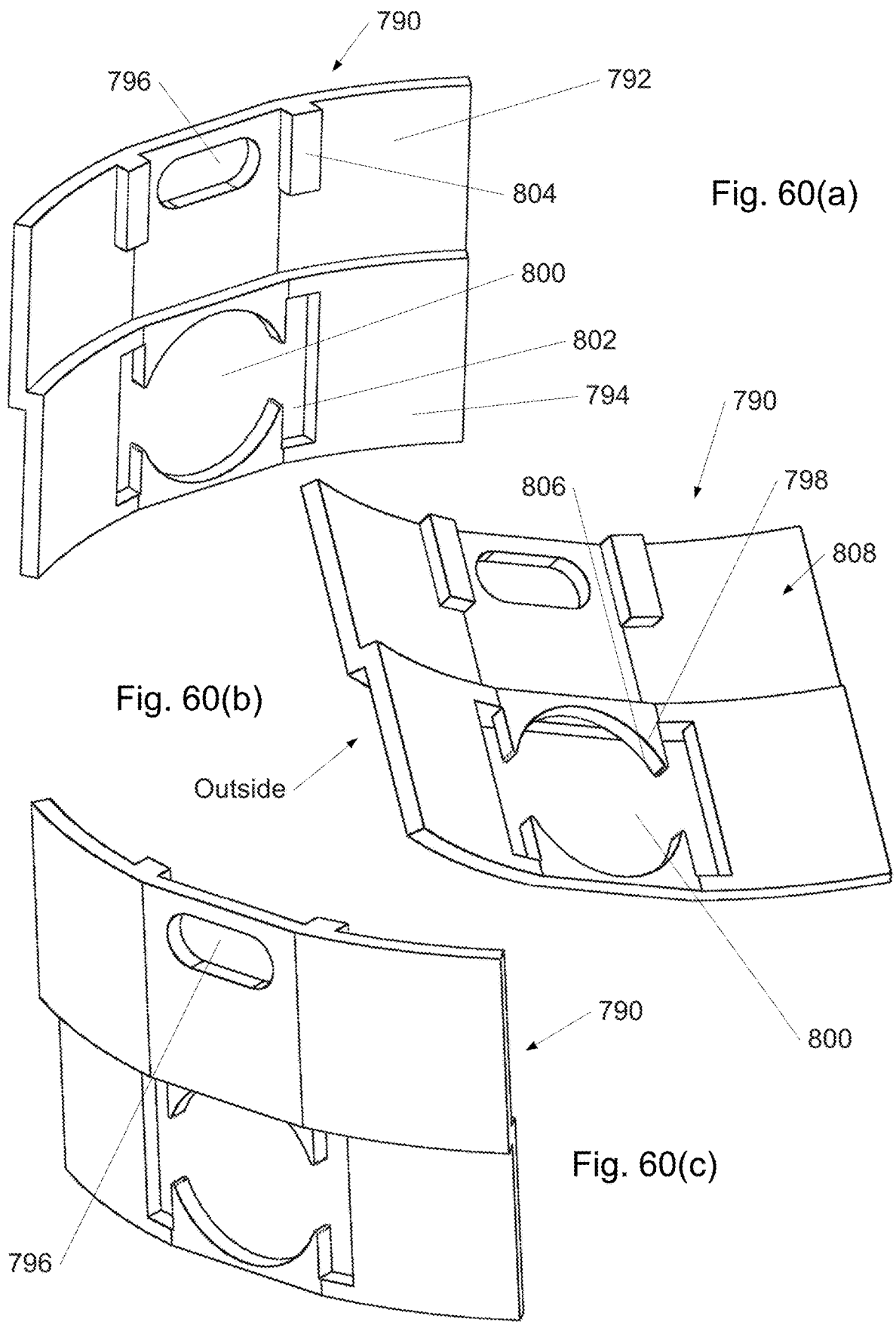

Fig. 60(h)
Fig. 60(i)
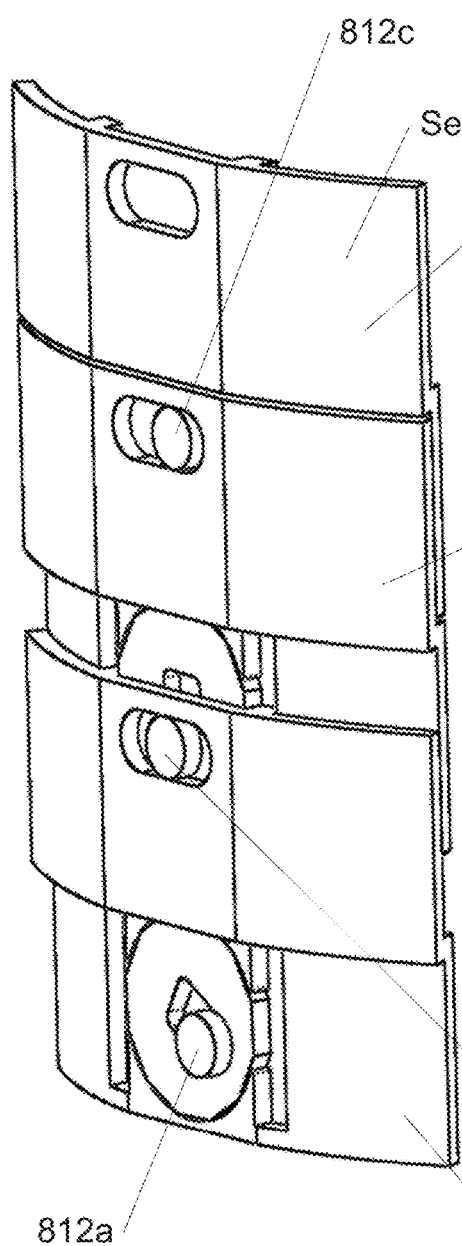
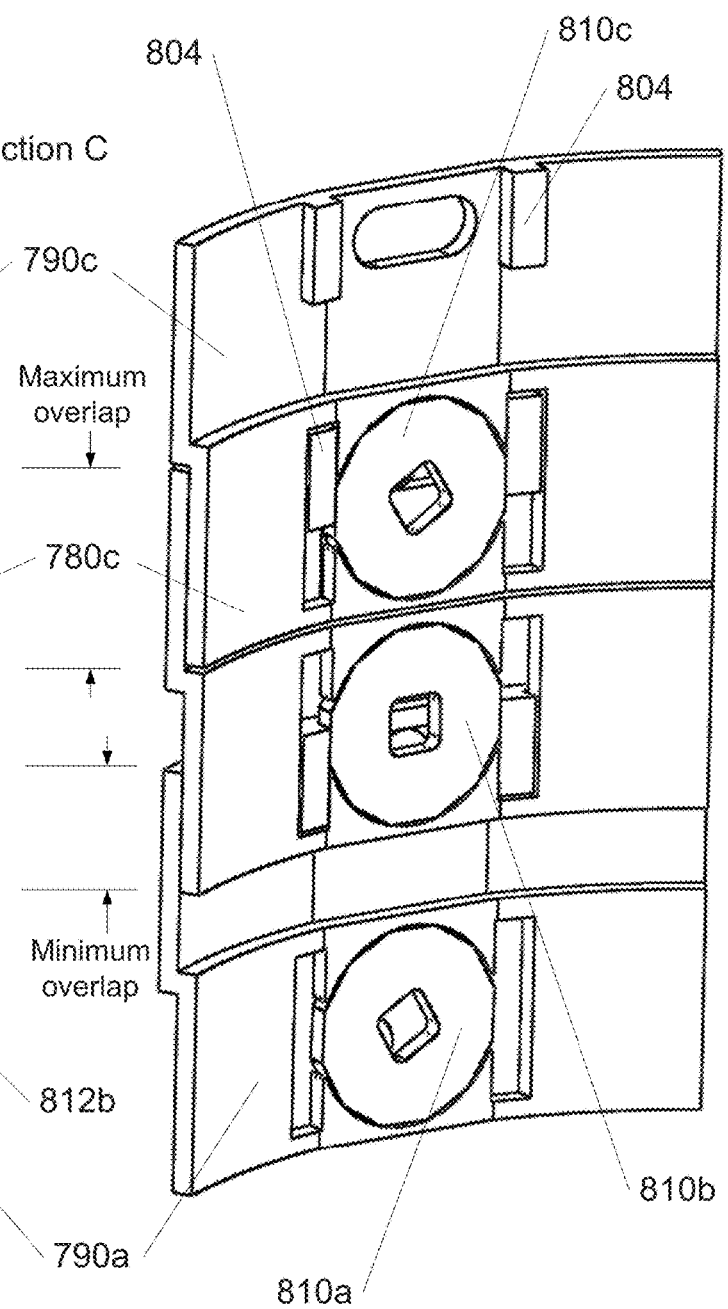

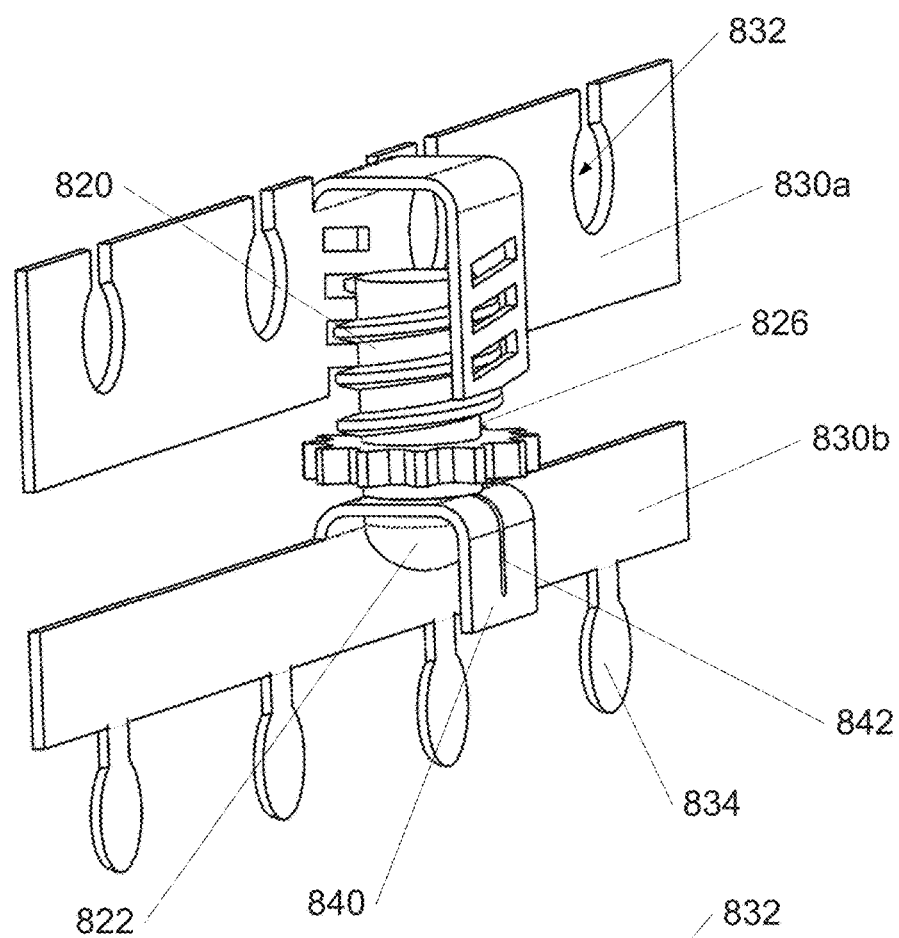
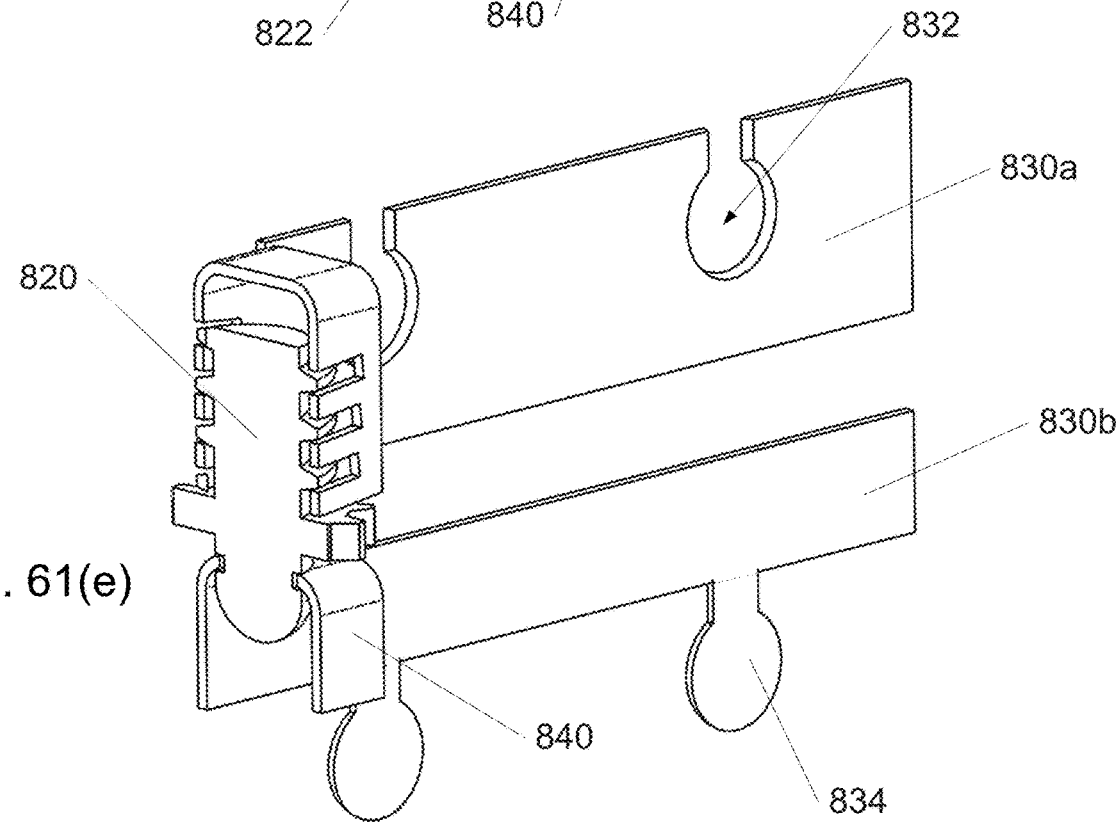
Fig. 61(d)
Fig. 61(e)

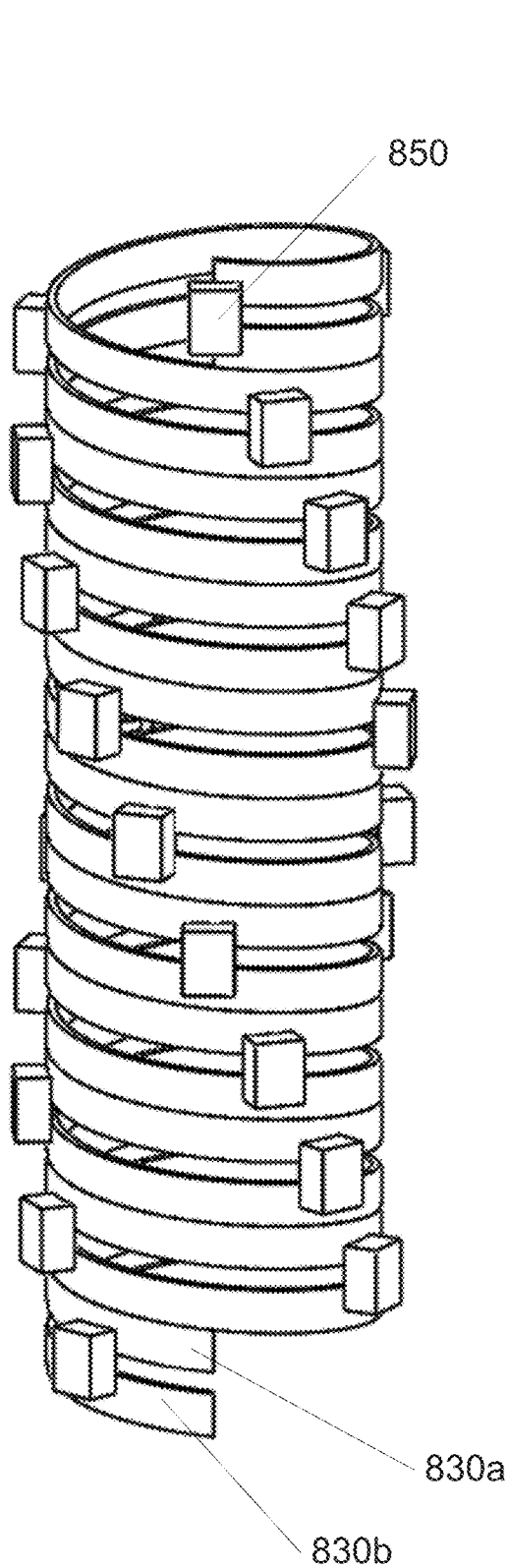
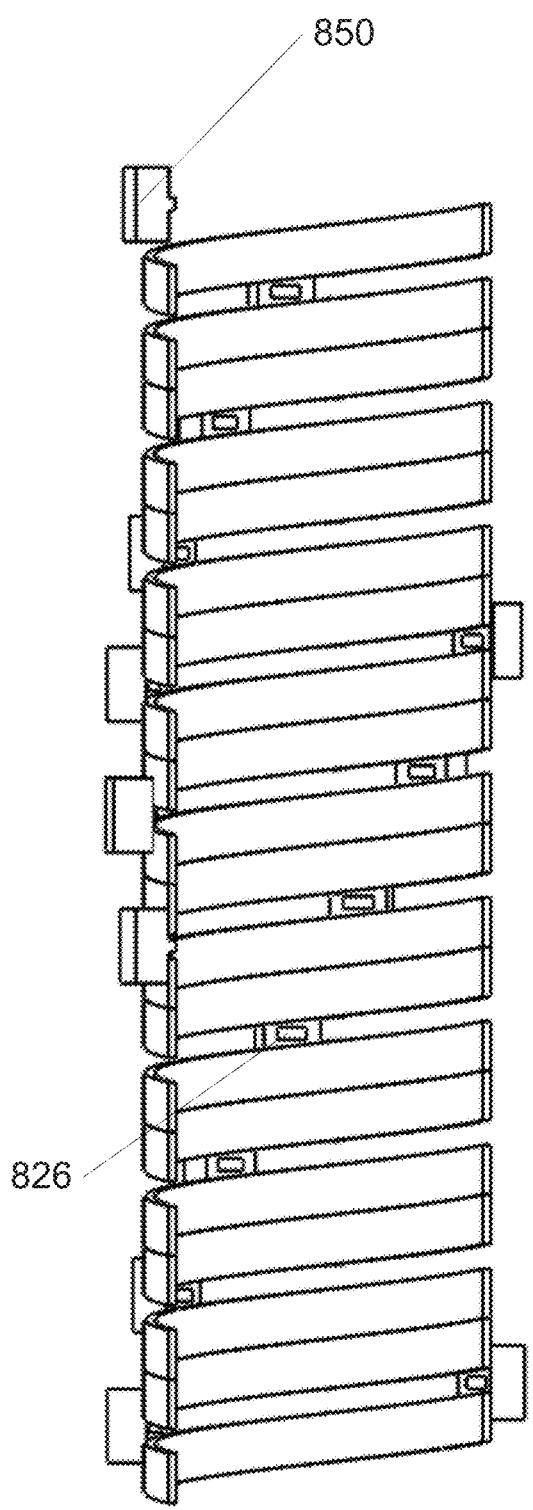
Fig. 61(o)
Fig. 61(p)

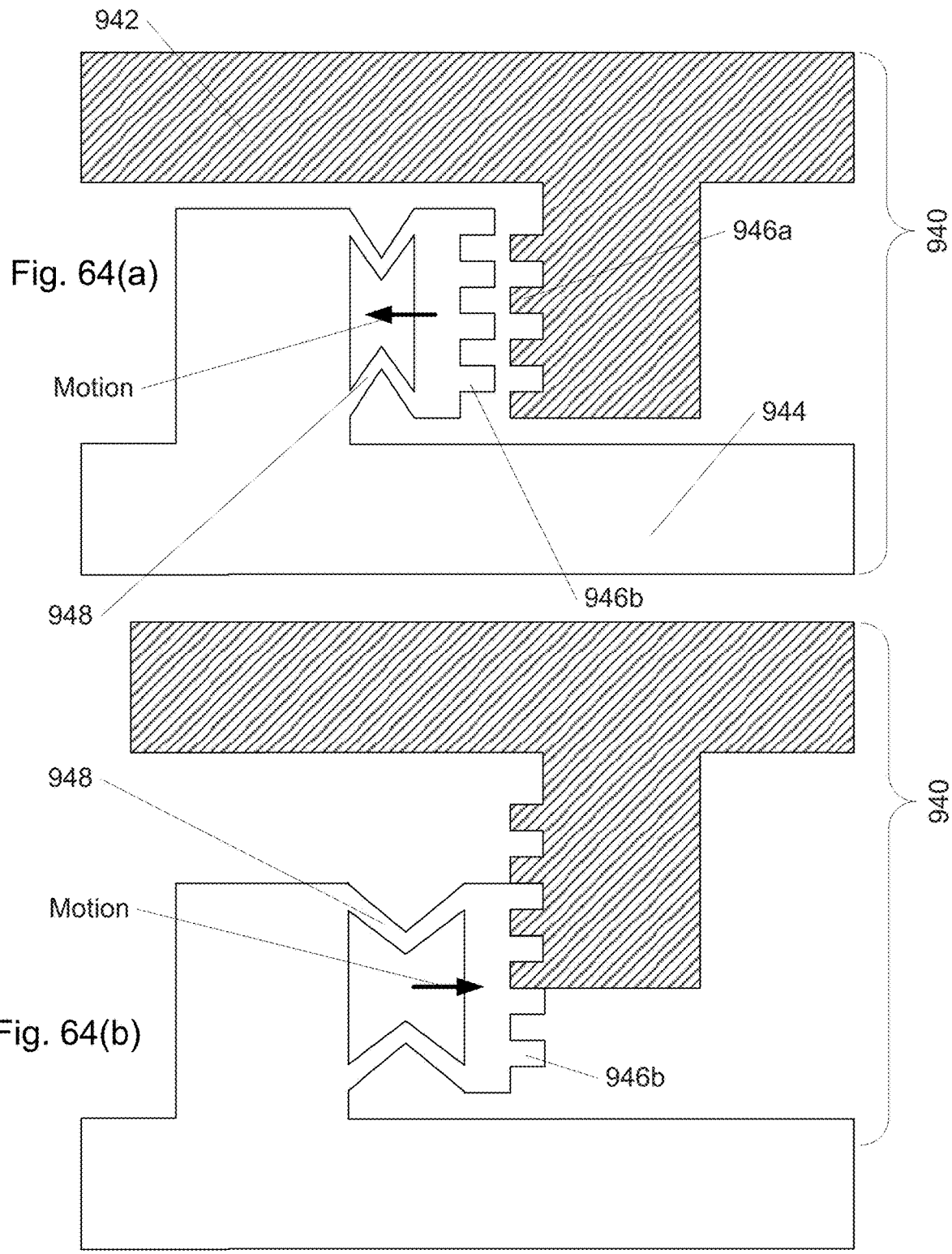

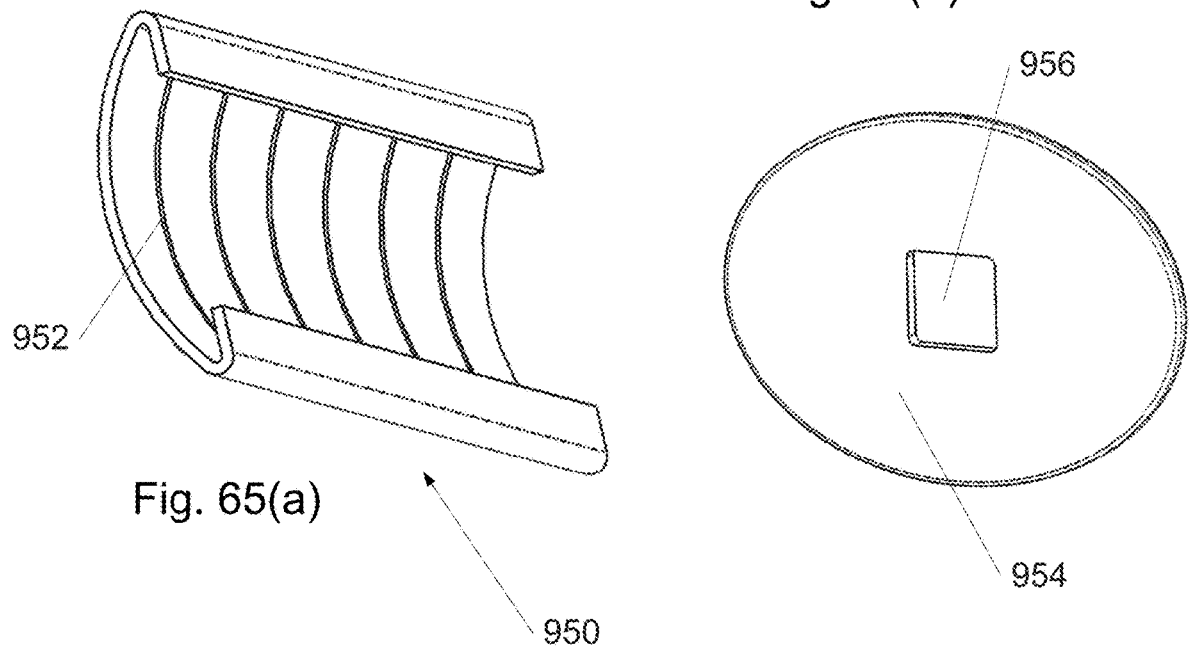
Fig. 65(b)
Fig. 65(a)
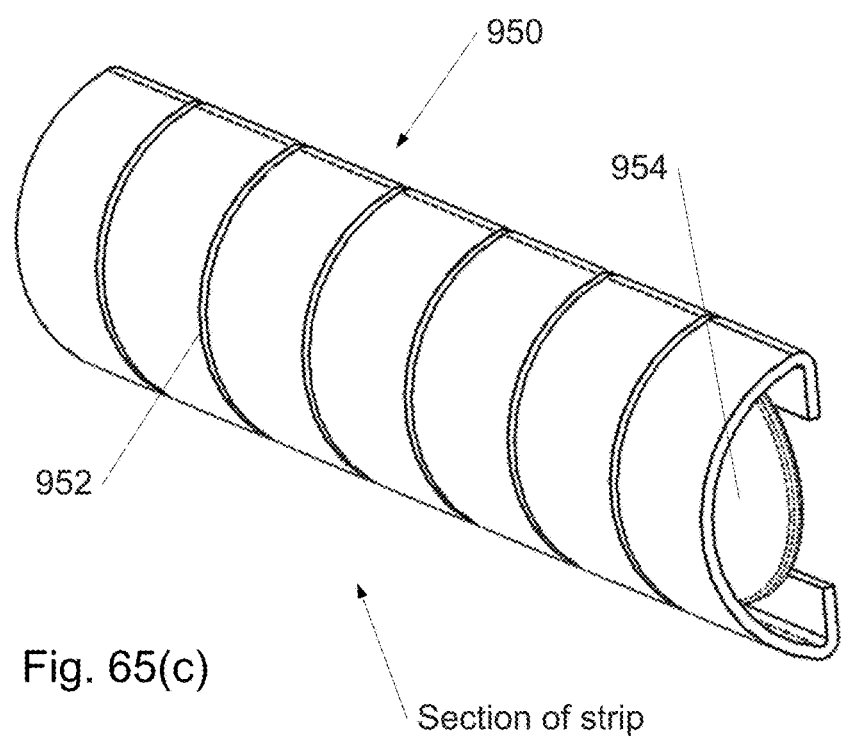
Fig. 65(c)
Section of strip

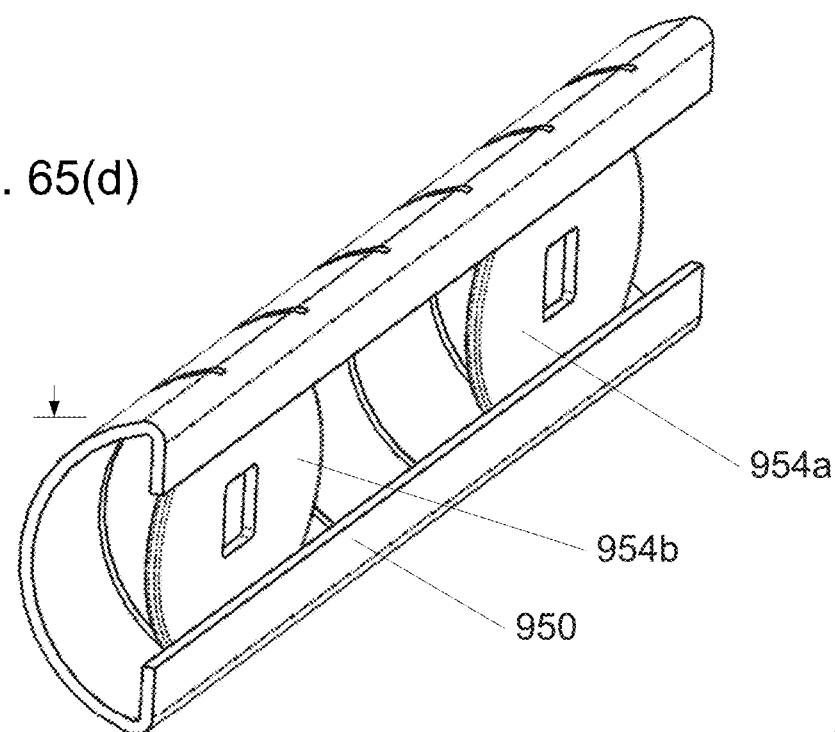
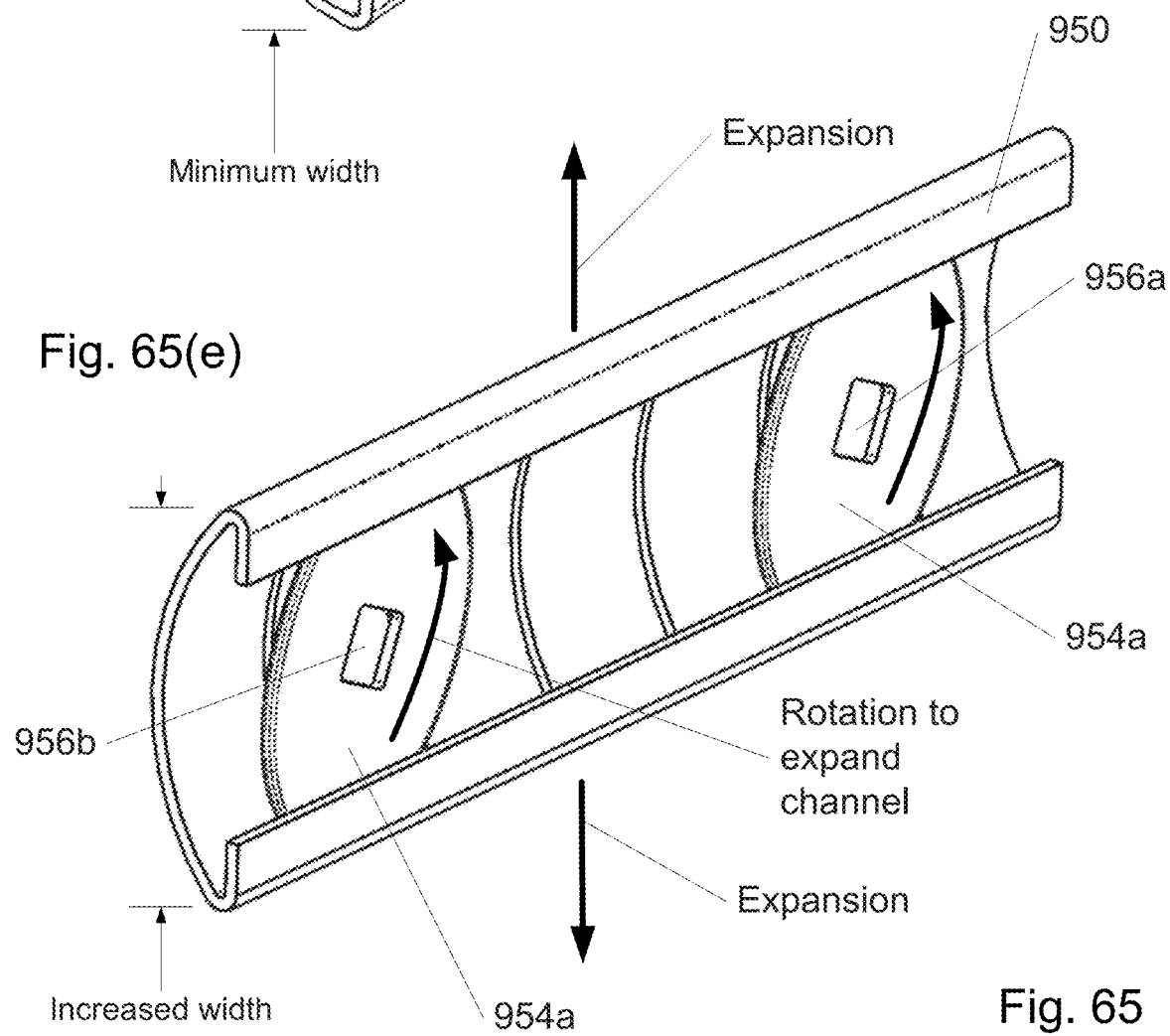
Fig. 65

Fig. 69(f)
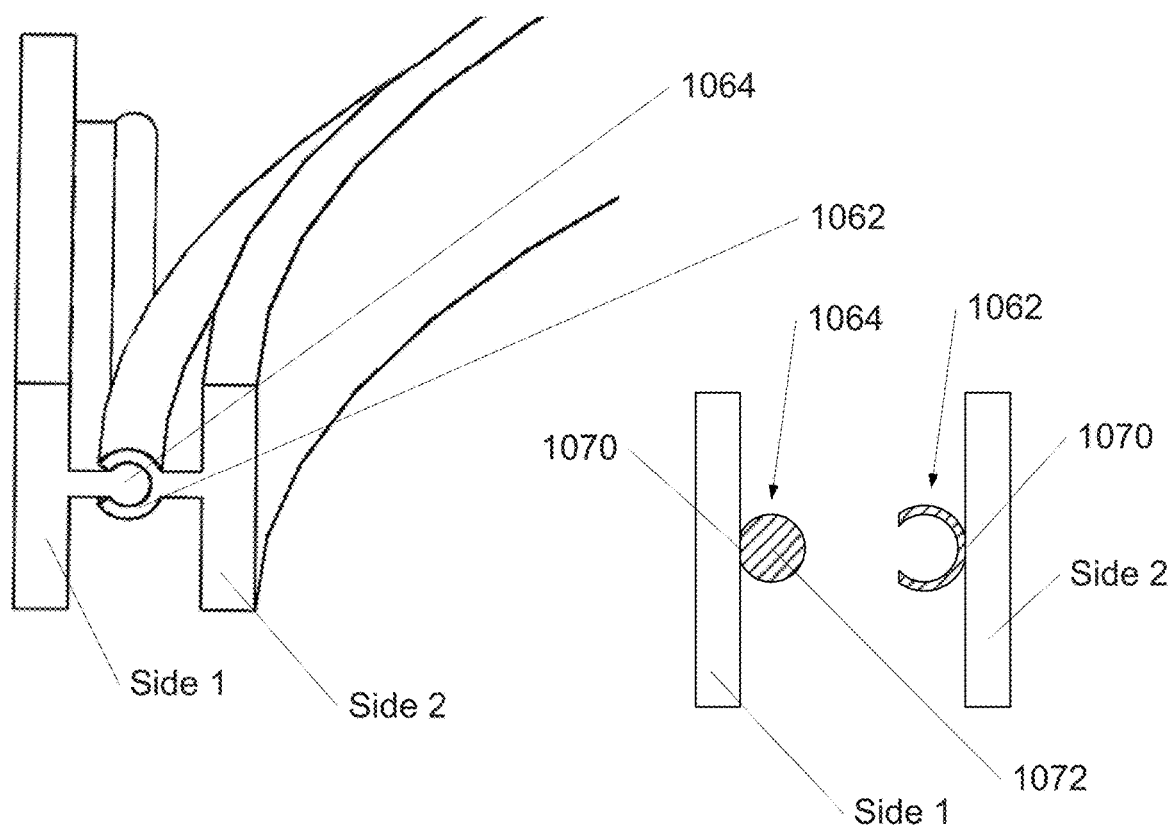
Fig. 69(h)
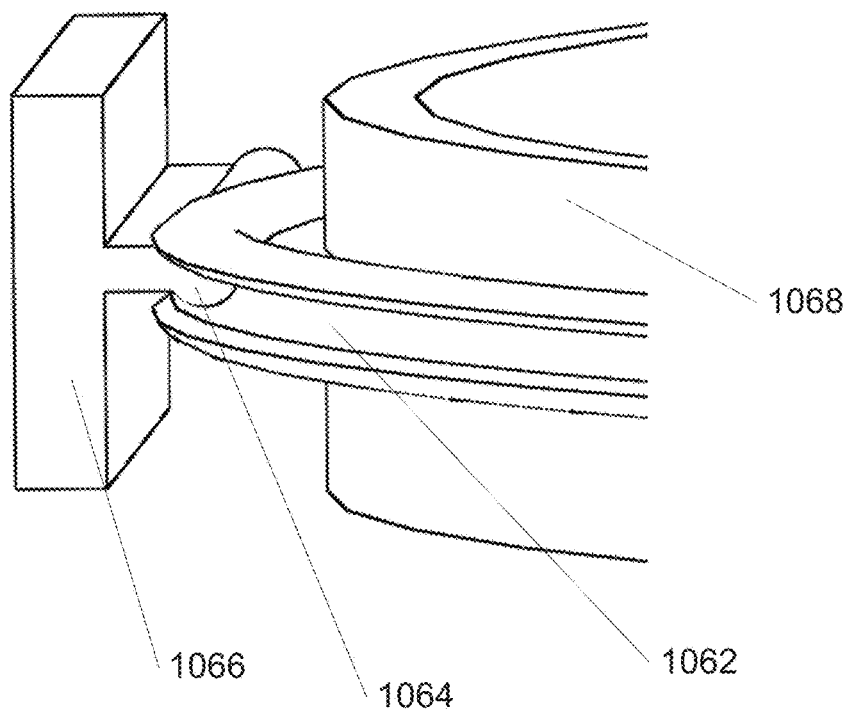
Fig. 69(g)

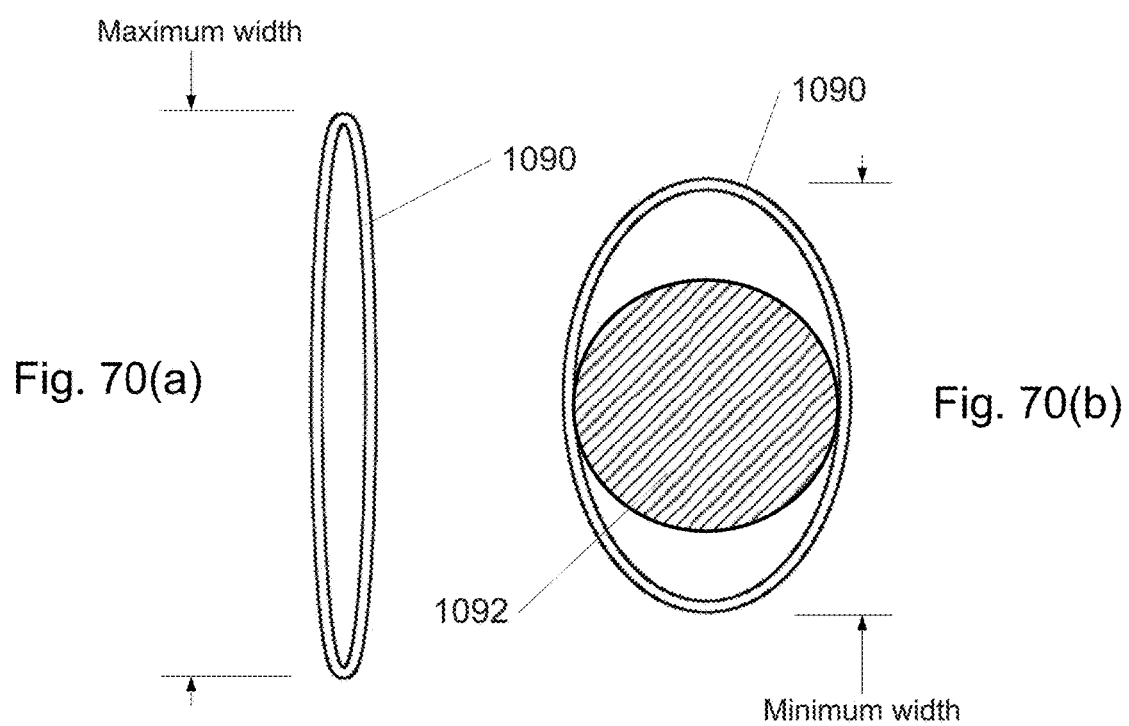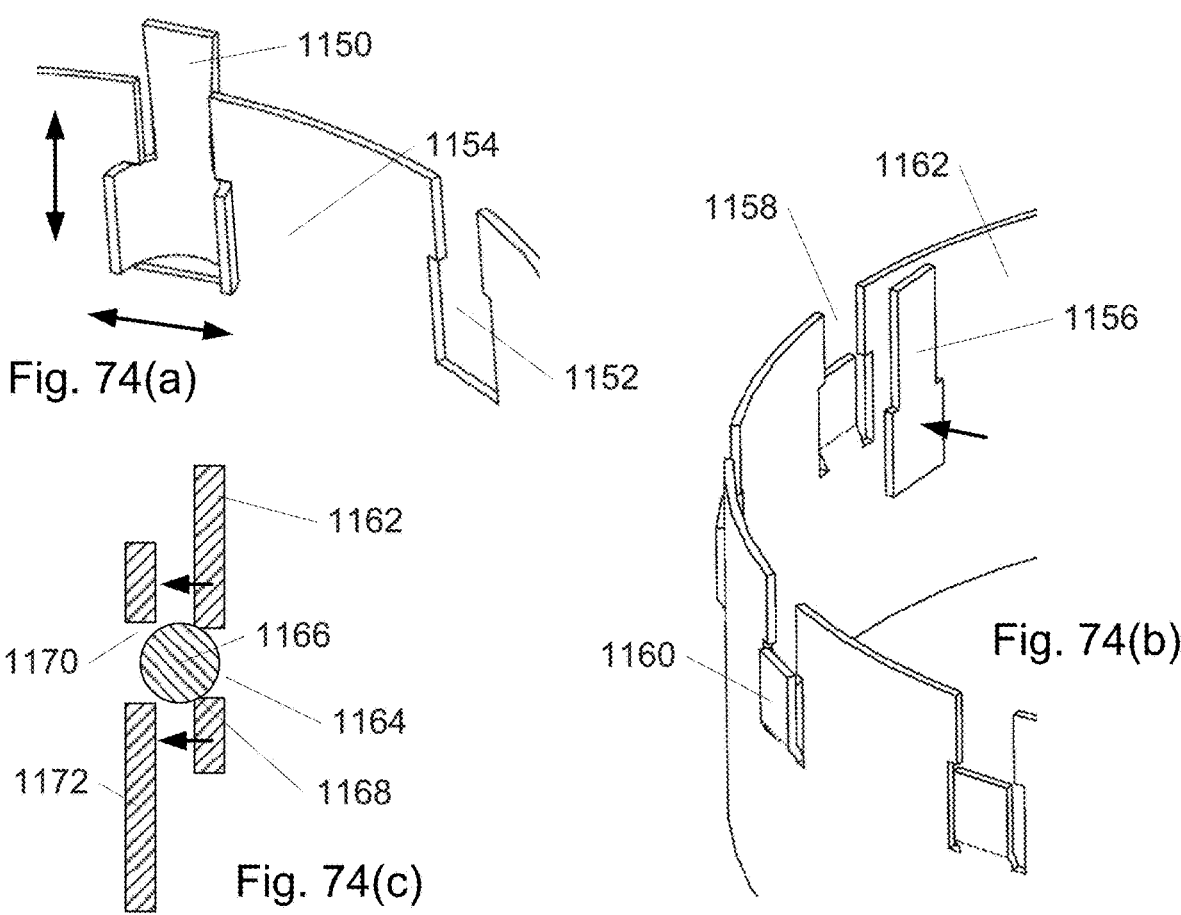

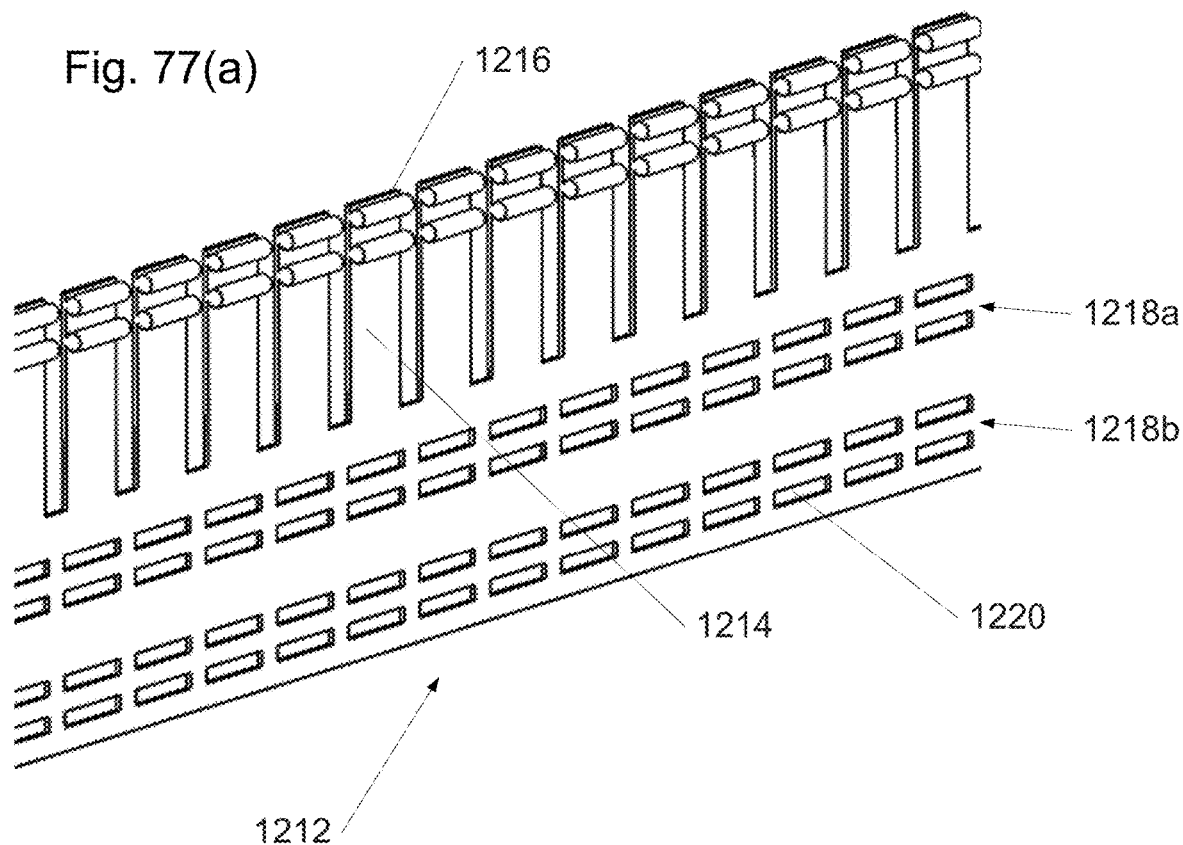
Fig. 77(a)
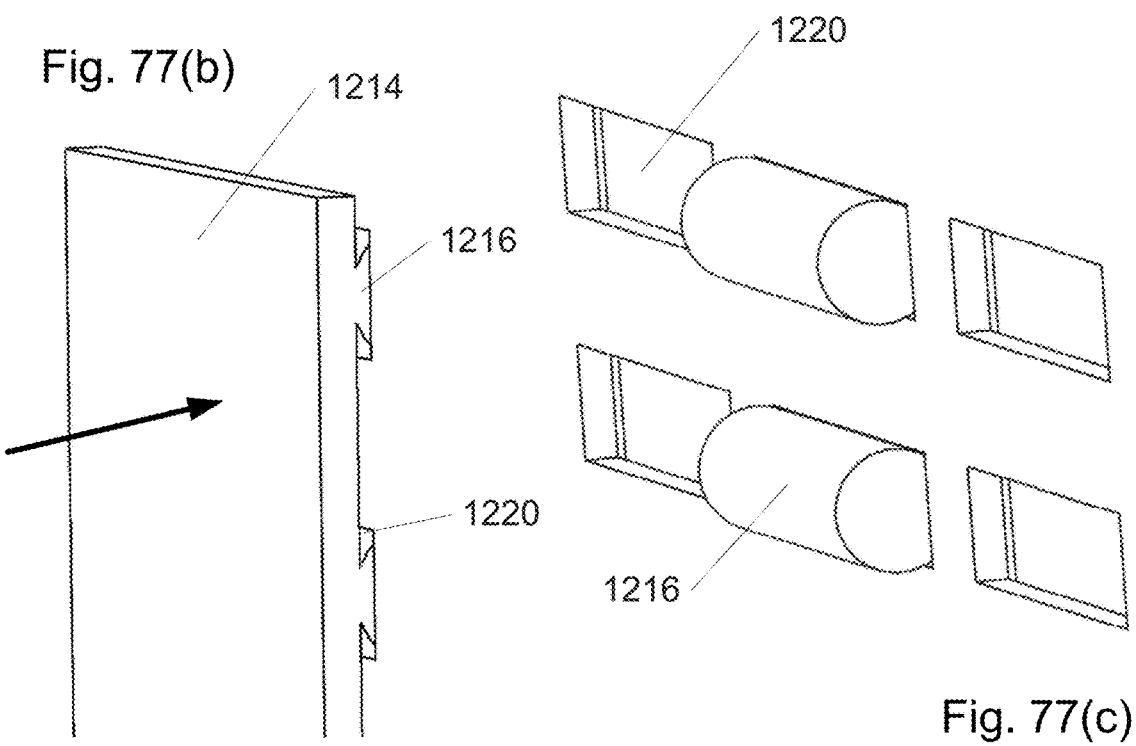
Fig. 77(b)
Fig. 77(c)

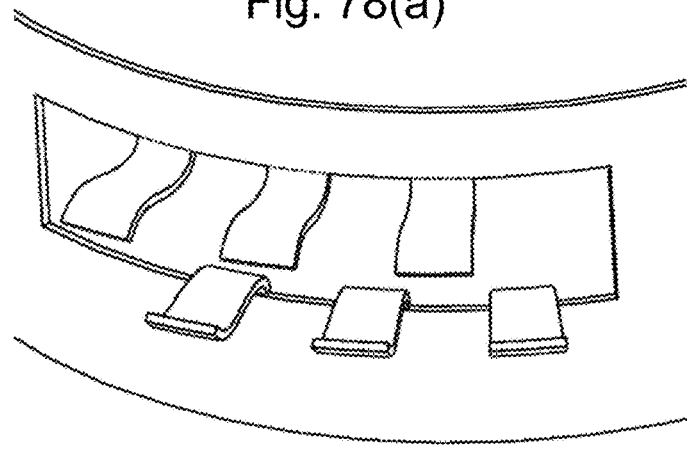
Fig. 78(a)
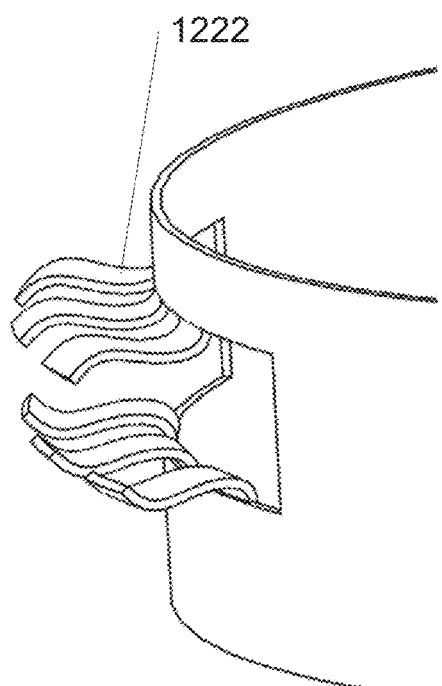
Fig. 78(b)
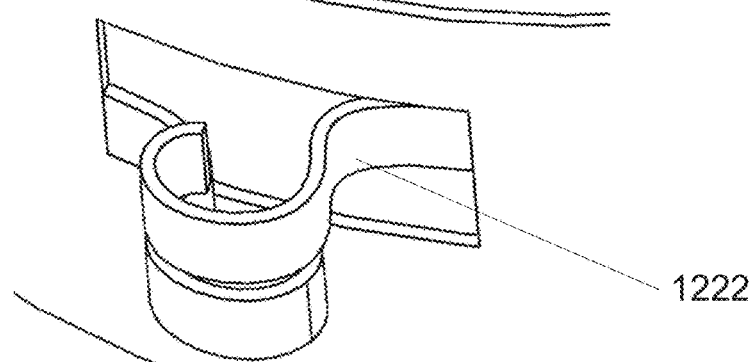
Fig. 78(c)
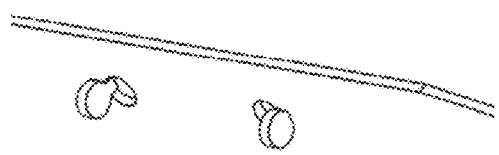
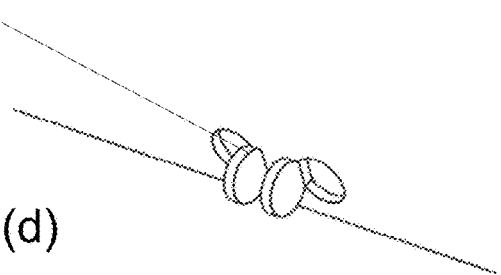
Fig. 78(d)

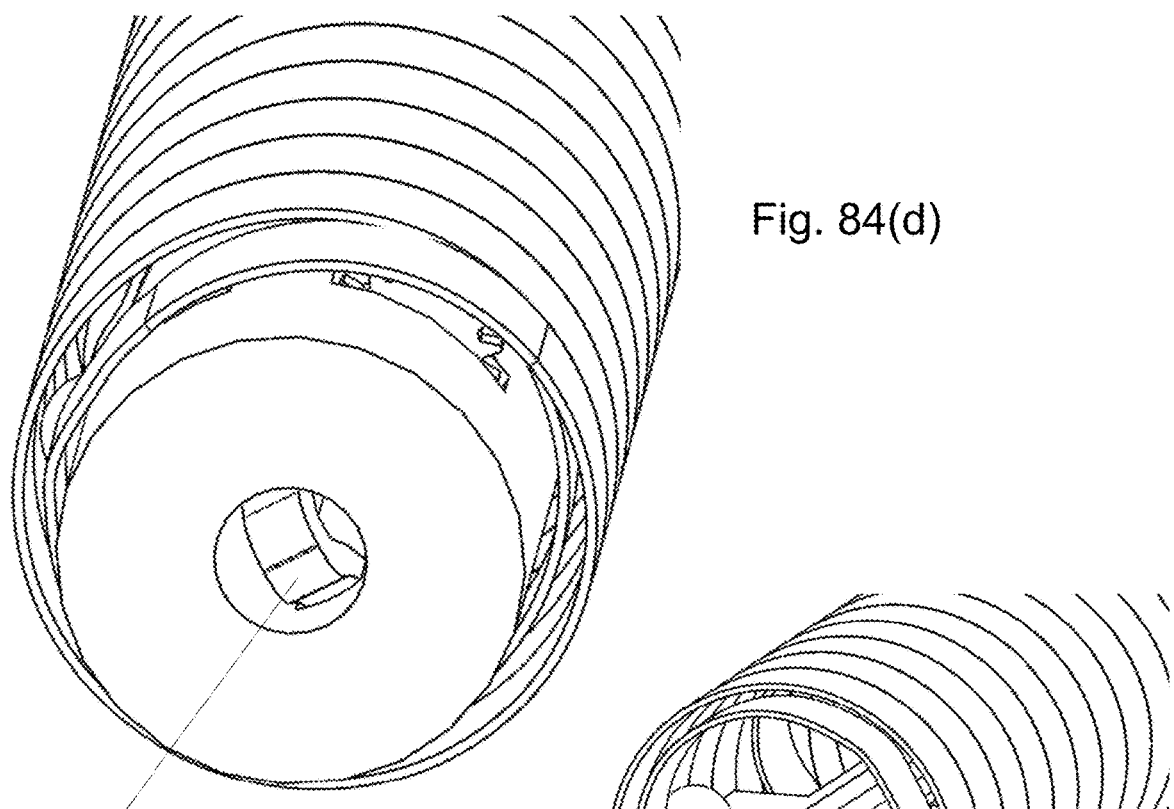
Fig. 84(d)
Fig. 84(e)
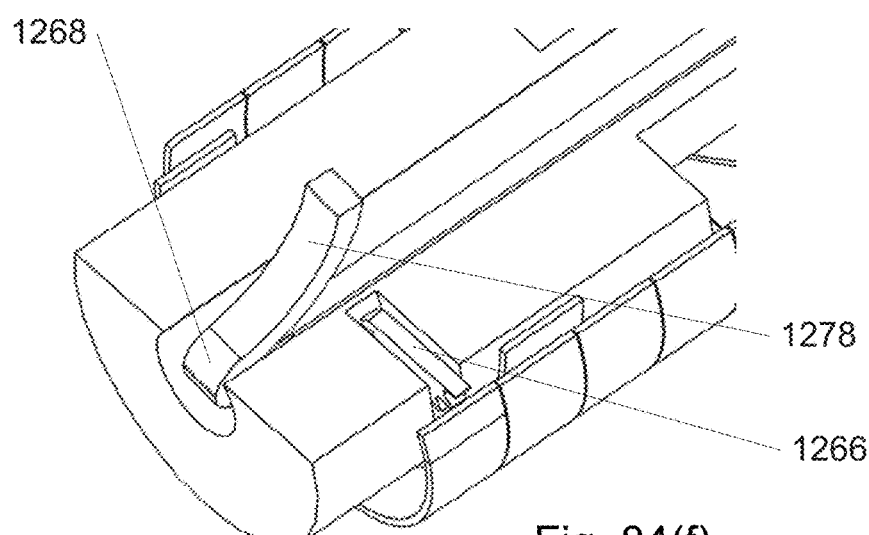
Fig. 84(f)

STEERABLE EXTENDABLE DEVICES

CROSS-REFERENCE TO RELATED APPLICATIONS

This application is a continuation-in-part of U.S. patent application Ser. No. 14/213,193, filed Mar. 14, 2104, now U.S. Pat. No. 9,282,993, issued Mar. 15, 2016, and claims priority to U.S. Provisional Application Ser. No. 61/791,692, filed Mar. 15, 2013 and Ser. No. 61/884,123, filed Sep. 29, 2013, the entire contents of each of which are incorporated herein by reference.

TECHNICAL FIELD OF THE INVENTION

The present invention relates generally to the fields of medical devices, robotics, oil and gas, civil engineering, disaster robotics, as well as other fields.

STATEMENT OF FEDERALLY FUNDED RESEARCH

None.

BACKGROUND OF THE INVENTION

This application relates in part to medical procedures, which comprise entering the patient's body with an instrument to remove, ablate, extract, aspirate, modify, or repair tissue and fluids; to perform diagnostic procedures; or to deliver therapeutic agents or devices. The application also relates to implanted devices and to non-medical devices.

Some medical procedures are minimally invasive; such procedures can improve outcomes, speed recovery, limit trauma, and allow earlier intervention. Cannulas and related, often hollow, tubular devices such as needles, catheters, tubes, and endoscopes, are commonly used in such procedures, allowing surgical tools (including powered tools such as microdebriders driven by rotating flexible shafts), diagnostic and therapeutic instruments, implants, and drugs to be introduced into the body and excised tissue and fluid to be removed. Yet due to obstructions such as bone or sensitive organs, current devices may be unable to access a target region, or only do so sub-optimally. A more invasive method, a riskier approach, or a worse outcome is thus sometimes unavoidable. Moreover, in a number of procedures for which multiple targeted regions within the body need to be accessed, it can be time-consuming and involve multiple punctures or incisions, even if access to a single region would be straightforward. These issues arise from the fact that many instruments are substantially rigid and straight and follow substantially straight paths within the body, whether within a hollow (i.e., gas- or liquid-filled) organ or lumen, or in solid tissue. Moreover, even instruments known to the art that are not rigid and/or not straight can also have difficulty in accessing certain regions of the body, as the following examples will illustrate.

There has been extensive research into steerable needles, cannulas, catheters, and endoscopes; snake-like robots; and other devices. To date such devices have been problematic and many remain experimental. Spinning steerable needles with asymmetric tips [1,2,3,4] offer small gauge sizes but have very large curvature/outer diameter (O.D.) ratios (e.g., 70:1 [5]), can only be deployed within solid tissue, and are difficult to control accurately due to varying tissue properties [6], etc. Concentric multi-tube superelastic nickel-titanium (Nitinol) needles [7,8,9,10,11] intended mostly for hollow regions offer relatively few shapes due to the small number of tubes; relatively large curvature/O.D. ratios [12]; limited stiffness; and small lumen/outside diameter ratios. Steerable catheters [13] and jointed, shape locking devices [14] have few degrees of freedom and sometimes large diameters. Snake-like robots [15,16,17] capable of following 3-D paths are typically 0.4-0.8" diameter and use costly components; their lumen or inner diameter (I.D)/O.D. ratios also tend to be small. Finally, everting endoscopes [18] grow distally and are flexible but not steerable.

Given the limitations of instruments known to the art, there is a need for new, more capable and dexterous instruments capable of curved motion along desirable paths within the body, either within hollow (e.g., gas- or liquid-filled) regions or through solid tissue. Such instruments would preferably be deliverable with minimal difficulty and tissue trauma or damage and have a small outside diameter (e.g., 1-10 mm). They could provide a unique platform technology with the potential to impact a wide variety of medical specialties and procedures, including sinus and skull base surgery (where narrow passages and nearby critical structures make minimally invasive procedures difficult or impossible with current straight or angled instruments, e.g. in the frontal sinus, anterior cranial fossa, cavernous sinus, and brainstem), urology (where, for example, repeated access to specific regions of the kidney can be difficult), and interventional radiology (e.g., for biopsy and drainage while avoiding critical structures, and local regional therapy). Moreover, there is a need (e.g., for cochlear electrodes and annuloplasty rings) for implantable devices that can be delivered in a minimally invasive manner and which have complex 3-D curved shapes; this capability is currently very limited and could be greatly expanded by using the approaches of some embodiments of the invention.

SUMMARY OF THE INVENTION

According to some embodiments of the invention, a stable, controllable cannula is provided that follows an optimal 3-D path—through gas or liquid-filled volumes or solid tissue—to reach virtually any target at any approach angle, and do so without iterative, time-consuming, and potentially traumatic manipulation by the clinician. FIG. 4(a-c) depicts this ideal sequence, in which the device extends along a path while steered and assembled robotically in-vivo so as to grow into a complex, often curvilinear 3-D shape within the body while the more distal regions of the device retain their original shape.

Such a device, which we term a "distally-assembled steerable cannula" (hereinafter, "DASC"), is fundamentally different from existing steerable needles, cannulas, catheters, and snake robots that rely on distally sliding and articulating. DASC is unique in several aspects. For example, it may be deployed within a patient's body entirely through distal growth, extending at its distal tip to follow a controlled 3-D path, while shape is maintained everywhere along the device. Moreover, it may be assembled in vivo from multiple, discrete pieces (interlocking segments or rings), be continuously assembled from a strip, or grow as an everting, steerable tube, offering an unprecedented number of possible 3-D shapes. These shapes may include multiple bends in multiple planes at various locations along the length of the cannula. Moreover, the cannula can vary its overall length up to a maximum. These attributes together can greatly facilitate operation within confined spaces. DASC provides an enormous number of degrees of freedom, yet does not require many actuators, since the mechanisms providing those degrees of freedom are self-locking and are accessed sequentially. DASC offers the ability to make tight turns (e.g., a 2:1 radius of curvature to O.D. ratio); for example, a 0.120" O.D. device could make a full 180° turn in a space only ~0.7" wide. DASC also provides an unusually large lumen/working channel (e.g., a 0.9:1.0 lumen/O.D. ratio)—comparable to a non-steerable catheter—enabling more instruments to be used simultaneously; improving endoscopic visualization, irrigation, and aspiration; and allowing more tissue to be excised (e.g., for biopsy or tumor resection).

DASC can serve as a stable, passive conduit that provides access and support to other devices (e.g., articulated endoscopes, forceps, bipolar diathermy and monopolar cautery devices, laser fibers, graspers, dissectors, scissors, knives, needles, needle drivers, spatulas, or other instruments, at least one of which can be used at a time, and which can be rapidly exchanged), for example, in endoscopic surgery, laparoscopic, single port, and natural orifice translumenal endoscopic surgery, or to infuse or aspirate liquids. However, unlike prior-art passive devices, DASC can be easily re-shaped distally without having to first withdraw it and re-insert it during a procedure. Thus, DASC can be disassembled partially and then reassembled such that the distal end moves to a new position and/or changes its approach angle to the target region, providing, for example, a stable platform for procedures which cover multiple sites or wide areas.

DASC can be image-guided (e.g., via pre- or peri-operative CT, fluoro (portions of DASC may be made radiopaque), MM, ultrasound, and/or direct visualization), can be "driven" precisely in real time by a clinician (e.g., using a joystick), or can automatically grow according to an optimal, pre-determined trajectory, with optional real-time correction. It could be optimized for rigidity (e.g., for tissue manipulation) or instead, for compliance, e.g., to approximate the modulus of tissue. The tip of a DASC device can be made to sense force, helping a clinical detect obstructions and choose an optimal trajectory for deployment.

In some embodiments, DASC grows from its distal end by sequentially assembling flexible segments or rings that interlock to form a rigid, self-supporting tube with a complex, programmable 3-D shape. The segments or rings are temporarily deformed and individually transported through the growing cannula by a flexible shaft or "smart stylet" (hereinafter the "stylet"), then assembled by the stylet at the distal end. Each ring is wedge-shaped in profile; by robotically mating the ring at a preset orientation with respect to the next-most-proximal ring, the local radius of curvature and direction of the cannula can be precisely controlled. A fully-deployed cannula may comprise over 100 rapidly-assembled segments or rings. Since each ring can be mated in a number (e.g., eight or more) orientations, the range of possible 3-D configurations—and thus cannula's reachable workspace and set of approach angles—is vast. DASC can be scaled down to an O.D. (outside diameter) as small as 0.04" (1 mm, 3 French) with a lumen ≥90% of the O.D., or can be scaled larger if required. As an example of a DASC suitable for sinus surgery, dimensions might be 0.12-0.16" O.D., 0.09-0.13" I.D. (inside diameter), 4-5" overall length, and 0.3-0.4" radius of curvature.

In one embodiment, the present invention includes an elongatable, steerable apparatus capable of growing from a proximal end to a distal end through a process of assembly wherein one or more segments are added to the distal end of the apparatus, the apparatus comprising: a first segment having a lumen therethrough, the first segment having a proximal end and a distal end; and a second segment having a lumen, a proximal end, and a distal end, wherein the second segment is deliverable via a segment transporter to the distal end of the first segment, wherein the segment transporter attaches the second segment to the first segment, wherein the second segment is capable of changing the growth direction (i.e., the local radius and plane of curvature) of the distal end of the apparatus and of one or more subsequent segments. In one aspect, additional segments are transferred to the distal end through the lumen formed of at least one of the first, the second and one or more subsequent segments. In another aspect, the growth is the result of everting a tube formed by two or more segments. In another aspect, the growth is the result of transferring additional segments to the distal end. In another aspect, at least the first, second or subsequent segments are at least one of triangular, circular, elliptical, polygonal, rectangular, square, or combination thereof. In another aspect, the at least first, second or subsequent segments comprise at least one of plastic, metal, rubber, latex, polymer, composite, elastomer, thermoplastic elastomer, synthetic rubber, natural rubber, melt processable rubber, propylene oxide elastomer, ethylene-isoprene elastomer, elastic polyvinyl chloride, silicone elastomer, elastic polyurethane, ethylene-vinyl acetate elastomer, or non-polymeric elastomer. In another aspect, at least the first, second or subsequent segments are metal and comprise at least one of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, superelastic nickel-titanium, and stainless steel. In another aspect, the segment transporter is defined further as a stylet that is comprised of at least one of a superelastic nickel-titanium, stainless steel, plastic, thermoplastic, elastomer, polyethylene terephthalate, polyethylene terephtalate glycol-modified, rubber, vinyl, latex, or silicone. In another aspect, at least one segment may be radiopaque. In another aspect, at least the first, second, or subsequent segments, may attach or interlock to each other by friction, abrasive contact surfaces, self-adhesive strips, hook and loop fasteners, hooks and eyes, ties, tabs, holes, buckles, belts, pins, elastic bands, rubber bands, snaps, clasps, magnets, zippers, DUAL LOCK™, or VELCRO™ tape fasteners. In another aspect, at least the first, second, or subsequent segments, are wedge-shaped and the addition of subsequent segments causes the extension of the apparatus at the distal end with a segment that is not wedge-shaped, a segment that is wedge-shaped on the distal or the proximal face, or a segment that is wedge-shaped on both the distal and proximal faces. In another aspect, at least the first, second, or subsequent segments, are wedge-shaped having a wedge angle that varies from 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees at the proximal or distal face, or on both faces. In another aspect, at least the first, second, or subsequent segments, are wedge-shaped and the segments interlock in increments of 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, 85, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 degrees about the longitudinal axis of the apparatus. In another aspect, at least the first, second, or subsequent segments, are wedge-shaped but also tapered along the longitudinal axis of the apparatus to expand or decrease an inner diameter of the apparatus. In another aspect, the central cannula is defined further as a having a proximal and distal end, wherein the segment transporter travels back and forth within the cannula to at least one of compress, swivel, transport, rotate, or add the subsequent segments to the distal end of the apparatus. In another aspect, the cannula is pre-loaded with some or all the segments necessary to reach a pre-determined length and shape.

In another embodiment, the present invention includes a method of lengthening and steering an apparatus capable of growing from a proximal end to a distal end through a process of assembly wherein one or more segments are added to the distal end of the apparatus, the apparatus comprising: obtaining a first segment having a lumen therethrough, the first segment having a proximal end and a distal end; and adding a second segment having a lumen, a proximal end, and a distal end, wherein the second segment is deliverable via a segment transporter to the distal end of the first segment, wherein the segment transporter attaches the second segment to the first segment, wherein the second segment is capable of changing the growth direction of the distal end of the apparatus and of one or more subsequent segments. In one aspect, additional segments are transferred to the distal end through the lumen formed of at least one of the first, the second and one or more subsequent segments. In another aspect, the growth is the result of everting a tube formed by the two or more segments. In another aspect, the growth is the result of transferring additional segments to the distal end. In another aspect, at least the first, second or subsequent segments are at least one of triangular, circular, elliptical, polygonal, rectangular, square, or combination thereof. In another aspect, the at least first, second or subsequent segments comprise at least one of plastic, metal, rubber, latex, polymer, composite, elastomer, thermoplastic elastomer, synthetic rubber, natural rubber, melt processable rubber, propylene oxide elastomer, ethylene-isoprene elastomer, elastic polyvinyl chloride, silicone elastomer, elastic polyurethane, ethylene-vinyl acetate elastomer, or non-polymeric elastomer. In another aspect, at least the first, second or subsequent segments are metal and comprise at least one of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, superelastic nickel-titanium, or stainless steel. In another aspect, the segment transporter is defined further as a stylet that is at least one of a superelastic nickel-titanium, stainless steel, plastic, thermoplastic, elastomer, polyethylene terephthalate, polyethylene terephthalate glycol-modified, rubber, vinyl, latex, or silicone. In another aspect, at least the first, second, subsequent segments, or the cannula is radiopaque. In another aspect, at least the first, second, or subsequent segments, may attach or interlock to each other by friction, abrasive contact surfaces, self-adhesive strips, hook and loop fasteners, hooks and eyes, ties, tabs, holes, buckles, belts, pins, elastic bands, rubber bands, snaps, clasps, magnets, zippers, DUAL LOCK™, or VELCRO™ tape fasteners. In another aspect, at least the first, second, or subsequent segments, are wedge-shaped and the addition of subsequent segments causes the extension of the apparatus at the distal end with a segment that is not wedge-shaped, a segment that is wedge-shaped on the distal or the proximal face, or a segment that is wedge-shaped on both the distal and proximal faces. In another aspect, at least the first, second, or subsequent segments, are wedge-shaped having a wedge angle that varies from 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees at one or both ends. In another aspect, at least the first, second, or subsequent segments, are wedge-shaped and the segments interlock in increments of 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, 85, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 degrees about the longitudinal axis of the apparatus. In another aspect, at least the first, second, or subsequent segments, are wedge-shaped but also tapered along the longitudinal axis the apparatus to expand or decrease an inner diameter of the apparatus. In another aspect, the central cannula is defined further as a having a proximal and distal end, wherein the segment transporter travels back and forth within the cannula to at least one of compress, swivel, transport, rotate, or add the subsequent segments to the distal end of the apparatus. In another aspect, the cannula is pre-loaded with some or all the segments necessary to reach a pre-determined length and shape.

In another embodiment, the present invention includes a cannula capable of growing from a proximal end to a distal end and capable of a non-linear configuration comprising: one or more segments having a lumen and substantially cylindrical in their uncompressed state and having a distal face and a proximal face that are non-parallel, wherein the one or more segments can be transformed into a non-cylindrical, substantially elliptical shape; a segment transporter that transports one or more additional segments in their non-cylindrical, substantially elliptical shape through the substantially cylindrical segments; and a coupling mechanism that engages the one or more segments to an adjacent segment, whereby at least one of the segments is transported through the lumen of the one or more substantially cylindrical segments to reach a distal location, and transformed to couple to the most distal of the segments, thereby growing the cannula. In one aspect, the segment transporter is capable of at least one of swiveling, rotating, coupling or transporting a segment. In another aspect, a swiveling axis of the segment is substantially parallel to a minor axis of the non-cylindrical, substantially elliptical shape of the segment. In another aspect, a distal face of a first segment is substantially perpendicular to a substantially cylindrical axis of the first segment, and a proximal face of a first segment is substantially non-perpendicular to the substantially cylindrical axis of the first segment; a distal face of a second segment is substantially non-perpendicular to a substantially cylindrical axis of the second segment, and a proximal face of a second segment is substantially perpendicular to the substantially cylindrical axis of the second segment; and wherein the swiveling axis is substantially perpendicular to a plane formed by the substantially cylindrical axis and a normal to the substantially non-perpendicular face of the segment. In another aspect, the segments comprise one or more holes along a distal edge or face of the segment and one or more tabs that extend from a proximal edge or face of the segments, wherein the one or more tabs fit within the one or more holes to couple two adjacent segments. In another aspect, each segment comprises two or more tabs that are equally spaced around the circumference of the segment. In another aspect, the tabs are substantially aligned with the major and minor axes of the substantially elliptical shape assumed by the rings when transformed. In another aspect, each segment comprises two holes that are substantially parallel to the swiveling axis. In another aspect, at least one first tab in the distal segment of a pair of adjacent segments enters a hole in the proximal segment of a pair of adjacent segments from the inside of the proximal segment, and at least one second tab on the non-opposite side of the distal segment enters a hole from the outside of the proximal segment to couple the segments. In another aspect, each of the first and second segments alternate.

In another embodiment, the present invention includes an elongatable, steerable cannula capable of growing from a proximal end to a distal end through a process of assembly wherein one or more segments are added to the distal end of the cannula, the cannula comprising: a first flexible segment substantially cylindrical in axial cross section when uncompressed and substantially elliptical when compressed, having a first lumen therethrough, the first segment having a first proximal face substantially perpendicular to a first substantially cylindrical axis and provided with one or more first male coupling elements, and a first distal face substantially non-perpendicular to the substantially cylindrical axis and provided with a first plurality of female coupling elements; a second flexible segment substantially cylindrical in axial cross section when uncompressed and substantially elliptical when compressed, having a second lumen therethrough, the second segment having a second proximal face substantially non-perpendicular to a second substantially cylindrical axis and provided with one or more second male coupling elements, and a second distal face substantially perpendicular to the second substantially cylindrical axis and provided with a second plurality of female coupling elements; a flexible shaft provided with grippers able to grip said first and said second segment to compress and allow to decompress said segments, swivel or allow to swivel said segments about axes substantially parallel to the minor axes of said first and second segments when compressed and substantially elliptical, and transport said segments through said lumen; wherein said flexible shaft transports said second segment through said lumen of said first segment, then rotates said second segment as required around an axis substantially coincident with the longitudinal axis of the flexible shaft, brings the proximal face of said second segment in contact with the distal face of said first segment, allows said second segment to decompress while allowing two of said second male coupling elements to enter two of said first plurality of female coupling elements from the inside and two of said second male coupling elements to enter two of said first plurality of female coupling elements from the outside; and wherein said flexible shaft transports said first segment through said lumen of said second segment, rotates said first segment as required around an axis substantially coincident with the longitudinal axis of the flexible shaft, brings the proximal face of said first segment in contact with the distal face of said second segment, then allows said first segment to decompress while allowing two of said first male coupling elements to enter two of said second plurality of female coupling elements from the inside and two of said first male coupling elements to enter two of said second plurality of female coupling elements from the outside. In another aspect, the segments comprise a superelastic nickel-titanium material. In another aspect, the first and second male coupling elements comprise interlocking male and female elements such that the adjacent segments are mechanically interlocked when the segments are decompressed. In another aspect, a plurality of first and second segments is arranged in an alternating pattern within the cannula. In another aspect, the angle between the first proximal face and second distal face is varied by varying the relative orientation of the first and second segments when coupled together. In another aspect, the relative orientation is varied as required by rotating the second segment substantially about an axis substantially coincident with the longitudinal axis of the flexible shaft prior to coupling the second segment to the first segment. In another aspect, the flexible shaft comprises a superelastic nickel-titanium material. In another aspect, the minor axis of the compressed, substantially elliptical second segment is substantially perpendicular to the plane defined by the substantially non-perpendicular second proximal face and the second substantially cylindrical axis, and wherein the minor axis of the compressed, substantially elliptical first segment is substantially perpendicular to the plane defined by the substantially non-perpendicular first distal face and the first substantially cylindrical axis. In another aspect, the second segment is swiveled about its minor axis and its major axis is substantially parallel to the first cylinder axis during transport by the flexible shaft, and wherein the first segment is swiveled about its minor axis and its major axis is substantially parallel to the second cylinder axis during transport by the flexible shaft. In another aspect, the second segment is rotated as required relative to the first segment prior to allowing the second segment to decompress, and wherein the first segment is rotated relative to the second segment prior to allowing the first segment to decompress. In another aspect, the grippers are supported by a fork that is compressed by a sliding tube. In another aspect, the grippers are supported by a flexible ring that is expanded by applying tension to a wire attached to its distal end.

In another embodiment, the present invention includes an elongatable, steerable cannula capable of growing from a proximal end to a distal end through a process of assembly wherein one or more segments are added to the distal end of the cannula, the cannula comprising: a first expandable segment substantially cylindrical in axial cross section having a first lumen therethrough, the first segment having a first proximal face substantially perpendicular to a first substantially cylindrical axis and provided with a first plurality of male coupling elements, and a first distal face substantially non-perpendicular to the substantially cylindrical axis and provided with a first plurality of female coupling elements; a second expandable segment substantially cylindrical in axial cross section having a second lumen therethrough, the second segment having a second proximal face substantially non-perpendicular to a second substantially cylindrical axis and provided with a second plurality of male coupling elements, and a second distal face substantially perpendicular to the second substantially cylindrical axis and provided with a second plurality of female coupling elements; a flexible shaft provided with an expanding member to expand and orient said first and said second segments, and transport said segments through said lumens; wherein said flexible shaft transports said second segment through said lumen of said first segment, then expands said second segment and allows second plurality of male coupling elements to enter said first plurality of female coupling elements from the inside; and wherein said flexible shaft transports said first segment through said lumen of said second segment, then expands said first segment and allows first plurality of male coupling elements to enter said second plurality of female coupling elements from the inside.

In one embodiment, the present invention also includes an elongatable, steerable cannula capable of growing from a proximal end to a distal end through a process of everting, the cannula comprising: an expandable tube having a relatively flexible inner wall of relatively small diameter and an relatively inflexible outer wall of relatively large diameter; a device for everting the tube to grow the cannula from its distal end by progressively transforming the inner wall into an outer wall; a steering mechanism for controlling the direction in which the cannula grows by varying the rate at which the inner wall is transformed into outer wall according to location around the circumference of the inner wall. In one aspect, the tube comprises braided superelastic nickel-titanium wire. In another aspect, the tube comprises an elastomer.

In another embodiment, the present invention includes a method of making an elongatable, steerable cannula capable of growing from a proximal end to a distal end through a process of assembly wherein one or more segments are added to the distal end of the cannula, the method comprising: obtaining a first flexible segment substantially cylindrical in axial cross section when uncompressed and substantially elliptical when compressed, having a first lumen therethrough, the first segment having a first proximal face substantially perpendicular to a first substantially cylindrical axis and provided with one or more first male coupling elements, and a first distal face substantially non-perpendicular to the substantially cylindrical axis and provided with a first plurality of female coupling elements; positioning a second flexible segment substantially cylindrical in axial cross section when uncompressed and substantially elliptical when compressed, having a second lumen therethrough, the second segment having a second proximal face substantially non-perpendicular to a second substantially cylindrical axis and provided with one or more second male coupling elements, and a second distal face substantially perpendicular to the second substantially cylindrical axis and provided with a second plurality of female coupling elements; inserting a flexible shaft provided with grippers able to grip said first and said second segment to compress and allow to decompress said segments, swivel or allow to swivel said segments about axes substantially parallel to the minor axes of said first and second segments, and transport said segments through said lumen; wherein said flexible shaft transports said second segment through said lumen of said first segment, rotates said second segment as required around an axis substantially coincident with the longitudinal axis of the flexible shaft, brings the proximal face of said second segment in contact with the distal face of said first segment, then allows said second segment to decompress while allowing two of said second male coupling elements to enter two of said first plurality of female coupling elements from the inside and two of said second male coupling elements to enter two of said first plurality of female coupling elements from the outside; and wherein said flexible shaft transports said first segment through said lumen of said second segment, rotates said first segment as required around an axis substantially coincident with the longitudinal axis of the flexible shaft, brings the proximal face of said first segment in contact with the distal face of said second segment, then allows said first segment to decompress while allowing two of said first male coupling elements to enter two of said second plurality of female coupling elements from the inside and two of said first male coupling elements to enter two of said second plurality of female coupling elements from the outside.

In another embodiment, the present invention includes a method of making an elongatable, steerable cannula capable of growing from a proximal end to a distal end through a process of assembly wherein one or more segments are added to the distal end of the cannula, the cannula comprising: obtaining a first expandable segment substantially cylindrical in axial cross section having a first lumen therethrough, the first segment having a first proximal face substantially perpendicular to a first substantially cylindrical axis and provided with a first plurality of male coupling elements, and a first distal face substantially non-perpendicular to the substantially cylindrical axis and provided with a first plurality of female coupling elements; positioning a second expandable segment substantially cylindrical in axial cross section having a second lumen therethrough, the second segment having a second proximal face substantially non-perpendicular to a second substantially cylindrical axis and provided with a second plurality of male coupling elements, and a second distal face substantially perpendicular to the second substantially cylindrical axis and provided with a second plurality of female coupling elements; and inserting a flexible shaft provided with an expanding member to expand and orient said first and said second segments, and transport said segments through said lumens; wherein said flexible shaft transports said second segment through said lumen of said first segment, rotates said second segment as required around an axis substantially coincident with the longitudinal axis of the flexible shaft, brings the proximal face of said second segment in contact with the distal face of said first segment, then expands said second segment and allows said second plurality of male coupling elements to enter said first plurality of female coupling elements from the inside; and wherein said flexible shaft transports said first segment through said lumen of said second segment, rotates said first segment as required around an axis substantially coincident with the longitudinal axis of the flexible shaft, brings the proximal face of said first segment in contact with the distal face of said second segment, then expands said first segment and allows said first plurality of male coupling elements to enter said second plurality of female coupling elements from the inside.

In another embodiment, the present invention includes a method of making an elongatable, steerable cannula capable of growing from a proximal end to a distal end through a process of everting, the cannula comprising: obtaining a flexible, expandable tube capable of being everted, positioning a device for everting the tube to grow the cannula from its distal end by progressively transforming the inner wall into an outer wall, rigidifying the outer wall as it is formed; and inserting a steering mechanism for controlling the direction in which the rigid outer wall grows by varying the rate, according to location around the circumference of the inner wall, at which the inner wall is transformed into the outer wall

BRIEF DESCRIPTION OF THE DRAWINGS

For a more complete understanding of the features and advantages of the present invention, reference is now made to the detailed description of the invention along with the accompanying figures and in which:

FIGS. 4(a)-(c) depict a target region and illustrates the ability of a distally assembled device to reach it.

FIGS. 5(a)-(d) and FIGS. 6(a)-(f) shows an embodiment of a distally assembled device.

FIGS. 8(a)-(g) show an embodiment of a distally assembled device.

FIGS. 10(a)-(g) show an embodiment of a distally assembled device.

FIGS. 12-15 depict an embodiment of a distally assembled device.

FIGS. 32(a)-(j) show a deployment sequence for a distally assembled device using rings.

FIG. 36 depicts a tab and hole.

FIG. 51 shows motions of head of FIGS. 48-49 due to screw rotation.

FIG. 52 depicts the head of FIGS. 48-49 holding an unswiveled ring.

FIG. 57(a)-(c) shows magnetically coupled rings with both proximal and distal wedge angles.

FIG. 60(a)-(i) shows sections and components of a strip from a continuously distally assembled/disassembled curved cannula in which the overlap is locally adjustable.

FIG. 64 shows a section of a strip from a continuously distally assembled/disassembled curved cannula in which the strip width is locally adjusted using interdigitated fingers.

FIG. 65(a)-(f) shows sections and components of a strip from a continuously distally assembled/disassembled curved cannula in which the strip width is locally adjusted using cams.

FIG. 69(a)-(k) shows sections and components of a strip from a continuously distally assembled/disassembled curved cannula in which the strip width is locally adjusted using a wedges.

FIG. 70(a)-(b) shows a section and components of a strip from a continuously distally assembled/disassembled curved cannula in which the strip width is locally adjusted using an expansion element.

FIG. 74(a)-(c) depicts various embodiments of interlocking elements.

FIG. 77(a)-(e) depicts strips with fingers and holes.

FIG. 78(a)-(d) shows features which can snap into holes.

DETAILED DESCRIPTION OF THE INVENTION

Figure 1:
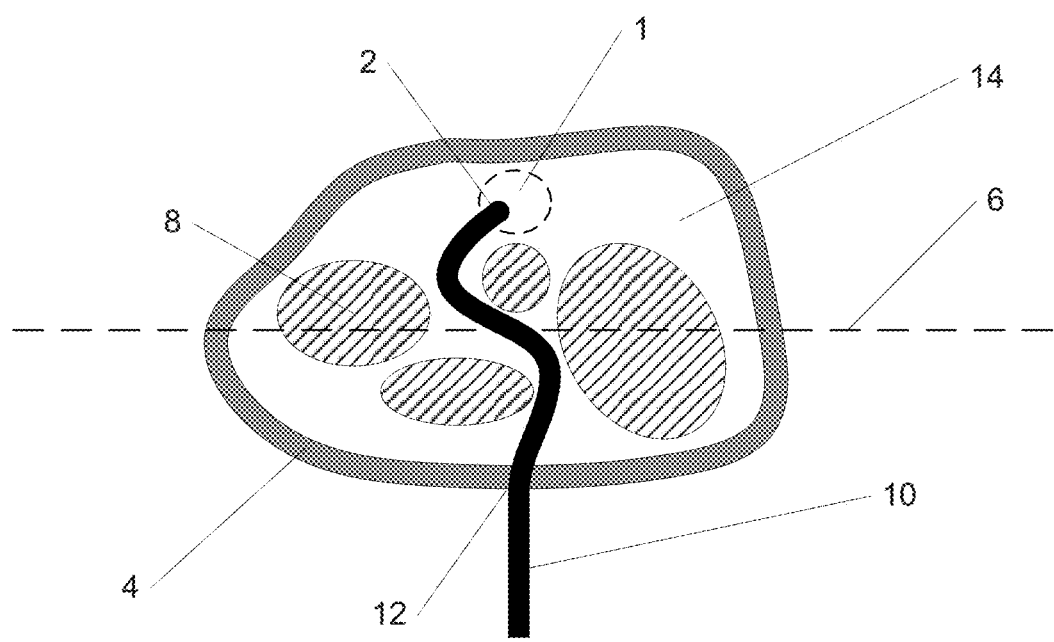
FIG. 1 depicts a schematic cross section of a section of a human body along with a medical device, a target region, and obstacles.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the units that may be used to add or reduce the length of an apparatus of the present invention may be referred to individually as a segment or ring, when there are two or more they can be referred to as segments or rings. The segment(s) or ring(s) the may be of any shape or shapes, including, e.g., triangular, circular, elliptical, polygonal, rectangular, square, or combinations thereof, including composite shapes, and extensions from the edge(s) of the segments or openings cut into the segments. Note also that the terms segment and ring may be used interchangeably herein.

The segment(s) can be made from, e.g., plastic, metal, rubber, latex, polymer, composite, elastomeric, a thermoplastic elastomer, a synthetic rubber, a natural rubber, a melt-processable rubber, a propylene oxide elastomer, an ethylene-isoprene elastomer, an elastic polyvinyl chloride, a silicone elastomer, an elastic polyurethane, an ethylene-vinyl acetate elastomer, or a non-polymeric elastomer, or combinations thereof. The segments or rings can be made from a wide variety of materials or composites, which can include polymer(s) selected from at least one of polyglycolic acid (PGA), polylactic acid (PLA), poly (dioxanone) (PDO), poly (l-lactide) (LPLA), poly (dl-lactide) (DLPLA), poly (glycolide-co-trimethylene carbonate) (PGA-TMC), poly (l-lactide-co-glycolide) (PGA-LPLA), poly (dl-lactide-co-glycolide) (PGA-DLPLA), poly (l-lactide-co-dl-lactide) (LPLA-DLPLA), poly(glycolide-co-trimethylene carbonate-co-dioxanone) (PDO-PGA-TMC), poly(ε-caprolactone), poly(dioxanone)(a polyether-ester), poly (lactide-co-glycotide), poly(SA-HDA anhydride), poly(orthoester), or polyglyconate. The segments or rings may be at least partially made from a metal, such as, e.g., titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, nitinol (nickel-titanium, e.g., superelastic), and stainless steel.

As regards the central cannula or segment delivery and removal device, it can include an expandable portion that can be, e.g., plastic, thermoplastic, elastomer, polyethylene terephthalate, polyethylene terephtalate glycol-modified, rubber, vinyl, latex, and silicone. Non-limiting examples of a stylet or assembly head is shown herein that include one or more clasps that permit the addition or removal of a segment or ring while also providing orientation for the segment or ring, e.g., to change the direction of the opening within the elongatable apparatus and thus the outside of the apparatus as well.

The segments can be attached to each other via a wide variety of fasteners or adhesives, which can be integrated into the segments themselves. Non-limiting examples of these fasteners or adhesives include tabs and openings in the top, bottom or side walls of the segment(s) that attach or interlock to each other by friction, mechanical interlocking, abrasive contact surfaces, self-adhesive strips, hook and loop fasteners, hooks and eyes, ties, tabs, buckles, belts, pins, elastic bands, rubber bands, snaps, clasps, magnets, zippers, DUAL LOCK™ (3M Company, St. Paul, Minn.), and VELCRO® tape fasteners.

As regards the change in direction by the addition of segments, the segments can be wedge-shaped such that when viewed perpendicular to the segment axis the segment comprising a "wedge angle", such that addition of a subsequent segment can cause the extension to be straight (i.e., continue in the same direction as the next most proximal segment), or cause a rotation (i.e., a change in direction) of the addition as a result of the wedge angle. In certain non-limiting examples, the wedge angle can vary from, e.g., 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees between segment(s) at one or both ends.

FIG. 1 depicts a hypothetical cross section of a portion of a patient's body, when the present invention is used in a medical context. Suppose that a physician needs to access target region 1 with the distal end 2 of an instrument, and is constrained to introduce the instrument through the skin 4 below dashed line 6. There may be no way do this using a straight instrument while avoiding contact with obstacles such as delicate or difficult-to-penetrate (e.g., bone) anatomical structures 8. Such structures may be surrounded by gas, liquid, or other tissue 14.

Figure 2A:
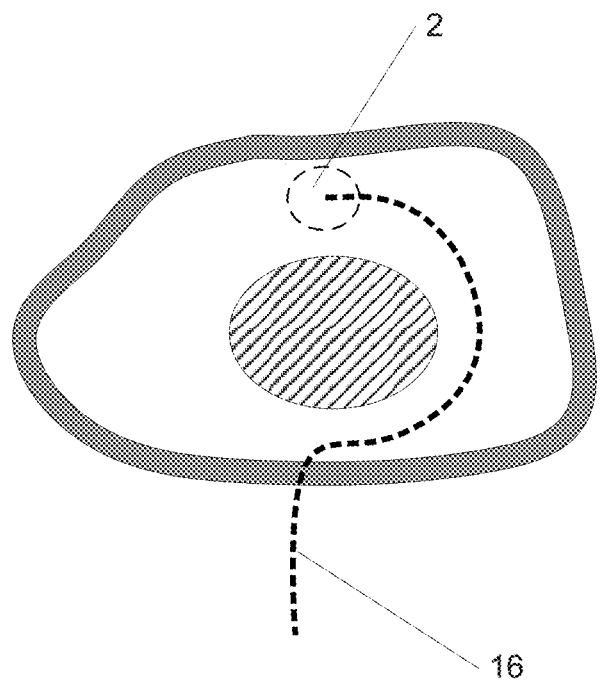
FIGS. 2(a)-(b) depict an ideal path to a target region and the inability of a first prior art device to reach it.
Figure 2B:
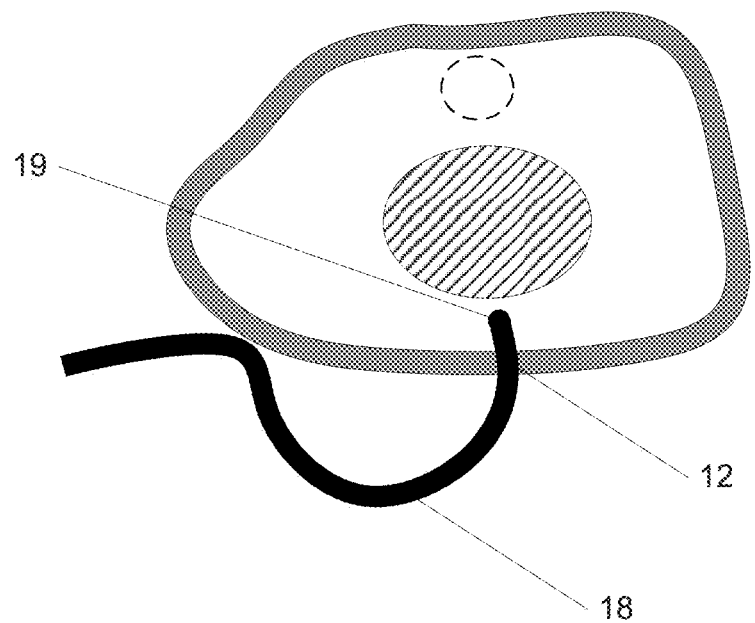
Figure 3A:
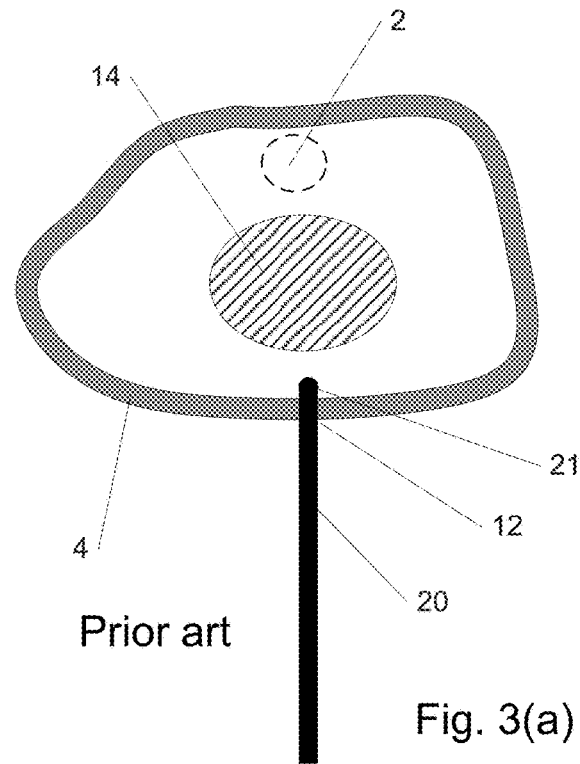
FIGS. 3(a)-(f) depict a target region and the inability of a second prior art device to reach it.
Figure 3B:
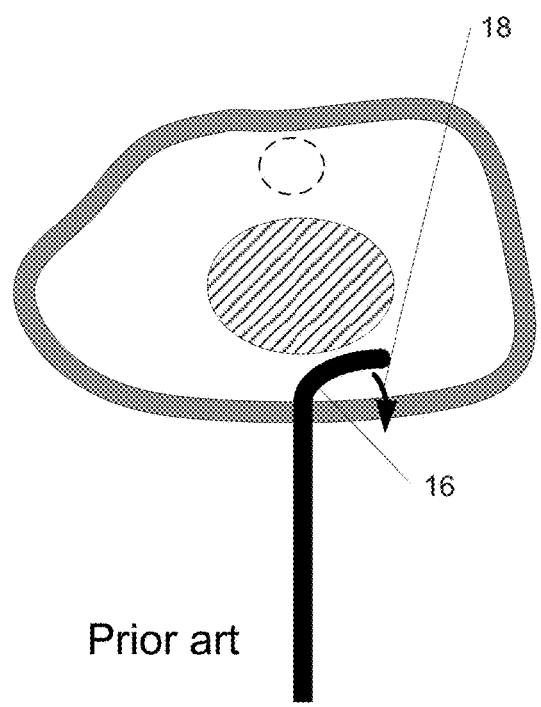
Figure 3C:
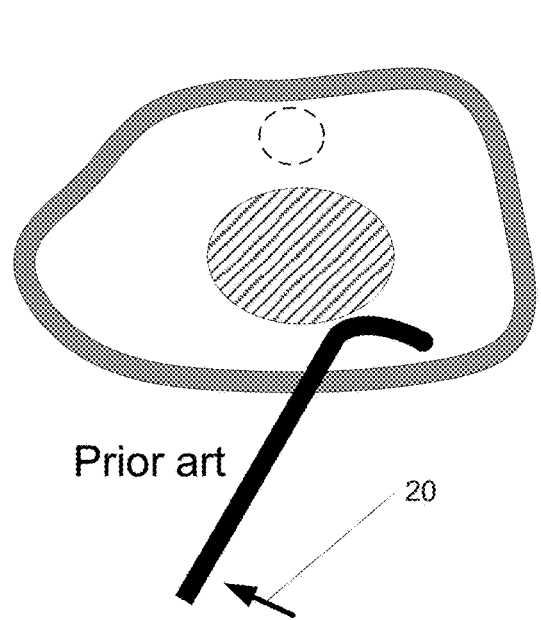
Figure 3D:
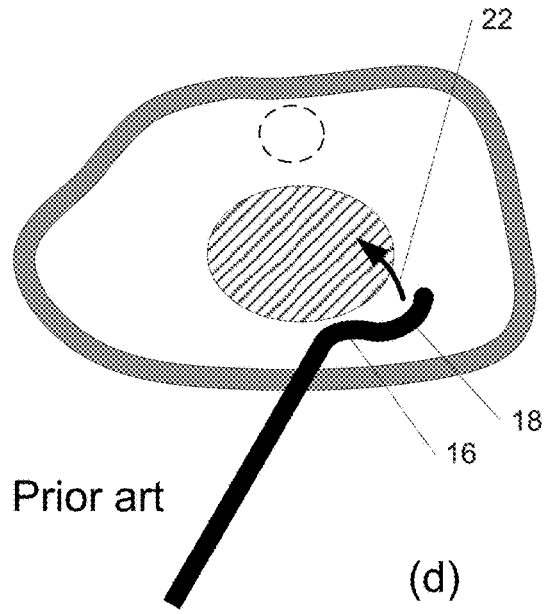
Figures 3E, 3F:
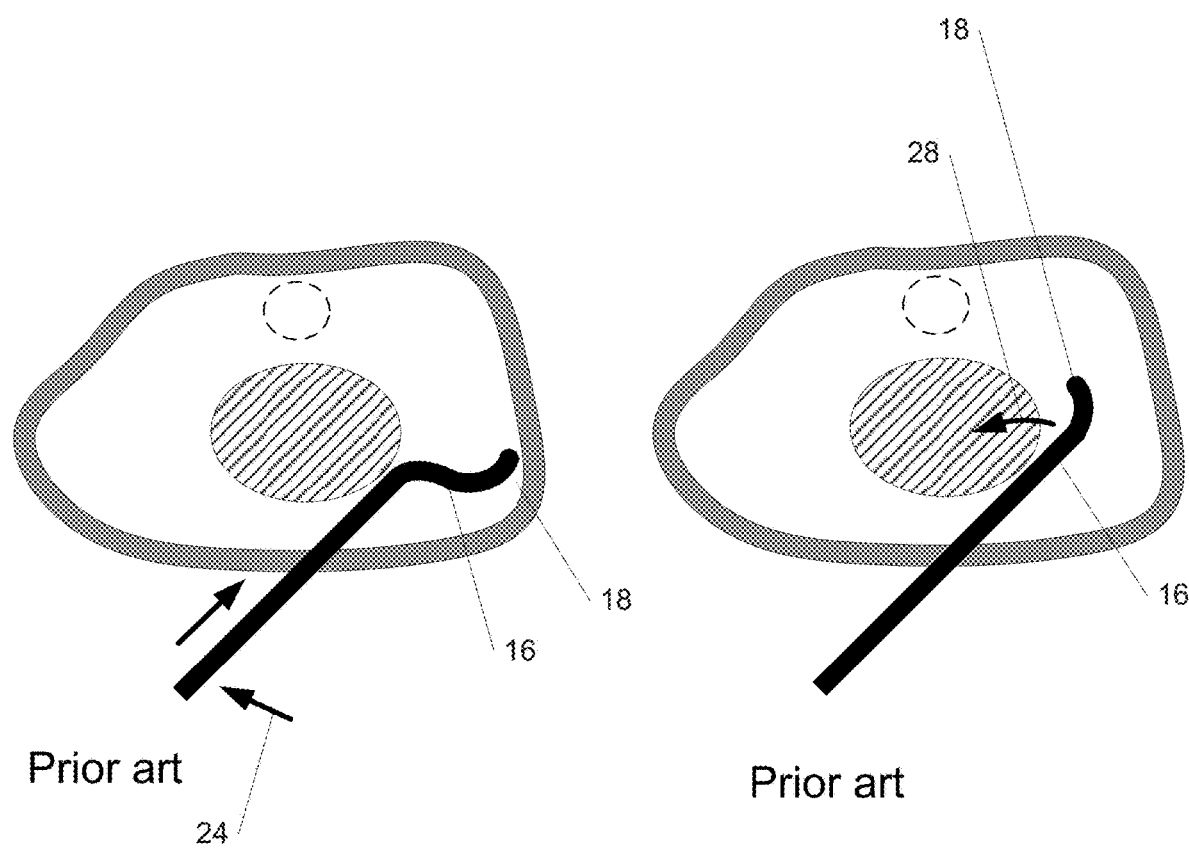

Known to the art are three basic methods by which an instrument 10 can be curved with the goal of its distal end reaching region 2. Referring to FIGS. 1, 2(a) and 2(b) depicting a simpler hypothetical cross section of a patient's body, in the first method, the preferred path to region 2 might be along path 16, avoiding structure 14. If the instrument 18 is substantially rigid but is pre-curved into a 3-D (or planar 2-D) shape as shown in FIG. 2(b), it may then be inserted through puncture site 12 with the goal of manipulating it so its distal end 19 reaches region 2. However, as shown in FIG. 2(b), such manipulation can be difficult or impossible. The instrument shape would correspond to the desired path once the distal end 19 has reached region 2, but in many cases the distal end 19 cannot reach region 2 due to instrument collisions with structure 14 or skin 4. The distal end 19 often cannot travel along path 16, and other parts of the instrument generally also cannot travel along path 16 (shown in FIG. 2(a)).

In some cases, the instrument can be curved into shapes other than the path shape such that with sufficient and skilled manipulation, the distal end 19 can ultimately reach region 2. However, such manipulation may be by trial-and-error, increasing procedural time and in some cases, patient exposure to X-rays or other radiation. Removal of the instrument would normally involve a similar process. Moreover, if the instrument is surrounded by tissue, it cannot as a whole penetrate and glide smoothly through the tissue by leading with distal end 19. Rather, a great deal of lateral movement of the instrument must occur, requiring the relatively broad side of the instrument to penetrate or deform surrounding tissue. This can be both difficult to accomplish (e.g., requiring significant force) and traumatic/damaging to the tissue.

FIG. 3 shows a second method for reaching region 2 with a curved instrument, in which the instrument is provided with the ability to flex and steer under control of the physician. Such an instrument most often is provided with a single steerable section near the distal end 21, but may be provided with additional steerable sections (a total of two such regions are assumed in the figure). A possible sequence of steps aimed at reaching region 2 with distal end 21 is now described. In FIG. 3(a), the instrument enters site 12 and in FIG. 3(b), the more proximal steerable region 16 is then bent in direction 18. In a later manipulation shown in FIG. 3(c), the proximal end of the instrument is moved in direction 20 to the side. In FIG. 3(d), the more distal steerable region 18 is then bent in direction 22. In FIG. 3(e), the proximal end of the instrument is moved in direction 24 and the instrument is slid in direction 26. Finally, in FIG. 3(f), section 16 is straightened out in direction 28. While the distal end 21 may ultimately reach region 2 through a combination of various manipulations of the kind described, it can be a slow, difficult, and iterative process to do so. Moreover, as with the first method, lateral movement of the instrument through tissue can make the required manipulations both difficult and traumatic.

A third method that might be considered for reaching region 2 is the method used, for example, in interventional cardiology. In this method, a guidewire—which can be provided with pre-curved or actively-steerable distal tips— would first be guided and delivered to region 2 and then a flexible instrument such as a catheter would be slid distally over the guidewire. However, since this method requires delivery of guidewire before the instrument is delivered, it is appropriate when the guidewire can itself follow a pre-existing path (e.g., such as within a lumen like an artery) or can be adequately controlled and steered (e.g., magnetically). The method is generally unsuitable for efficiently and accurately accessing region 2 when it is located, as in the figure, within a gas- or liquid-filled cavity or within solid tissue.

1st Embodiment

In a 1st embodiment of the invention, an instrument enters the body and is delivered along a desired path such as path 16 of FIG. 2(a) as illustrated in FIGS. 4(a-c) to reach region 2. The path may be determined, for example, using imaging such as CT or MM. In FIG. 4(a), instrument 30 enters the skin 4 through puncture site 12 and begins to follow path 16, curving as it grows or elongates with its distal end 32 in the lead. In FIG. 4(b), the instrument has lengthened further and in FIG. 4(c) distal end 32 has reached region 2 as desired. Such a "distal growth" behavior allows distal end 32 and the instrument to precisely and quickly follow the path without trial-and-error and with minimal difficulty, force, or potential tissue damage. Moreover, the instrument may be shortened or retracted once used along the same path.

FIG. 5 is a cross-sectional view illustrating how the instrument of the 1st embodiment extends from its distal end, rather than being pushed from its proximal end as with prior-art instruments. New material (or components) required to extend the distal end further along path 16 is supplied to the distal end, e.g., by transportation through the center of the instrument, though in some embodiment variations, material is transported along the exterior of the instrument.

In FIG. 5(a), a base tube section 34 is provided, forming the proximal end of the instrument. The geometry shown is rotationally symmetric around axis 35. In FIG. 5(b), a radially-collapsed tube section 36 enters section 34 at its proximal end and is moved distally, in direction 38. When section 36 has reached a suitable location along section 34 as in FIG. 5(c), it expands in direction 40 as shown in FIG. 5(d), in some embodiment variations slightly deforming section 34 as it reaches its final diameter, and interlocking rigidly with section 34. The result is a substantially straight tube, or cannula, comprising two sections, in which the base tube has remained at the same location and a new section— using material supplied at the proximal end—has been joined to the distal end of the cannula. Thus, the distal end is dynamic, not static: a particular section that is the most distal at one time may not be at a later time when another section has extended past it more distally. The most distal portion of the instrument is in some embodiment variations not a section such as section 36, but rather, another component such as a cap. Such a component can begin adjacent to one section and become successively transferred to each new section as the cannula elongates, or can be deployed after the last section has been delivered.

As shown in FIG. 5, in some embodiment variations the instrument is a cannula with a lumen 41 extending along the axis of the instrument through which fluid may be supplied or withdrawn, or through which therapeutic or diagnostic instruments and implants may be passed. In other embodiment variations, the instrument does not have such a lumen once the instrument is fully extended, or in use the lumen may be mostly obscured (e.g., by a stylet or distal tip). Therapeutic and diagnostic devices may also be slid over the exterior of the deployed DASC device, rather than through it, or may use DASC as a rail along which the device is advanced and/or retracted.

For use in a gas or liquid environment, the instrument needs to be relatively rigid, so each section preferably forms a rigid, well-interlocked joint with its neighboring section. Rigid interlocking may be achieved by friction; protrusions on one section interacting with features such as protrusions, cavities, or perforations on another; by textures, or by other suitable means. In the case of a permanent cannula, sections may be attached by adhesive, welding, brazing, soldering, riveting, and other methods known to the art.

The expansion of section 36 can be accomplished by a variety of means. In some embodiment variations, it is the result of the section springing back to its natural diameter after having been compressed. In other embodiment variations it is the result of a deformation that plastically deforms the material of section 36 outwards (e.g., section 36 may be designed similar to a metal stent known to the art), after allowing for elastic springback/recoil. For example, an expanding balloon or bladder may be used to deform the section to an approximately circular shape. In still other embodiment variations, it is the result of section 36 being elastically deformed outwards and held in its expanded position (e.g., by a ratcheting mechanism or clips; or if, for example, designed as a braided superelastic nickel-titanium tube, by maintaining axial tension). In FIG. 5(*d*), section 36 has been joined to section 34 at an angle, forming a short section of a curved cannula instead. By adding additional sections similar to section 36—though not necessarily of the same length, diameter, or material—at the desired relative angles, a long, distally-assembled cannula following a complex 3-D path may be constructed.

FIG. 6 depicts how the steps in FIG. 5 may be accomplished in some embodiment variations in which the diameter of section 36 is normally small and must be actively deformed outwards to achieve a larger diameter. In FIG. 6(*b*), section 36 fits over balloon 42 and moves along with it (e.g., section 36 is snugly fitted over balloon 42, which in some embodiment variations is slightly inflated). Balloon 42 is supported by flexible hollow shaft 44 and connected to wires 46. To allow balloon 42 to tilt in any direction, thus allowing the instrument to follow a 3-D path, at least two wires 46 may be provided. However, in some embodiment variations, means other than wires are used to tilt balloon 42, or wires may be contained within shaft 44. Balloon 42 is advanced distally through section 34 in direction 38. Once section 36 has reached a suitable location along section 34 as in FIG. 6(*c*), balloon 42 is tilted (if applicable) by pulling on at least one wire 48 in direction 49, and is inflated to expand section 36 in direction 40 as shown in FIG. 6(*d*), interlocking sections 36 and 34. In practice, the expansion or tilting can be initiated prior to section 36 reaching its correct distal position. Having expanded section 36 to interlock with section 34, in FIG. 6(*e*) balloon 42 detaches from section 36 and collapses in direction 50. In FIG. 6(*f*) balloon 42, now in some embodiment variations fully collapsed, retracts distally in direction 52, where it can fit inside an additional section, expand slightly to secure it, and then repeat a process similar to that of FIGS. 6(*b-f*) to build a long cannula.

In embodiment variations in which sections are naturally of larger diameter and spring back after having been compressed, means of keeping the sections compressed until they are delivered to the distal end of the cannula may be used. For example, a balloon may be provided with hooks on its surface that engage features on the inside surfaces of section such as section 36. Once so engaged, by collapsing the balloon or allowing it to collapse, section 36 is forced to become compressed so it can fit through other sections. In some embodiment variations, sections such as section 36 may comprise an elastic tube, for example, a braided wire tube designed to reduce in diameter when elongated axially, and increase in diameter when compressed axially, or an elastomeric tube. In the case of sections, which are normally expanded (i.e., having a larger diameter when no forces act on them), they may be delivered through other sections by temporarily stretching them axially, and interlocking them to other sections by releasing the axial tension.

In some embodiment variations, the cannula can be disassembled and retracted (e.g., after completion of a clinical procedure) by approximately reversing the steps shown in FIG. 6, e.g., with the most distal section disassembled and retracted first. In such a process, various means of compressing the sections to a diameter small enough to pass proximally through other sections may be used, including the hooked balloon already described. In the case of sections composed of elastomeric material or wire braid, for example, these can be reduced in diameter by stretching them axially, and then retracting them through other sections. In the case of a ratcheting mechanism that holes the sections open, the ratchet for each section would be released to allow disassembly.

In some embodiment variations, sections transported distally are enlarged further than shown in FIGS. 5-6 so as to fit over and interlock with the exterior surface of other sections, in lieu of fitting over and interlocking with the interior surface as already described. In the case of sections that are elastically stretched to a larger diameter, interlocking of a newly-added section to another section may be achieved or enhanced by means of the newly-added section simply collapsing onto the other section.

The steps shown in FIGS. 5-6 may be, in some embodiment variations, performed manually by a physician or other personnel, or in other embodiment variations may be performed automatically or semi-automatically, making the instrument a robotic system. Such a system can for example manipulate using computer-controlled motors and actuators the position of shaft 44, the tension on wires 46, and the pressure of balloon 42 in FIG. 6, such that the cannula is extended along a path or retracted. Such control may be based on a predetermined path within the patient's body, or under real-time control of the physician, e.g., using a joystick to steer the cannula as it lengthens, and a throttle (e.g., a 1-axis joystick) which controls the speed of forward or reverse motion (extension/growth/assembly, or else retraction/disassembly). Other human interface devices that can be useful to determine the shape of the cannula include a helical spring-shaped "analog" controller made from wound strip or wire, which is directly manipulated. The user can then control the cannula shape by deforming the controller into the shape desired for the cannula. Sensors (e.g., capacitive, inductive, magnetic, piezoresistive) in the controller (e.g., every 120° around the circumference of the helix, can measure local strain, distance between turns, etc. to determine its three-dimensional shape. The sensors may be wireless, but can be wired. Instead of having a large number of sensors and/or a large number of wires, a stylet equipped with sensors or merely electrical contacts can be slid within the controller to measure its shape (or transmit data from fixed sensors) sequentially (or more at a time). The shape of the controller can also be measured optically using optical motion tracking methods or 6 degree of freedom electromagnetic sensors known to the art. Techniques applicable to sensing the shape of a controller can also be used, of course, to sense the shape of the cannula itself (e.g., to verify it has not distorted due to forces acting on it, given the existence of clearances between parts, material compliance, etc. in the structure). For example, as the stylet rotates, if its axial motion is driven by its engagement (e.g., with sprocket and sprocket holes) with the strip, then by monitoring the axial motion, the shape of the cannula can be inferred. In some embodiments, the shape of the cannula can be determined (e.g., with strips which can deform in width such as those of FIG. 63) by adjusting the axial motion of the stylet as the cannula is wound.

Figure 7:
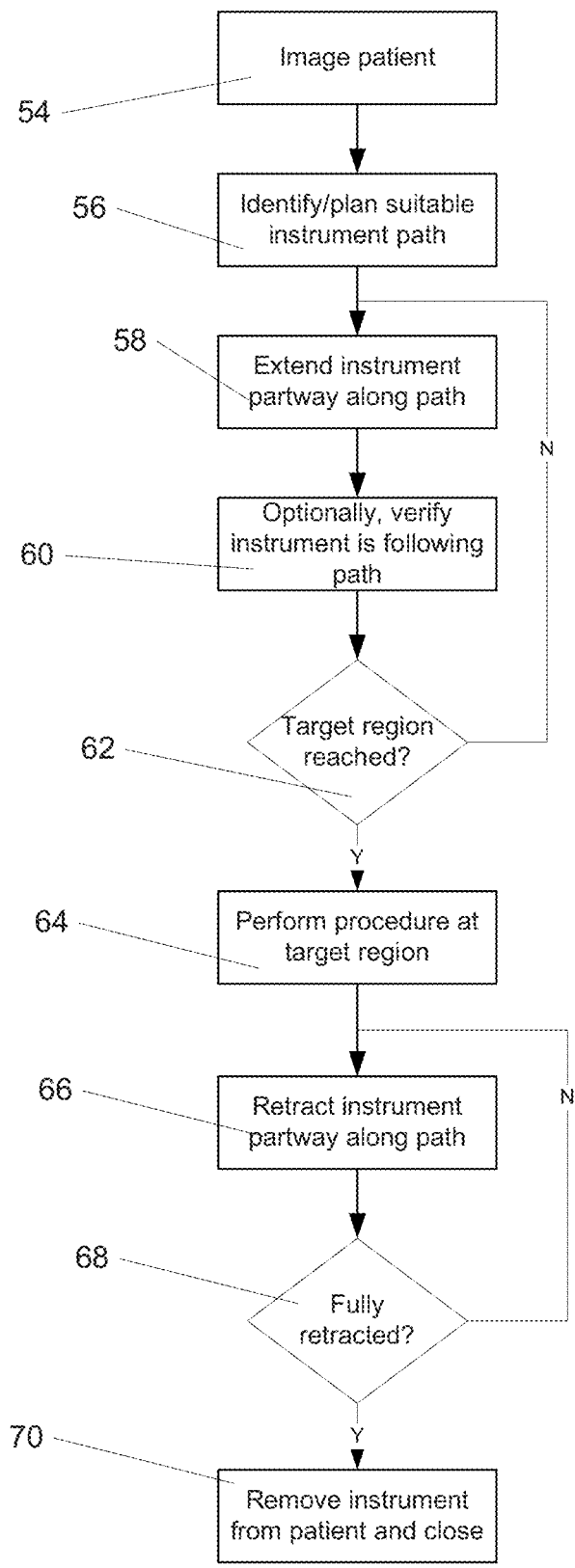
FIG. 7 is a flow chart describing how a distally assembled device may be used in some embodiments.

FIG. 7 is a flow chart describing how a device such as that described herein may be used in some embodiments. Referring to the flowchart symbols of FIG. 7, imaging (54) may be performed on the patient prior to the procedure, using modalities such as CT, MM, and ultrasound, and the image data aligned to the patient, e.g., using fiducial marks known to the art. In some embodiment variations, imaging is performed while the instrument is advanced as well, or in lieu of performing it beforehand. A suitable path along which the instrument is to be delivered is then identified/planned (56) and the instrument is extended partway (e.g., one section at a time) along the path (58). Optionally, verification that the instrument is adequately following the commanded path may be performed (60), and adjustments made (e.g., to the angle of the next section to be added). A decision (62) is then made whether the target region is reached. If not, then the instrument is extended further. If it has, then the procedure (e.g., delivery of drug, biopsy, ablation, etc.) is performed at the target region (64). The instrument then is retracted partway (e.g., one section at a time) along the path (66). A decision (68) is then made whether the instrument is fully retracted and able to be removed from the patient. If not, then the instrument is retracted further. If it has, the instrument is removed and the puncture/incision is closed.

2nd Embodiment

Figure 8E:
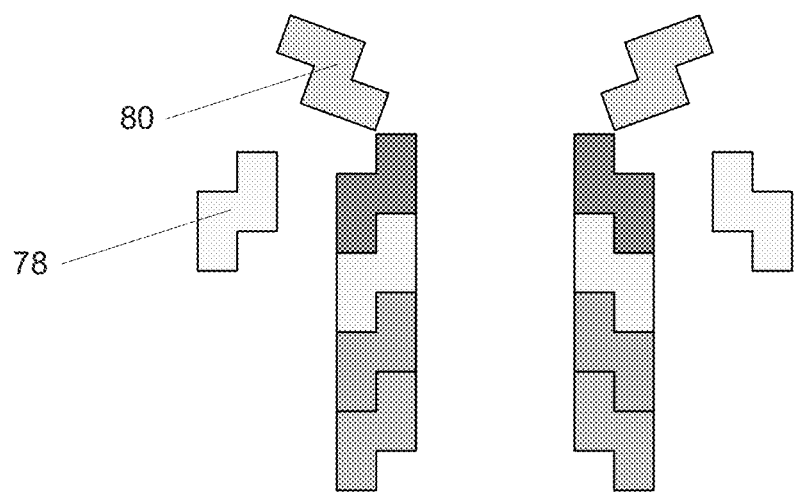
Figure 8F:
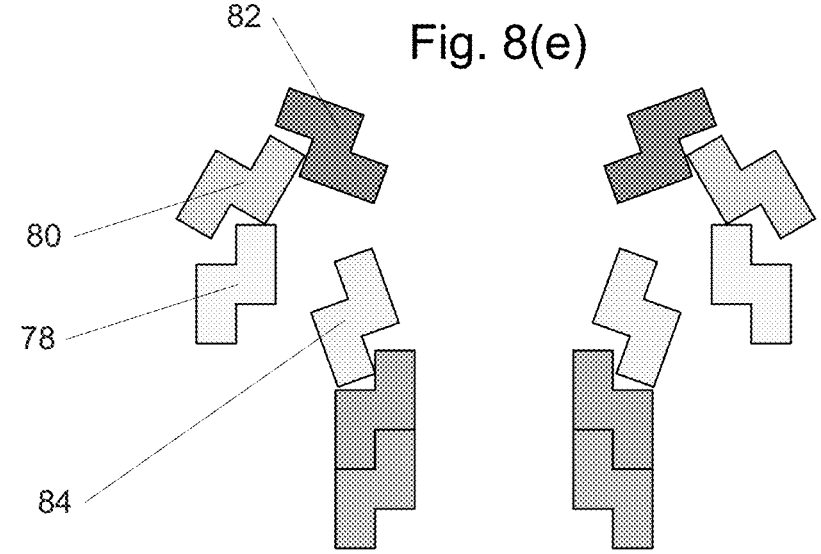
Figure 8G:
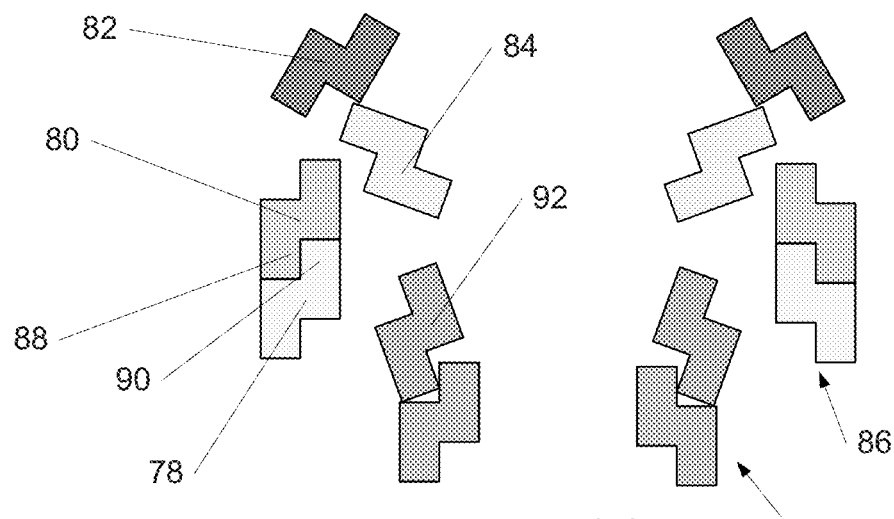

FIG. 8 depicts a cross-sectional view of a 2nd embodiment of the invention similar in some aspects to the 1st embodiment. The geometry shown is rotationally symmetric around axis 71. In this 2nd embodiment, in lieu of tubular sections as in the 1st embodiment, rings 72 are provided as shown in FIG. 8(*a*) which can fit into one another due to their shape, and which are capable of stretching to a larger diameter and everting. The ability to stretch, in some embodiment variations, may be provided by segmenting the ring in the plane of the ring (e.g., into pie-like slices) and joining these together with compliant elements such as flexures, which may be integral to the ring. As a whole, the rings stack and nest to form tube 74. Initially the proximal end of tube 74 is aligned to reference plane 76. In FIG. 8(*b*), tube 74 has moved distally and distal ring 78 has begun to evert and stretch. In FIG. 8(*c*) and all remaining sub-figures within FIG. 8, tube 74 has moved further distally. Also, ring 78 has continued to evert and stretch while tube 74 has moved further proximally. In FIG. 8(*d*), ring 78 is mostly everted and stretched while ring 80 is beginning to evert and stretch. In FIG. 8(*e*), ring 78 has completely everted and stretched, forming the first and most proximal ring of a new, larger-diameter, outer tube. Meanwhile, ring 80 has everted and stretched further. In FIG. 8(*f*), ring 80 has nearly completely everted and stretched and is beginning to nest against ring 78. Meanwhile, ring 82 has partially everted and stretched and ring 84 is beginning to evert and stretch. In FIG. 8(*g*), ring 80 has completely everted and nested against ring 78, forming the second ring of outer tube 86. Stretched as it is in this position, the lower portion 88 of ring 80 presses against the upper portion 90 of ring 78, clamping ring 80 to ring 78 securely. As shown, rings 80 and 78 are parallel to one another, forming a straight section of outer tube 86. However, ring 80 may also be at an angle when it clamps onto ring 78, causing outer tube 86 to be curved. Also shown in FIG. 8(*g*) are other rings such as 82, 84, and 92 in different stages of stretching and everting. The overall result is that the inner tube 74 moves distally to supply rings to outer tube 86, extending the cannula towards the target region of the patient's body. In one variation, eversion and stretching of the rings is due to them being affixed to an elastomeric tube (not shown) which is itself everted and stretched to form an inner wall (associated with the inner tube) and an outer wall (associated with the outer tube). The stretching and eversion of the elastomeric tube may be caused simply by pushing the inner wall of the tube distally. In this variation or in some other variations, the rings and/or the tube are temporarily attached to wires (not shown) which, if differentially tensioned, cause rings to clamp onto one another in a non-parallel, angled manner, curving the resulting structure in that region.

The steps shown in FIG. 8 may be, in some embodiment variations, performed manually by a physician or other personnel, or in other embodiment variations may be performed automatically or semi-automatically, making the instrument a robotic system.

3rd Embodiment

FIG. 9 is a cross-sectional view of a 3rd embodiment of the invention similar in some aspects to the 1st embodiment. In this 3rd embodiment, the sections that are assembled at the distal end include surfaces which are sections of a sphere, to facilitate sections interlocking with one another at multiple angles through ball joint-like structures. FIG. 9(*a*) shows an instrument comprising four sections interlocked at various angles, the most distal of which is section 94. The geometry shown of section 94 and other sections is rotationally symmetric around axis 95. Sections such as section 94 may have a spherical interior surface 96 and a spherical exterior surface 97. The particular shape of the overall instrument is provided as an example only. In FIG. 9(*b*), section 96, initially collapsed to a relatively small OD (outside diameter) 98 is supported by balloon 100 attached to base 102 and flexible hollow shaft 104. Wires 106 are attached to base 102 (or balloon 100) to control the angle of balloon 100 and section 96. In FIG. 9(*b*), section 96 has entered the most proximal section and begins to move distally. In FIGS. 9(*c-d*) it continues to move distally, being pushed by shaft 104 in direction 108 through the lumen formed by the already-interlocked sections. If required to minimize collisions with such sections, wires 106 may be pulled 110 relative to shaft 104 to steer section 96 through the lumen. When balloon 100 is tilted as shown, shaft 104 doesn't necessarily bend near its top or base 102 apparently swivel as shown; rather, shaft 104 may bend more gradually along its length.

In FIG. 9(*e*), section 96 has reached its destination and is ready to expand. In FIG. 9(*f*) balloon 100 has expanded, significantly increasing the OD 112 of section 96. The ratio between OD 112 after expansion and OD 98 prior to expansion can be significant (e.g., 1.5-5). To allow a change in diameter of sections, in some embodiment variations sections may be segmented (e.g., into pie-like slices) and joined together with compliant elements such as flexures, which may be integral to the segment.

Before section 96 has expanded completely and interlocked with section 94, it is tilted in the desired direction by pulling on at least one of the wires 106. Tension on wires 106 may be removed when not needed, as is the case with one of wires 106 after full expansion of balloon 100 in FIG. 9(*e*). In FIG. 9(*g*), balloon 100 has deflated, released section 96, and is moving proximally in direction 114 in preparation for supporting and transporting another section. Section 96 remains expanded and interlocked with section 96 by various means discussed already with respect to the 1st Embodiment: plastic deformation allowing for elastic springback, a ratcheting mechanism, etc.

Figures 9A, 9B, 9C, 9D:
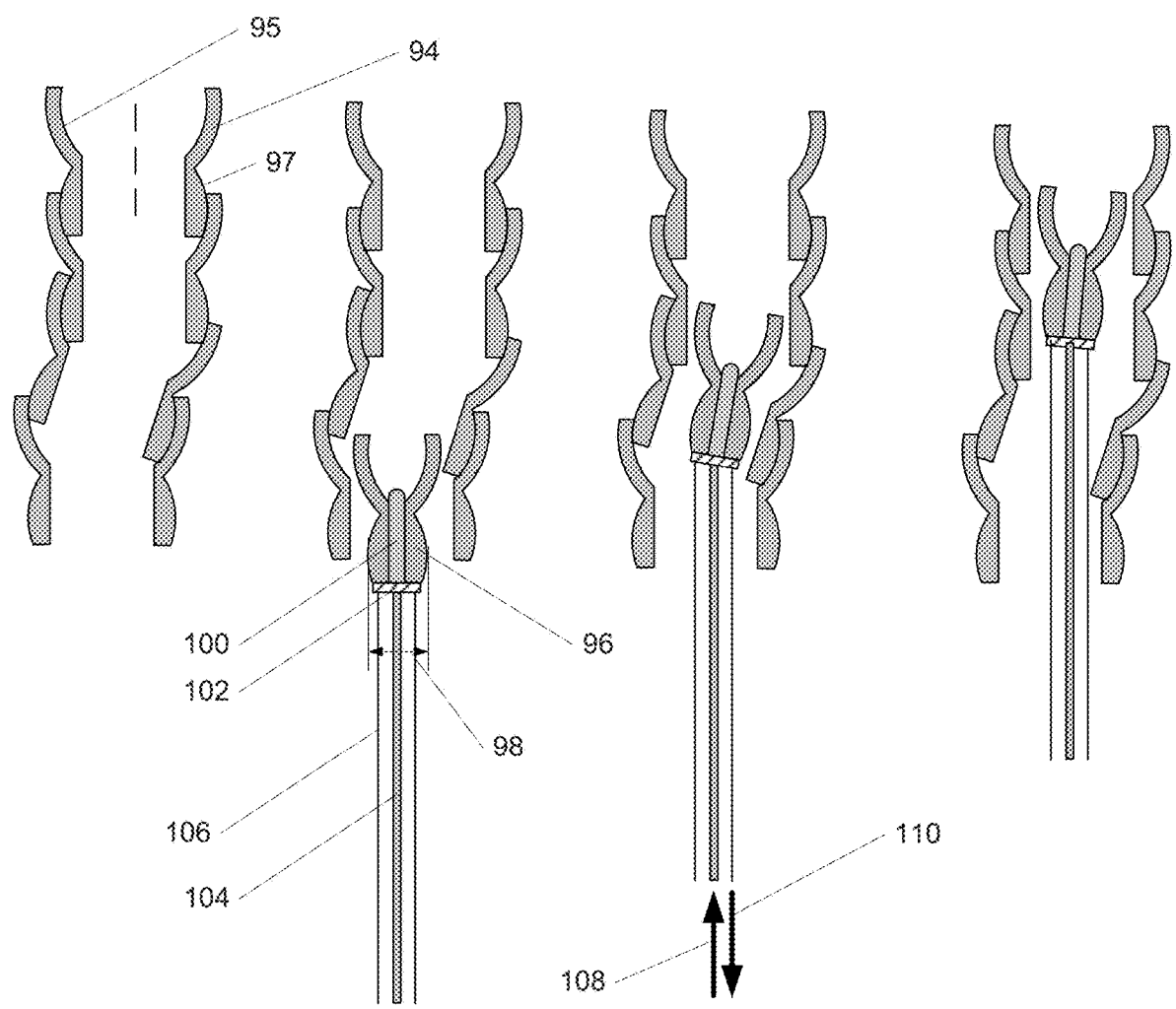
FIGS. 9(a)-(h) show an embodiment of a distally assembled device.
Figures 9E, 9F, 9G, 9H:
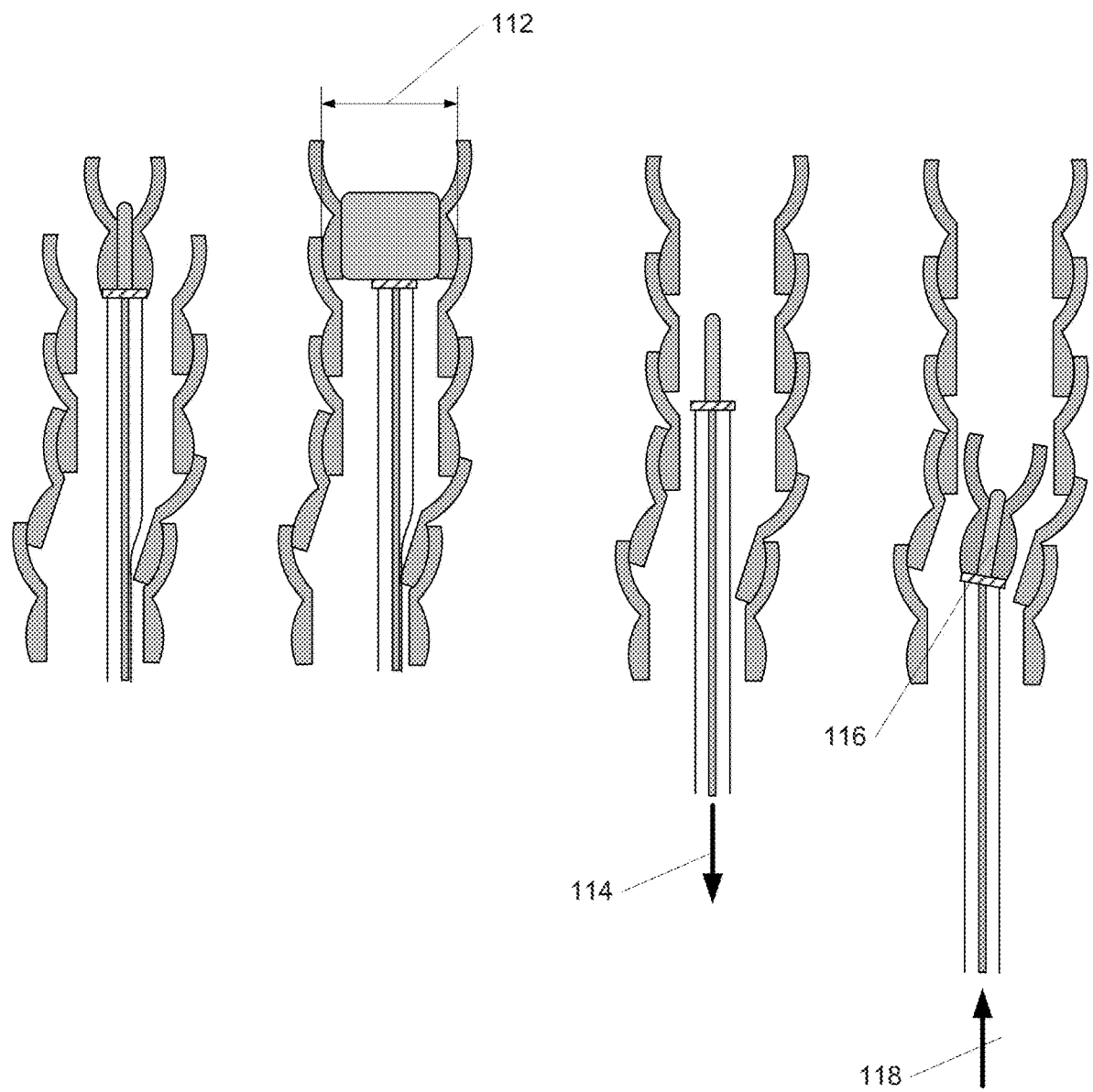

FIG. 9(*h*) shows balloon 100 supporting section 116 and transporting it distally in direction 118, repeating the cycle begun in FIG. 9(b). In one variation, base 102 is omitted, for example, so that balloon 100 can pass in a proximal direction through section 116, and then expand slightly to secure it before progressing distally again.

In this variation and in some other variations, the edges of sections are more rounded, chamfered, or tapered than shown in FIG. 9, minimizing the likelihood of getting caught on other sections when moving in either direction.

Once the distal assembly process has been completed to access the target region and the clinical procedure has been completed, disassembly of the instrument can be achieved by approximately reversing the assembly sequence, using the balloon and its associated components to remove and retract each section, beginning with the most distal section.

The steps shown in FIGS. 9(a)-(h) may be, in one variation, performed manually by a physician or other personnel, or in other embodiment variations may be performed automatically or semi-automatically, making the instrument a robotic system.

4th Embodiment

FIG. 10 is a cross-sectional view of a 4th embodiment of the invention similar in some aspects to the 1st, 2nd, and 3rd embodiments. The geometry shown is rotationally symmetric around axis 119. In this 4th embodiment, the sections that are assembled at the distal end include surfaces which are sections of a sphere as in the 3rd embodiment. As with the 2nd embodiment, a given segment engages an external surface of the next most proximal segment, instead of an internal surface as with the 1st and 3rd embodiments. Unlike the 2nd embodiment, there is no eversion of the elements. To allow a change in diameter of sections, in some embodiment variations sections may be segmented as already described. In FIG. 10, the instrument is shown straight (all sections aligned in parallel) and not curved for simplicity.

FIG. 10(a) shows an instrument comprising an initially-expanded base section 120 and expandable sections such as distal section 122 supported by balloon 124 and flexible hollow shaft 126. Shaft 126 passes through section 120 and also passes through other sections such as sections 128 and 130. In some embodiment variations, wires connecting to balloon 124 are provided to tilt the axis of sections as they are delivered.

In FIG. 10(b), balloon 124 has expanded enough to expand the diameter of section 122 so its proximal concave spherical surface can be fit over the distal convex spherical surface of section 120. In FIG. 10(c), balloon 124 has been retracted proximally in direction 132 such that the two spherical surfaces are in proximity and in FIG. 10(d), balloon 124 has deflated, allowing section 122 to clamp securely and interlock with section 120. In FIG. 10(e), balloon 124 has been further retracted in direction 132 such that it can enter the lumen of section 128. In FIG. 10(f), balloon 124 has slightly inflated, allowing it to pull section 128 as shown in FIG. 10(g) distally in direction 134. The configuration shown in FIG. 10(g) is equivalent to that of FIG. 10(a): one cycle of distal assembly has been achieved, and is about to repeat again.

As before, disassembly of the instrument can be achieved by approximately reversing the assembly sequence beginning with the most distal section. The steps shown in FIG. 10 may be, in some embodiment variations, performed manually, or in other embodiment variations, performed automatically or semi-automatically.

5th Embodiment

FIG. 11 is an isometric view of a 5th embodiment of the invention similar in some aspects to previous embodiments and in particular, the 4th embodiment. Each section in the 5th embodiment is comprised of pie-like segments 136 as in FIG. 11(a). Each segment in some embodiment variations has a distal surface 138 that is a section of a sphere. Multiple (e.g., 6) segments are joined to a stretchable (e.g., elastomer) band 138 as shown in FIG. 11(b), forming a section 142.

Figure 11A:
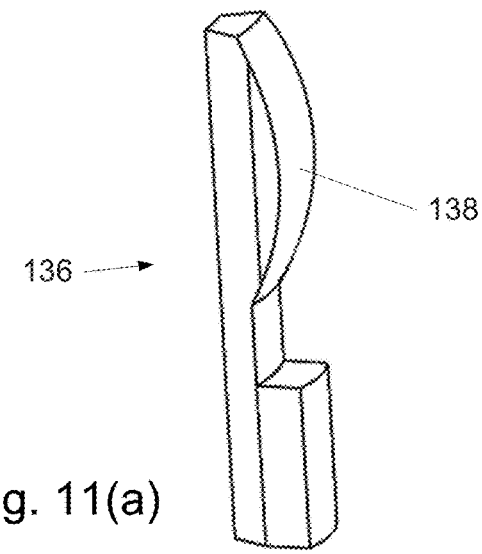
FIGS. 11(a)-(d) show an embodiment of a distally assembled device.
Figure 11B:
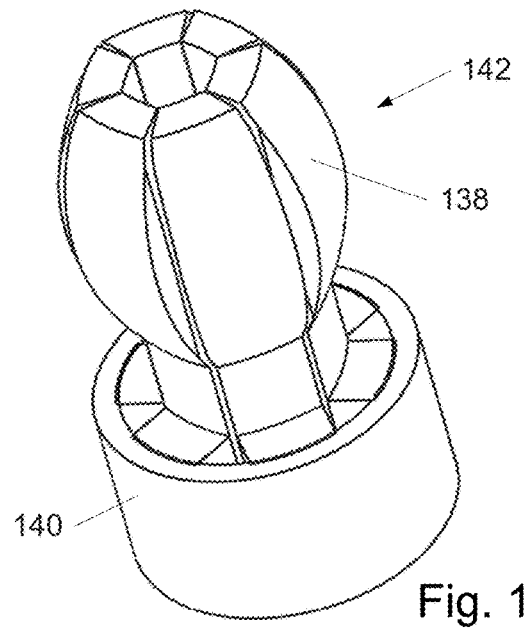
Figure 11C:
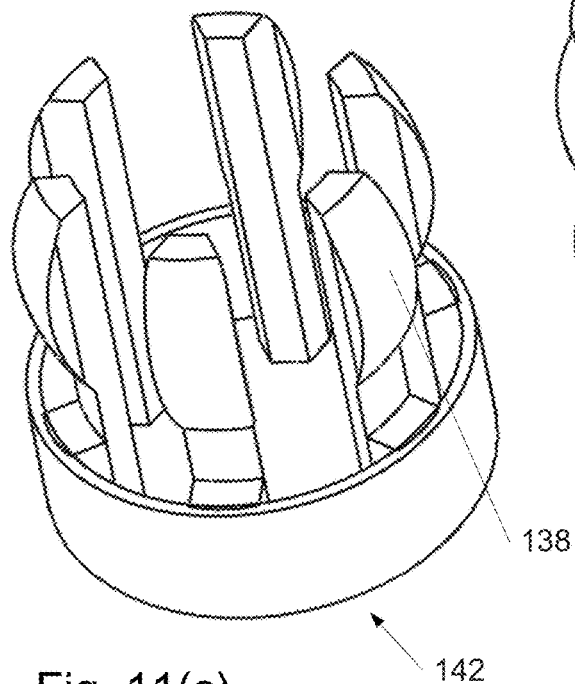
Figure 11D:
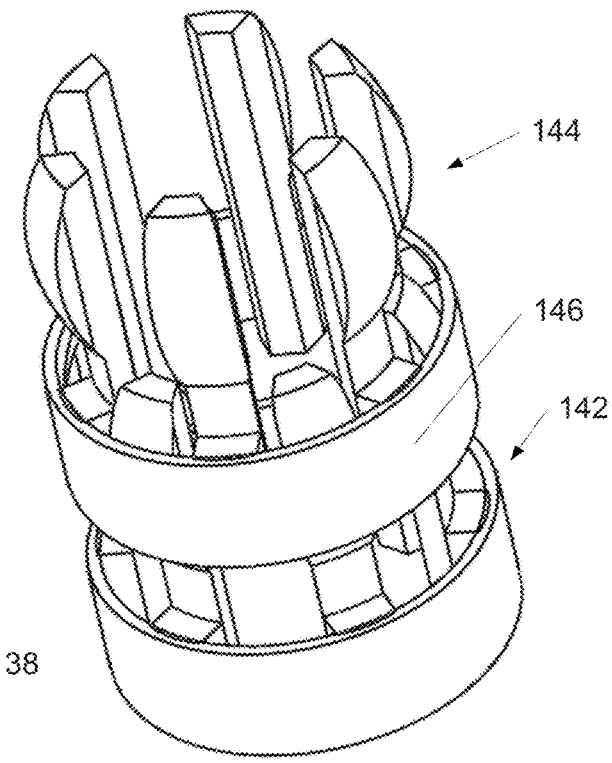
Figure 13A:
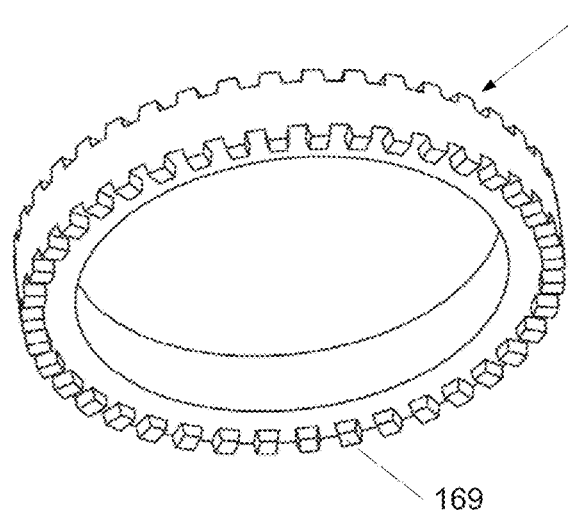
Figure 13B:
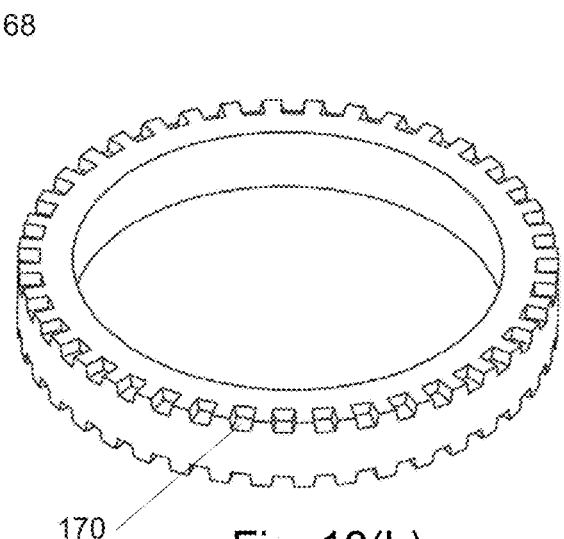
Figure 13C:
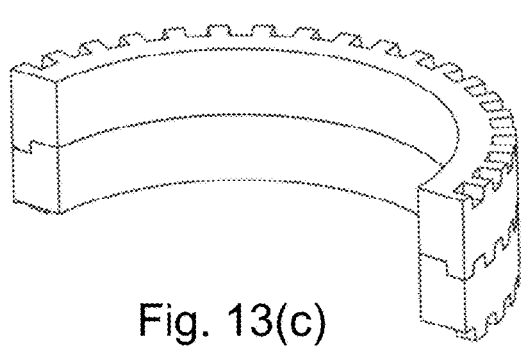
Figure 13D:
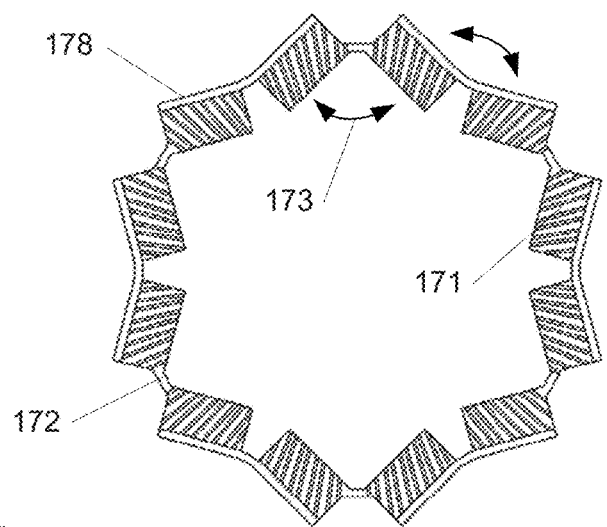
Figure 13E:
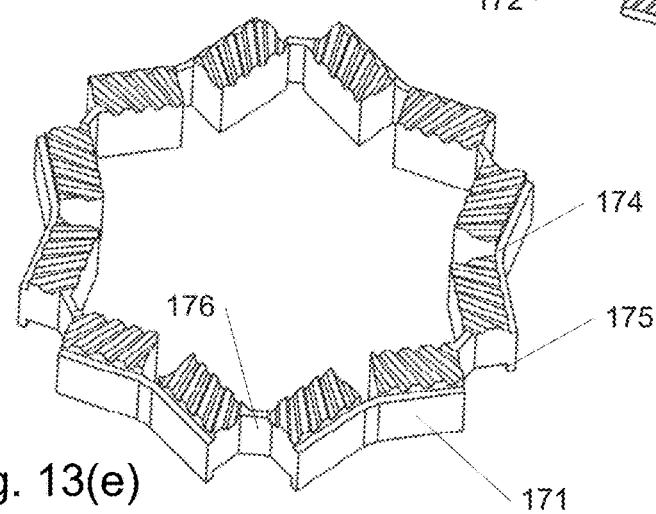
Figure 13F:
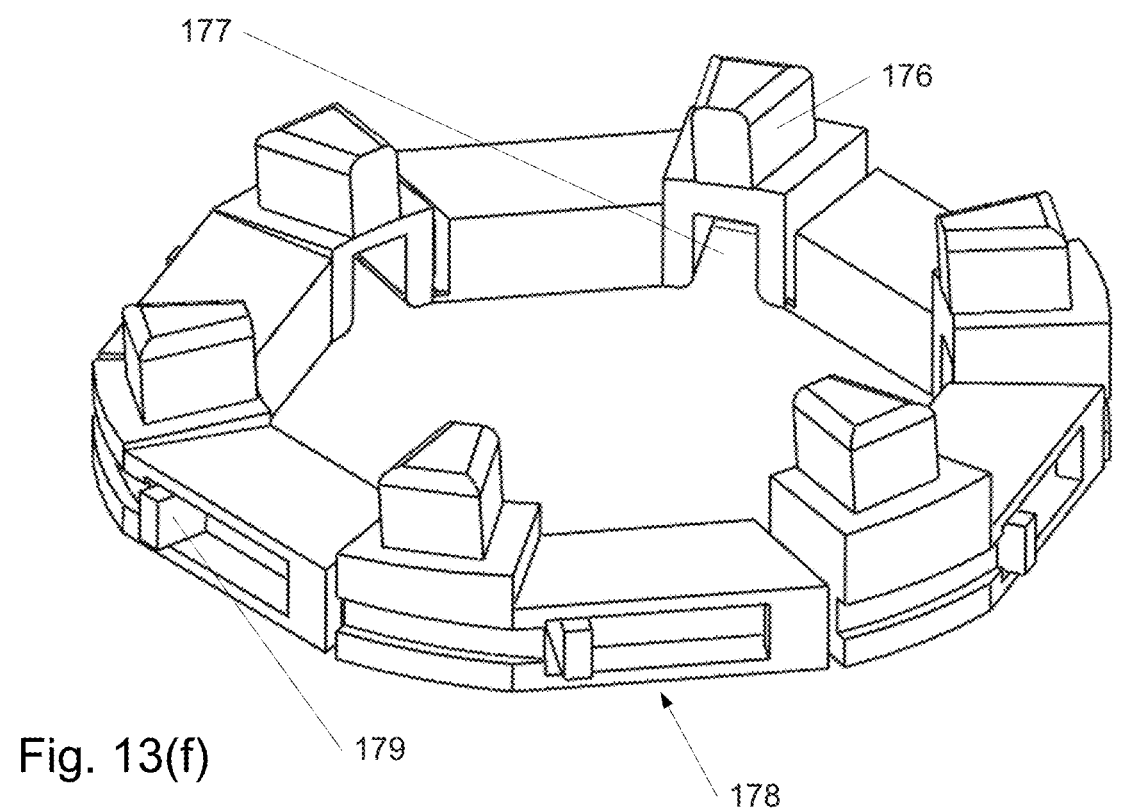
Figure 13G:
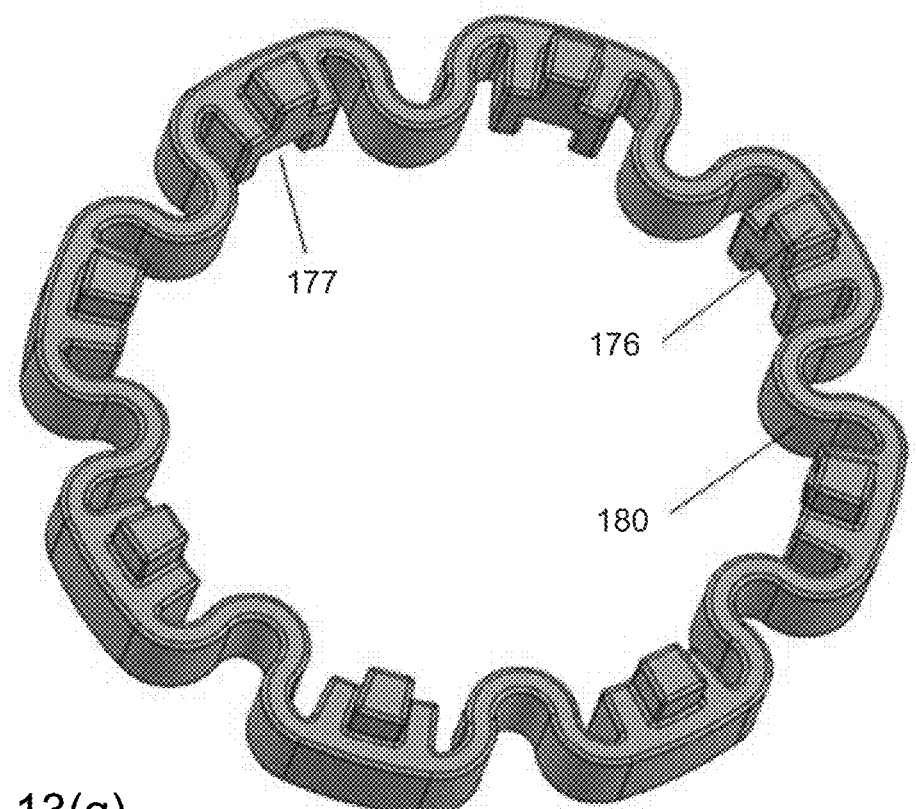

In the configuration shown in FIG. 11(b), the section has a relatively small OD. However, by stretching band 138, section 142 can expand considerably as in FIG. 11(c). As shown in FIG. 11(d), once band 140 is expanded, another section 144 initially in a compressed configuration (similar to that shown in FIG. 11(b)) can pass distally through section 142, then expand its OD, and then move in a proximal direction such that the proximal ends of segments in section 144 can fit in between the segments of section 142 as shown in FIG. 11(d). At that time, band 146 of section 144 can also make contact with surfaces 138 of section 142.

In some embodiment variations, friction between band 146 and surfaces 138 of section 142 can join sections 142 and 144 together with sufficient stiffness. In other embodiment variations, other means of interlocking are used. In some embodiment variations, after all sections are distally assembled into an instrument, the OD of the most proximal section (which has been maintained by a suitable mechanism) is reduced, causing the ODs of all the more distal segments to also be reduced. As the OD of a section is reduced, the proximal ends of a given segment come into contact with the distal ends of the section just proximal to it. Such contact, as the segments clamp one another, leads to additional friction and in some embodiment variations other interlocking features may be provided. For example, protrusions on the sides of the proximal ends of segments in section 144 may fit into holes on the facing surfaces: the distal end of segments from a section 142. Interlocking mechanisms such as this preferably are designed to allow for positive interlocking regardless of the relative orientation of neighboring sections.

6th Embodiment

FIG. 12 shows a 6th embodiment of the invention similar in some aspects to previous embodiments. In the 6th embodiment, the instrument is distally assembled from a set of rings (e.g., circular or polygonal) made from a deformable material (e.g., a metal). FIGS. 12(a-b) show plan views of rings. A ring initially unexpanded/compressed into a small OD 152 as in FIG. 12(a) can expand as shown in FIG. 12(b), e.g., through the use of balloon 150, to form a ring with an ID (internal diameter) larger than OD 152. This allows another ring in compressed form to pass through it in a distal direction; in some embodiment variations rings can be transported through other rings while supported by the balloon, similar to other embodiments already discussed.

FIG. 12(c) shows an elevation view of a single expanded ring in some embodiment variations, and FIGS. 12(d-e) show elevation views of multiple rings in the same embodiment variation. In FIG. 12(d), rings have been stacked, beginning with proximal ring 154, with no offset between them, forming a straight cannula. In contrast, in FIG. 12(e), rings have been stacked with offsets to follow curve 156. With a large enough number of rings (which may be thicker than shown in the figures) and appropriate offsetting (not so much as to make the lumen through the ring stack smaller than is needed to pass a collapsed ring), a long cannula may be distally assembled to follow a complex 3-D path.

FIG. 12(f) shows an elevation view of a single expanded ring in some embodiment variations, and FIGS. 12(g-h)

show elevation views of two rings in the same embodiment variation. In this embodiment variation, the top surface 158 and bottom surface 160 are not parallel, giving the ring a wedge shape with a wedge angle theta between the surfaces. Such rings may be paired as in FIGS. 12(*g-h*). When paired and relatively oriented such that the thinnest section of distal ring 162 overlies the thickest region of ring 164, the top and bottom surfaces of the ring pair are parallel. Distally assembling a cannula from a set of paired rings arranged as in FIG. 12(*g*) would yield a straight cannula. In contrast, as shown in FIG. 12(*h*), by rotating ring 162 relative to ring 164, the top and bottom surfaces become non-parallel. Distally assembling a cannula from a set of paired rings arranged as in FIG. 12(*h*) would yield a curved cannula. The amount of relative rotation of two rings in a pair determines the amount of non-parallelism of the ring pair, and the amount of local curvature of the cannula. Meanwhile, the direction of the normal to the top surface 166 determines the direction of the local curvature of the cannula. Unlike the offset stacked rings of FIGS. 12(*c-e*), the lumen through a cannula made from wedge-shaped rings is not reduced by offsetting. Wedge-shaped segments refer to the mating faces of the segments. The non-parallelism of the proximal mating face with respect to the distal mating face on the same segment allows the apparatus to assume a curved shape, and the orientation of the wedge with respect to the next most proximal segment determines the amount of curvature and its direction.

To form a rigid cannula, rings should not move relative to their neighbors. Among the methods available to prevent such movement are interlocking protrusions on, for example, the bottom of odd-numbered rings, which fit into other protrusions, cavities, or perforations on, for example, the top of even-numbered rings. For example, radially-arranged gear-like teeth on both the upper and lower surfaces of rings can engage one another in one of many discrete orientations. FIGS. 13(*a-b*) show, respectively, bottom and top isometric views of an expanded ring with gear-like teeth 169 along the bottom edge and recesses 170 to accommodate those teeth along the top edge. FIG. 13(*c*) shows a cross-sectional view of two such rings stacked such that the teeth of the upper ring fit into the recesses in to lower one. As shown, the rings are interlocked as long as some axial tension or preload is provided to keep the rings from separating: one cannot rotate with respect to the other, nor can one slide radially with respect to the other, since the teeth recesses for the teeth are only near the edge. It is intended that the rings in FIG. 13(*a-c*) combine in pairs like the rings in FIG. 12(*f-h*) and be wedge-shaped in elevation view as shown in those figures; this taper is not shown in FIGS. 13(*a-c*).

Also not shown in FIGS. 13(*a-c*) is evidence of the rings having initially been compressed so as to pass through the center of other rings. FIGS. 13(*d-e*) show a segmented ring comprising relatively rigid segments 171 and relatively flexible hinges 172, which illustrates, as with FIG. 12(*a*), how a ring can initially be compressed and then open up as shown by arrows such as arrow 173 into a shape similar to that of FIGS. 13(*d-e*), or even be further expanded to become more circular. As with the rings of FIGS. 13(*a-c*), these rings can have teeth along the outer edges of the bottom surface, and recesses along the outer edges of the top surface, preventing relative rotation of rings when stacked. In the variation shown, the teeth are towards the inner edges on top and bottom, and a groove 174 is provided on the top surface outer edges to receive a ridge 175 on the bottom surface outer edges, preventing radial sliding/shear.

FIGS. 13(*f-g*) depict two other variations of expanding rings. In FIGS. 13(*f-g*), the rings are shown unexpanded and having cavities 177 to receive bosses 176, allowing rings to join together somewhat like LEGO® blocks. The ring of FIG. 13(*e*) has telescoping sections 178 including travel stops 179. Such a ring could be produced by additive manufacturing, such as the MICA FREEFORM™ process (Microfabrica, Van Nuys, Calif.) or other processes having adequate resolution, depending on ring size. When expanded, the telescoping sections extend to enlarge the ring and allow an unexpanded ring to pass through it; the travel stops prevent the ring from over-expanding and/or breaking into separate parts. The ring of FIG. 13(*f*) includes flexures/living hinges 180 which allow it to be elastically (or plastically) deformed into a shape in which the flexures are far less bent, and in some cases, straight, again allowing an unexpanded ring to pass through an expanded ring. Such a ring could be produced by high-resolution injection molding from a material such as polypropylene, by companies such as MTD Micro Molding (Charlton, Mass.), depending on ring size.

In some embodiment variations, the rings of FIG. 13 are normally contracted, but can be stretched by a balloon (or other device) into an expanded configuration as shown in FIG. 13(*d-e*). In such an embodiment variation, the teeth and recesses of FIG. 13(*a-c*), and the ridge and groove of FIG. 13(*d-e*) also maintain the rings in an expanded configuration once the rings are stacked and the balloon has been removed, much like the $4^{th}$ embodiment. Before moving proximally to stack a ring against another ring, the balloon can be rotated (e.g., by twisting the shaft to which it is attached) so as to adjust the relative orientation of each ring, thus achieving the desired amount and direction and curvature, as already discussed. In some embodiment variations, the rings of FIG. 13(*d-e*) are made from superelastic nickel-titanium or a polymer such as polypropylene or polyethylene such that the hinges can bend easily and without fracture. In some embodiment variations, the hinges can rotate at pivot points, not simply bend compliantly. In such embodiment variations, an elastic member (e.g., a band) may be provided to spring the ring either open or closed, or springs (e.g., torsional or leaf) may be incorporated at the pivot joints.

In some embodiment variations, rings may interlock using interlocking textured surfaces such as VELCRO® or an array of small mushroom-like protrusions (e.g., the DUAL LOCK™ fastener from the 3M Company, St. Paul, Minn.). The gear teeth already discussed provide a finite, quantized number of relative angles between rings, but in some embodiment variations, even fewer (e.g., 3-6) relative angles may be required. In such cases, providing rings with just a few protrusions on one surface and corresponding depressions on the opposite surface may suffice.

In some embodiment variations, rings may be held tightly against one another by one or more tensioned wires which run through the rings from most proximal to most distal; as a new ring is added, the wire(s) are transferred to the most distal ring. In some embodiment variations, rings are held against one another by magnetism. For example, the rings may be made of a ferromagnetic material, and placed in a magnetic field, or a magnet may be in contact with the most proximal ring and the magnetic flux conducted through the entire stack as more rings are added, making each new ring hold onto the previously-added ring. In some embodiment variations, magnetically-assisted contact may be used during the distal assembly process, but when all rings are deployed, another means of clamping the rings tightly against one another may be employed, such as one or more wires which run the length of the stack.

In some embodiment variations, the rings or at least one of their mating surfaces are compliant (e.g., an elastomer) such that when the rings are in contact, a seal is made between rings, thus allowing liquid or gas to be channeled without leakage from one end of the ring stack/cannula to the other.

In some embodiment variations, rings that are both offset as in FIGS. 12 (c-e) and wedge-shaped as in FIGS. 12(f-h) may be used.

FIG. 14 shows in cross-section apparatus used in some embodiment variations to deliver a distally-assembled cannula comprised of rings, such as that described in FIGS. 12(f-h) or FIG. 13.

The geometry shown is rotationally symmetric around axis 181. As shown in FIG. 14(a-b), a plate 182 is connected to a tube 183 in which a stack of unexpanded rings such as ring 184 is loaded, supported by support 185. Balloon 186 is provided with gripping shoes 188 (shown in FIG. 14(b), a detail view of FIG. 14(a)) which engage one ring at a time in the stack (currently ring 184) when the balloon is slightly inflated as shown. Balloon 186 is attached to flexible hollow shaft 190, which can rotate and translate as indicated by the arrows.

Figure 14A:
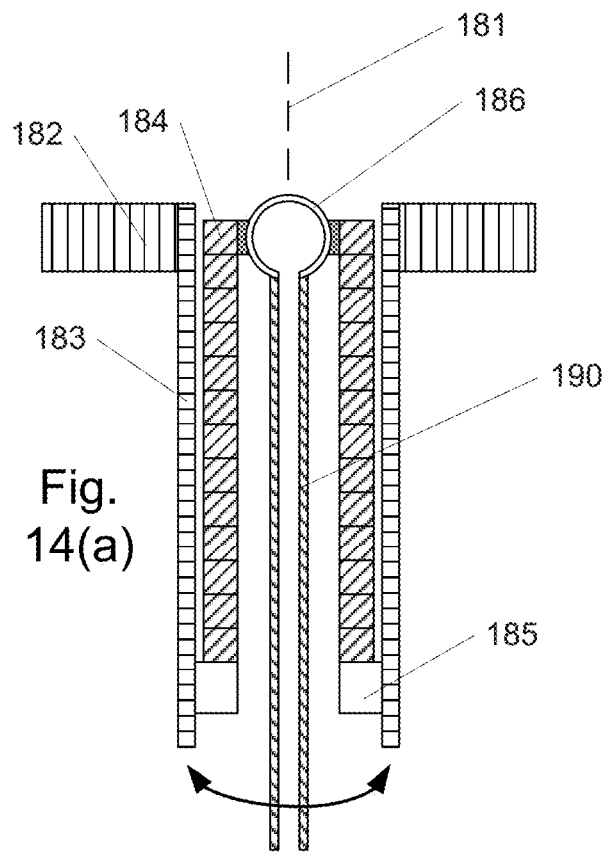
Figure 14B:
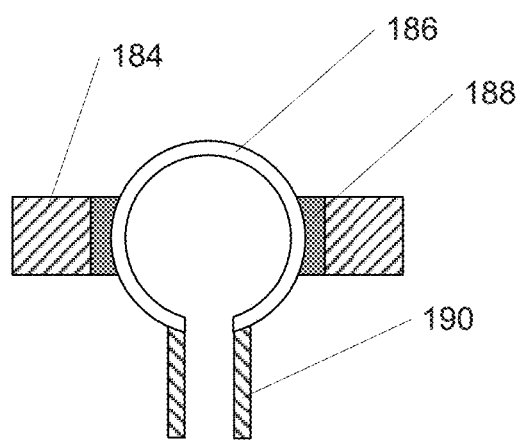
Figure 14C:
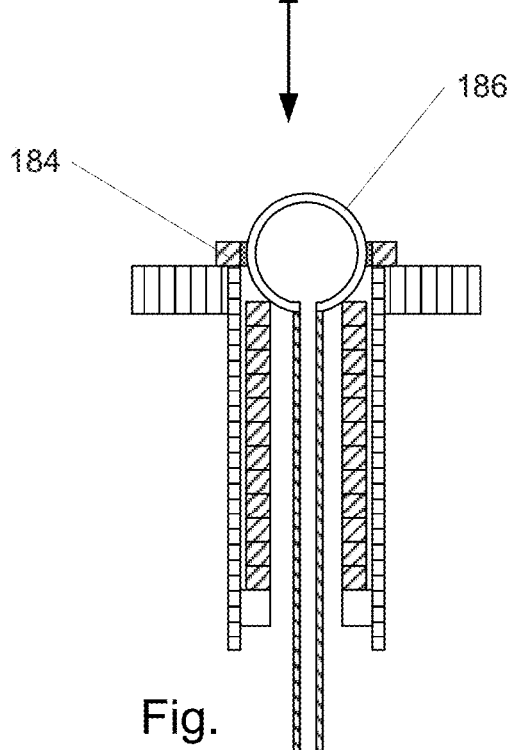
Figure 14D:
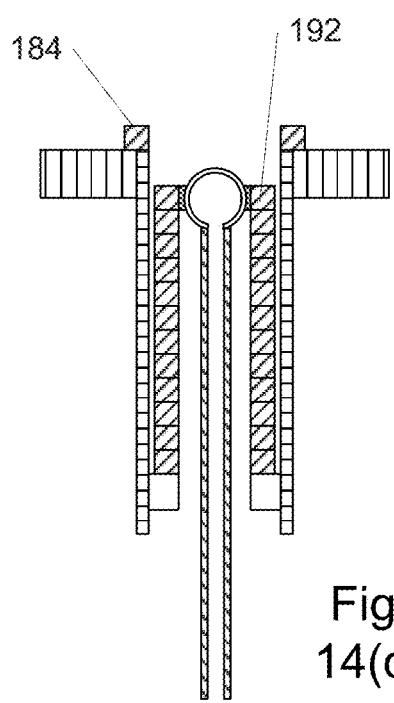

In FIG. 14(c), balloon 186 has been translated distally, carrying with it ring 184, and then inflated by passing fluid through shaft 190, expanding ring 184. Ring 184 is rotated to the correct orientation by torqueing shaft 190 and placed against plate 182 (which may have features that keep the ring expanded) and balloon 186 is then collapsed and retracted distally where shoes 188 can fit into ring 192, the next ring on the stack. If the device is deployed within tissue, the balloon may also serve to dissect (e.g., blunt dissection) and/or displace tissue to as to make room for additional rings and create a pathway for the device. The distal assembly process is then repeated, with ring 192 being stacked in expanded form and with the desired orientation onto ring 184, where it is slightly more distal than ring 184. The process is further repeated until as many rings are stacked in expanded form as are needed. Disassembly of the cannula involves a process of approximately reversing the steps required to assemble it, and in some embodiment variations unexpanded rings end up inside tube 183 as before.

In some embodiment variations, rings may be pre-oriented or pre-selected such that when assembled, they form a cannula of the desired 3-D curvature, and little or no balloon rotation is required. In such variations, is may be important to prevent the rings from inadvertently rotating to an improper orientation before being assembled. One means of accomplishing this is to make the rings a shape other than round (e.g., polygonal) on their OD and make the inside of tube 183 have a matching shape that prevents ring rotation. In some embodiment variations, for example in the case of pre-oriented rings which require little or no rotation, the rings can have different wedge angles, rather than have all the same wedge angle.

In some embodiment variations, rings may not have substantially co-planar tops and bottoms. For example, segments such as segment 174 in FIG. 13 can have different heights, thus influencing the stacking orientation of adjacent rings.

Figures 15, 15A, 15B:
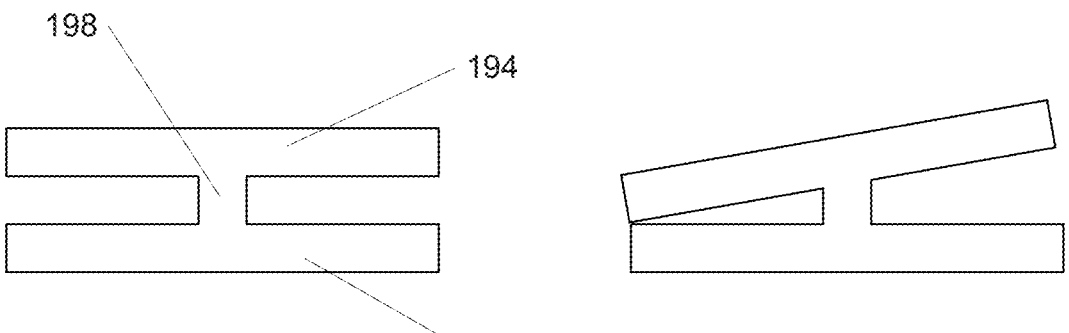

FIG. 15 shows a partial method of manufacture for wedge-shaped rings. In FIG. 15(a), a ring is produced in one piece, and then machined to form an upper ring 194, a lower ring 196, and a bridge 198 joining them. Then, in FIG. 15(b), the upper plate is reoriented relative to the lower plate by plastically deforming the bridge.

In some embodiment variations, in lieu of rings expanded radially as shown in FIG. 12(a), rings may be in the form of flat spirals, which are expanded (or contracted) by twisting them, balloon expanding them, etc. In the expanded, strained configuration, if not plastically deformed, they may be maintained in that configuration by ratcheting mechanisms, clips, etc.

7th Embodiment

We now turn to a set of embodiments which may be more suitable for producing steerable instruments which are not necessarily rigid on their own (if unsupported by surrounding tissue or other material) and may therefore be better suited for applications in which it is desirable to access a target region embedded in surrounding tissue.

Figures 16A, 16B:
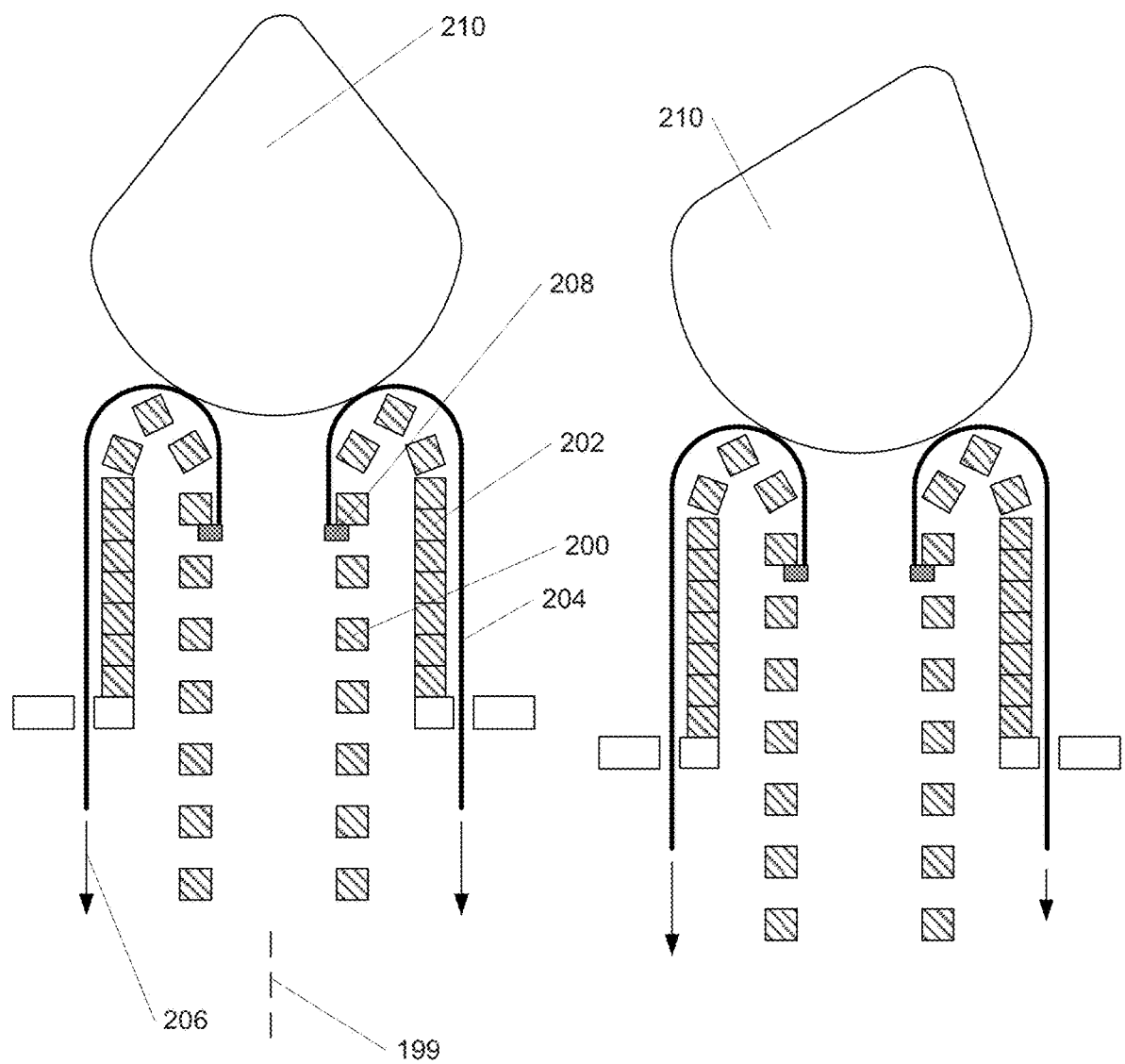
FIGS. 16(a)-(b) show an embodiment of a distally assembled device.

FIG. 16 shows a cross-sectional view of a 7th embodiment of the invention similar in some aspects to previous embodiments. The geometry shown is rotationally symmetric around axis 199. As shown in FIG. 16(a), a tube (e.g., a braided tube of Nitinol (nickel-titanium) wire) is everted and has both inner walls 200 and outer walls 202, the latter forming a cannula. Wire turns of the tube 200 located on inner walls are axially expanded and radially collapsed, whereas wire turns 202 on outer walls are radially expanded and axially collapsed. If the wire turns 202 are fully collapsed, the cannula may be self-supporting and suitable for use surrounded by fluid. As the inner walls move distally in the process of extending the cannula, inner turns 200 evert and are transformed into outer turns 202. In some embodiment variations, the distal motion may be implemented by pushing inner turns 200 distally (e.g., if surrounded by a tube, not shown, to prevent inner turns from prematurely collapsing axially and expanding radially). In other embodiment variations, the motion may be implemented by pulling on wires 204 in the direction 206. The distal ends of wires 204 engage inner turns 200 through the use of repositionable hooks 208 or other means, such that pulling on wires 204 pulls inner turns distally. Wires 204 are curved over the everting tube as shown, with the tube acting to reverse their direction of motion. In some embodiment variations, a ring or set of rollers, not shown, located between wires 204 and everting tube reduces friction between wires 204 and tube and prevents deformation of tube. At the distal end of the instrument is a tip serving to penetrate tissue with minimal force, and acting as a stylet to prevent tissue coring (tissue entering the lumen formed by the inner walls). Once the cannula has obtained the full length desired, tip 210 can be collapsed and removed, displaced, drilled through, etc. if it interferes with the procedure.

To extend straight ahead, penetrating through tissue, wires 204 are pulled an equal distance. In order to extend the instrument along a curved path, not all wires are pulled an equal distance or with an equal tension. For example, as shown in FIG. 16(b), the left wire is pulled more or tensioned more than the right wire. This has the effect of forcing turns on the left side to pile up faster on the outer tube, tending to tilt the tube to the right. Moreover, tip 210, if in contact with the wires as shown, can be rotated by them even though there is some slip between wires 204 and tip 210; the direction of tip rotation, with bottom of tip 204 (which may be a section of a sphere) acting as a pulley, is also toward the right. As the cannula lengthens and penetrates into tissue, the biasing of the everting tube and tip caused by uneven wire motion or tension causes the cannula to curve in its trajectory. As the cannula extends, it forms a liner for the tunnel through the tissue, reinforcing it and supporting it against collapse. In some embodiment variations, the liner may be largely or completely non-porous, allowing fluid transport. In some embodiment variations (e.g., when a braided tube is used), a thin, separate continuous liner is provided which everts along primary tube and provides a leak-proof conduit.

The length of the everting tube can be adjusted prior to cannula delivery such that inner turns 200 are completely everted and the resulting lumen is larger—determined by the ID of the outer turns—than it would be if not completely everted.

Retraction of the cannula can be accomplished by pulling the tube formed by inner turns 200 proximally. Or, if the tube has completely everted in order to maximize the lumen, wires can be provided that are affixed to the proximal ends of the tube; pulling these can reverse the eversion of the tube.

8th Embodiment

Figure 17:
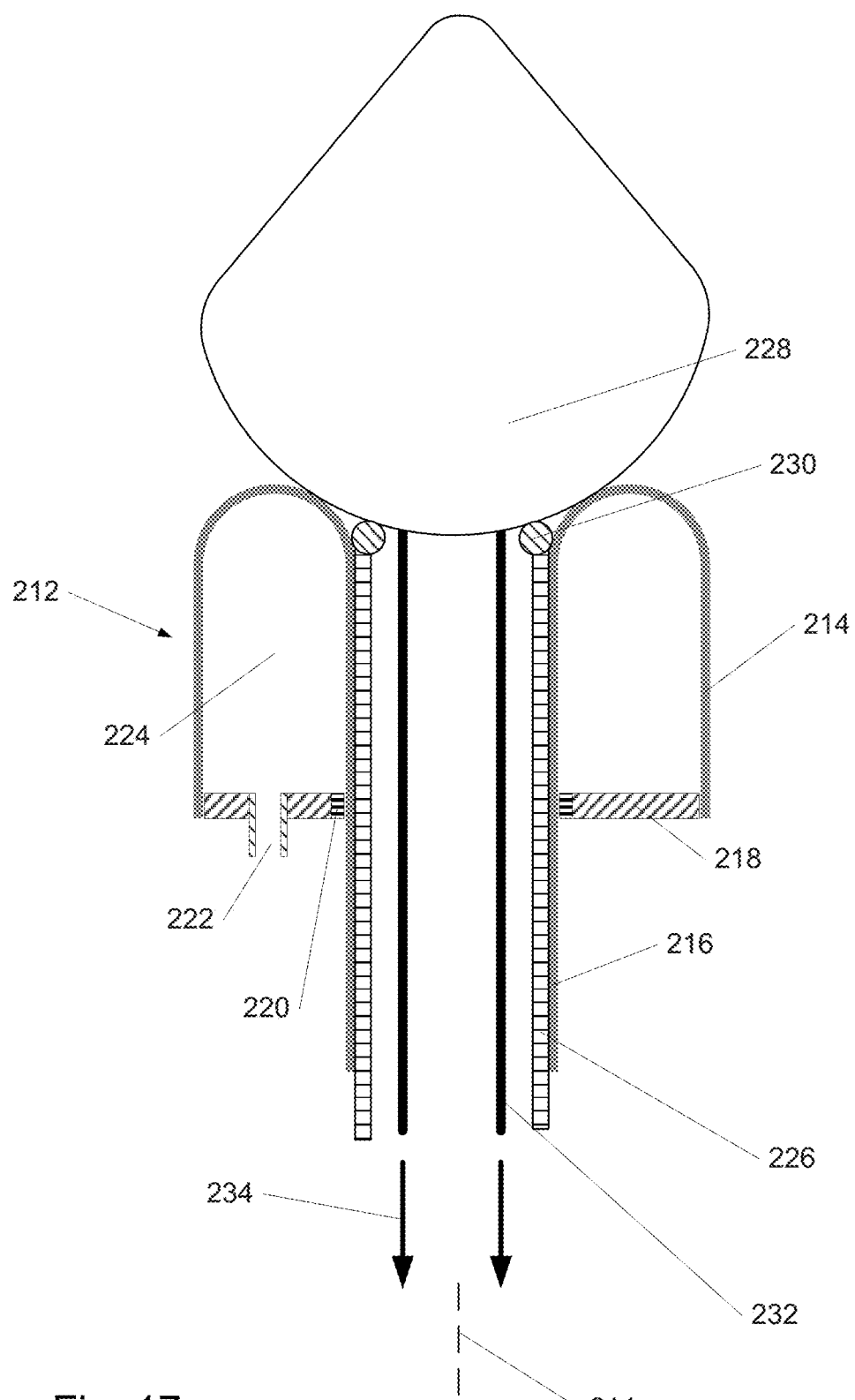
FIG. 17 shows an embodiment of a distally assembled device.

FIG. 17 shows a cross-sectional view of an 8th embodiment of the invention similar in some aspects to previous embodiments. The geometry shown is rotationally symmetric around axis 211. An everting flexible tube 212 (e.g., silicone rubber, Goretex) is provided, comprising outer walls 214 and inner walls 216. Outer walls 214 and inner walls 216 are bridged by rigid ring 218 which is optionally equipped with sliding seal 220 on its inner edge. Ring 218 is perforated to form a fluid inlet 222. When fluid (e.g., having a lubricating, low-friction property) is pumped into space 224 between outer walls 214 and inner walls 216, the pressure causes tube 212 to evert further and elongate. Outer walls 214 may in some embodiment variations be reinforced (e.g., by braid) to minimize bulging due to the fluid pressure. Also, in some embodiment variations, radially stiff and strong tube 226 is provided adjacent to inner walls 216 to prevent inward bulging and loss of ring/seal contact pressure. In some embodiment variations, compartment formed by tip 228 (see below) and inner walls 216 may be pressurized to minimize inward bulging of inner walls 216 and loss of ring/seal pressure. Tube 226 may also help to support tip 228, in some cases through ring 230. While tube 212 everts, tip 228 may be tilted and steered by applying differential tension to wires 232 attached to tip, in direction 234.

9th Embodiment

Figure 18:
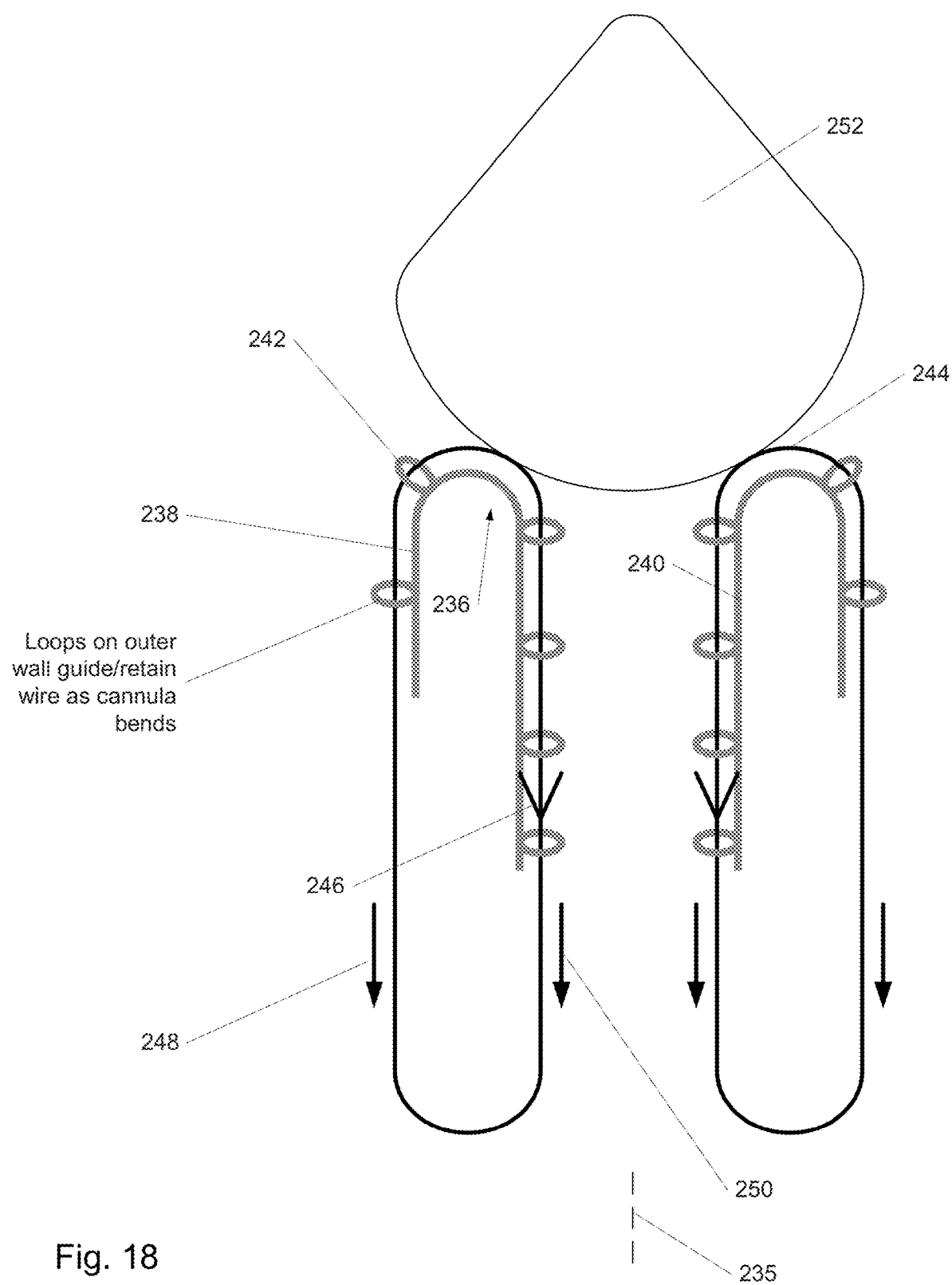
FIG. 18 shows an embodiment of a distally assembled device.

FIG. 18 shows a cross-sectional view of a 9th embodiment of the invention similar in some aspects to previous embodiments, and particularly to the 7th embodiment. The geometry shown is rotationally symmetric around axis 235. An everting flexible tube 236 is provided, which may for example be a continuous elastomeric tube or a braided metal wire tube, and having outer walls 238 and inner walls 240. In some embodiment variations, loops 242 are spaced (e.g., regularly) along the inside of inner walls 240, ending up on the outside of outer walls 238 as tube 236 everts. Running through loops 242 are wires 244 equipped with barbs 246. Wires 244 extend proximally and may be joined into continuous loops as shown. Loops 242 serve to advance inner walls 240 distally, extending the instrument, and also guide wires 244 on the outside of outer walls 238, such that when the instrument curves, wires 244 remain adjacent to outer walls 238.

When wires 244 are pulled in direction 248, barbs 246 engage loops 242 and pull inner walls 240 distally, further everting tube 236. After thus pulling inner walls 240 a short distance, wires 244 are then pulled in direction 250 a short distance such that barbs 246 pass in a proximal direction (i.e., proximally) through the next most proximal loops, engaging them in preparing for the next cycle, in which wires 244 are again pulled in direction 248. When all wires 244 are manipulated (e.g., alternating between pulling in directions 248 and 250) at the same rate, tube 236 everts and extends straight, forcing tip 252 into tissue. When wires 244 are not all manipulated at the same rate, tube 236 will tend to bend away from the direction in which the rate is higher, forcing tip 252 into tissue in a new direction. In some embodiment variations, tip 252 may also be tilted, e.g., through the use of wires such as wires 232 in FIG. 17. In some embodiment variations, in lieu of loops 242, if tube 236 has openings or recesses in its side (e.g., as a braided wire tube would), a ball (or bead or other shape) affixed to wire 242 can be used to pull inner walls 240 directly. In such a case, the ball can be maintained within the openings/recesses by a stylet or tube (possibly elastomer) adjacent to the wires inside the instrument, or by a balloon. Such a balloon may periodically be lowered in pressure to allow the ball to be easily repositioned by pulling wire 244 in direction 250 so it can engage a more proximal opening/recess.

10th Embodiment

Figure 19:
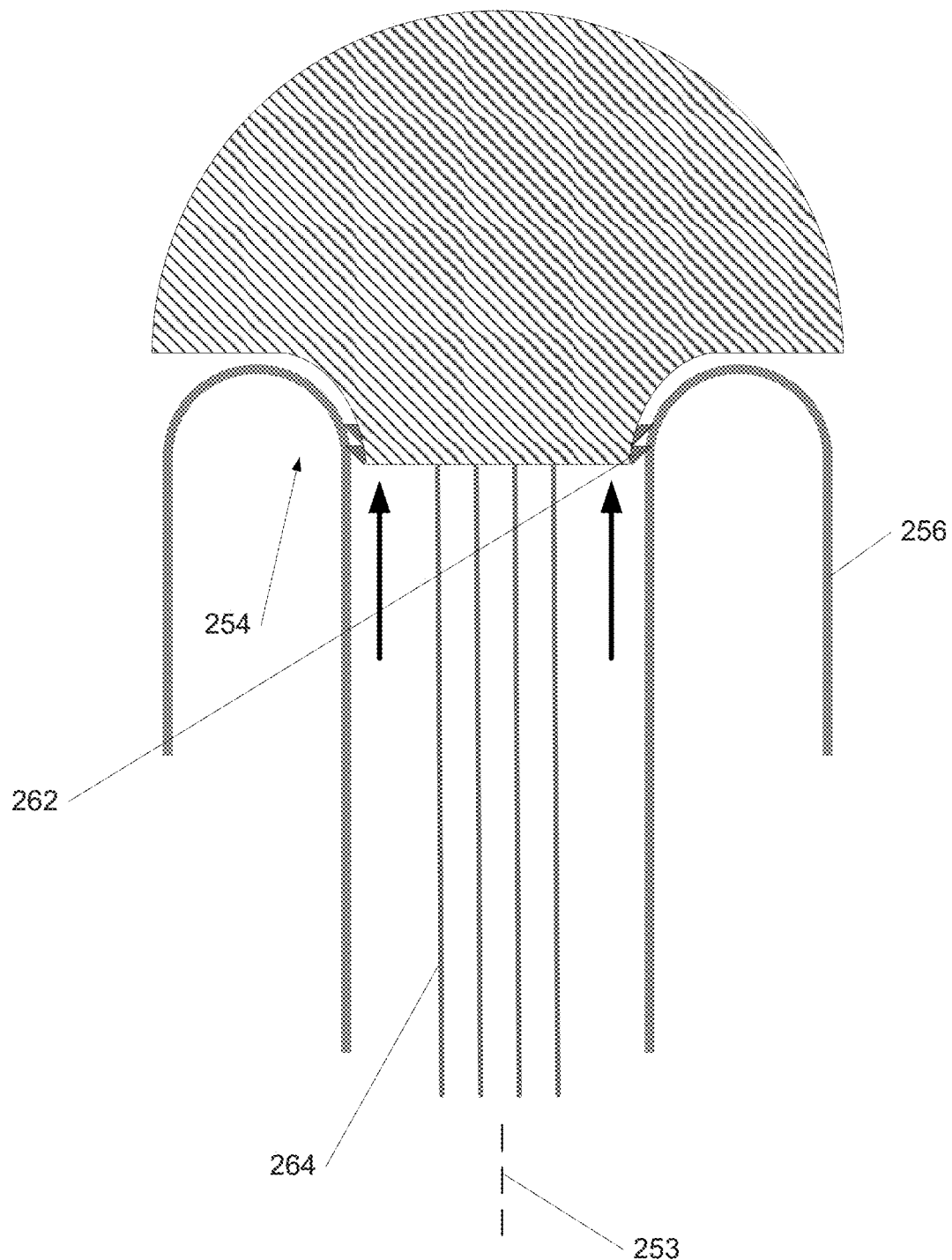
FIG. 19 shows an embodiment of a distally assembled device.

FIG. 19 shows a cross-sectional view of a 10th embodiment of the invention similar in some aspects to previous embodiments, and particularly to the 9th embodiment. The geometry shown is rotationally symmetric around axis 253. Again an everting tube 254 is provided, having outer walls 256 and inner walls 258. A distal tip 260 (here shown rounded, however other shapes are possible, such as that of FIG. 18) is provided with actuators 262 which make contact with inner walls 258 and pull them in a distal direction (e.g., using an inchworm or rolling motion). Actuators 262 receive power through electrical wires 264. When actuators 262 are actuated at a uniform rate, tube 254 everts uniformly and extends distally along a straight path. When actuators 262 are actuated at a non-uniform rate, the distal extension is along a curved path whose direction and radius of curvature depend on the relative actuation rates.

11th Embodiment

Figure 20:
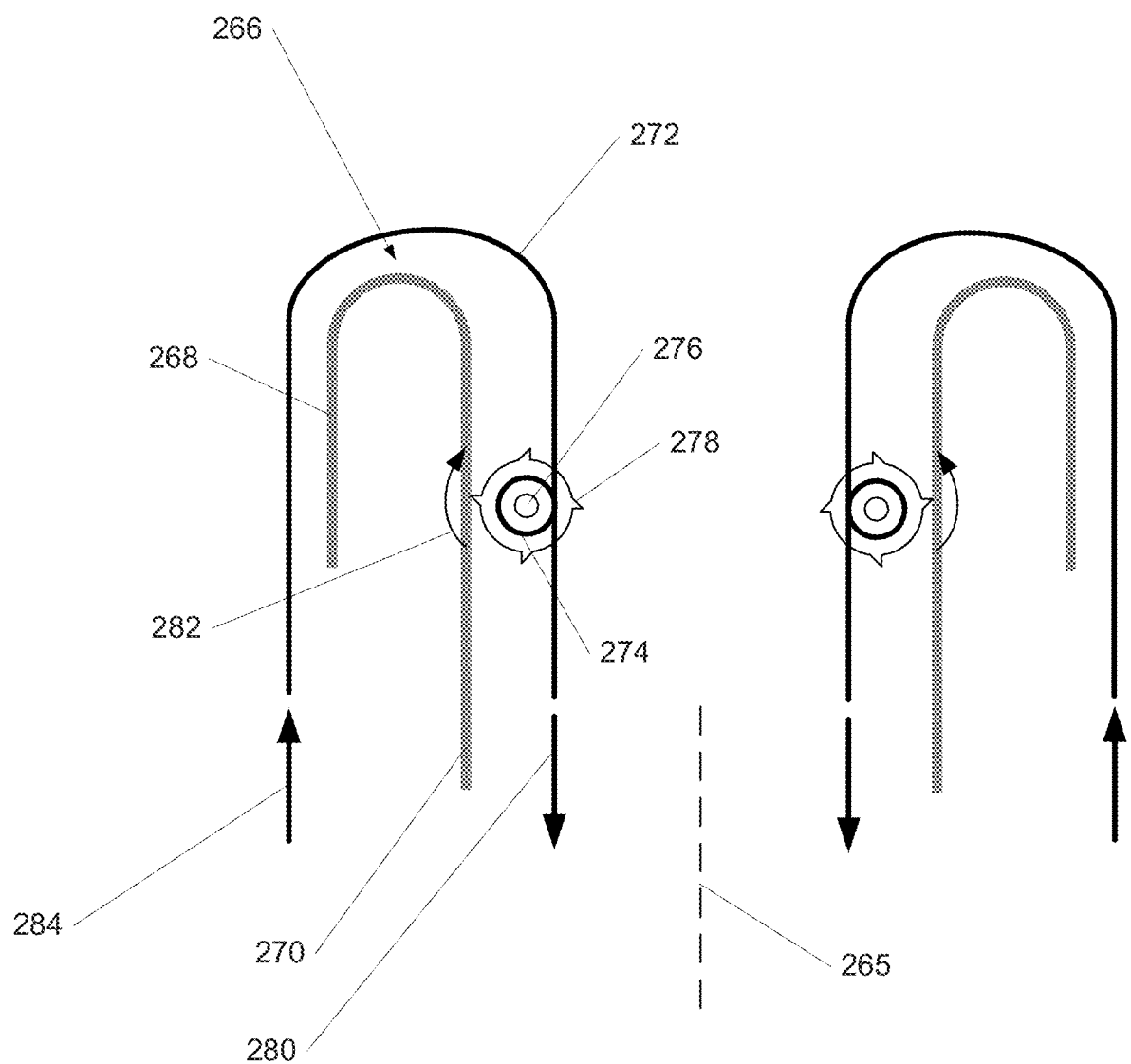
FIG. 20 shows an embodiment of a distally assembled device.

FIG. 20 shows a cross-sectional view of an 11th embodiment of the invention similar in some aspects to previous embodiments, and particularly to the 9th embodiment. The geometry shown is rotationally symmetric around axis 265. Again an everting tube 266 is provided, having outer walls 268 and inner walls 270. Wires 272 are provided, which run in the direction shown, and which may be joined into loops as in FIG. 18. A distal tip (not shown) may also be provided. Wires 272 are wrapped around wheels 274. Wheels 274 turn on axles 276 mounted to distal tip or to a flexible tube or shaft (not shown) running down the lumen of the instrument, adjacent to the wheels. Wheels may be provided with teeth 278. When wires 272 are pulled in direction 280, wheels 274 are rotated in direction 282, causing inner walls 270 to be pushed distally, thus further everting tube 266. Wire motion can be continuous in one direction in some embodiment variations. In other embodiment variations, in which wheels 274 are provided with a ratcheting mechanism that only allows rotation in direction 282, wire motion can be reciprocating, alternating between motion in direction 280 and motion in direction 284. In such embodiment variations, retracting of the device requires removing or reversing the ratcheting mechanism.

When wires 272 are pulled or cycled at a uniform rate, tube 266 everts uniformly and extends distally along a straight path. When wires 272 are pulled or cycled at a non-uniform rate, the distal extension is along a curved path whose direction and radius of curvature depend on the relative pulling/cycling rates.

12th Embodiment

Figure 21:
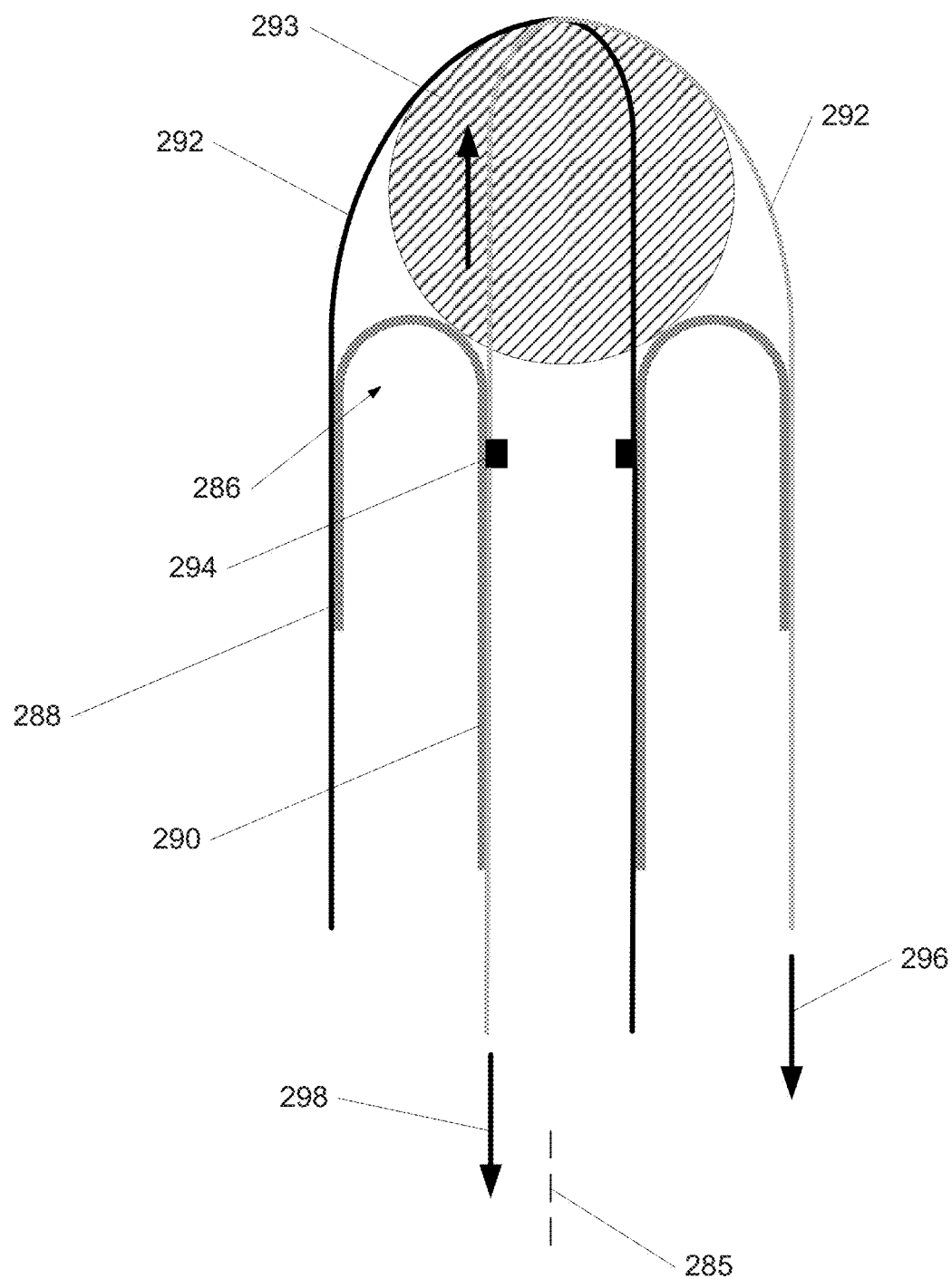
FIG. 21 shows an embodiment of a distally assembled device.

FIG. 21 shows a cross-sectional view of a 12th embodiment of the invention similar in some aspects to previous embodiments and particularly to the embodiments of FIGS. 16 and 18. The geometry shown is rotationally symmetric around axis 285. Again an everting tube 286 is provided, having outer walls 288 and inner walls 290. Wires 292 are provided which extend upwards along outer walls 288 and over a surface 293 which redirects them downwards, where they attach to temporary anchors 294 and then continue proximally out of the instrument. Wires 292 may be joined into loops such as wires 244 in FIG. 18. Surface 292 may be, for example, spherical, and may be the distal tip of the instrument, or a portion thereof. Anchors 294 may be of the type described in the 9th embodiment (e.g., balls which enter depressions in inner walls 290) or of another design, such that anchors 294 will securely grasp inner walls 290 when wires 292 are pulled in direction 296, but will loosen their grip when pulled in direction 298.

When wires 292 are pulled in direction 296, anchors 294 grasp inner walls 290 and pull inner walls 290 distally, further everting tube 286. After pulling inner walls 290 a short distance, wires 292 are then pulled in direction 298 a shorter distance such that anchors 294 can grasp a more proximal region on inner walls 290 in preparation for the next cycle, in which wires 292 are again pulled in direction 296. When all wires 292 are manipulated (e.g., alternating between pulling in directions 296 and 298) at the same rate, tube 286 everts and extends straight, forcing the tip into tissue. When wires 244 (in FIG. 18) are not all manipulated at the same rate, tube 286 will tend to bend away from the direction in which the rate is higher, forcing the tip into tissue in a new direction. In some embodiment variations, the tip may also be tilted, e.g., through the use of wires such as wires 232 in FIG. 17.

Everting versions of the cannula such as this one may in some embodiments incorporate a shape memory polymer that can transition from a rigid to a flexible state (e.g., when heated), or simply a thermoplastic which can soften when heated. Then, for example, heat can be applied to the inner walls (e.g., by radiant heater, hot air, laser, embedded resistive wires) as they evert to form the outer walls, making them flexible enough to both bend and stretch, which facilitates eversion. Once everted, the structure can rigidify. If the inner walls are also rigid, it can facilitate pushing them distally. However, if too flexible, they cannot conform to the outer walls of the cannula, which may in general be curved. Thus in some embodiment variations it is beneficial to keep the inner walls mostly flexible (e.g., by heating them with a hot air stream that is directed through the inner walls from proximal to distal end or vice-versa.

Everting versions of the cannula such as this one may in some embodiments incorporate a granular material between two walls of a double-walled tube; in some embodiment variations this is isolated within individual compartments which may be toroidal in shape and disposed axially along the tube. By apply vacuum to the regions of the tube which form outer walls and sealing the regions to hold vacuum, they can become rigid and hold their shape by virtue of jamming. Everting versions of the cannula such as this one may in some embodiments incorporate an electrorheological or magnetorheological fluid between two walls of a double-walled tube; in some embodiment variations this is isolated within individual compartments which may be toroidal in shape and disposed axially along the tube. By apply an electric or magnetic field to the regions of the tube which form outer walls, they can become rigid and hold their shape by virtue of greatly increased viscosity.

13th Embodiment

Figure 22A:
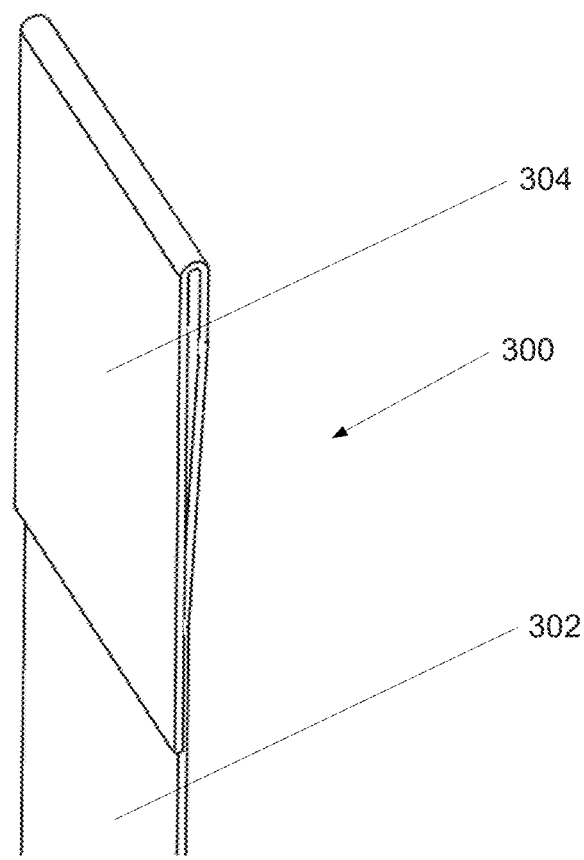
FIGS. 22(a)-(b) show an embodiment of a distally assembled device.
Figure 22B:
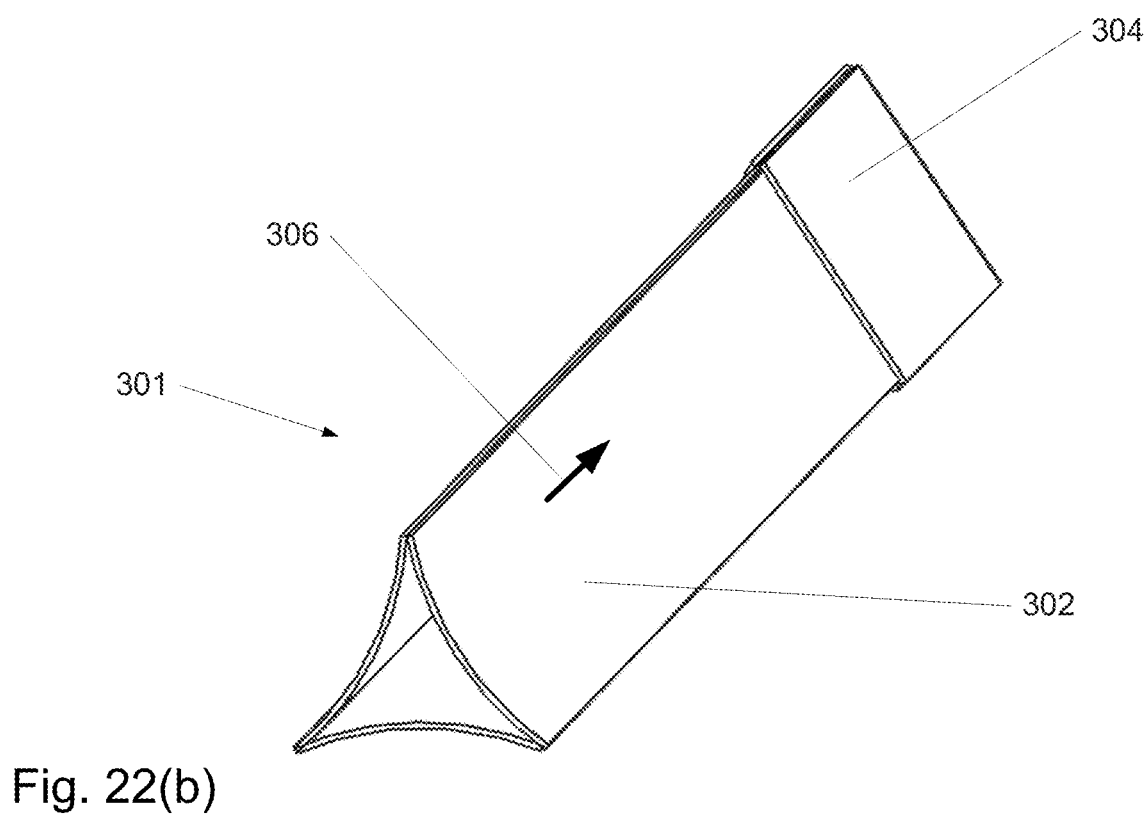

FIG. 22 shows a cross-sectional view of a 13th embodiment of the invention similar in some aspects to previous embodiments. In FIG. 22(a) a strip 300 of flexible material is provided. A curved region 302 of strip 300 is folded back on itself to form a substantially flat region 304. Three strips 300 are shown in FIG. 22(b) joined into a triangular tube 301, with regions 304 on the outside and regions 302 on the inside. In some embodiment variations strips 300 are curved in regions 302 to allow strips 300 sufficient space inside flat regions 304 when assembled into tube 301. In some embodiment variations, strip 300 is stretchable and when stretched, becomes narrower, thus allowing it to move easily within the triangular tube with less friction and without curving. For example, strip 300 may comprise an expanded metal-like material perforated with many holes (e.g., diamond-shaped). As a result of being stretched, the narrower wall of triangular tube 301 will still form a stiff tube, but the triangular cross section will not necessarily be equilateral.

If regions 302 are fed distally in direction 306, regions 304 will elongate in direction 306 as material from region 302 flows to the distal end of the tube 301, around the bend, and ends up on the outside as part of region 304. Strips 300 are joined by adhesive, seam welding, magnets, zippers, VELCRO®, DUAL LOCK™, etc. in such a way that if all strips 300 are fed distally at the same rate, the tube 301 resulting from joining them at their edges is straight. However, if strips 300 are fed at different rates, the tube 301 resulting from joining them at their edges will be curved. By adjusting the relative feed rates and/or the amount of stretch if strip 300 is stretchable, evolving/everting tube 301 can thus be made to curve along a 3-D path. In some cases, such as when the strip is made of an expanded metal-like perforated material, it may be compressed along its axis as well as being expanded. In some embodiment variations, more than 3 strips are used. For example, 6 strips may be fed distally, folded back onto themselves, and joined along their edges to form a tube with a hexagonal cross section. In such a case, the strips need not be curved initially, since there is adequate room to accommodate their width. Since unlike a triangular tube a hexagonal tube can collapse, appropriate bracing or reinforcement can be used, such as joining the strips using a method that provides rigid seams that maintain the strips at the correct relative angles.

14th Embodiment

Figure 23:
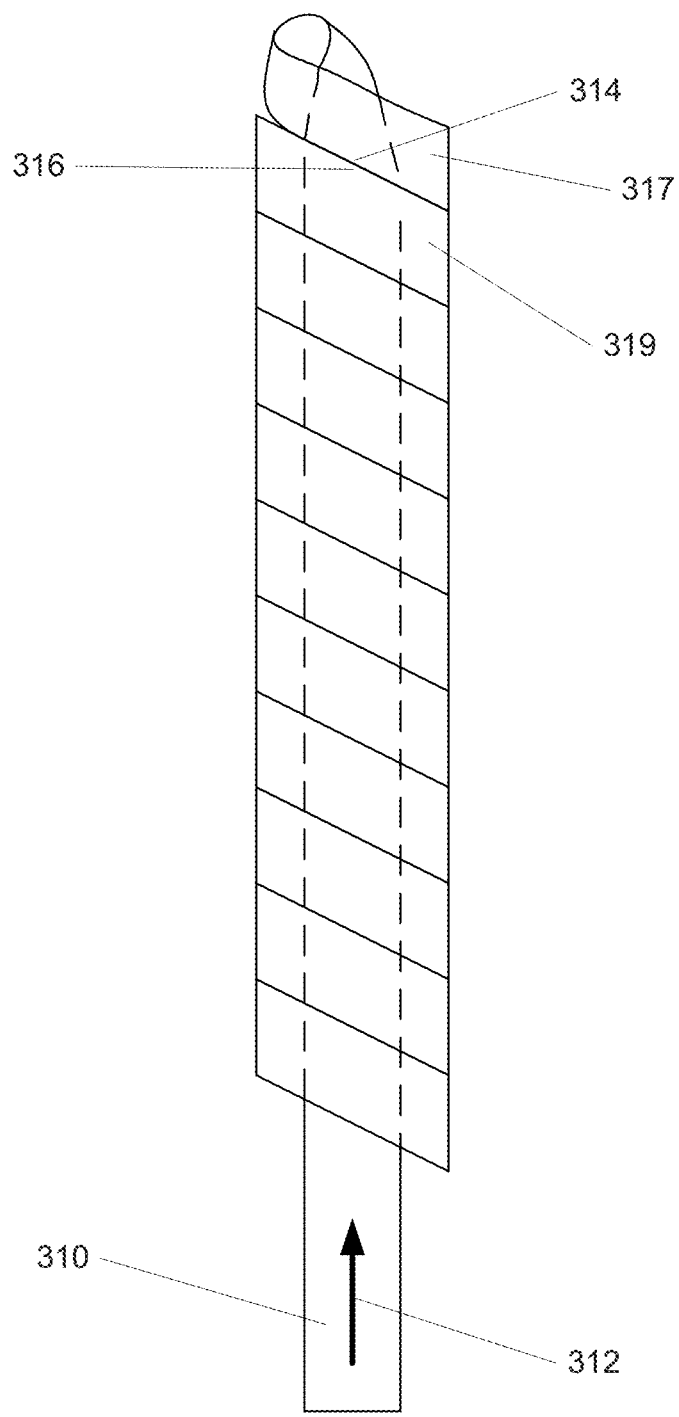
FIG. 23 shows an embodiment of a distally assembled device.

FIG. 23 shows a cross-sectional view of a 14th embodiment of the invention similar in some aspects to previous embodiments, and particularly, the 13th embodiment. In the figure, a strip 310 of flexible material, long compared with its width, is provided. The strip is advanced distally in direction 312 through the lumen of the tube or cannula (e.g., round in cross section) that is formed by winding the strip in an approximately helical pattern and joining the most distal winding 317 and the adjacent, next-most distal winding 319 together to form a seam and distally grow the tube. In some embodiment variations, proximal edge 314 of winding 317 (in FIG. 24) and distal edge 316 of winding 319 are joined edge-to-edge. In some embodiment variations the seam is formed with some degree of overlap (not shown) of the edges of the windings. Windings 317 and 319 may be joined by adhesive, welding, magnets, zippers, VELCRO®, DUAL LOCK™, mechanical features such as tabs and holes, or other methods. The resulting tube 308 has a structure similar to a roll used to hold paper towels. As the seam is formed, prior to forming of the seam, or after forming of the seam, the amount of overlap or the width of the strip may be adjusted locally. In regions of the tube where the amount of overlap or the width of the strip is substantially uniform around the circumference of the tube, the tube will locally grow along a straight path. However, in regions of the tube where the overlap or width of the strip substantially varies around the circumference of the tube, the tube will locally curve and grow along a non-straight path.

For windings in when the strip width or amount of overlap is constant, the cannula is straight. However, for windings in which width or overlap varies around the circumference, the winding becomes effectively tapered, producing a curvature in the cannula whose radius and plane depend on the location and magnitude of the variation.

15th Embodiment

Figure 24A:
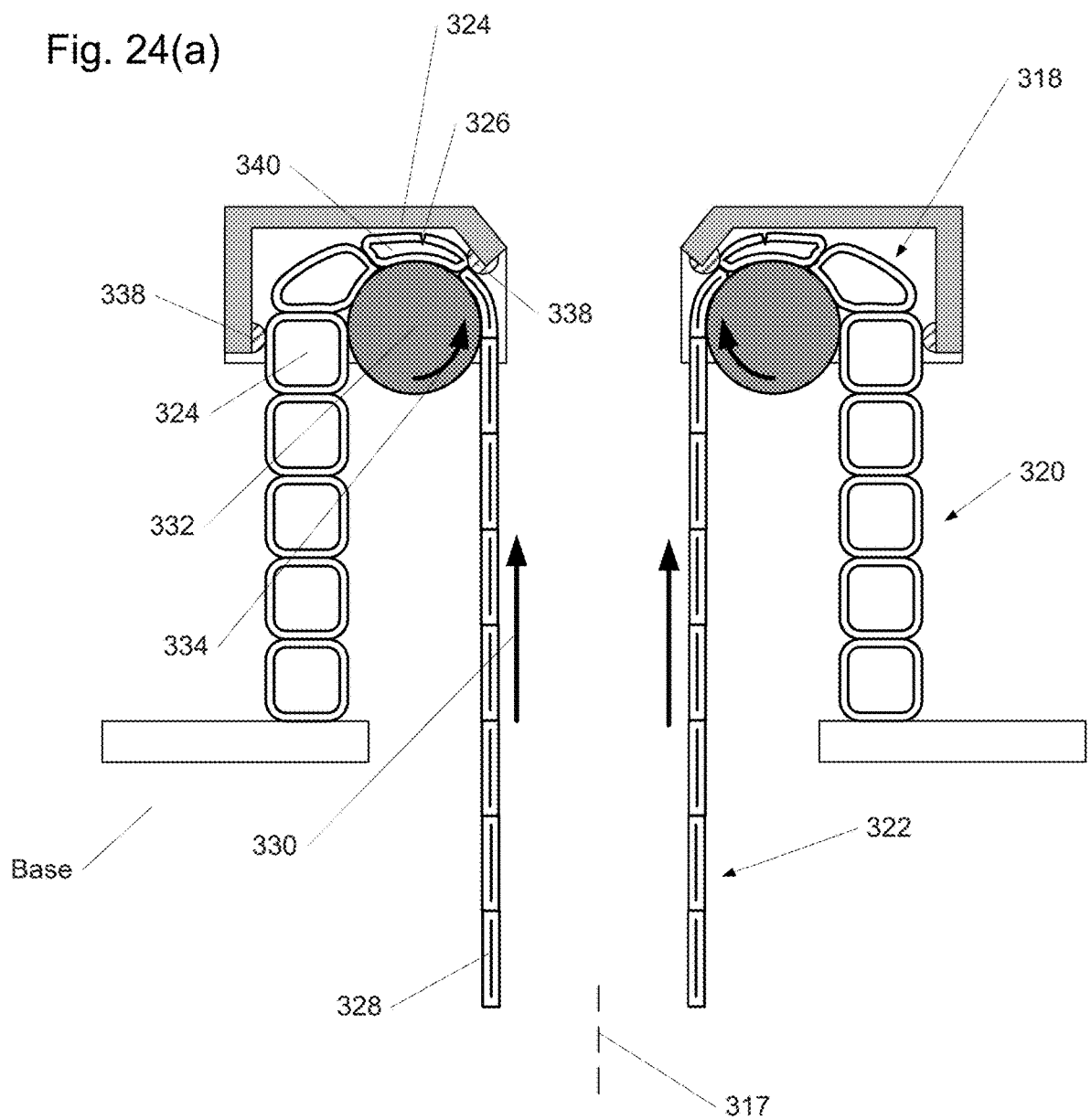
FIGS. 24(a)-(b) show an embodiment of a distally assembled device.
Figure 24B:
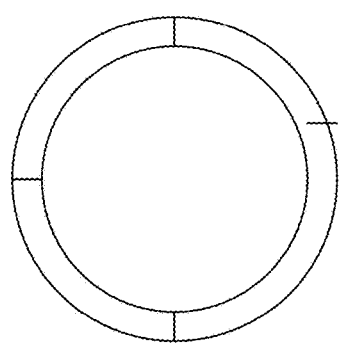

FIG. 24(a) shows a cross-sectional elevation view of a 15th embodiment of the invention similar in some aspects to previous embodiments. The geometry shown is rotationally symmetric around axis 317. In the figure, tube 318 is able to evert, having outer walls 320 and inner walls 322. The walls of tube 318 are comprised of flexible (e.g., elastomeric) sacs, which can be inflated with fluid such as sac 324. As shown in FIG. 24(b), in some embodiment variations, sacs have a partial-toroidal shape; in plan view, they appear as sections of tori spanning less than the normal 360 degrees for a full torus: for example, 90 degrees (as shown) or 120 degrees. Sacs are provided on their surface with slits 326 that allow them to be filled when slits 326 are widened as shown in the figure. Alternatively in some embodiment variations, sacs can be pierced by fixed or moving needles and then re-seal themselves upon withdrawal of the needles. Initially, forming at least part of inner walls 322, sacs are unfilled such as sac 328. As sacs move distally in direction 330, either pulled by rotating rollers 332 rotating in direction 334, they ride over rollers 332 (driven, for example, by motors, not shown) and enter chambers 324 sealed at its entrance and exit by seals 338. Within chambers 324, sacs such as sac 340 are inflated with fluid (in the figure, all sacs are shown equally inflated for simplicity). For example, while sac 340 is bent over roller 332, slit 326 on upper surface is widened and fluid can enter sac. When sac 340 has progressed further (e.g., to a position such as sac 324 exiting the chambers), slit 326 will have closed, trapping fluid inside sac 340. In some embodiment variations, sacs can be actively sealed (e.g., by the application of heat if meltable, or adhesive). Chambers 324 are also of a partial-toroidal shape, each corresponding to a partial toroidal sac. The pressure to each of chambers 324 can be varied, such that the pressure inside each sac when it exits chambers 324 can also vary. If sacs are elastomeric, an increase in pressure will cause them to increase in size. In some embodiment variations, the increase in size is somewhat isotropic; however, in other embodiment variations, the increase in size is anisotropic, and primary along the direction of axis 317. This may be accomplished through the use of reinforcing bands in each sac wall, or other structures, and may be preferred, in that it allows sac height along axis 317 to vary more dramatically.

If all sacs at a given level (i.e., position along eversion/symmetry axis 317) are inflated to the same pressure, then assuming they are equivalent, tube/cannula 318 will grow in a direction parallel to axis 317. However, if the pressures are not equal, sacs with higher pressure and greater axial height will bend the growth direction away from themselves, causing the cannula to bend or curve as desired, along a 3-D path.

Retraction of the cannula can be accomplished by reversing rollers 332; sacs will enter chambers 324 and be emptied of their fluid contents and collapsed as they return to form inner walls 322 moving proximally.

In some embodiment variations, rather than providing sacs with a slit that can open to admit fluid, and chambers to fill sacs with fluid, sacs can be sealed and pierced by a needle (e.g., protruding from the surface of rollers 332). While so pierced, fluid can be injected into each sac. When the needle retracts, the sacs (e.g., if elastomeric) can re-seal, maintaining their charge of fluid within.

16th Embodiment

Figure 25:
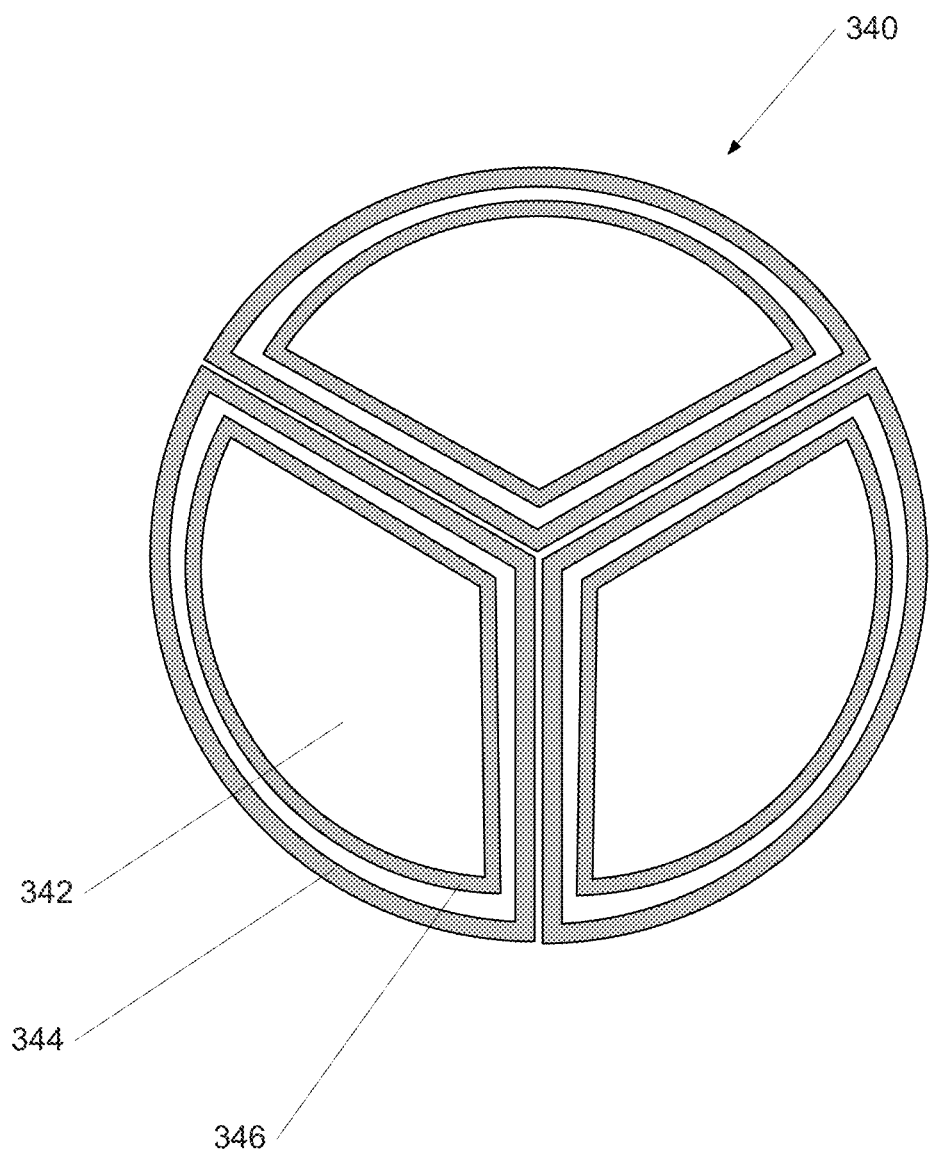
FIG. 25 shows an embodiment of a distally assembled device.

FIG. 25 shows a cross-sectional axial view of a 16th embodiment of the invention similar in some aspects to previous embodiments. Tube 340 is comprised of several (e.g., 3-4) smaller tubes 342 joined or grouped together, each of which itself is cable of everting, e.g. in the manner shown in FIG. 17. Each tube 342 has outer walls 344 and inner walls 346. If each tube 342 everts at the same rate as it grows distally, tube 340 will grow to follow a straight path. But if the tubes do not all evert at the same rate, tube 340 will grow to follow a curved path. Adjusting the relative growth rates of tubes 342 thus causes tube 340 to follow the desired 3-D path in space. Tube 340 can be equipped at its distal end with a tissue-penetrating, non-coring tip (not shown).

17th Embodiment

Figure 26A:
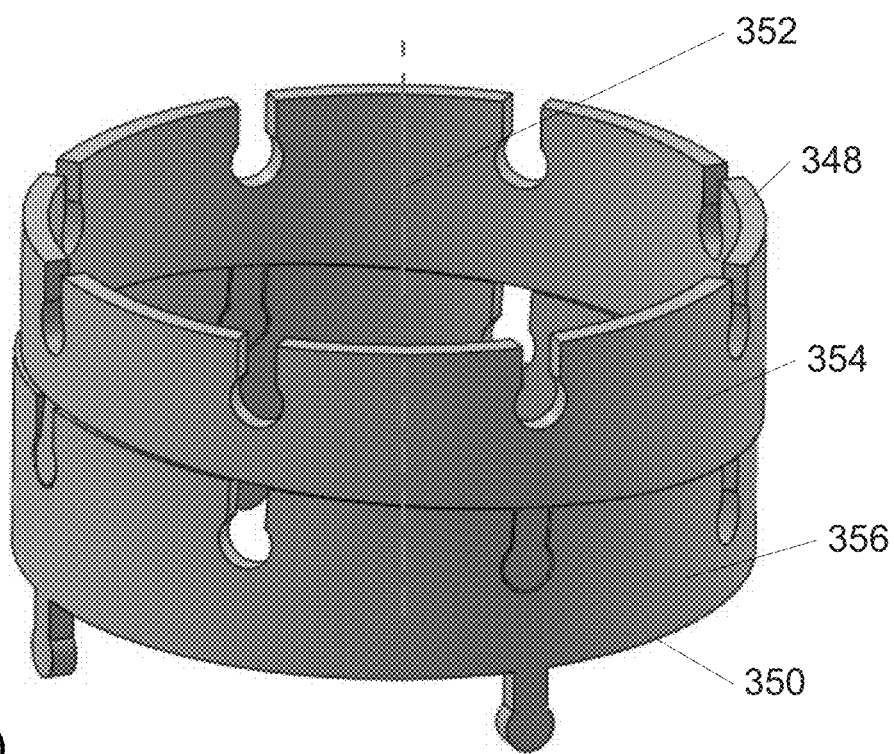
FIGS. 26(a)-(b) show rings associated with shows an embodiment of a distally assembled device.
Figure 26B:
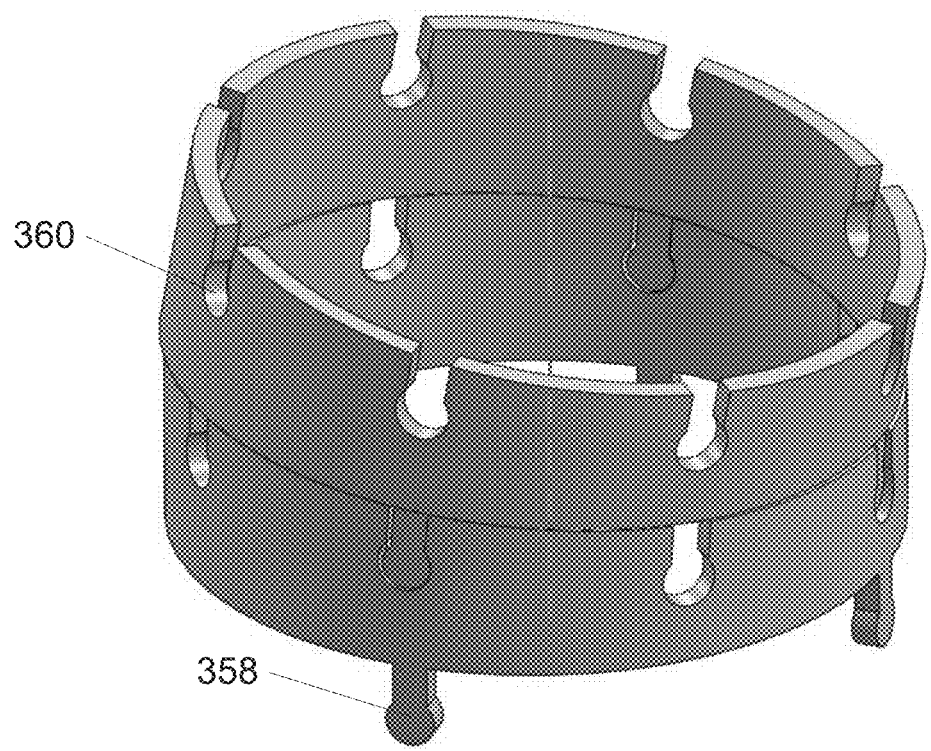
Figure 27:
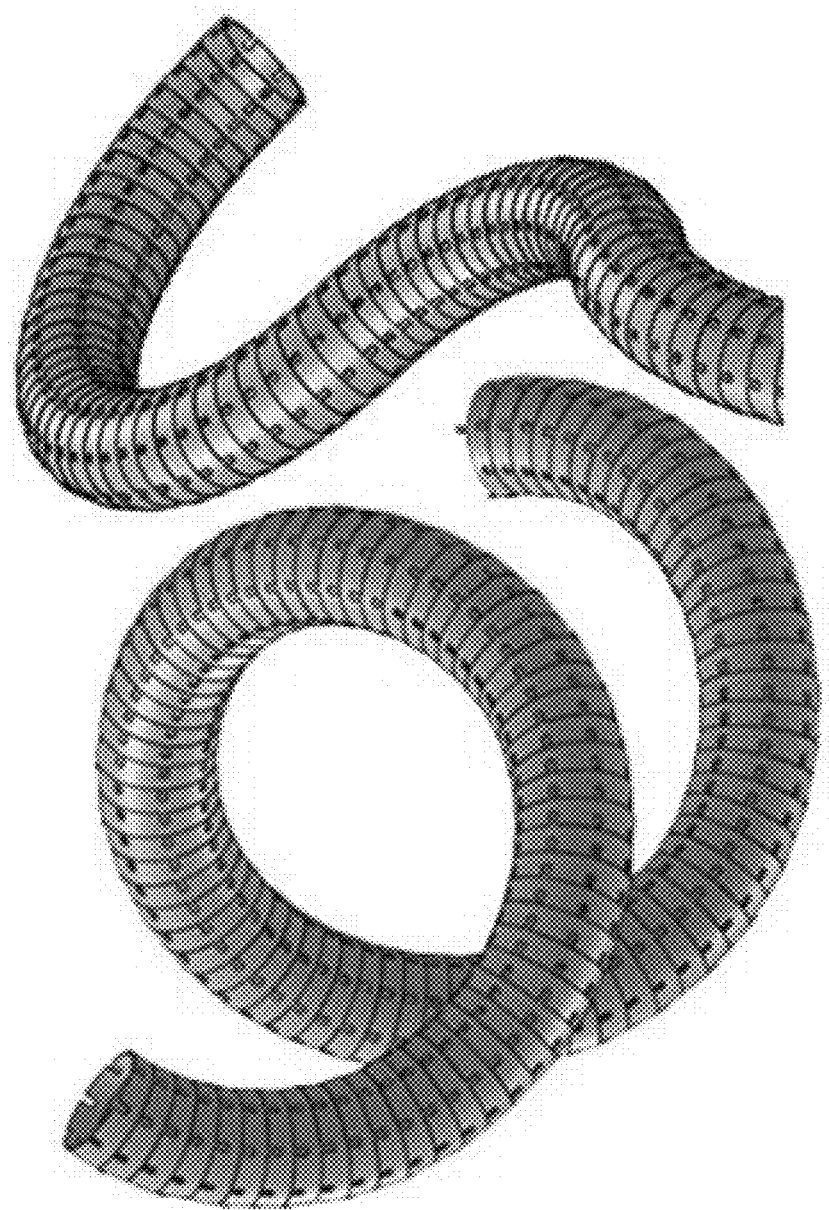
FIG. 27 shows cannulas produced using multiple rings.

FIGS. 26-41 depict a 17$^{th}$ embodiment of the invention similar in some aspects to the 6th embodiment. To distally grow DASC, material must be supplied to the distal end, preferably through the cannula. FIG. 26 shows a design in which material is provided in the form of rings with a wedge-shaped profile and which can couple or interlock. Preferably though not necessarily, these rings are of two different types as shown in the figures, and are used in alternation (i.e., in pairs), allowing straight cannula sections to be formed when the rings are suitably aligned as in FIG. 26(a). The distal face 348 or proximal face 350 of each rings is formed at a specified wedge angle relative to ring axis 352 (e.g., 5° as in FIG. 26), and are therefore not parallel. For distal ring 354 of the pair, distal face 348 is normal to the ring axis and proximal face 350 is at an angle other than 90 degrees; for proximal ring 356, proximal face 350 is normal to the axis and distal face 348 is at an angle other than 90 degrees (typically the same angle as that of the distal ring's proximal face). The relative orientation of the rings can be set so proximal face 350 and distal face 348 are parallel (FIG. 26(a)), at twice the wedge angle (FIG. 26(b)), or at intermediate angles. The angle between proximal and distal faces dictates the local curvature of the cannula, while the orientation of proximal ring 356 dictates the tilt direction of distal face 348 of distal ring 354. Thus, by adjusting the orientation of both rings independently, both curvature and direction can be controlled. With the eight-hole rings shown, five unique curvatures, each with eight directions, are possible. Each ring has four male coupling elements or tabs 358 extending perpendicularly from its proximal face and is perforated with a set of female coupling elements or holes 360 (here, eight) communicating with distal face 348 (in some embodiment variations, tabs 358 are provided on distal face 348 and holes 360 are provided communicating with proximal face 350). Tabs 358 and holes 360 mechanically interlock rings 354 and 356, providing stability in shear, torsion, and tension, and enabling a strong, rigid structure to be built. Two of tabs 358 are located close to the minor axis of the deformed, elliptical ring, and two close to its major axis. The wall thickness of the rings and tabs must be great enough to allow the rings to interlock, since tabs 358 will not necessarily be flush or tangent to the ring surface. Since the proximal face of ring 354 and the distal face of ring 356 may not be circular in shape due to the wedge angle (e.g., if the rings are cut from a tube), in some embodiment variations the rings are slightly deformed (e.g., plastically) to make these faces circular in shape. If a second pair of rings is mated to the first pair, the first pair's distal face establishes the plane of the proximal face for the second pair, and so on. FIG. 27 shows two cannulas, the lower one helical, both having complex 3-D shapes comprising dozens of rings such as rings 354 and 356 (shown in FIG. 26). Notably, these cannulas differ only in the relative orientations of their rings.

Figure 28:
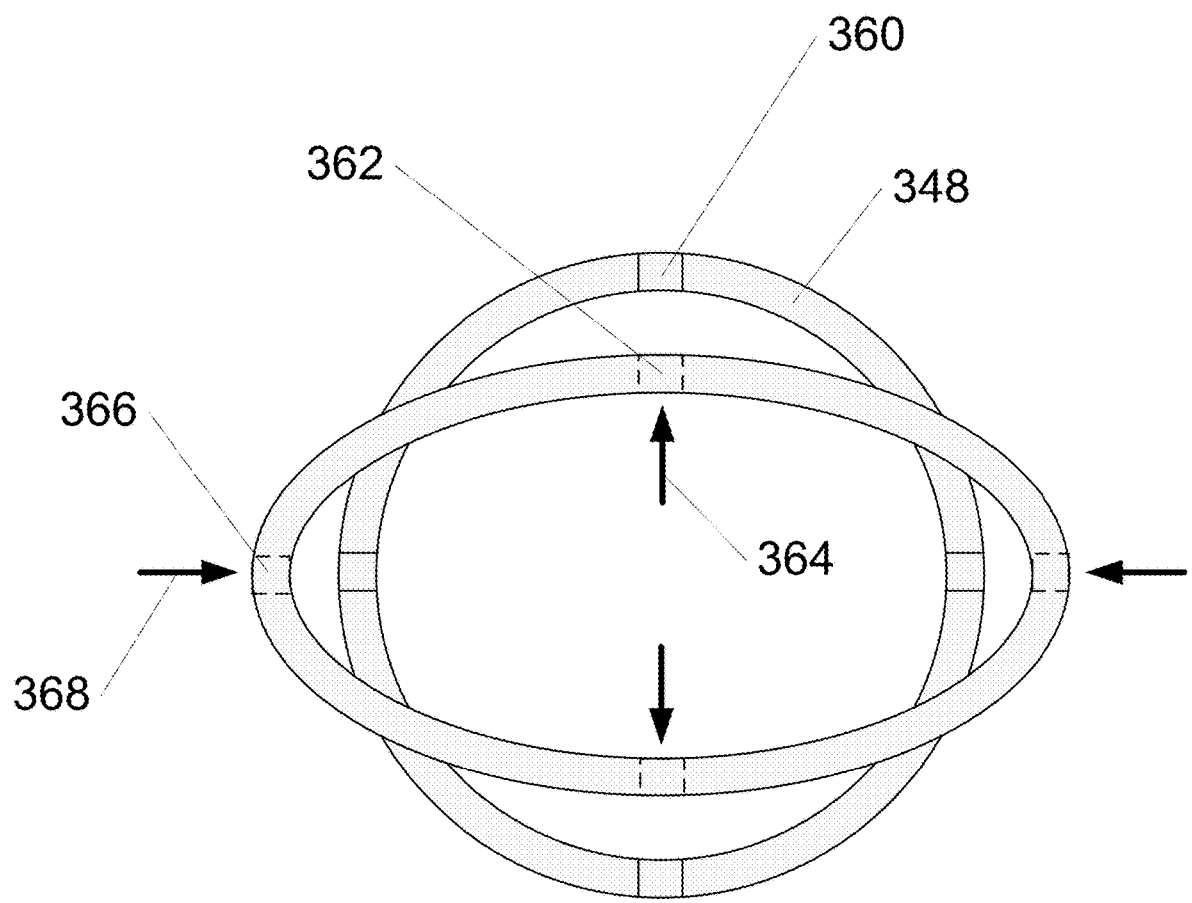
FIG. 28 shows how rings couple together.

Unlocking or locking the rings requires one ring to be temporarily compressed into a substantially elliptical shape. FIG. 28 is an axial view of a deformed elliptical ring in contact with a circular ring below. When the upper ring is allowed to relax into a circle, two opposite tabs 362 (shown in phantom view) from the top ring, located along the minor axis of the ellipse, move outwards in the direction of arrows 364 to enter holes 360 communicating with distal face 348 of the lower ring from the inside. Simultaneously, the remaining two opposite tabs 366 move inwards in the direction of arrows 368 to enter holes 360 from the outside. The four tabs thereby lock the rings together, and keep them interlocked until and unless at least one ring of the pair is deformed so as to cause tabs and holes to separate. In some embodiment variations, one of the tabs may be eliminated, yet the rings may still be interlocked and stable in shear, while in some embodiment variations, two of the tabs may be eliminated and an interior or exterior tube is provided, such that the rings when interlocked are still stable in shear. In some embodiment variations, more than four tabs may be used; for example, tabs may be provided in pairs, with the members of each pair relatively closely spaced. Typically the upper ring is unlocked by re-compressing it to extract tabs 362 and 366 from holes 360, after which the upper and lower rings can be separated.

Figure 29:
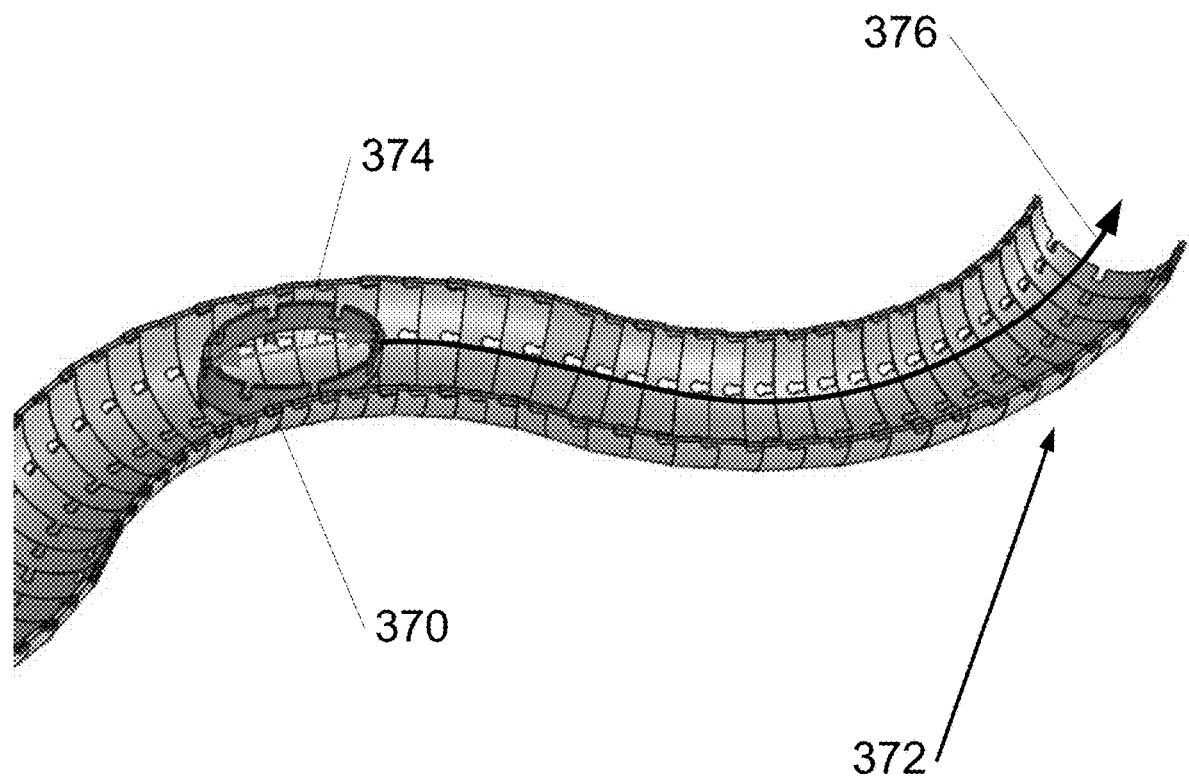
FIG. 29 depicts how rings are transported through the cannula.
Figure 30:
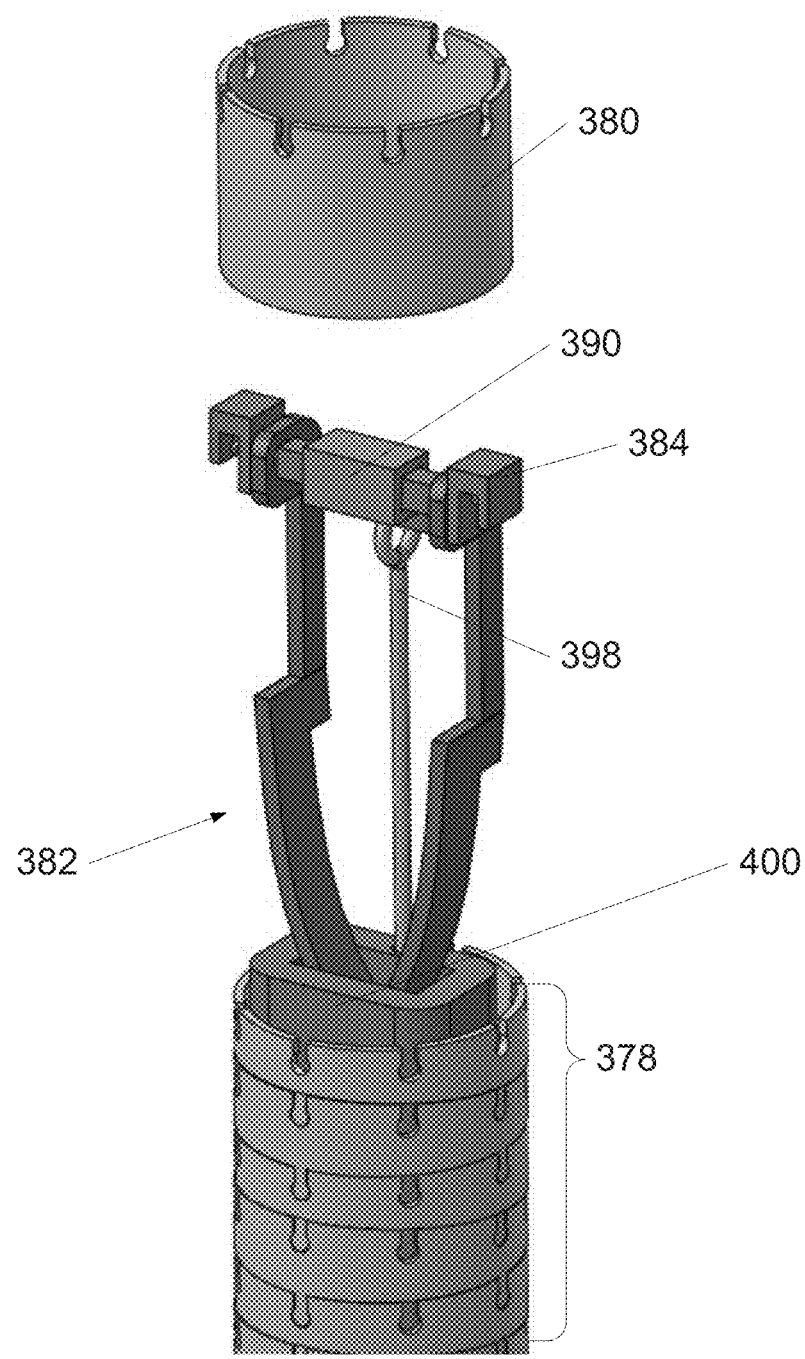
FIG. 30 depicts the head of a stylet and other components.

In the compressed state rings 370 can be transported through the cannula lumen toward distal end 372 (or towards the proximal end) by swiveling them so that the major axis 374 of the ellipse is substantially aligned with the direction of travel 376 (FIG. 29). Assembling/disassembling the cannula is accomplished using a robotically-actuated stylet that can compress, swivel, transport, and rotate rings based on high-level commands (e.g., "bend with 10 mm radius in a 7 o'clock direction"). The stylet includes a flexible shaft that is pushable and torqueable within the cannula, and a distal head. FIG. 30 shows the head of the stylet, along with stack of rings 378 ready for use, and base 380 that serves as a foundation for the cannula. Stack of rings 378 may be incorporated into a cartridge, not shown, that is easily loaded and unloaded from the DASC system; the rings may held ready for use either interlocked as shown in FIG. 30, or held separate from one another. Cartridges may vary in the size of rings they contain, the number of rings, the type of rings (e.g., hole count), ring radiopacity, etc. For access to deep anatomy, base 380 may be very long and rigid or flexible. In some embodiment variations, base 380 comprises a standard straight, flexible, or pre-shaped catheter. In some embodiment variations, stack 378 may be internal to the patient, not external, speeding assembly.

Figure 31A:
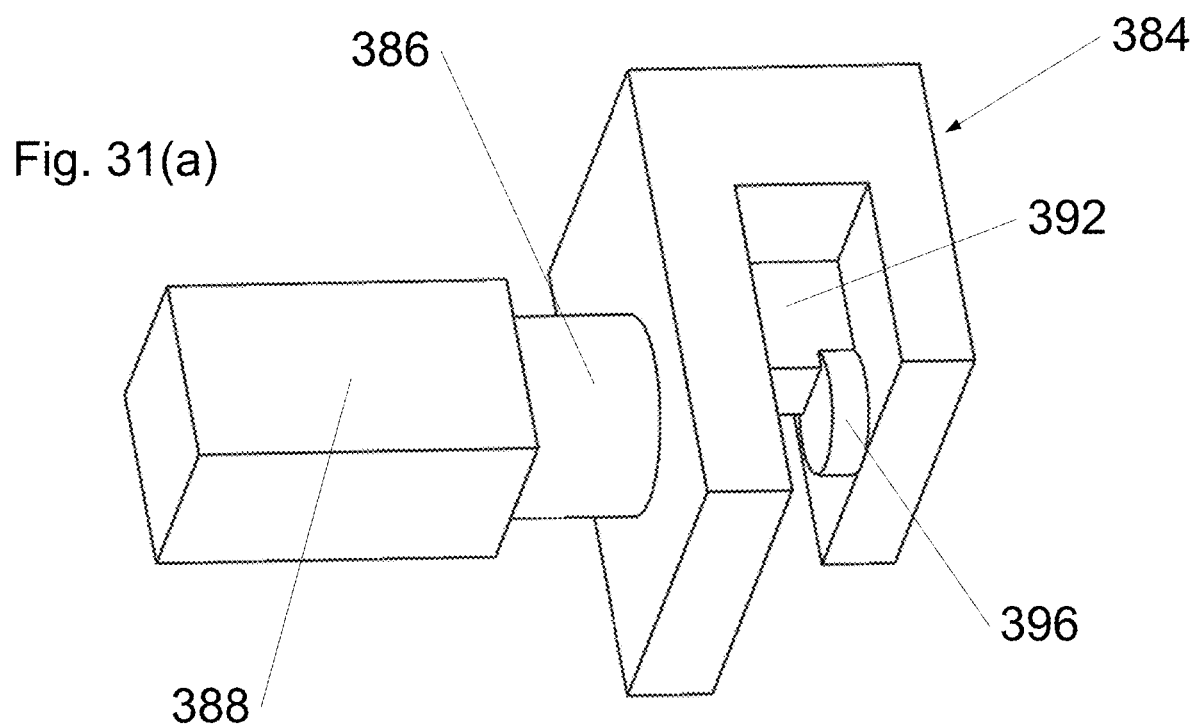
FIGS. 31(a)-(b) show details of grippers and ring.
Figure 31B:
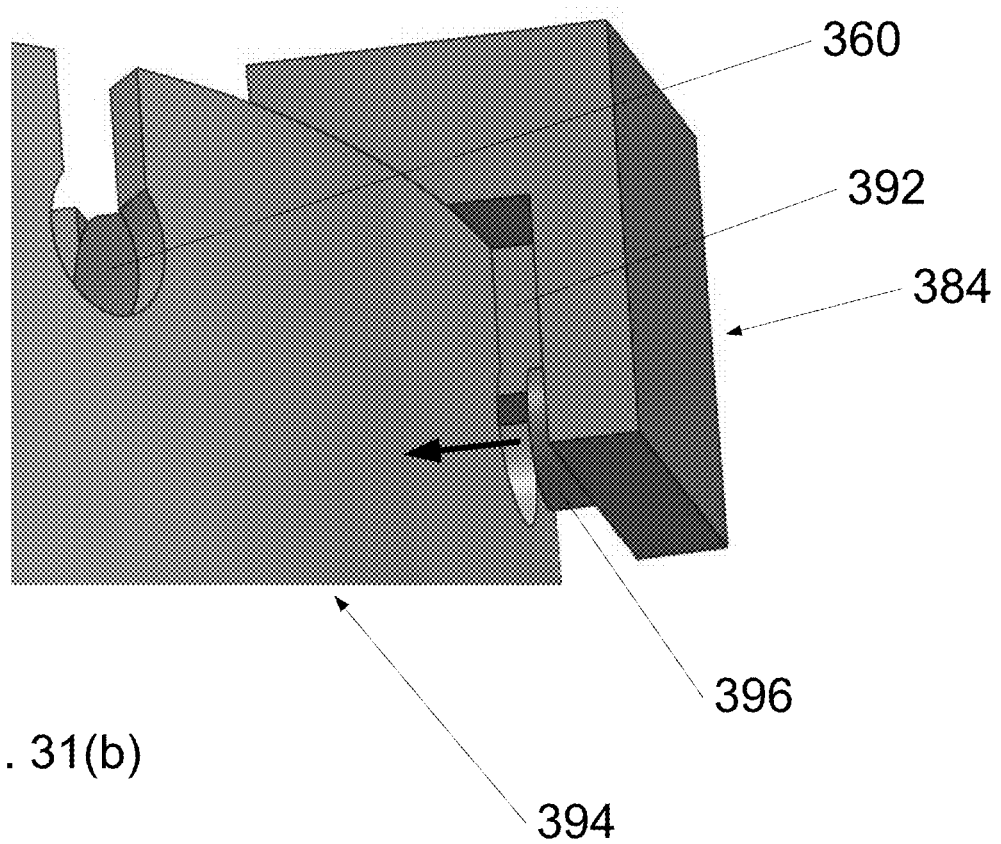

The stylet head includes deformable fork 382 tipped with two swiveling grippers 384. Each gripper 384 has a cylindrical boss 386 allowing rotation with respect to fork 382, a non-rotating (e.g., square as shown in FIG. 31(a)) boss 388 that slides within swivel block 390 (FIG. 30), allowing the fork to expand and compress, fin 392 tapered for easy insertion into the slot-shaped distal portion of hole 360 in ring 394, and cylindrical boss 396 which engages the circular portion of hole 360 in ring 394 (near ring 394's minor axis). Boss 396 enters the circular portion of hole 360 when gripper 384 is pulled inwards by compressing fork 382 (FIG. 31(b)), securely grasping ring 394; fin 392 allow grippers 384 to rotate ring 394 without slippage when a swivel wire 398 (FIG. 30) is slid to rotate swivel block 390 and thus rotate grippers 384. Passing over the proximal region of fork 382 is compression tube 400; when this is advanced, the flexible regions of fork 382 are compressed and grippers 384 are forced inwards, capturing and compressing ring 394. Not shown are flexures (e.g., attached to the stylet head) that center the stylet within the cannula and can help it glide through.

Assembly of the cannula (e.g., within a hollow region) proceeds in a preferably-automated fashion as follows: In FIG. 32(a), the stylet has retracted in direction 402 so that grippers 384 can engage the most distal ring 404 in the stack. In FIG. 32(b), compression tube 400 has compressed fork 382 in direction 406 so that grippers 384 compress ring 404 and unlock it from the remaining rings in stack 378. In FIG. 32(c), the stylet and ring have been advanced in direction 408 toward base 380. In FIG. 32(d), ring-swiveling wire 398 has been advanced in direction 410, causing swivel block 390 to pivot ring 404 as shown by arrow 412 until its major axis is roughly parallel to the substantially cylindrical axis of base 380, allowing ring 404 to move as shown by arrow 414 through base 380 until ring 404 has passed through base 380 as in FIG. 32(e). In FIG. 32(f), wire 398 has been retracted as shown by arrow 416, swiveling ring 404 as shown by arrow 418 until its major axis is roughly orthogonal to the axis of base 380. The stylet has also been rotated as shown by arrow 420 about its long axis to orient ring 404 at the correct angle relative to base 380; this operation may also be done prior to the stylet head and ring entering the cannula, or during the distal travel of the head and ring (e.g., to save time). However, if it is done during travel of the head and ring, the stylet may need to provide more torque to accommodate increased friction.

In FIG. 32(g), the stylet has been pulled proximally in the direction of arrow 422, mating ring 404 and base 380 (ring 404 may be allowed to pivot freely, or swiveled to the required angle); a tensile load cell can be used to detect this event. In FIG. 32(h), compression tube 400 has been retracted, letting fork 382 and ring 404 expand as shown by arrows 424; as ring 404 expands, its tabs enter the holes of base 380, locking ring 404 and base 380 together. In FIG.

32(*i*), the stylet has advanced in direction 426 until grippers 384 are past the distal edge of ring 404. In FIG. 32(*j*), the tube has been advanced to compress fork 382 in direction 428 to fit through the lumen of ring 404 and base 380, after which the stylet is withdrawn in direction 430 to fetch the next ring in the stack. This cycle repeats for every ring, with newly-added rings coupled to rings already coupled to one another, or in the case of ring 404, to base 380. With all rings delivered and the cannula thus assembled, the stylet is retracted to open the lumen for the procedure; before use, a liner (e.g., a PTFE, silicone elastomer, polyethylene, or polypropylene tube) can be pushed through the cannula (e.g., while twisting) to render it fluid-tight if needed; the liner outside diameter may be close to or significantly smaller than the cannula/ring inside diameter. In some embodiment variations, the liner may include multiple lumens, be deployed into the cannula by everting, and/or be reinforced by a braid or coil. In some embodiments, the liner is anchored to one or more rings (e.g., the most distal ring) and then pushed distally or pulled proximally so as to help stiffen the cannula, by pre-loading rings against one another. In some embodiment variations, the rings stored in the stack may be advanced gradually as rings are removed, such that the most distal ring is always as close as possible to the distal end of the cannula; this can be accomplished by a compression spring as in an ammunition magazine, etc. In some embodiment variations, rings are not removed from the distal end of the stack, but rather, from the proximal end, and transported through the stack as well as through the growing cannula.

With the procedure completed, disassembly proceeds roughly by reversing this process. The fork is compressed and advanced to the most distal ring, and the stylet rotated to match the ring's orientation when interlocked (the angle is stored in memory). The grippers engage the ring, compress it to unlock it, move it distally to swivel it, then retract and release it into a container (e.g., a waste container if the rings are disposable/single-use).

To maximize the reliability of ring interlocking and ensure that tabs enter holes properly, in some embodiment variations in the step shown in FIG. 32(*h*) the ring may be allowed to return to nearly circular form and the stylet rotated such that the tabs snap into the nearest holes. The angle to which the ring is rotated prior to this snapping behavior can be chosen so that the nearest holes are also the desired holes. Torsional compliance of the shaft can prevent shaft damage after the snapping occurs; in some embodiment variations the torsion on the shaft is measured to determine when the snapping has occurred, and further rotation of the shaft may be temporarily ceased. In some embodiment variations, the risk of incorrect ring orientation can be mitigated by using one or more optical fibers to detect holes in the ring and thus determine the angle at which the ring is orientated before the ring is mated. The holes used for interlocking and/or additional holes provided for optical detection can be detected optically using ambient light or light supplied by a local source (e.g., light emitting diode) or optical fiber (e.g., the same fiber used for detection). A special "index" hole having an unusual aspect (e.g., size, shape, or position) may be provided to provide absolute vs. relative orientation. In some embodiment variations, mechanical methods of aligning the head to the holes may be used. For example, the stylet head may incorporate spring-loaded balls (e.g., four arranged in a circle and separated by 90 degrees) or other mechanical "feelers". The balls can be pressed against the inside of the most distal ring before mating a new ring; as the stylet head is turned, the balls "pop" in and out of the holes, using them as detents to align the head/new ring to the distal ring, and ensuring that the new ring can reliably interlock to the distal ring. Or, the tabs can have domed and/or tapered surfaces on the surfaces facing the holes, such that by expanding the rings partway and rotating the stylet head, the tabs can "snap" into the holes.

Methods of determining the orientation of the stylet head relative to the distal ring may also be used to ensure that the stylet head is correctly oriented with respect to the ring before an attempt to re-capture the ring by engaging, compressing, and decoupling it is made. Preferably the correct holes of the ring (i.e., those aligned with the minor axis of the deformed ring) are engaged by the grippers, though in some embodiment variations, holes near the correct holes may be suitable, or other holes used. In some embodiment variations, if ring coupling is completed and it is determined that the wrong or sub-optimal hole was used, the ring may be decoupled, re-oriented, and coupled again; this approach may also be used for iterative assembly of the cannula. DASC can be adjusted once assembled to change its shape by simply decoupling and re-orienting rings relative to one another, then recoupling them.

In some embodiment variations, to verify the ring is interlocked before it is released by the grippers, and mitigate the risk of dropping a ring into the patient, the stylet is advanced and the compressive force on it measured (e.g., using a load cell): if the force is less than expected, the ring can be automatically re-compressed, adjusted if needed, and re-interlocked. A similar method may be used in some embodiment variations during disassembly to minimize the risk of dropping the ring: to verify the ring is captured by the stylet head before the ring is decoupled from the next most distal ring, the stylet may be advanced proximally and the compressive force on the stylet measured. In some embodiments, bosses 396 may include relatively long protrusions which capture the ring by its holes even when grippers 384 are not engaged.

Figure 33A:
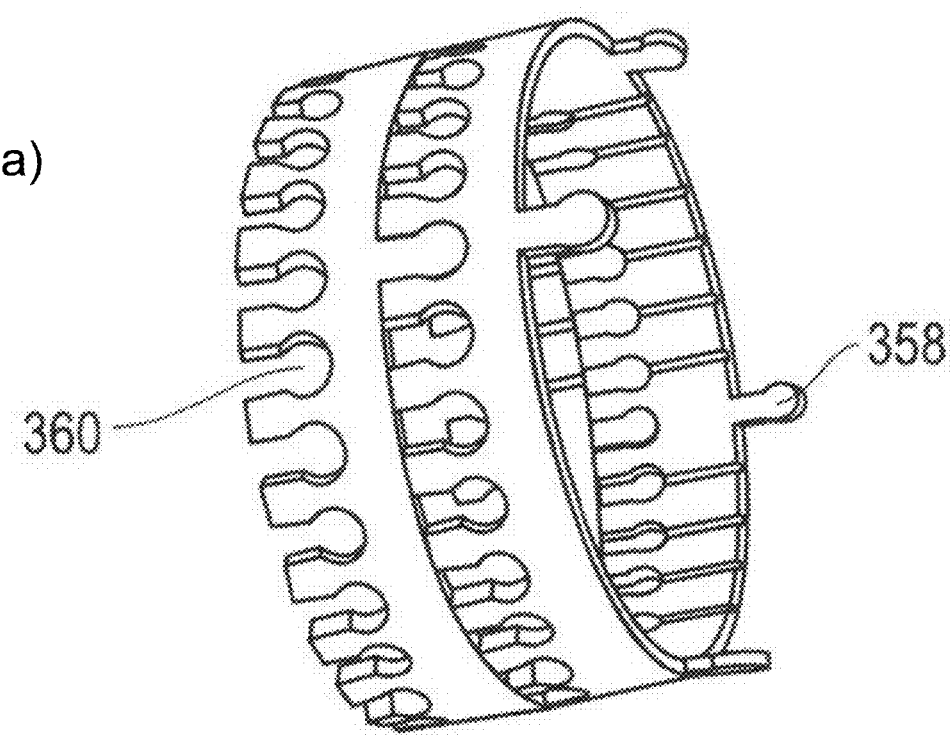
FIGS. 33(a)-(b) comprise photographs of scaled up rings and stylet head.
Figure 33B:
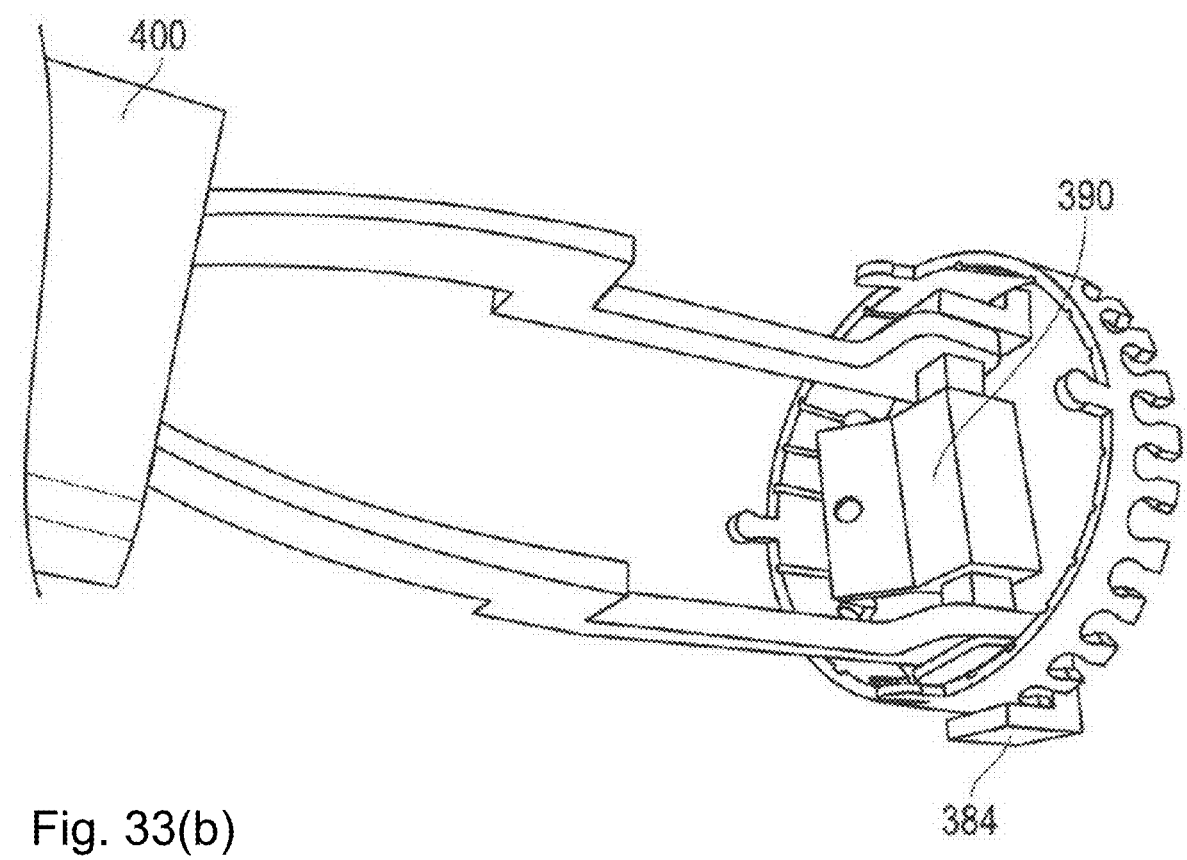
Figure 34:
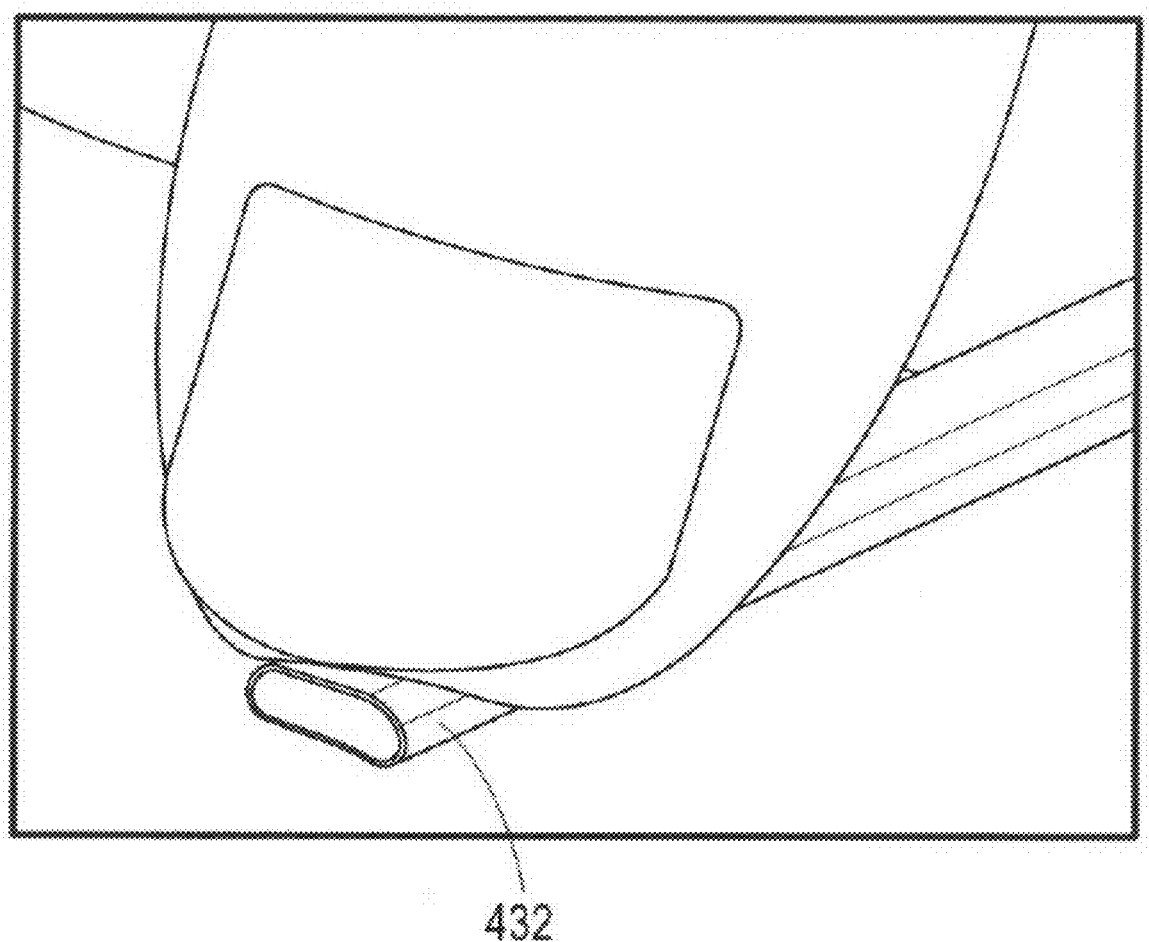
FIG. 34 is a photograph of a compressed Ni—Ti tube.
Figure 35:
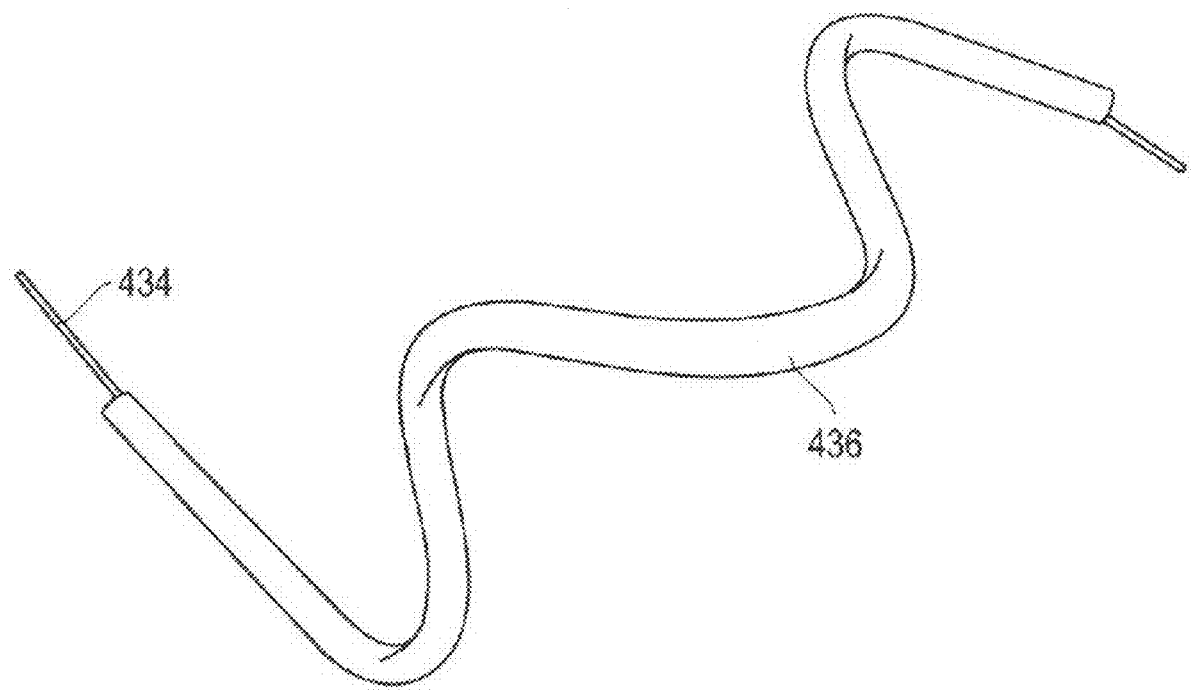
FIG. 35 is a photograph of a cable tube in an aluminum tube.

Scale models of rings and stylet head similar to those in FIG. 30 were made using additive manufacturing as shown in FIGS. 33(*a*-*b*). As shown in FIG. 33(*a*), rings having tabs 358 and holes 360 interlocked securely. A ring was also fitted to grippers 384 (FIG. 33(*b*)), swiveled by swivel block 390, and compressed by compression tube 400. Rings preferably elastically recover when compressed, although in some embodiment variations, rings can be plastically deformed when compressed and expanded (expansion should then account for springback), or can be hinged. While polymer rings can be useful, metal is in many cases preferable for strength. Experiments were performed with 304 stainless rings cut from 14 gauge/0.003" wall and 8 gauge/0.008" wall hypotube; these plastically deformed when compressed. In contrast, 0.172" outer diameter (O.D.)/0.004" wall superelastic Ni—Ti tube 432 (Johnson Matthey, Wayne, Pa.) recovered elastically and completely even when squeezed more than needed (FIG. 34). Superelastic Ni—Ti is a good choice for metal DASC rings as it is widely-used in medical devices, strong, suitable for MRI-guided interventions, long-term implantable, and laser-machinable. However, less costly materials such as spring steel may be suitable. As a potential stylet torqueable, flexible shaft, tests were performed using 0.035" O.D./0.019" I.D. superelastic Ni—Ti cable tube 434 (ACTONE®, Asahi Intecc USA, Santa Ana, Calif.); this was easily passed through bent aluminum tubing 436 about 9" long with 0.132" inner diameter (I.D.) (FIG. 35). Cable tube 434 could be rotated smoothly with good torque control. Similar products such as torque coils, some intended for bidirectional torquing, may be used.

One design parameter is the number, size, and shape of the holes (and the corresponding size and shape of the tabs). While eight (or as few as four) are adequate for some cannula shapes, other shapes (e.g., spirals) need more rings (e.g., 20-30 holes) for finer control of ring relative orientation, allowing a smoother shape. Fewer holes allow for stronger tabs such as the design of FIG. 36. In general, tabs and holes do not require a slot-shaped section as with the tabs and holes of FIG. 26; all that's needed is an undercut shape, which might be circular, truncated circular, T-shaped, L-shaped, keyhole-shaped, trapezoidal as in FIG. 36, where tab 438 fits into hole 440, etc. Another design parameter is wedge angle, which affects minimum radius of curvature. The wedge angle can vary widely; however, angles in the range of 2-10° may be preferable.

Rings can be manufactured from tubular stock by CNC milling, laser cutting, laser/waterjet cutting (e.g., using the LASER-MICROJET® process of Synova S.A. of Ecublens, Switzerland), micro-waterjet, photochemical machining, and other methods. As shown in FIG. 26, the sidewalls of the holes and tabs are preferably substantially perpendicular to a plane tangent to the ring at the centerline of the hole or tab, since sidewalls with significant draft/taper make it difficult to insert tabs into holes from both the inside and outside. Two tabs of the distal ring of FIG. 26(a) are not in the plane of the tubing from which they are cut, and need to be bent and/or heat set after cutting to make them perpendicular to the proximal face. The compression tube and fork (both as short as possible to navigate small cannula radii), grippers, swivel block, and any other parts that must fit inside the rings can be manufactured by methods including computer numerical control (CNC) milling, micro electrical discharge machining, laser cutting, and photochemical machining. For future 1-2 mm O.D. cannulas, the microscale metal additive manufacturing process known as MICA Freeform may be applicable to manufacturing such parts, given MICA FREEFORM™'s small features, 2 μm tolerance, and ability to produce working assemblies. Materials for these components include metals, polymers, and ceramics; magnetic resonance imaging (MRI) compatibility may be a consideration in choosing the best materials.

Figure 37:
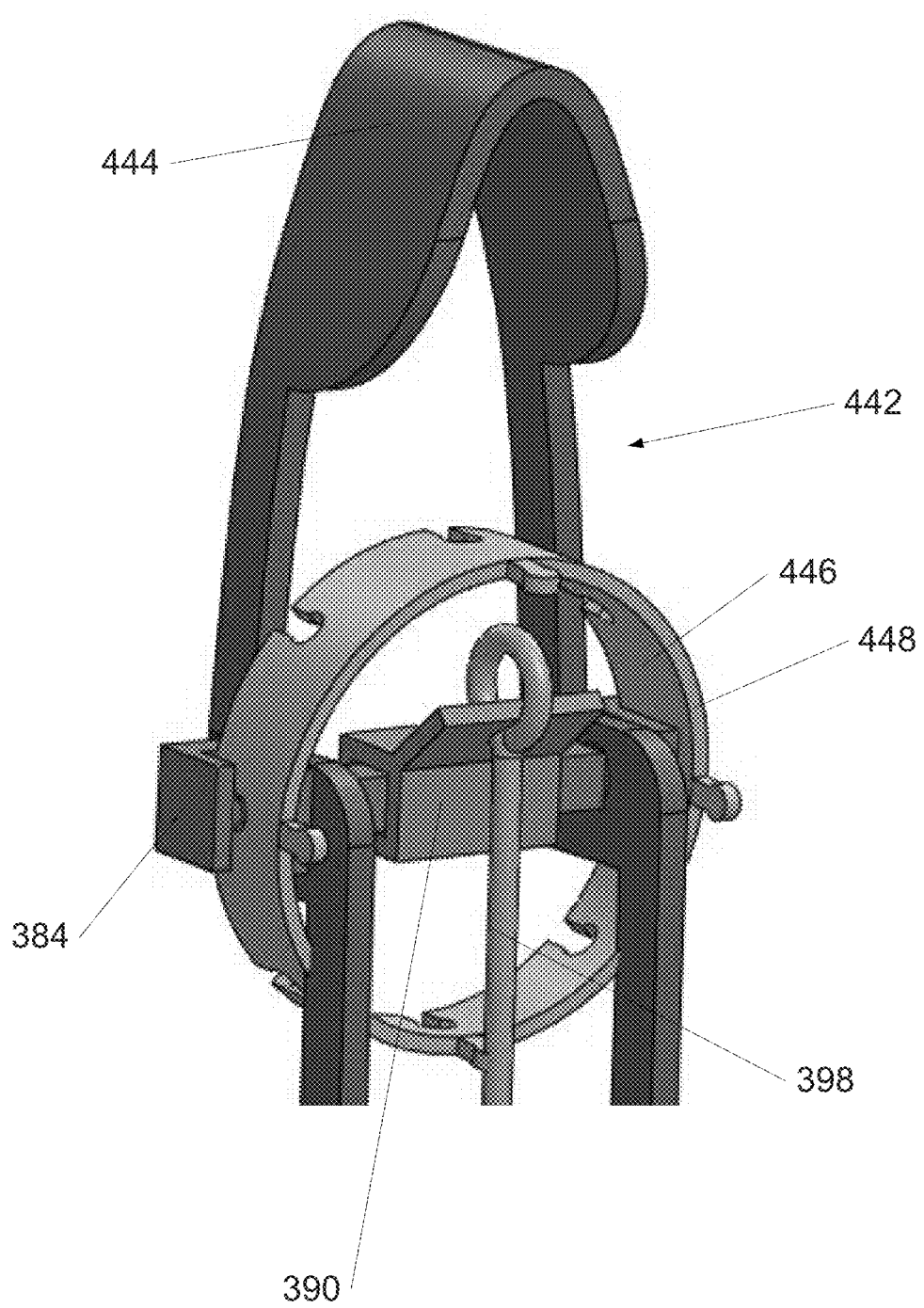
FIG. 37 depicts a stylet head.

In some embodiment variations, for example, those in which DASC grows within solid tissue vs. a liquid or gas-filled space, the fork may be modified to facilitate penetrating, cutting, and/or displacing tissue and to prevent tissue from interfering with the motion of the rings and other components. FIG. 37 shows a stylet head in which the distal end of fork 442 has been extended distally and the two flexures brought together to form a distal tip 444 which can penetrate, cut, dissect, and/or displace tissue, and which is large enough to shield ring 446 and other moving components from tissue contact, but which still allows fork 442 to be compressed or expanded. In some embodiments the distal head is rotated to enhance tissue penetration or cutting. In some embodiment variations in which the distal ring can make contact with tissue, tissue may be cut or displaced by swiveling ring 446 (which may have one edge/surface, such as the proximal face 448 sharpened at least partially) or spinning the distal head with the ring at a particular angle. In some embodiment variations, other devices for tunneling or burrowing through tissue may be provided at the distal end of the stylet, such as RF ablation electrodes, microdebrider-like teeth, pressurized water jets, or lasers.

Figure 38:
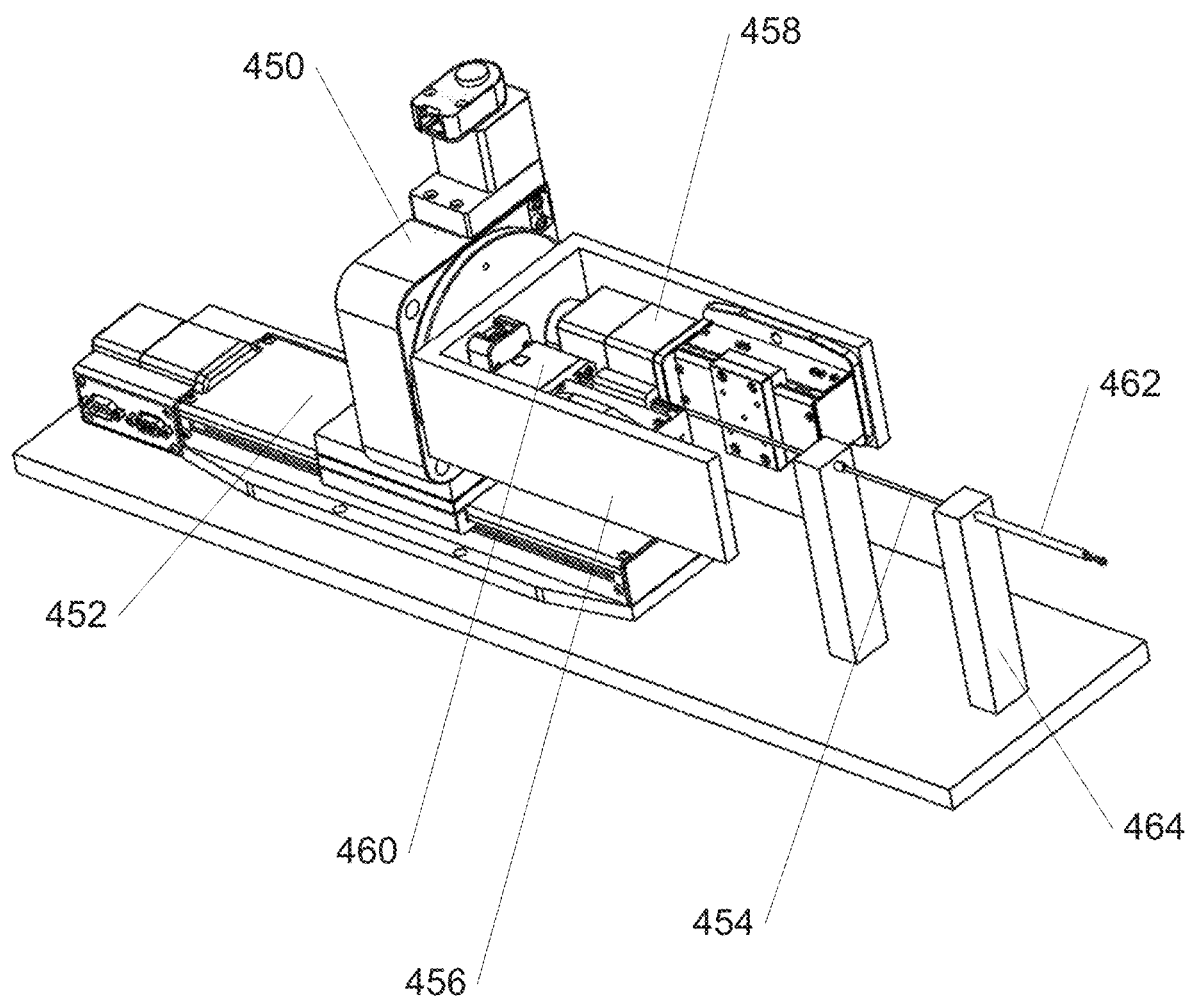
FIG. 38 depicts a robotic system.

FIG. 38 depicts a robotic system for DASC in which a set of reusable components such as stages and brackets—ultimately housed in a console unit—are interfaced to the stylet which may be disposable/single-use. A single console may accommodate different rings and accompanying stylets, which vary in ring diameter, type, length, etc. A single console may assemble and disassemble multiple cannulas. The console actuators may also be used to actuate a device used in conjunction with DASC, such as a steerable catheter passed through the DASC lumen. The console is preferably fixed in position relative to the patient. As shown in the figure, the required motions for ring assembly and disassembly can be provided, for example, by four motorized stages. Rotary stage (e.g., with slip rings) 450 mounted on linear stage 452 can serve to rotate stylet shaft 454 about its longitudinal axis to orient each ring before mating. Linear stage 452 can serve to translate the stylet distally and proximally. Rotary stage 450 can also have mounted to it, e.g. through bracket 456, two small linear stages or actuators: stage 458 to actuate the ring-swiveling wire, and stage 460 to translate the compression tube, which compresses the fork. Assembled cannula 462 may be supported by support 464. In some embodiment variations, in lieu of a linear stage, stylet shaft 454 may be wound around a spool which is rotated to extend or retract the shaft and thus translate the stylet head, i.e., a winch configuration. This configuration also allows for a very long stylet shaft. The spool can itself be rotated around an axis substantially parallel to the unwound shaft, twisting the shaft to reorient rings before mating/interlocking. To facilitate this with a shaft that is springy such as ACTONE cable tube, means such as a pad in contact with the wound shaft may be provided to keep the shaft in close contact with the spool.

Support of flexible stylet shaft 454 before it enters cannula 462, especially when the latter is short (e.g., just the most proximal/base ring or tube) is important to avoid sagging and buckling. Support can be provided by telescoping tubes, bellows, everting tubes, or winding shaft 454 onto a spool as just described.

In some embodiment variations, the stylet head is rotated by means other than twisting the stylet shaft. For example, the head can incorporate female threads with a steep pitch, and a region of the stylet shaft with matching male threads passes through the female threads. By translating the shaft axially, the head would be forced to rotate. Proximal axial translation can be achieved by pulling on the shaft with distal translation achieved by a return spring, or by a lengthening and shortening a small bellows (e.g., Servometer, Cedar Grove, N.J.) using fluid pressure/suction.

In some embodiment variations, procedures needing more than a single cannula can use one set of actuators to assemble several cannulas in sequence. In some embodiment variations, the same actuators used to assemble/disassemble the cannula can be used to manipulate surgical tools inside the assembled cannula, or can steer the cannula's distal end in real time if flexible rings and pull wires are provided.

In some embodiment variations, the edges and corners of stylet and rings can be radiused to minimize the risk of stylet or ring catching while traversing other rings, or excessive friction (e.g., in areas of small radii). In some embodiment variations, the style head axial length is made as short as possible. In some embodiment variations, the most distal portion of the stylet head is designed to easily glide past rings when the stylet head moves distally, while keeping other components away from the inner surfaces of the cannula, where they might get caught; a proximal portion of the head might be used for a similar purpose when the head is moving proximally. In some embodiment variations, the stylet head is coated with parylene or AMC148-18 (Advanced Materials Components Express, Tyrone, Pa.)—a hard, biocompatible, low-friction coating, or provided with a biocompatible lubricant to reduce friction. In some embodiment variations, the stylet shaft is twisted by a known amount while it moves through the cannula to reduce static friction. In some embodiment variations, the stylet head is vibrated (e.g., axially) to reduce friction while passing through the cannula. In some embodiment variations, the shaft is covered with a low friction coefficient (e.g., polytetrafluoroethylene (PTFE)) sheath to make movement easier. In some embodiment variations, a liner, preferably of a low friction coefficient material such as PTFE 15 provided in the cannula to make movement easier. The liner can be extended gradually more distally as each ring is added (e.g., by the stylet or ring pulling it along) and can be withdrawn prior to or during cannula disassembly, for example, by pulling the liner from its proximal end. In embodiments in which the liner is not needed to aid cannula assembly but provided to make the cannula watertight, etc., the liner can be deployed after all rings are assembled, attached to the final/most distal ring, etc., and can be made from materials with higher friction coefficients such as silicone.

In some embodiment variations, the stylet head is pulled forward using a screw-like motion. The head can include a thread-like element (e.g., male or female), which engages projections or another thread (e.g., female or male) that is continuous or discontinuous on the inside of the rings or the inside of a liner. By twisting the stylet shaft, the head is twisted and advances distally or retracts proximally inside the rings. Once the head has moved distally past the most distal ring, it is free to rotate to orient the next ring or to prepare to decouple the most distal ring.

In some embodiment variations, rings may vary in size, shape, type, or function. For example, the most distal ring may incorporate a closed or partially-closed end, as long as the ring can still be deformed to pass through the cannula (unless added separately). A ring may include multiple apertures and mounting surfaces for smaller rings, allowing a single cannula to branch into one or more smaller cannulas, or allowing a steerable catheter or other device to be passed through it in a controlled fashion. The most distal ring and most proximal rings in the cannula may only have tabs but no holes, or vice-versa.

Figure 39A:
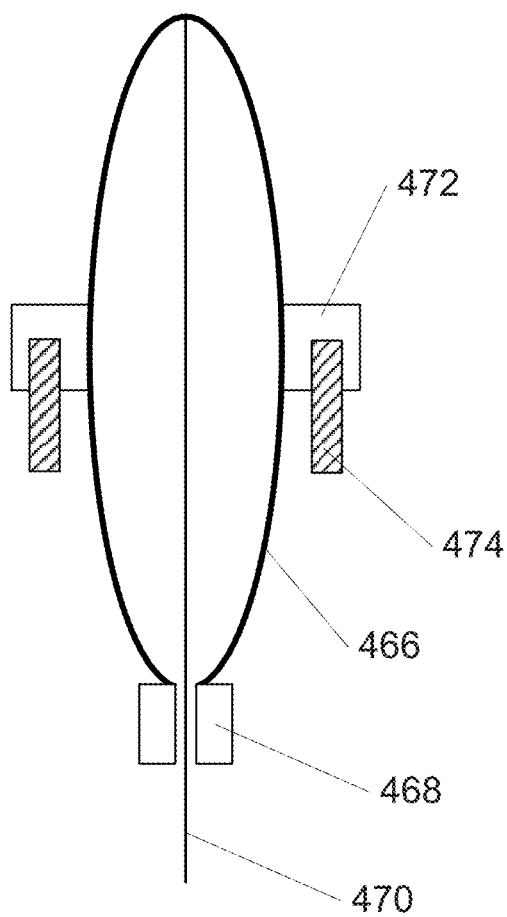
FIGS. 39(a)-(b) show apparatus for changing the shape of rings.
Figure 39B:
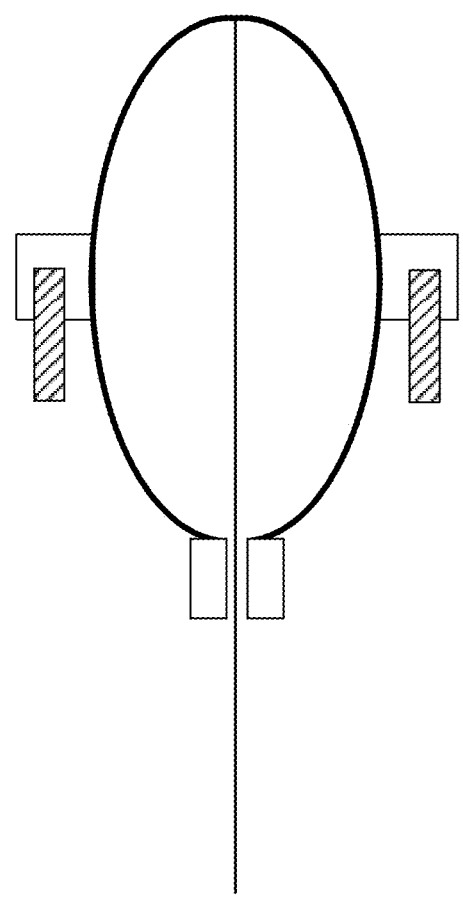

In general, the stylet/ring combination should be as flexible as possible so as to best navigate the cannula when moving both distally and proximally. In some embodiment variations, alternatives to a compression tube may be used to compress and expand the rings. For example, two concentric tubes may be used. One tube is fixed to the stylet shaft (and may be the shaft) while the second is coupled to the grippers through spiral leaf springs such that when the second tube is rotated relative to the first tube in the direction that tightens the spiral, the grippers are pulled radially inwards (and possibly also rotated; this can be compensated). Both tubes can be ACTONE™. Alternatively as shown in the cross-sectional view of FIG. 39, the grippers can be attached to a flexible loop or band 466 (e.g., elliptical in shape as shown) that is supported proximally by hollow stylet shaft 468 (e.g., a cable tube) and whose distal end is attached to pull wire 470. In its relaxed/unstressed state, loop 466 is elongated axially as shown in FIG. 39(*a*), causing grippers 472 to collapse ring 474: the force supplied by loop 466 is enough to deform ring 474. In FIG. 39(*b*), pull wire 470 has been pulled proximally, shortening loop 466 axially but widening it radially, and allowing ring 474 to expand to its normal circular shape. Such an arrangement may be less stiff than the compression tube arrangement described above and involves less friction as it is purely compliant. Loop 466 also may serve to penetrate, cut, dissect, and/or displace tissue, and shield ring 474 and other moving components from tissue contact as in the embodiment of FIG. 37. Other approaches may be used, such as an expanding mechanism which expands the ring along the as-expanded major axis of the ellipse by pushing against the ring from its inside; an expanding balloon with bell cranks or other linkages to modify the direction of force; a balloon that is coupled to the grippers and contracted by reducing its internal pressure; flexible elements such as wires coupled to the grippers and pulled into a tube to draw the grippers inwards, and so forth.

In some embodiment variations, the gripper of FIG. 31, which is shaped so as to pass over the distal edge of the ring and compress by pushing its exterior surface inwards, is replaced by means of gripping the ring using holes, from its inside, or from its edges. For example, features may be provided on the inside of the ring, which can be grasped by suitable features on the stylet head to compress the ring. Or, a shape capable of expanding (e.g., a flexible tube or split cylinder with a translating wedge or ball) can be inserted through the holes in the ring, and then expanded to grasp the ring from its edges and pull it inwards. Or, a split cylinder having an inner region and an outer region eccentrically mounted can be inserted through a hole in the ring from the inside, and the outer portion rotated by an angle less than 360 degrees so that it can no longer be withdrawn from the hole and can pull the ring inwards along with it.

In some embodiment variations, the rings are deformed into a shape which allows movement through the cannula using a mechanism that pushes them outwards rather than pulls them inwards; such a mechanism would normally have the axis of pushing perpendicular to the axis of swiveling (which is normally parallel to the minor axis of the deformed, elliptical ring).

In some embodiment variations, the rings are elliptical in their relaxed/unstressed state and are held circular by virtue of adjacent rings or preferably, a locking mechanism. However, rings dependent on adjacent rings to maintain their shape may not interlock stably. Moreover, the force applied to rings that are more proximal by rings that are more distal and elastically deformed will tend to distort these more proximal rings. It may therefore be preferable that rings have the shape desired for the cross section of the cannula (e.g., circular) while in their relaxed state.

In some embodiment variations, in lieu of four tabs that interlock the rings three tabs may be used; this too may provide stable interlocking of the rings. However, it is challenging to deform the ring into a shape that enables it to pass through the cannula and also allows easy locking and unlocking of the tabs.

In some embodiment variations, in lieu of four tabs just two are provided, preferably parallel to either the major or minor axis of the elliptically-deformed ring. If the tabs and rings both have draft in the correct directions to allow the tabs to be inserted into the holes, the interlocked rings may be stable. However, with only two tabs holding the rings together, the cannula may be weaker, especially when subject to a bending force, compared with one having more tabs. In some embodiment variations, rather than use the tabs to provide stable interlocking in all axes (including shear), the rings are provided with additional features to provide stability that would otherwise be missing. For example, if rings include a smaller diameter tube at their proximal end which fits into the next most proximal ring distal end, stability in shear is provided, and a tab design similar to that of FIG. 26 can be satisfactory using only two tabs approximately 180 degrees apart.

In some embodiment variations, all the holes or all the holes incorporate a thin (e.g., stamped) region which prevents tabs entering holes from the outside from exiting the holes from the inside, or vice-versa, or comprise holes that are blind. In either case, stability can be achieved with just two tabs.

Figure 40:
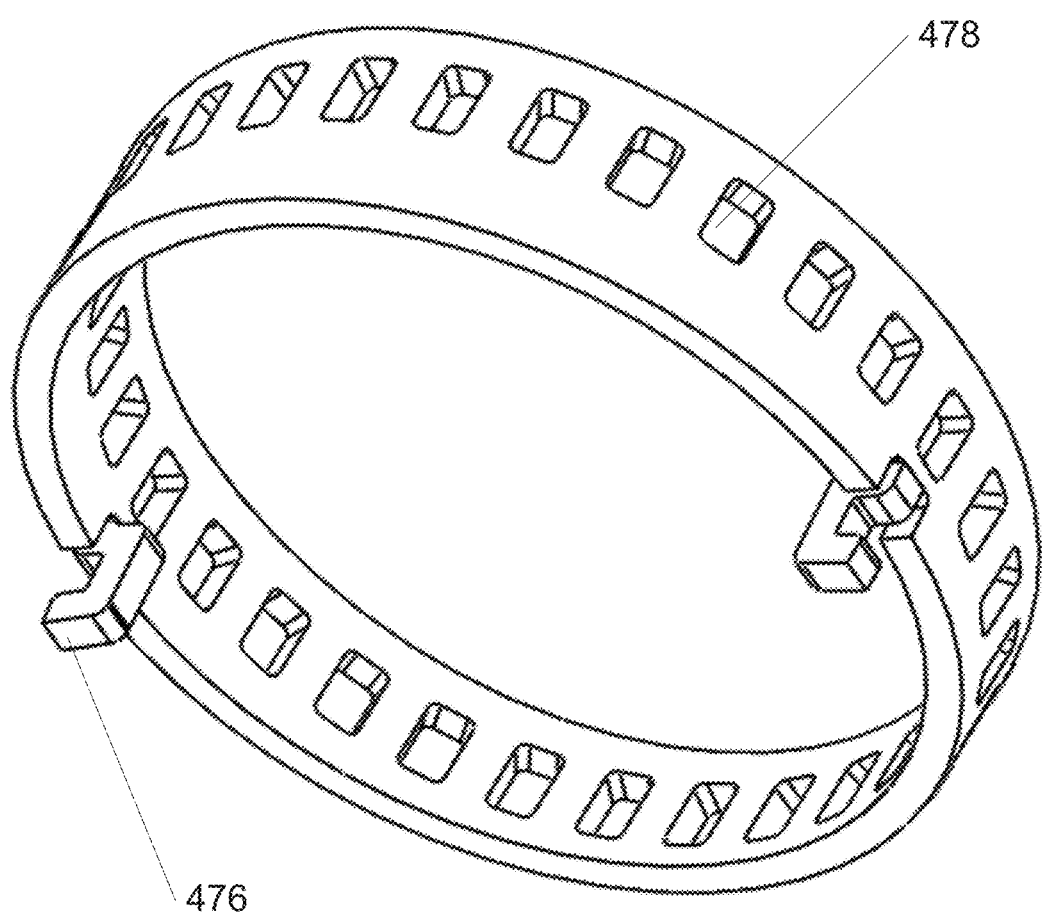
FIG. 40 shows a ring.

In some embodiment variations, the tabs can have a more complex form than those shown in FIG. 26 such that only two tabs can provide stability in shear, torsion, and tension. FIG. 40 shows a ring having tabs 476 that are C-shaped and which extend partly into the ring lumen (alternatively, such tabs can be on the outside of the ring). Such tabs can be manufactured after cutting the ring from tubing via bending. When the ring is deformed inwards at the tabs, the tabs are able to enter holes 478 in the adjacent ring from the inside, and interlock the rings stably. Or, tabs 476 can have a chamfered/ramped profile such that they are pushed inwards as the mating surfaces of the rings approach one another, allowing tabs 476 to snap into holes 478 without compressing the ring.

In some embodiment variations, the rings are not stable in shear when interlocked but are stabilized by a separate element, such as a tube (e.g., PTFE) or rod, which is slid incrementally over or through the cannula as rings are added or removed. An internal tube may be preferable to an internal one, as it avoids liquid contact with the rings if liquid is being transported by the cannula, creates a smooth, low-friction lumen through which to pass instruments, and reduces the risk of traumatizing tissue when passing a tube over the cannula. The tube could be advanced or retracted by a separate actuator or intermittently engaged and released by the stylet to advance and retract it.

In some embodiment variations, the proximal end of the ring has male threads and the distal end has female threads (or vice-versa) such that one ring can be screwed into another to interlock them, and also serve to adjust the relative angle of the rings. The axis of each thread should be perpendicular to the surface of the ring at the end that is threaded; thus, the axes of the two threads will not be parallel. In some embodiment variations, even-numbered rings have male threads at both ends or throughout, and odd-numbered rings have female threads at both ends or throughout, or vice-versa.

In some embodiment variations the cannula isn't circular in cross section, but elliptical, and the rings aren't deformed to pass through the cannula, but are elliptical in their relaxed state and simply re-oriented to fit through the cannula. Such rings can only mate with one another in two possible orientations (e.g., forming a zero or maximum curvature pair), limiting the range of possible DASC shapes if all rings are identical. However, if multiple versions of the rings are provided in which the orientation of the wedge angle relative to the ellipse major and minor axes varies, more complex 3-D shapes can be provided if the DASC robotic system is able to select and deliver the appropriate ring at each location.

In some embodiment variations—rather than being deformed into an elliptical shape prior to passing through the cannula (or having an elliptical state in their relaxed state), rings can be circular or otherwise shaped and sufficiently compliant such that when oriented with the ring axis approximately 90 degrees to the cannula axis, the ring is compressed into a sufficiently narrow shape by the cannula itself (i.e., the rings that comprise it) so it can pass through it. When rings are so oriented, their distal/leading surface is curved, facilitating passage and compression. To enhance this effect, rings may be stiff axially but flexible radially.

Figure 41:
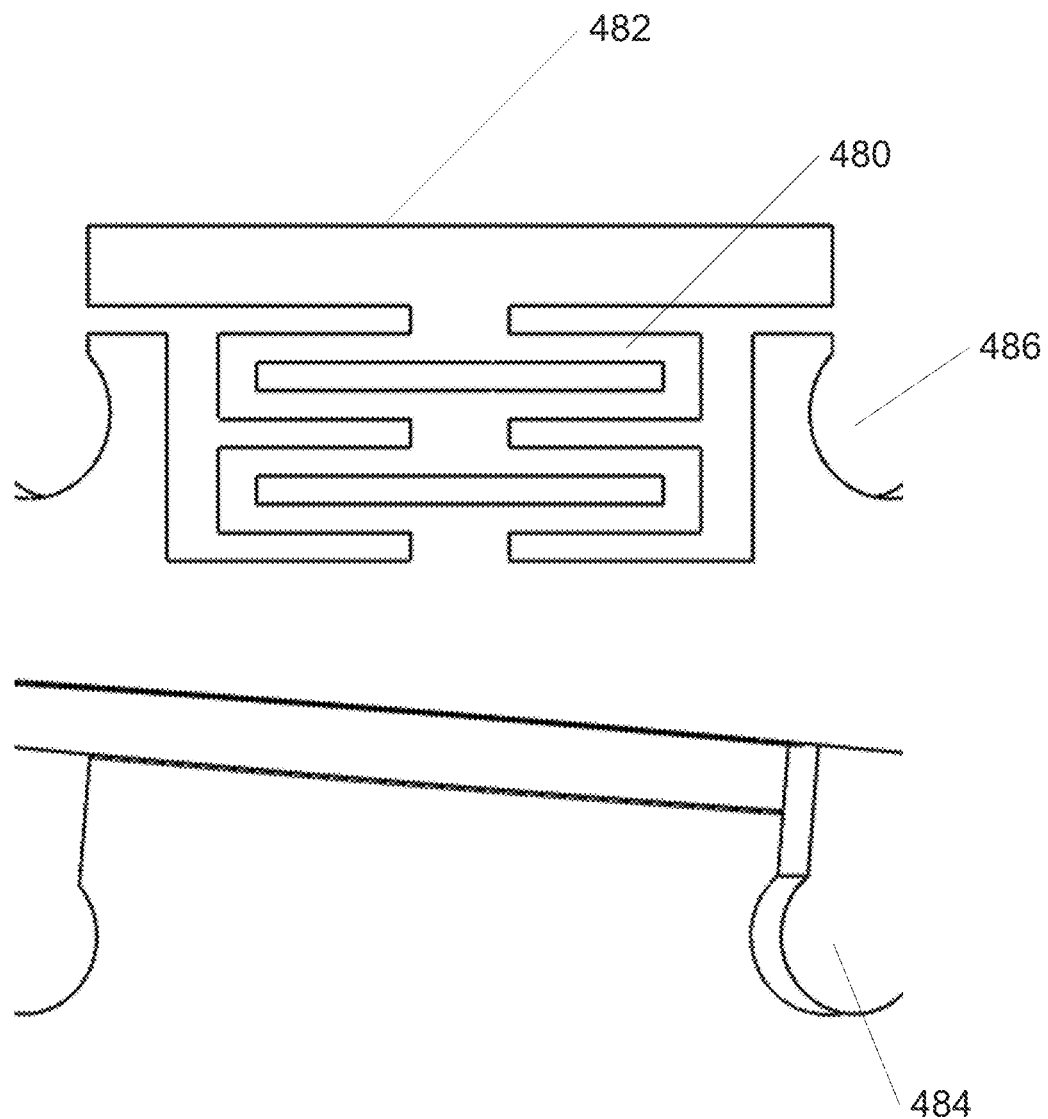
FIG. 41 shows a detail of a ring with flexures.

In some embodiment variations, cannula rigidity may be enhanced by reducing clearances between rings and/or by designing the rings to be mutually preloaded as-assembled (e.g., by tensioning the stylet shaft), and/or by post-tensioning the rings to preload the rings in compression to resist tensile and bending forces using wires running from the most proximal to the most distal ring. If desired, the cannula can also be preloaded in tension, to better resist compressive forces. In some embodiment variations, rings may not be coupled (e.g., by tabs and holes) but simply held together by tension in one or more wires. FIG. 41 shows a close-up view of a ring incorporating side flexures 480 (e.g., laser-cut) to provide preloading of distal face 482 against the adjacent ring when the rings are interlocked. The mating, preloaded ring faces minimize axial backlash, while the simultaneous preloading of circular tab 484 against the circular (or v-shaped) distal surface of hole 486 preloads the joint in shear and torsion. In some embodiment variations, tabs such as tab 484 may be made flexible so that they may be preloaded against holes such as hole 486. If desired, means of preloading such as the flexures of FIG. 41 may also be used to couple rings together if suitable (e.g., L-shaped) catches and holes are provided: rings may be pushed together, given a twist, and then released.

In some embodiment variations, a single cannula is comprised of rings that are different from one another. Such variations may include shape, diameter, height, and wedge angle; number, shape, and type of tabs and holes; incorporation of flexural and/or preloading features; and material, among other variations. For example, some regions of the cannula, such as the distal end, may incorporate metallic rings that are flexible due to the incorporation of flexural elements (e.g., like the flexures of FIG. 41) or because they are made from a flexible material such as an elastomer. Such regions can be passively flexible, allowing compliance and reduced trauma if contacting tissue, during a procedure, for example, or in an implanted device. Or, if provided with means of actuation, such regions can have adjustable stiffness or be able to be articulated or steered. For example, a flexible region near the distal end of the cannula can allow the distal tip to be deflected in real time, much like a flexible endoscope tip, by providing tension wires or cables to at least one ring and pulling on these with appropriate tensions. Flexible regions may be entirely comprised of flexible rings (e.g., with parallel faces), or have only some of the rings flexible, e.g., a series of alternating flexible and (axially) rigid rings may be used.

In some embodiment variations, in lieu of the ring shapes of FIG. 26 in which one face is normal to the ring axis and one is at another angle to the axis, both faces can be an angle other than 90 degrees to the axis.

In some embodiment variations, direct imaging of the cannula as it is being extended can be achieved by incorporating a fiber optic bundle in the stylet, such as surrounding the stylet shaft, or forming the shaft. Alternatively, an imaging sensor such as, e.g., a complementary metal-oxide-semiconductor (CMOS) or charge coupled display (CCD) device, or an ultrasonic transducer, could be incorporated into the stylet, such as attached to the top surface of the swivel block, allowing panning and tilting of the field of view to be achieved by swiveling the block and tilting the stylet shaft, respectively. For example, while the block is oriented as in FIG. 32(f), a sensor mounted parallel to the currently most distal surface of the block would image the path ahead, allowing the clinical controlling the cannula to select a ring orientation, through an appropriate interface, before mating/coupling the ring. In the stylet head configuration of FIG. 37, the tip of the fork can incorporate an imaging system, such as an imaging sensor and optics. To aid in visualization, fluid such as saline or air can be provided to the region between imaging sensor and tissue to wash away debris, displace blood, etc.

In some embodiment variations, DASC can be assembled over a guidewire or other structure, or within a catheter or other structure. To allow for assembly over a structure, the stylet can be designed differently than shown in FIG. 30 and may be hollow, and the rings can be notched to allow them to be swiveled as much as in FIG. 32(d), or simply swiveling to a different angle so as not to intersect the structure. With appropriate sensing (e.g., optical, mechanical) the local direction of the structure (e.g., guidewire or cannula) can be sensed and the appropriate ring orientation selected such that the trajectory of the DASC cannula substantially matches that of the structure inside or surrounding it. In the case of the structure being an anatomical structure such as a blood vessel, duct, or cochlea, DASC can be extended so as to remain centered in the lumen, minimizing wall contact and potential issues such as damage to the intimal surface, thrombus, and inflammation.

In some embodiment variations, DASC rings may be pre-oriented according to the desired cannula shape such that they may be delivered through the cannula and joined to the growing distal end with little or no rotation by the stylet required.

In some embodiment variations, DASC rings may comprise a shape memory allow and transform from one shape into another by heating or cooling. For example, a ring may be circular in axial cross section at elevated temperature, and elliptical in axial cross section at a lower temperature. For example, the ring may remain relatively cool while it is transported through the cannula, but upon exiting and coming into contact with body tissue or fluid, the ring may warm and transform its shape. A source of heating or cooling may also be used; for example, the stylet may be heated or cooled and by contact with a ring thereby heat or cool the ring.

In some embodiment variations, DASC rings comprise different numbers of tabs and holes, and transform into shapes that are not substantially elliptical. For example, a ring may transform into a rounded triangular shape having tabs at the vertices and at the midpoint of each side, and couple with another ring (e.g., circular) by deforming such that the tabs at the vertices enter holes in the other ring from the outside, and the tabs at the midpoints enter the holes from the inside.

In some embodiment variations, DASC rings are designed for low radial stiffness but high axial stiffness. For example, a ring can be corrugated or scored (e.g., by etching, milling, laser engraving) so that it deforms easily into an ellipse. The corrugation and/or scoring can be very localized since the major and minor axes of the ellipse are normally the same for all rings: as few as two scoring lines aligned with the major axis can be sufficient.

In some embodiment variations, the proximal end of DASC is outside the patient's body, while in other embodiment variations, the proximal end is within the patient's body, for example, attached to a rigid tube, flexible catheter (e.g., one that is anchored), anatomical structure such as bone, implant, etc.

In some embodiment variations, the holes in the rings are blind so that the rings may form a substantially leak-proof conduit when assembled. Alternatively, the holes may be through holes, but a liner is affixed (e.g., by bonding) to the rings on the interior and/or exterior to provide sealing. To improve sealing, the rings may be made from a soft material such as an elastomer, or have elastomeric mating surfaces. In some embodiment variations, rings made from a hard material such as metal alternate with rings made from a soft material such as silicone rubber, to provide sealing. In some embodiment variations, the soft rings are essentially gaskets which are individually placed during DASC assembly or attached to rings on either the proximal or distal faces, or both.

In some embodiment variations in which DASC remains in the place, e.g., as an implant, DASC can be detached once deployed, by methods including mechanical decoupling, fracturing, electrolytic dissolution, melting, and so forth.

18th Embodiment

A corrugated, bellows-like tube may be provided initially in an axially-compressed state, compressed configuration. The tube may be extended by advancing the distal end distally, carrying with it the folded corrugations, while allowing corrugations to unfold and lengthen from the proximal end. By varying the extent of unfolding at different circumferential locations, the direction in which the distal end moves can be controlled, steering the tube as it lengthens.

19$^{th}$ Embodiment

An everting flexible tube/cannula as in the 8$^{th}$ Embodiment, comprised of a material that can be stiffened locally can be deployed into a cannula of complex 3-D shape by incrementally or continuously feeding the inner walls in a distal direction by an amount that may differ circumferentially, and stiffening the tube locally upon its eversion to form outer walls. For example, the tube may comprise a photopolymer (e.g., a photopolymer-impregnated tube of carbon or glass fiber) that is initially flexible but which is rigidified by exposure to ultraviolet or visible light, e.g., produced by a ring-shaped light that surrounds the inner walls at the growing distal end. Materials stiffening due to cooling, evaporation, chemical reaction, etc. can also be used. The resulting outer walls are thus rendered stiff, retaining the local curvature, if any, produced when the inner walls were everted and passed the ring. Unless the stiffening is reversible, such a cannula may be permanently deployed. If light is used to rigidify the tube, it can be shielded by suitable design of baffles from those regions which have not yet been everted and given the desired direction and radius of curvature.

In a similar manner, the outer walls of a braided everting tube (e.g., made from superelastic nickel-titanium) may be locally stiffened and locked into position once formed by locking the wires of the braid to one another, preventing relative motion. For example, selected wires may be resistance or laser welded to one another on the outer walls; this can be done as the inner walls are fed distally by an amount that may differ circumferentially, and everted to form the outer walls.

20$^{th}$ Embodiment

Figures 46A, 46B, 46C:
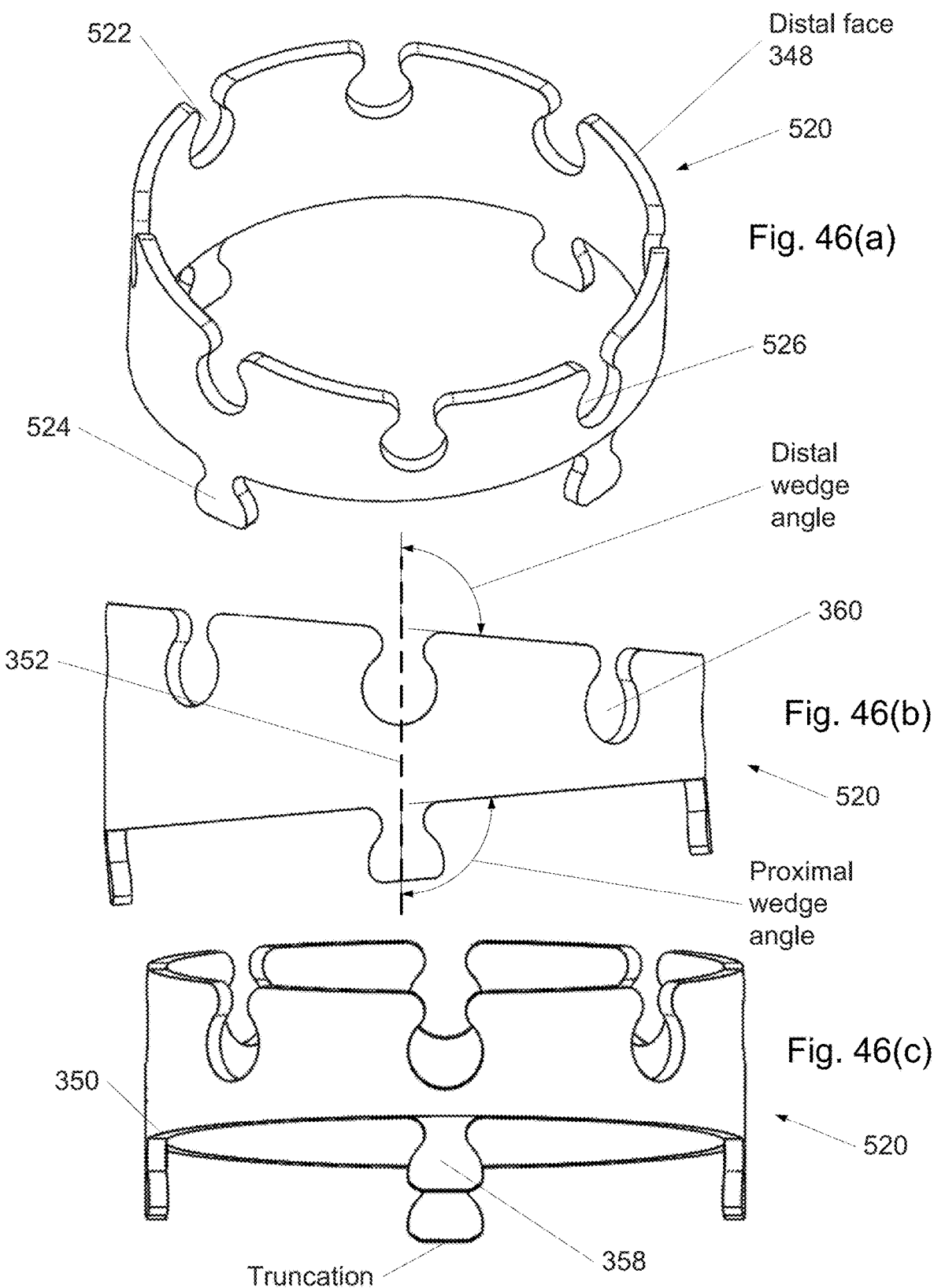
FIG. 46(a)-(c) depicts rings with both proximal and distal wedge angles.
Figure 47:
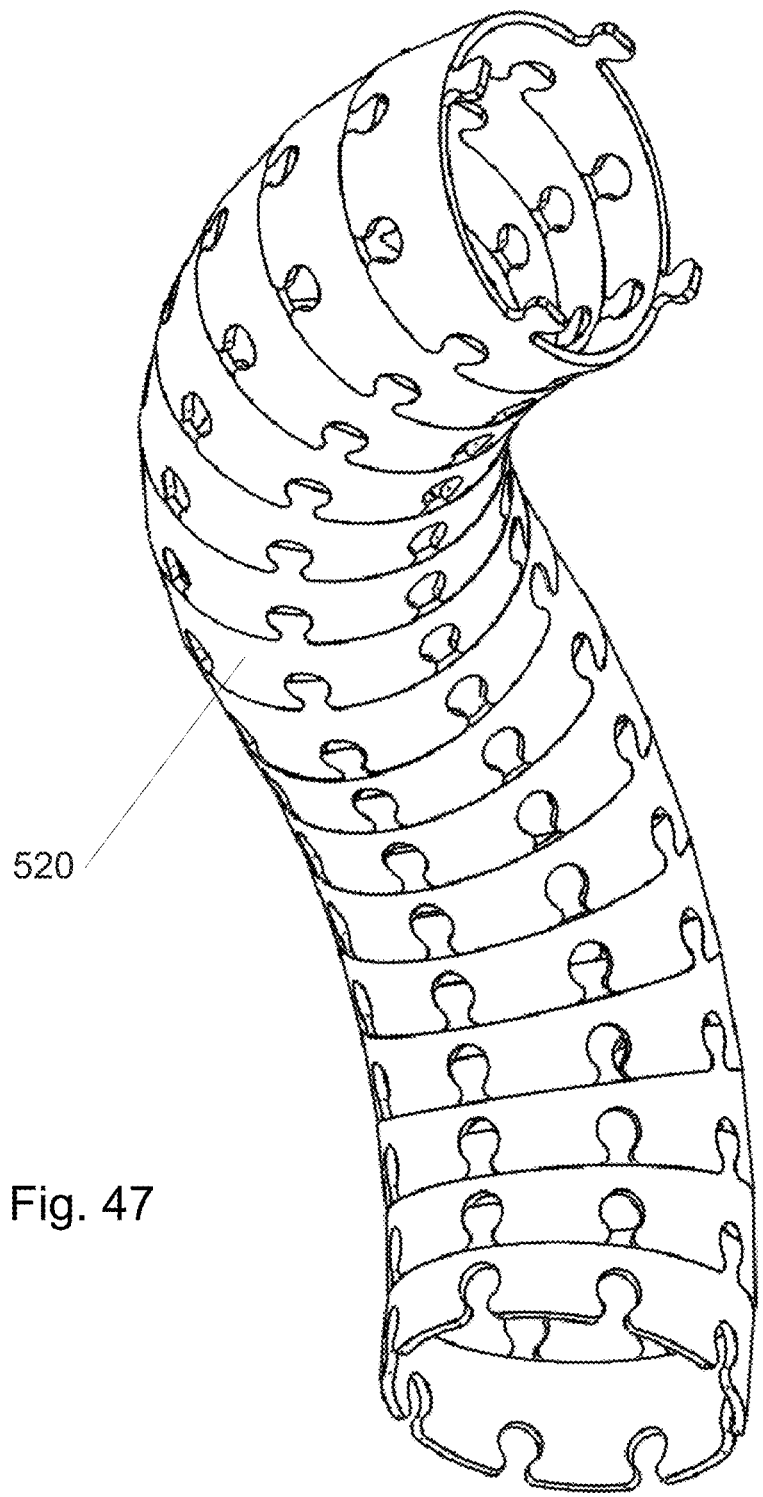
FIG. 47 shows a cannula comprising rings with proximal and distal wedge angles.

The 20$^{th}$ Embodiment shares some similarities with the 7$^{th}$ Embodiment above. FIG. 46 depicts a ring 520 used in some embodiments which is wedge-shaped and equipped with interlocking holes 522 and tabs 524 somewhat like shown of FIG. 26. However, in the case of the present ring 520, there is wedge angle (relative to the ring axis 352) at both the distal face 348 and the proximal face 350. In the embodiment variation depicted, the two wedge angles are the same, but in some embodiment variations they may be different. FIG. 46(a) is a 3-D view of the ring, while FIGS. 46(b)-(c) are elevation views. In the ring shown in FIG. 46, eight holes are provided; however, a different number of holes may be used in some embodiment variations. One hole (the "narrow hole" 526) is positioned at the narrowest portion of the wedge, and one (the "wide hole" 522) is positioned at the widest portion of the wedge. As shown in the 3-D view of FIG. 47, multiple such rings 520 can be combined with various relative orientations to form cannulas with complex 3-D shapes, much like the rings of FIG. 47, in which both the direction and amount of curvature are controlled. In FIGS. 46-47, the tabs on the ring are shown to be of a different shape than those of FIG. 26 (e.g., having a truncation), which can facilitate insertion of the tabs into the corresponding holes.

Figure 48:
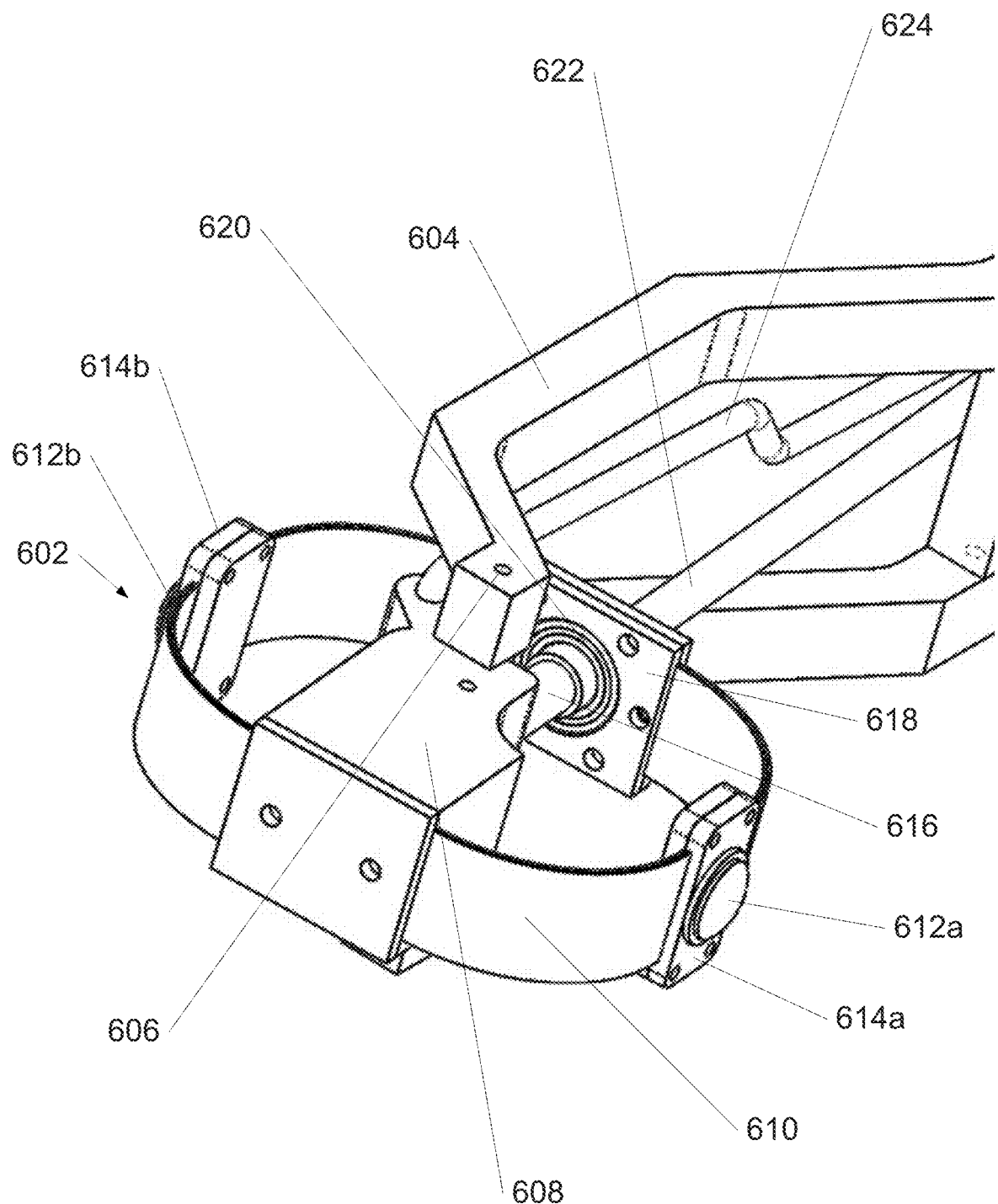
FIGS. 48-49 shows a stylet head used to manipulate rings for a cannula.
Figure 49:
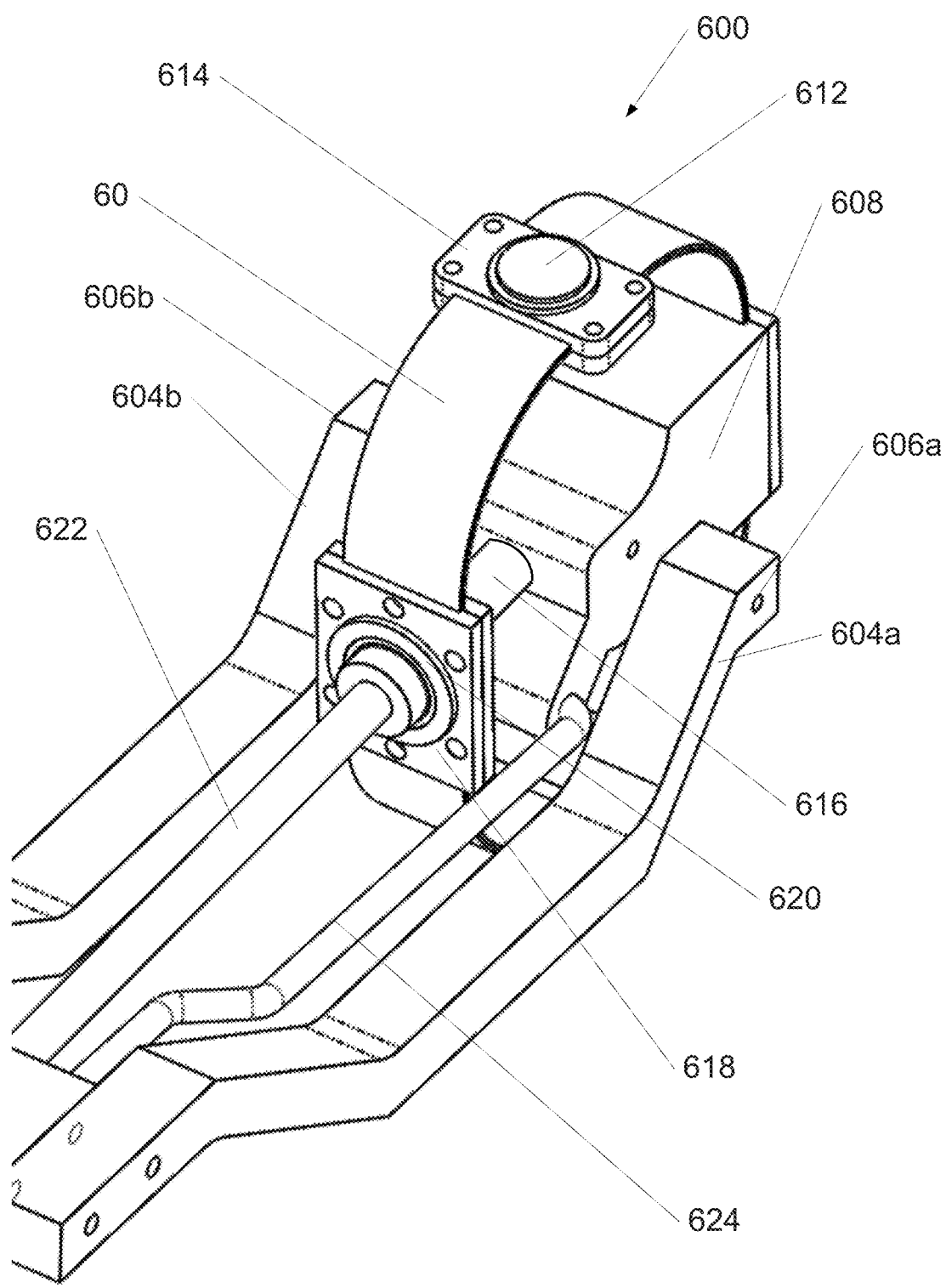
Figure 50:
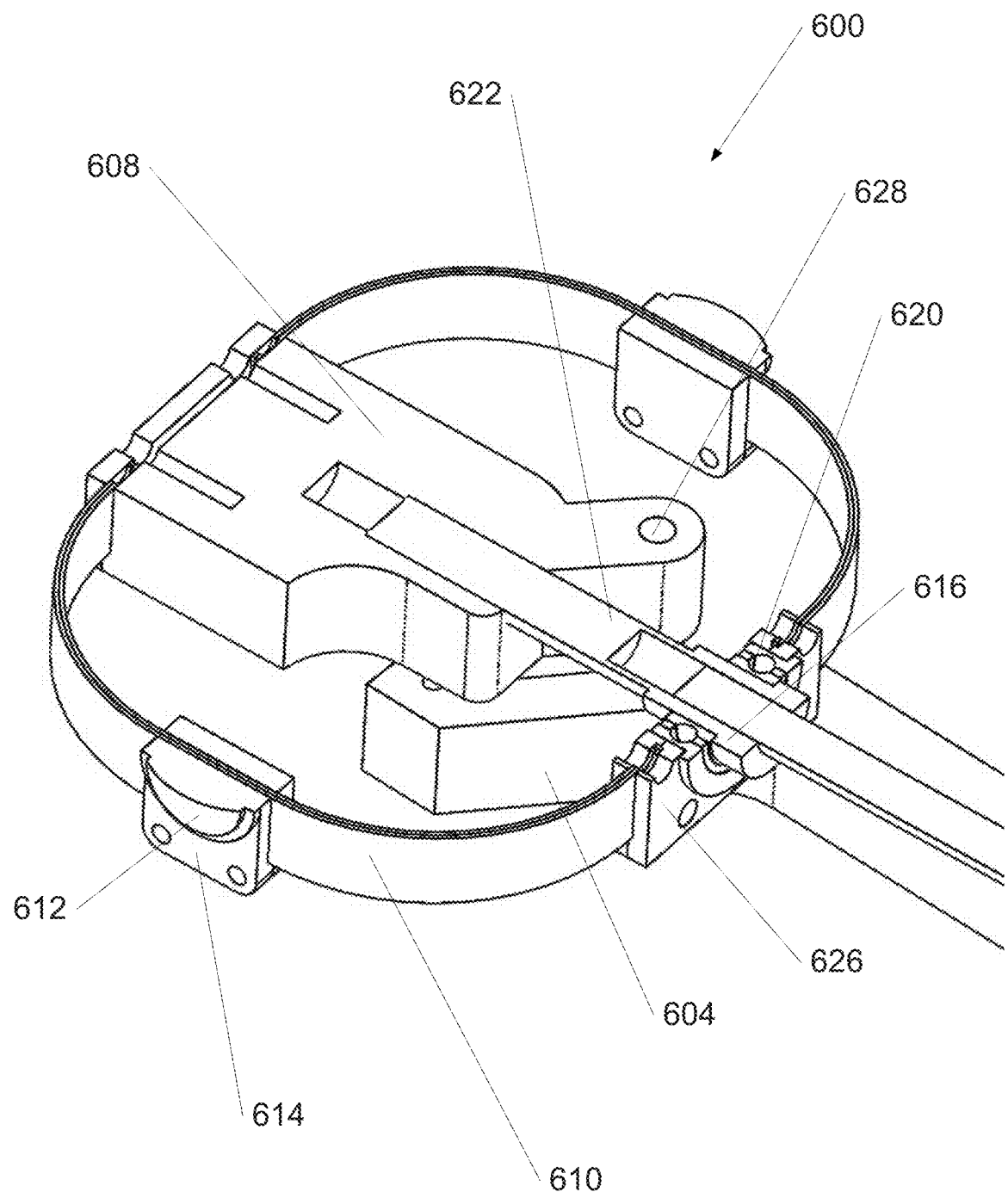
FIG. 50 depicts a cross-sectional view of the head of FIGS. 48-49.

FIGS. 48-50 depict 3-D views of the head of a stylet 600 used in some embodiments to assemble rings such as those of FIG. 26 or FIG. 46. The distal end 602 of the stylet 600 is shown and is depicted with a fork 604 that ends in a pivot 606 that is connected to a swivel block 608, which is connected to a loop 610, which is connected to a pair of bosses 612a,b on boss supports 614a,b. The swivel block 608 is connected via a screw 616 that rotates at its base 618 via a bearing 620. The motion of the loop 610 and bosses 612a,b is controlled by a flexible shaft 622 and a swivel wire 624. FIG. 49 shows an oblique side view of the stylet 600, with forks 604a,b that end in pivots 606a,b that are connected to a swivel block 608, which is connected to a loop 610, which is connected to boss 612 on boss support 614. The swivel block 608 is connected via a screw 616 that rotates at its base 618 via a bearing 620. The motion of the loop 610 and bosses 612a,b is controlled by a flexible shaft 622 and a swivel wire 624. FIG. 50 is a sectional 3-D view of the stylet 600, shown with swivel block 608 connected to fork 604. The swivel block 608 is connected to a loop 610, which is connected to a boss 612 on boss support 614. The swivel block 608 is connected via a screw 616 that rotates at its base 618 via a bearing 620 at base 626. Also shown is swivel wire hole 628. In operation, the head serves to deform the ring into a new shape and swivel it so it can be transported through the cannula. However, here, the deformation is accomplished by expanding the ring from the inside, rather than compressing it from the outside as in FIG. 32. The head comprises a loop of flexible material (e.g., spring steel) analogous in some manner to that of FIG. 39, and which may be manufactured in several pieces that are held together by other components of the head such as the base and the swivel block. On both sides of the loop is a boss support and boss similar that boss 396, but rounded or otherwise tapered so as to more easily center itself on the hole in the ring, with less critical alignment required. The swivel block pivots on a fork at the distal end of the stylet, and is caused to swivel by pushing or pulling on a swivel wire. A flexible shaft is supported by a bearing at the base, and is connected to a screw such that rotating the shaft rotates the screw. The swivel block is threaded to receive the screw.

As shown in the elevation view of FIGS. 51a and 51b, assuming a right-hand thread on the screw 616, clockwise rotation of the shaft/screw 616 (as seen from the shaft) causes the screw to enter the swivel block 608 (FIG. 51(a)), and counterclockwise rotation causes it to retract from the swivel block 608 (FIG. 51(b)). As the distance A decreases (FIG. 51(a)), elastic (or plastic) flexing of the loop 610 causes the distance B, between bosses 612a,b, to increase, while as distance A increases (FIG. 51(b)), flexing of the loop 610 causes the distance B to decrease. The rings in FIG. 51a,b are shown in the process of changing shape, but still undistorted. If a ring such as that of FIG. 46 is held by the stylet head 600, increasing distance B will cause it to expand and transform from a circular shape into one that can fit through the cannula once swiveled, e.g., an ellipse or oval. Screw 616 stably maintains loop 610 in its deformed shape and thus maintains the ring in an expanded state with the desired amount of expansion, without requiring a constant tension be applied to the expander, which can complicate swiveling of the expander and ring.

Figure 53A:
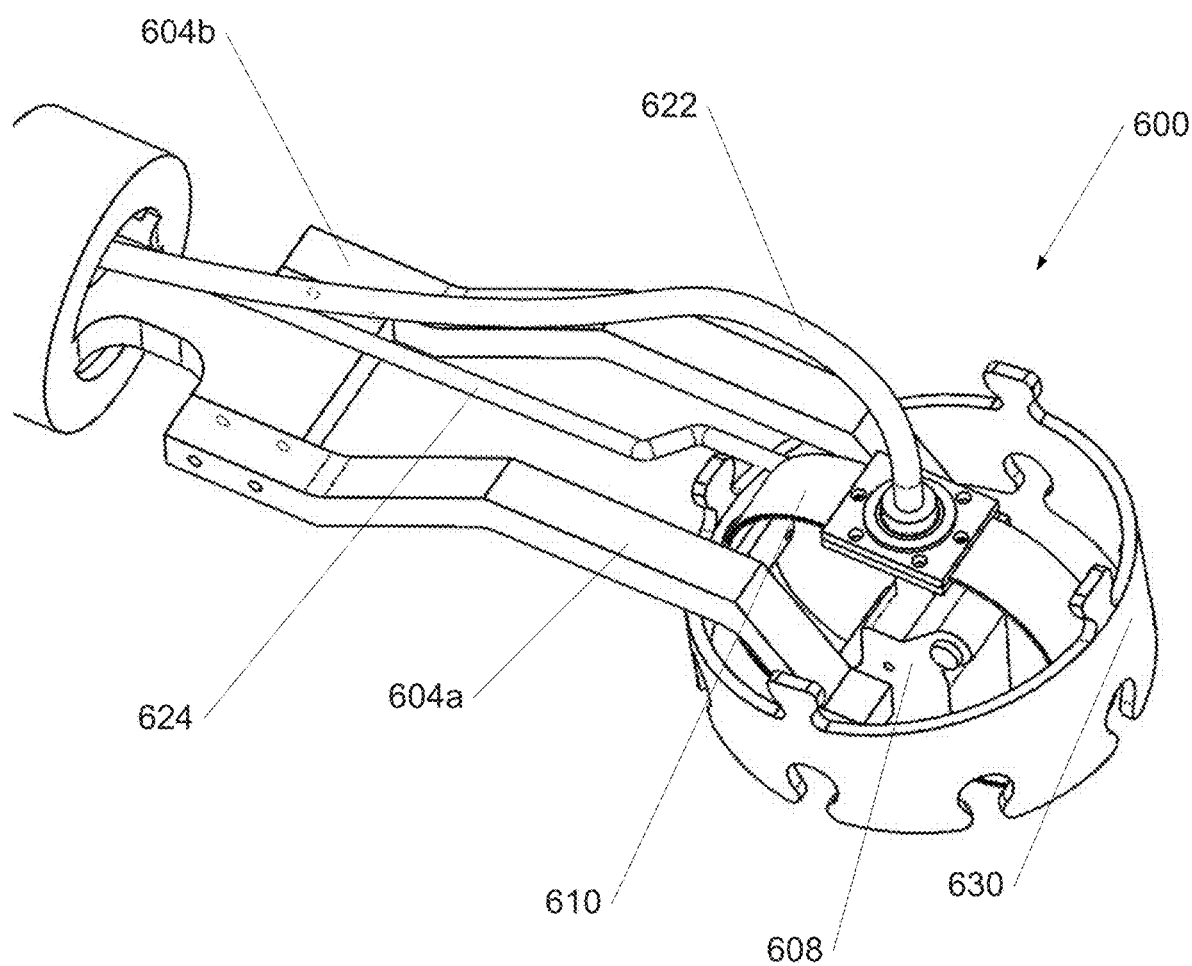
FIG. 53(a)-(b) depicts the head of FIGS. 48-49 holding a swiveled ring.
Figure 53B:
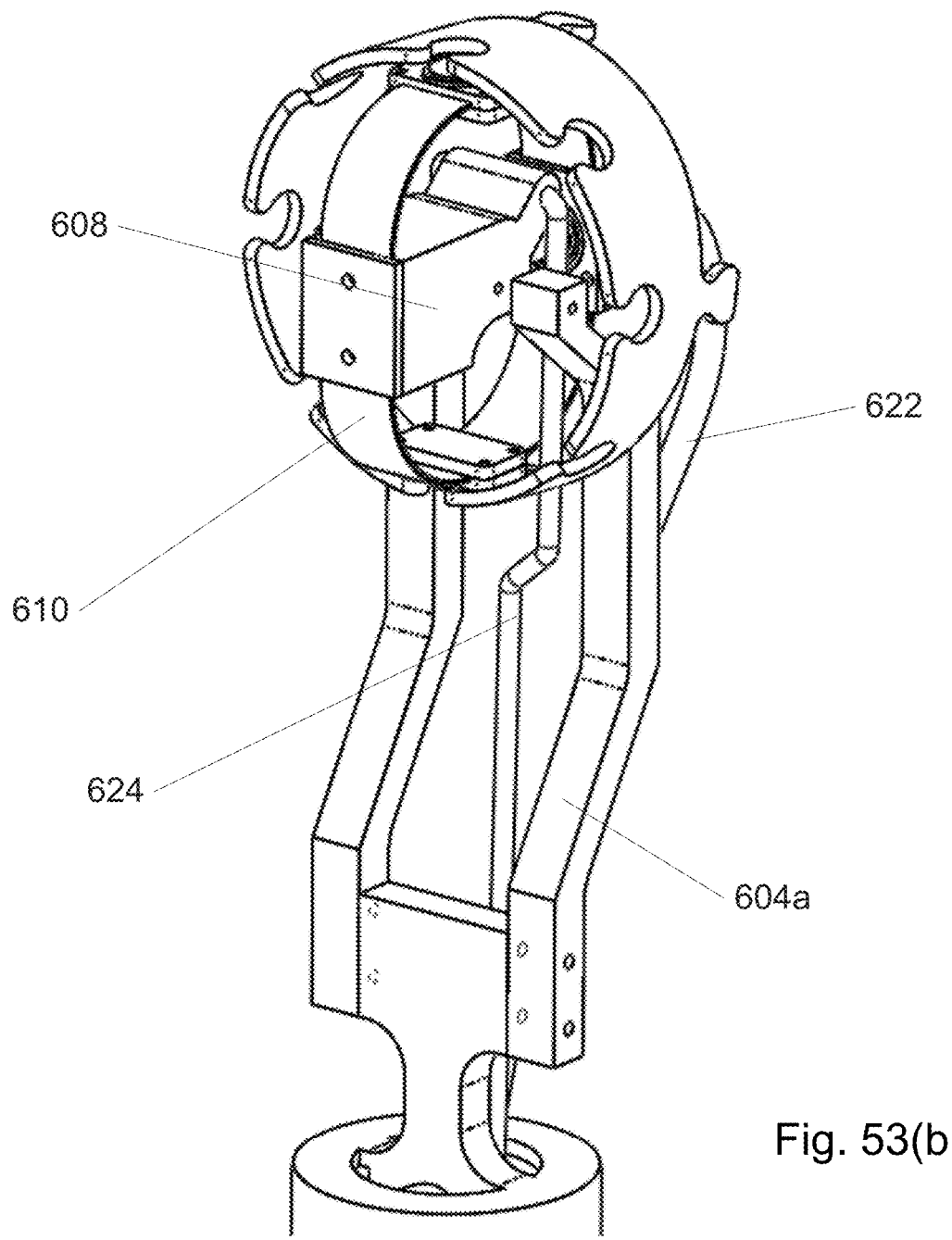

In the 3-D views of FIGS. 52(a)-(b), a ring 630 such as that of FIG. 46 is positioned on the stylet 600 of FIG. 48, such that the bosses 612a,b of the stylet 600 engage the wide and narrow holes on opposite sides of the ring 630. Also depicted are the swivel wire 624, the forks 604a,b, and the flexible shaft 622. In FIG. 52(b), axis of ring 630 is substantially parallel to the cannula and longitudinal axis of the stylet 600. However, in the 3-D view of FIGS. 53(a)-(b), the swivel wire 624 has been pushed, causing the ring 630 to swivel so that axis is now substantially perpendicular to the cannula and axis of the stylet 600, and the flexible shaft 622 is bent in the process. In some embodiments, a spring (e.g., a torsional spring positioned between swivel block 608 and fork 604) is provided which acts to orient the stylet head as shown in FIGS. 53(a)-(b) unless tension is applied to swivel wire 624; this avoids the need to push on swivel wire 624, which can cause buckling if flexible shaft 622 excessively resists bending. In other embodiments, a spring (e.g., a torsional spring positioned between swivel block 608 and fork 604) is provided which acts to orient the stylet head as shown in FIGS. 52(a)-(b) unless tension is applied to flexible shaft 622. In such embodiments, swivel wire hole 628 can be located on the side of swivel block 608 opposite flexible shaft 622 as opposed to the arrangement shown clearly in FIGS. 50-51. In the orientation of FIG. 53(a)-(b), the stylet 600 shows that if the ring 630 has been stretched into a narrower shape (not shown) by action of the screw, it will be able to pass through the cannula. The forks 604a,b, the loop 610, the swivel block 608, the flexible shaft 622 and the swivel wire 624, are depicted. In practice, the following sequence of steps can be used in some embodiments to assemble a new ring onto the distal end of the cannula, assuming the ring is already positioned on the stylet head when the stylet is withdrawn from the cannula:

1. Swivel the ring (by translating the swivel wire distally, relaxing tension on it, etc.) until its axis is substantially perpendicular to the stylet axis and expand the ring by rotating the flexible shaft (e.g., clockwise). These steps may be performed in either order. The loop and ring remain expanded without further involvement by the flexible shaft; however, the flexible shaft must translate along its long axis to allow swiveling to occur. This translation may be actively provided or it may be passive. If passive, the shaft can be elastic, or have an elongatable, torqueable section (e.g., telescoping), or its actuator (e.g., a motor) can be mounted so as to allow movement, for example. Translation of the shaft is also important when mating the ring to the next most proximal ring, since the swivel block may need to swivel slightly to ensure that the proximal surface of the ring to be mated is parallel to the distal surface of the next most proximal ring.

2. While the ring is expanded, translate it and the stylet head through the cannula from its proximal to its distal end.

3. Pull the swivel wire to swivel the ring until its axis is substantially parallel to the stylet axis and rotate the stylet around its longitudinal axis to orient the ring as required. These steps may be performed in either order, and rotation may be accomplished prior to translating the ring.

4. Move the stylet and ring proximally to mate the ring with the next most proximal ring and rotate the shaft (e.g., counterclockwise) to allow the ring to regain its unstressed, circular shape while allowing the tabs to enter the holes in the adjacent ring. Further rotate the shaft to decouple the ring from the stylet head, allowing the latter to be returned proximally (after swiveling) to fetch another ring if needed.

Figure 54:
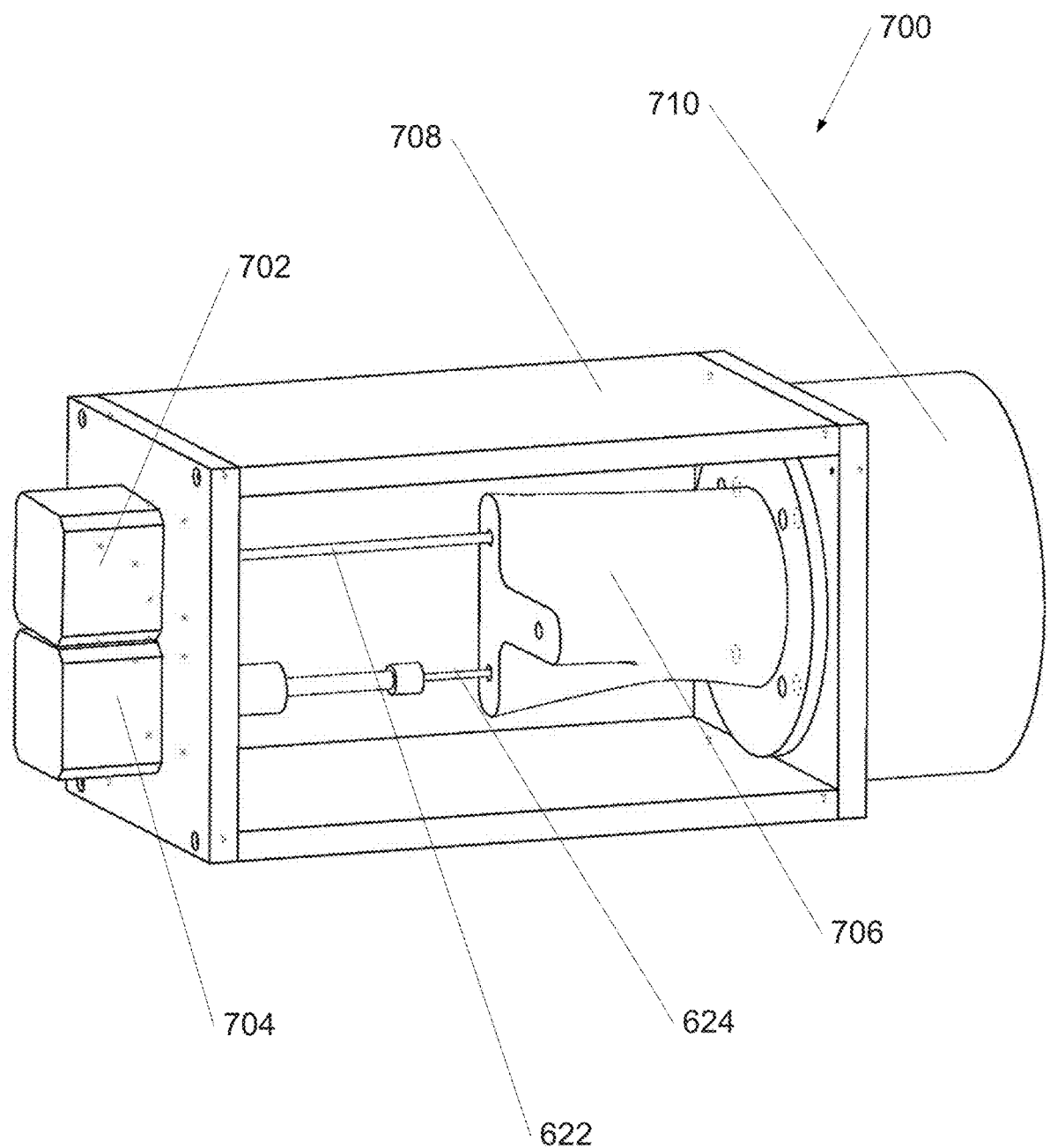
FIG. 54 depicts actuators which actuate a stylet.

FIG. 54 depicts a 3-D view of apparatus 700 used at the proximal end of the stylet of FIG. 48 in some embodiments to produce the required motions of the swivel wire 624, the flexible shaft 622, and overall rotation of the stylet (to orient the ring). Apparatus 700 has some similarities with that of FIG. 38. A motor 702 is provided to rotate the flexible shaft 622 and ultimately the screw, changing the shape of the ring. A linear actuator 704 is provided to pull and push on the swivel wire 624. A guide 706 may be provided with curved internal channels shaped to guide the flexible shaft 622 and swivel wire 624 into the (hollow) stylet of relatively smaller inside diameter. A frame 708 provides mounting for all components to a rotary stage 710 to which the stylet is also mounted, allowing overall rotation.

Figure 55:
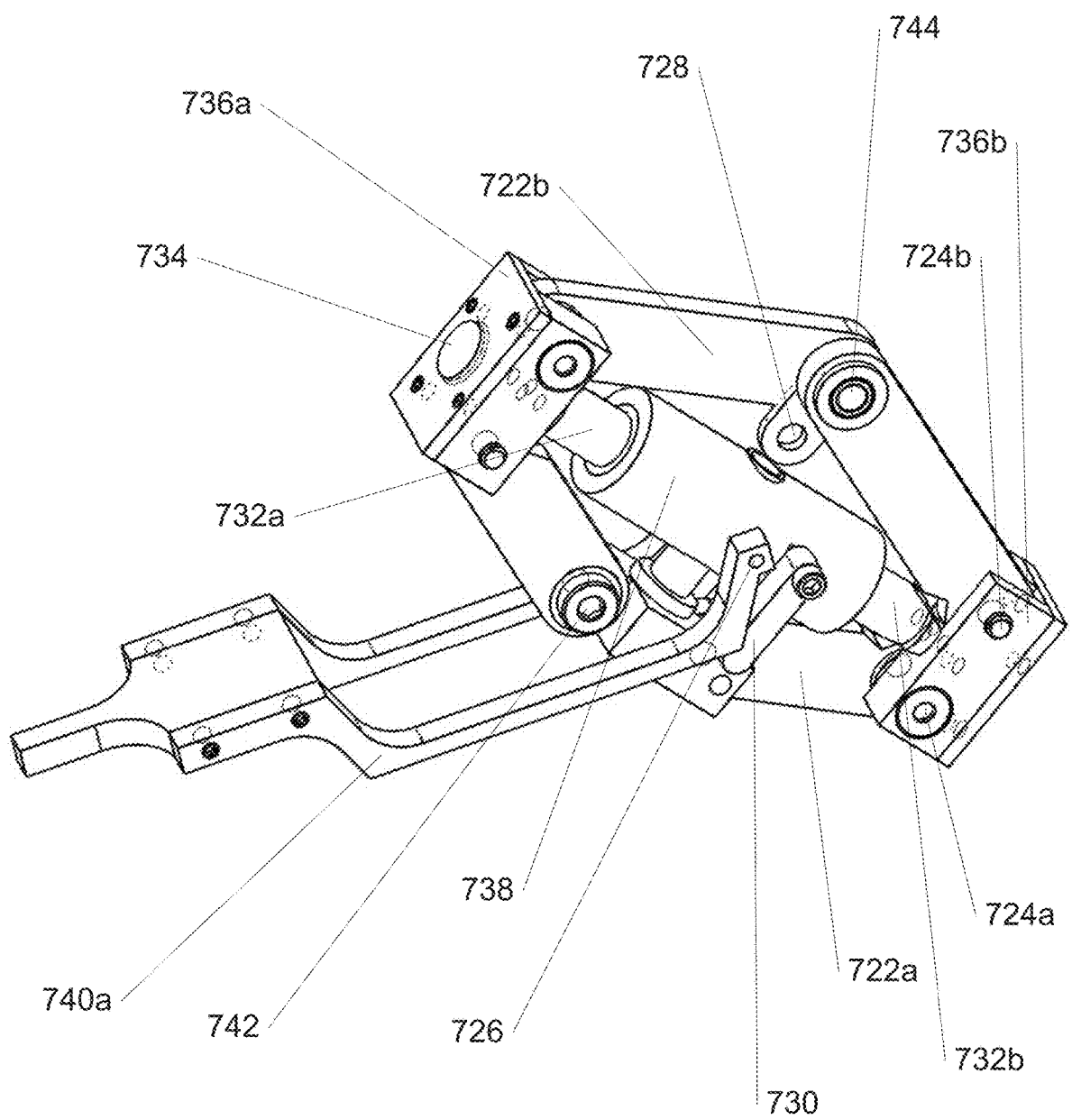
FIG. 55 shows an alternative stylet head used to manipulate rings for a cannula.

FIG. 55 depicts a 3-D view of a stylet head 720 used in some embodiments which is similar in some respects to that of FIG. 48, but using articulated arms 722a,b pivoting on screws 724a,b to provide an expansion of the ring (not depicted) in addition to swiveling around the pivot 726 (by pulling on the swivel wire tab shown) on forks 740a,b. Pulling on the expansion tab 728 with a wire 730 causes rotation of the upper and lower arms 722a,b and the pistons 732a,b attached to the boss 734 on boss supports 736a,b, which are withdrawn from the central cylinder 738, which guides them as they slide. Also depicted are screws 742 and 744. The overall effect is to increase the distance between the bosses 736a,b, expanding the ring (not depicted). In some embodiment variations, rather than pulling on an expansion tab, fluid may be supplied to the cylinder 738 under pressure (e.g., through the forks 740a,b) to hydraulically force the pistons 732a,b outwards and expand the ring (not depicted).

Figure 56:
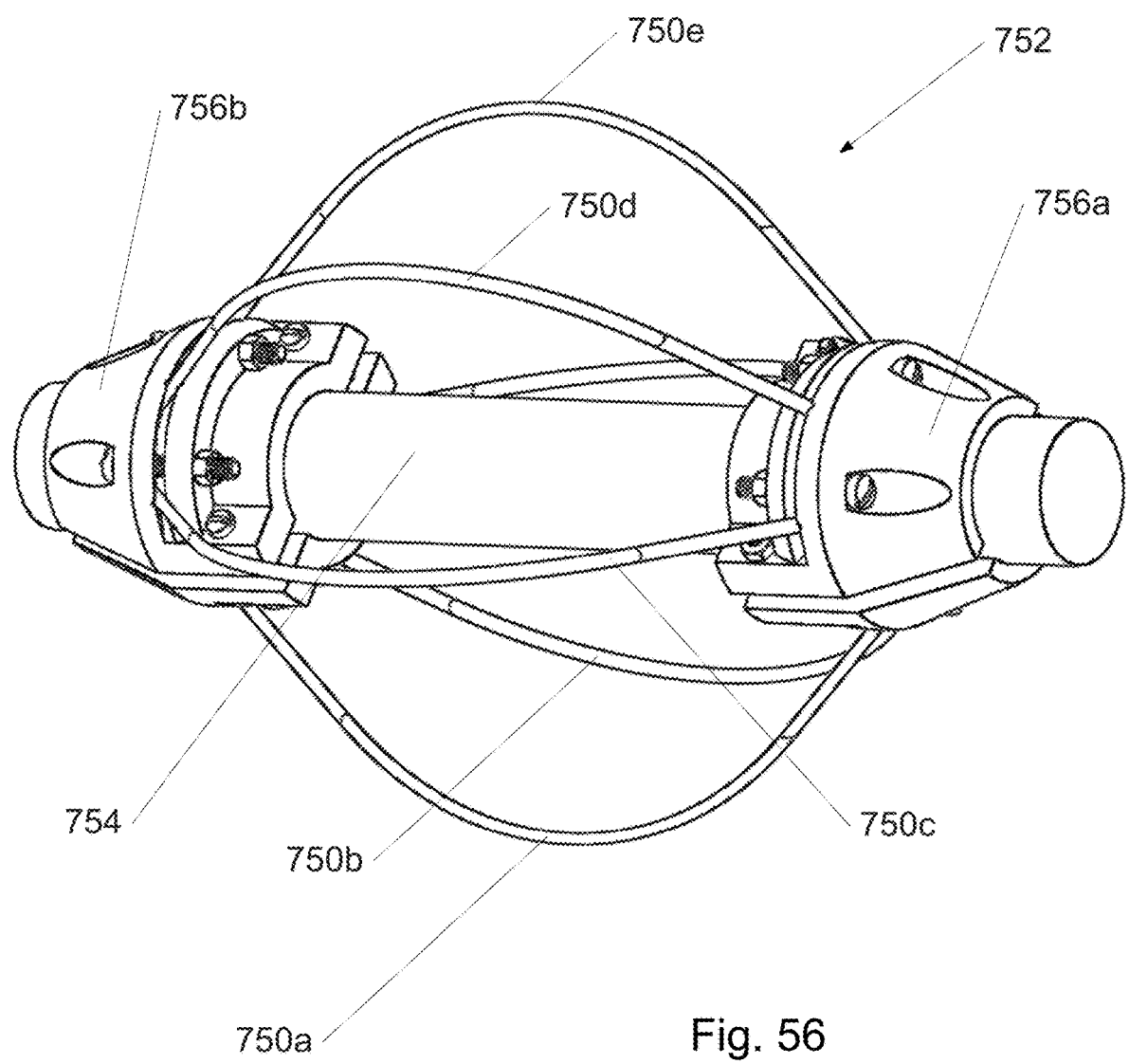
FIG. 56 depicts a centering device surrounding the shaft of a stylet.

Stylet heads such as those of FIG. 48 (also of the 17$^{th}$ Embodiment) are preferably kept centered within the lumen of the cannula, for example when the stylet head is near the distal end of the cannula for ring attachment or detachment, which can require good centering. Also, means of centering the flexible stylet at intervals along its length can minimize stylet buckling within the lumen as it is pushed distally down the cannula. Various approaches may be used for centering and buckling control such as an inflatable balloon (e.g., toroidal) surrounding the stylet, which may be inflated and deflated as needed; a brush with bristles emanating from stylet in various directions; balls, omnidirectional wheels, low-friction material such as PTFE and spring-loaded rollers or wheels. One approach to a centering device is shown in the 3-D view of FIG. 56, which features a series of flexures 750a-e, which surround the stylet 752, extending in different orientations to center and stabilize in two orthogonal planes simultaneously. Flexures 750a-e can take the form of spring wire, for example, optionally covered with a low-friction material such as PTFE, and are preferably shaped so as to not catch on any features of the cannula (e.g., apertures in the rings) while they move within it. Flexures 750a-e can be fastened to the stylet shaft 754 using suitable flexure mounts 756a,b as shown. However, in some embodiments the mounts support the flexures 750a-e but are not themselves affixed to the stylet shaft 754, thus allowing the latter to rotate (to orient the ring) without having to also rotate the center device: due to friction this may be difficult, and twisting of the centering device may distort the flexures, therefore materials can be selected to overcome these two forces, e.g., shape memory alloys such as, Ag—Cd, Cu—Al—Ni, Cu—Sn, Cu—Zn, Cu—Zn—X (X=Si, Al, Sn), Fe—Pt, Mn—Cu, Fe—Mn—Si, Co—Ni—Al, Co—Ni—Ga, Ni—Fe—Ga, Ti—Nb, Ni—Ti, and/or Ni—Ti—Z (Z=Hf, Pd, Ga).

FIG. 57 depicts 3-D views of several configurations of a cannula 760 with rings 762 which are similar to those of FIG. 46), but which use magnets instead of interlocking tabs and holes to connect with one another. While this may be less strong (in certain circumstances) than using tabs and holes, for example, the attraction of one magnet for another, if discrete magnets are used, allows for self-alignment. Magnets may be used to temporarily position a ring 762 before a more durable mating method is applied (e.g., adhesive or welding in the case of a permanent structure). FIG. 57(a) shows a cannula 760 comprising a series of rings 762 with both proximal 764 and distal 766 wedge angles in which the wedge orientations provide the minimum radius of curvature (with the narrow 768 and wide 770 holes aligned). FIG. 57(b) shows a cannula 760 having the maximum radius of curvature (it is substantially straight, with the narrow 768 and wide 770 holes aligned but alternating). FIG. 57(c) shows a cannula 760 having a moderate curvature, in-between the radii of FIGS. 57(a) and 57(b). As shown in FIG. 57(c), a slight curvature can be achieved by relatively orienting rings 762 so that the tabs are offset just one hole away from the position which provides a straight cannula: i.e., the narrow 768 and wide 770 holes are slightly offset. If desired, the offset can alternate from side to side of the central position as shown, which on average provides a curve within a single plane. Magnets can also be used in some embodiments to align rings similar to those of FIG. 26, which do not have both proximal and distal wedge angles, etc. While the rings 762 can be rotated along the longitudinal access, the spacing or angle between magnet slots 772 can be selected to maximize the options for rotation and hence a change in the radius of curvature of the cannula 760.

While in some embodiment variations rings may be themselves magnetized along the ring axis and thus are attracted to one another, in the embodiment shown, relatively small rectangular magnets (e.g., NdFeB, not shown) are fastened into slots in the mating surfaces of the rings. All the magnet poles facing outwards from the proximal faces of the rings are of one polarity (e.g., North) while all the magnet poles facing outwards from the distal faces of the rings are of the opposite polarity (e.g., South), thus ensuring that rings are attracted to their immediate neighbors. Since there are multiple (here, eight, but many more are possible) magnets distributed around the faces of the rings at substantially equal angles to one another, it is possible to join one ring to another with multiple (e.g., eight) orientations, thus achieving the same effect of controlling the local curvature and direction of the cannula as if one used rings with interlocking features such as tabs and holes. The rings are equipped with diametrically opposite wide and narrow holes to engage a stylet head such as that shown in FIG. 48. To unmate one ring from another, the stylet head, after engaging holes in both rings, can twist or translate one ring relative to the other to shear the mating surfaces and reduce the magnetic attraction.

In some embodiment variations, the magnets are not as small as shown or necessarily flush with the inner and outer surfaces of the rings, and may be joined to the inner or outer surfaces of the rings, with no slots required. In some embodiments, magnets may serve as an aid to orienting rings relative to one another, but the mechanical strength of the joint is provided in large part by interlocking elements such as tabs and holes. The use of magnets on rings can apply to other embodiments such as the 17$^{th}$ Embodiment, as well as the 20$^{th}$ Embodiment.

Continuous Distal Assembly and Disassembly:

The distally assembled cannula, or tube, described in the 14$^{th}$ Embodiment can grow in a continuous manner as material in strip form is delivered continuously to its distal end through its lumen. The distal portion of the strip forms the proximal end of the tube and the proximal portion of the strip forms the distal end of the tube as the assembly process progresses. The strip forms a series of approximately helical windings in which a section of the strip is joined to another section of the strip, together forming a cannula. A winding is assumed to be a full 360° of rotation of the strip around the longitudinal axis of the cannula; however, the beginning and end of a winding (i.e., the 0° and 360° locations) may be somewhat arbitrary. In regions where the cannula is curved, the windings may not be parallel to one another. This is distinct from approaches such as those of the 17$^{th}$ and 20$^{th}$ embodiments, which achieve growth intermittently as each ring is added. Continuous (or even quasi-continuous) growth offers a number of potential benefits over intermittent growth, such as a) much faster assembly and disassembly (since there is no need to grasp and swivel a ring, transport it over a distance, swivel and release it), enabling a faster process and making very high aspect ratio (length to diameter, e.g., 300:1) cannulas feasible; b) no risk of a dropped element (e.g., ring); c) reduced alignment requirements; d) less costly (e.g., reel-to-reel) manufacturing processes and potentially less costly materials (e.g., stainless steel versus superelastic nickel-titanium); e) more compact storage of material (e.g., on a spool); f) the ability to adjust the cannula shape after assembly in some embodiments, allowing very rapid motions if permitted by the available working space; g) a stylet which remains distal during assembly and disassembly, facilitating real-time monitoring of the cannula growth direction and the assembly/disassembly process (e.g., helping with alignment, identifying problems); and h) in some embodiments, the ability to produce a cannula of different diameters, or of variable diameter (e.g., tapered).

In the 14$^{th}$ Embodiment, a winding (i.e., a section of the strip) may be joined to another winding with a variable amount of overlap, thus modulating the local effective width of the strip, as is required to change the growth direction (i.e., the local radius and plane of curvature) of the cannula. Whereas varying the amount of overlap is one approach to varying the effective width and is used in some embodiments for this purpose (and can also increase cannula strength and stiffness), in other embodiments each winding of the strip is joined with a non-varying overlap (e.g., in an edge-to-edge fashion) to its proximal neighbor, and the actual local width of the strip is modulated. Both approaches may also be used in the same cannula.

Figures 58A, 58B, 58C:
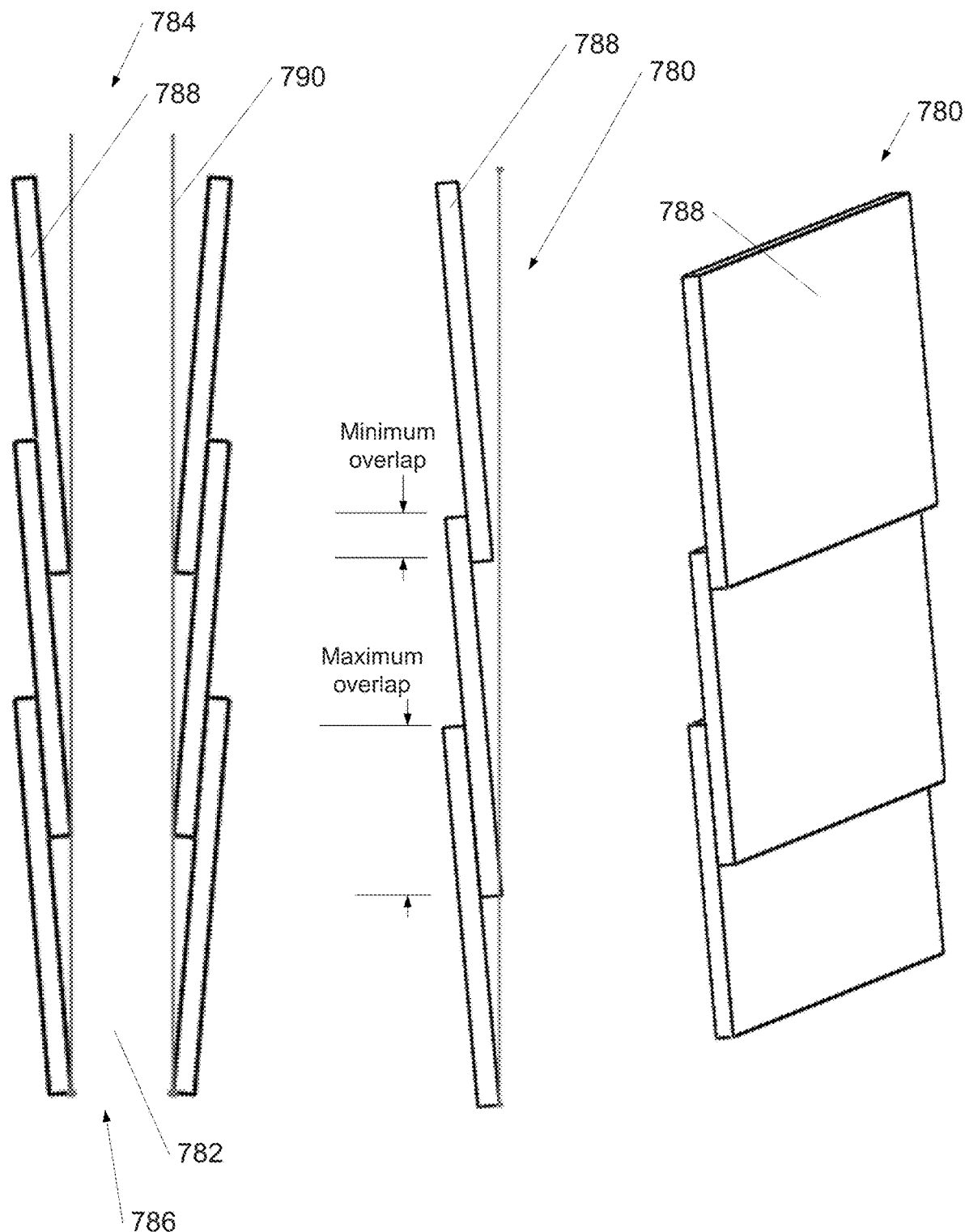
FIGS. 58(a)-(c) and 59 depict sections of overlapping windings in continuously distally assembled/disassembled curved cannulas.

In assembling a cannula as in FIG. 23, the diameter of the cannula 780 that can vary along its length: decreasing gradually if material is added from the interior of the cannula 782 as shown, or increasing gradually if material is added from the outside. Cannula 780 is depicted with a distal end 784 and a proximal end 786. While this may be desirable, it is possible in some embodiments to grow the cannula 780 with a constant diameter. FIGS. 58($a$)-($b$) depict elevation sectional views, and FIG. 58($c$) a 3-D sectional view, of a cannula 780 such as that in FIG. 23 in which the strip is angled such that each winding of the strip 788 (assumed to be added from the cannula interior as in FIG. 23) is larger in diameter 790 (e.g., by twice the thickness of the strip) near the distal edge of the strip 788, compared with its diameter near the proximal edge. Thus each winding of the strip 788 is approximately conical. In FIG. 58($a$), the overlap of one strip 788 with respect to another is uniform, so the cannula 780 grows straight. In the partial section elevation view of FIG. 58($b$) and the 3-D view of 58($c$), the amount of overlap varies over a range, which produces curved growth of the cannula 780.

Figure 59:
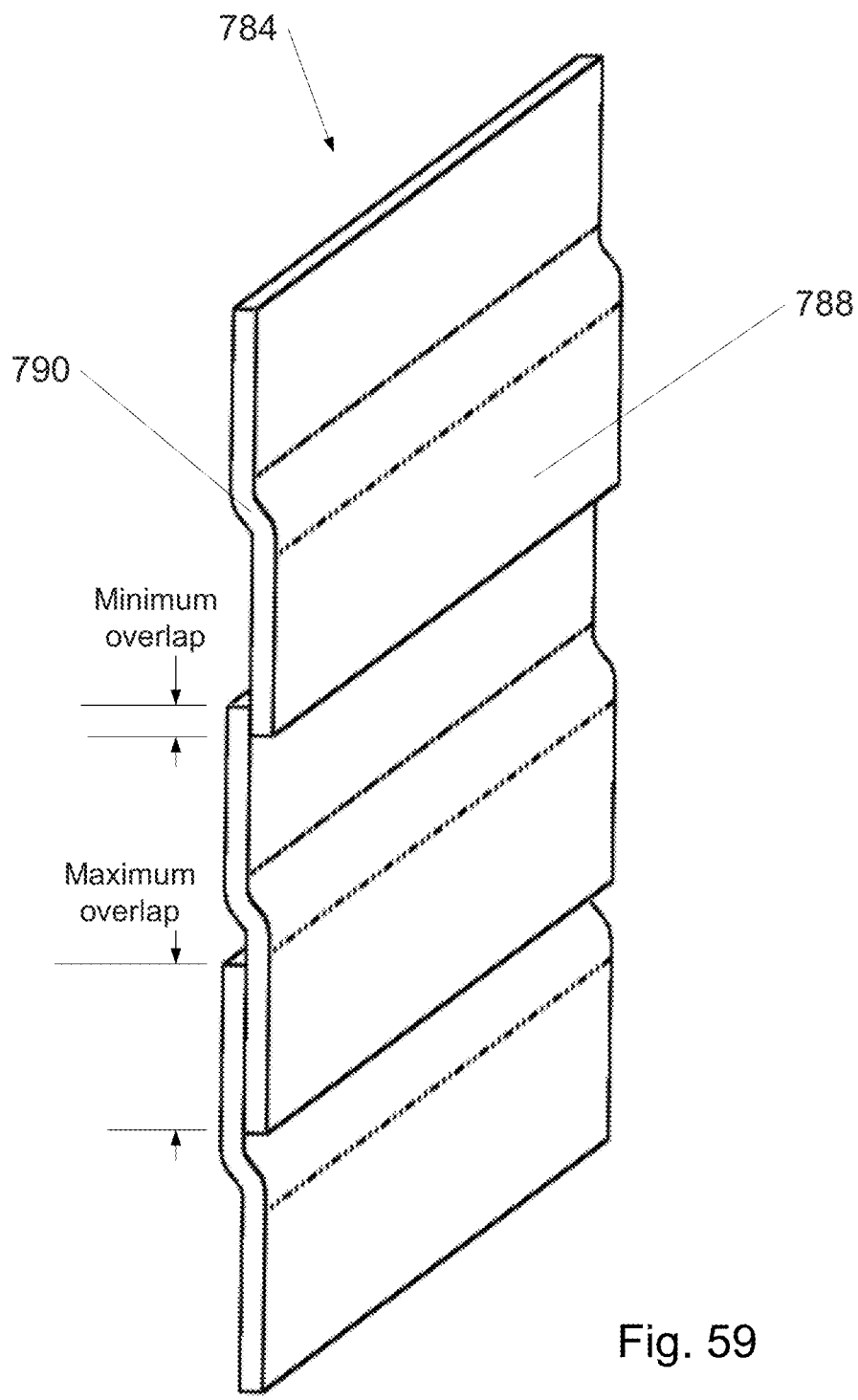
Figure 60D:
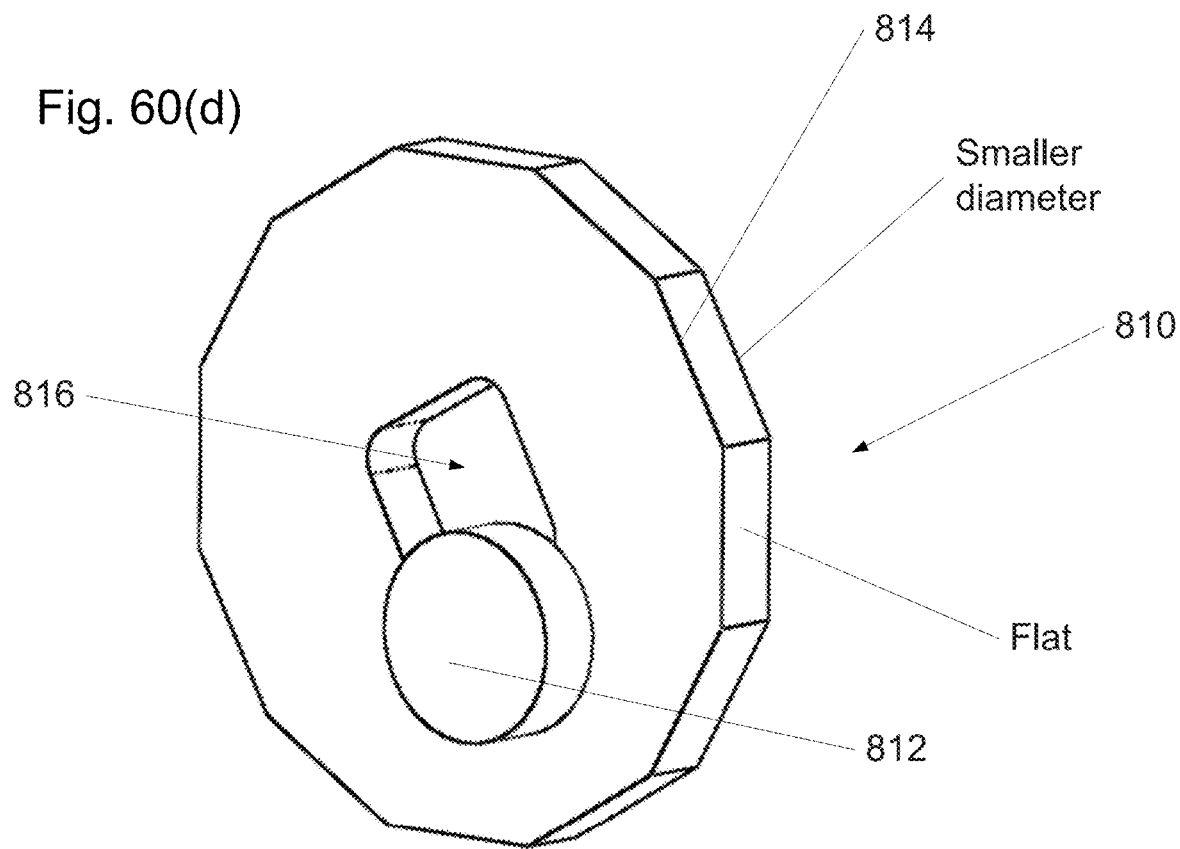
Figure 60E:
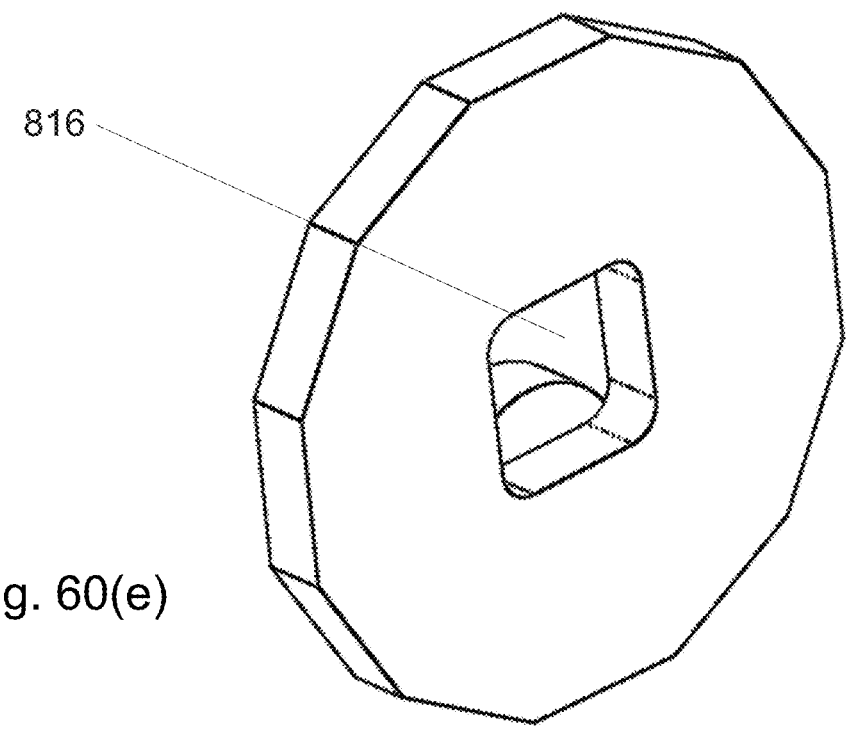
Figure 60F:
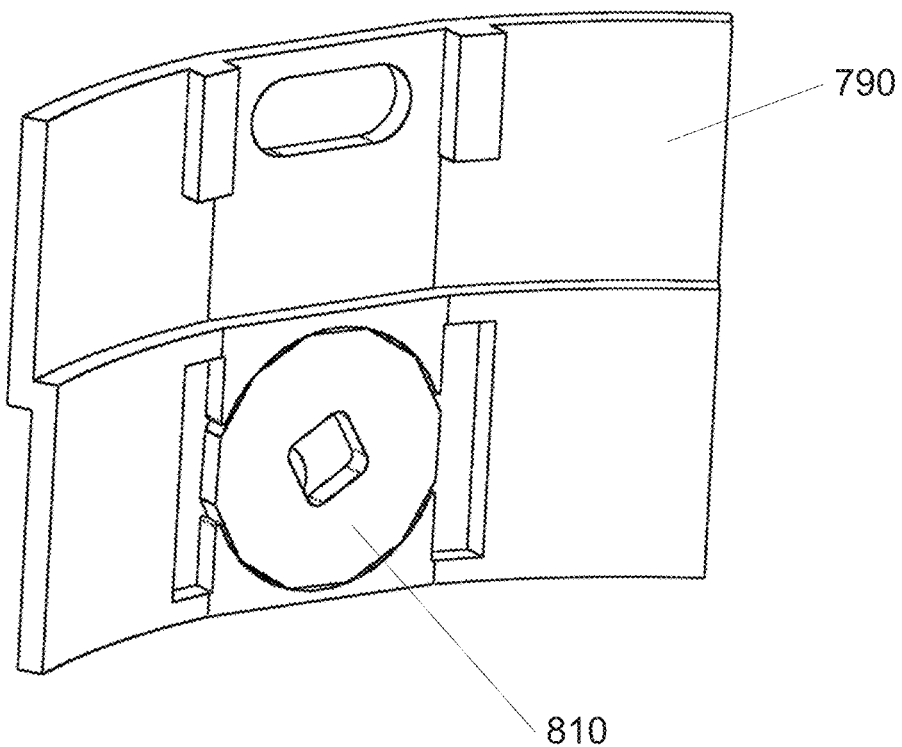
Figure 60G:
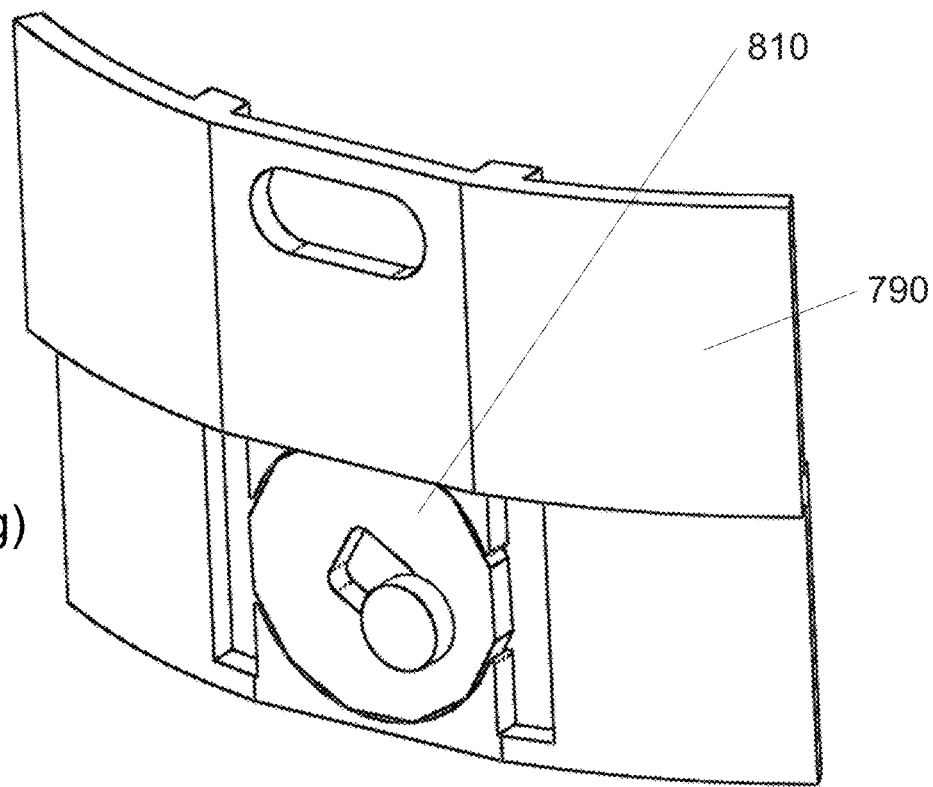

FIG. 59 depicts in 3-D sectional view a cannula 780 similar to that of FIG. 23, formed from a strip 788 having a transition 790 in one region which allows the distal portion 784 of the strip 788, when formed into a winding, to have a slightly larger diameter than the proximal portion, thus accounting for the strip thickness while maintaining a constant diameter. The overlap of adjacent strips can be varied to change the growth direction of the cannula 780. Methods of adjusting the overlap are varied, and may include drilling or punching holes in one region of the strip 788 as needed to accommodate pins in another, incorporating multiple grooves or teeth on mating surfaces of the strip, or approaches discussed in various embodiments below.

A strip with parallel edges can be wound around a straight cylinder to form a helical winding, and no distortion of the strip is required. A strip having one sinusoidal edge can be wrapped perpendicularly (i.e., not helically) around a cylinder to form a ring that is wedge-shaped, akin to the rings of FIG. 26, and again no distortion of the strip is required. A strip having two sinusoidal edges that are 180° out of phase with one another can be wrapped perpendicularly around a cylinder to form a ring that is double wedge-shaped, akin to the rings of FIG. 46, and once again no distortion of the strip is required. A strip that, when wound so that the proximal edge of one winding can be connected to the distal edge of an adjacent winding, and which gives rise to a cannula that is curved, may therefore have a complex shape. If the strip is manufactured ahead of time with a variable width as in the 34$^{th}$ embodiment to generate a cannula of a specific 3-D configuration, it can easily be given such a shape. If on the other hand, the strip is intended to generate an arbitrary 3-D configuration when needed, it must be more generic. In some embodiments, to provide adequate flexibility to the strip to avoid distortions, the strip of embodiments discussed hereinafter, or other embodiments, may be designed and manufactured to be flexible (via plastic deformation, elastic deformation, or using stiff, stable, adjustable elements) within the plane of the strip. In other words, if the strip is lying on a flat surface, such a strip should allow its edge to be non-straight (e.g., sinusoidal or curved) and/or non-parallel, with minimal tendency for the strip to distort in a direction normal to the flat surface. Various structures can be used, e.g., perforations, cuts, scores, integrated flexures, and/or adjustable screws, that allow the strips to have non-straight or non-parallel edges when appropriate are not illustrated or further described herewithin, but may be incorporated in some embodiments.

To further elaborate on methods for joining one section of the strip to another—some easily reversible and some not easily reversible—as described above in connection with FIG. 23, adhesives include for example two-part, cyanoacrylate, epoxy, urethane, hot melt, radiation (e.g., ultraviolet)-cured, thermally-cured, and evaporatively-cured adhesives, applied to adjacent edges and/or surfaces of the strip. Welding methods include for example laser welding, arc welding, spot welding, seam welding, resistance welding, gas welding, MIG and TIG welding, and ultrasonic welding, again applied to adjacent edges and/or surfaces of the strip. Mechanical attachment methods include for example pressing together adjacent edges and/or surfaces covered with VELCRO®, DUAL LOCK™, interlocking tabs and holes as in the rings of the 17$^{th}$ and 20$^{th}$ Embodiments, interlocking (e.g., LEGO®-like) bosses and cavities or teeth and holes; arrays of interlocking bosses (e.g., rectangular, circular) or interdigitated fingers; balls in holes, flat or curved metal tabs and slots or holes; use of fasteners such as zippers, zippers with multiple mating configurations (e.g., multiple depressions on one tooth to receive the protrusion on a mating tooth), ZIPLOC®-type zip fasteners, screws, rivets, staples, and anchors; deforming the adjacent strip edges or surfaces and mutually entangling them; use of tongue in groove or dovetail joints; magnets (which can be used for attachment by themselves, used as an assist to attachment by other means, and/or used as an aid to alignment); vacuum or air pressure; particle jamming; stitching or sewing with a wire or thread; and so forth. It should be noted that since the act of winding/bending the strip to form a portion of a cannula may produce a restoring force tending to straighten it, and this force may be used to keep several mechanical methods of attachment positively engaged. Moreover, if the strip can only detach from an adjacent strip by a displacement along the cannula axis (e.g., approximately along the width of the strip), it may be prevented from doing so by suitable interlocking.

In some embodiments of a continuously distally assembled/disassembled curved cannula, adjustment of the local overlap or width is performed as the strip is being wound into a cannula: i.e., the adjustment is performed at one circumferential location at a time before or as the winding is joined to its proximal neighbor. In some embodiments, the adjustment may be performed after one or more windings has been already created. For example, a winding (assumed to be 360°) for example with parallel strip edges to produce a straight direction of the cannula can be formed and joined to the adjacent winding, and then the direction can be altered into a curve by making the winding wedge-shaped after it has been fully formed and joined. If the stylet needs to temporarily stop winding the strip to grow the cannula while making this adjustment, the result is quasi-continuous growth, since there are brief pauses.

A stylet of suitable design, translating and in some embodiments, rotating inside the cannula as it grows, can be used to attach one winding of the strip to its next-most distal (i.e., proximal) neighbor. The stylet can also be used to modulate the overlap of one winding with respect to another, and/or the local width of the strip. The stylet may be moved by proximally-located motors and other actuators much as with the stylet of the 17$^{th}$ Embodiment.

In some embodiments, the cannula may be formed from a set of strips (e.g., joined end-to-end or side-to-side) rather than from a single strip. Materials suitable for the strip or sub-components therefore for a continuously distally assembled/disassembled curved cannula include but are not limited to metals such as stainless steel, nitinol (nickel-titanium, e.g., superelastic), titanium, vanadium, aluminum, nickel, tantalum, zirconium, chromium, silver, gold, silicon, magnesium, niobium, scandium, platinum, cobalt, palladium, manganese, molybdenum and alloys thereof, and zirconium-titanium-tantalum alloys, as well as polymers such as thermoplastics, thermosets, elastomers, etc. Examples include polycarbonate, polypropylene, polyethylene, acetal, nylon, fluoropolymers, thermoplastic elastomers, silicone, natural rubber, vinyl, and latex. Amorphous materials such as glass and amorphous metals, as well as ceramic materials may also be used.

21$^{st}$ Embodiment

Referring to the 3-D views of FIGS. 60(*a*)-(*c*), show various views of individual strips 790 can be provided in some embodiments for continuous distal assembly/disassembly of a curved cannula which incorporates a mechanism which can adjust the amount of overlap of one strip 790 relative to another adjacent strip (not depicted), and positively lock the selected amount overlap in place. FIG. 60(*a*)-(*c*) are 3-D sectional views of a section of strips 790 having a mostly bent form (except for the central region, which in some embodiments may be flat as shown): as it would appear once comprising a portion of a winding of the cannula. The strip 790 comprises an upper band 792 and a lower band 794 joined with an overlap. Holes, cuts, or slots (not shown) may be provided in the overlap region at intervals, and/or holes, cuts, or slots on the bands, to reducing the bending stiffness of the strip 790. The lower band 794, intended to be bent into a winding of smaller diameter 798, includes a circular cutout 800 to accommodate a polygonal wheel and two rectangular cutouts 802 to accommodate sliding bosses 804. The upper band 792, bent to form a larger diameter 806, includes a slot 796 to accommodate a pin on the wheel and sliding bosses.

As shown in FIG. 60(*b*), a portion of the upper band 792 overlaps the circular cutout 800 in the lower band 794. The circular cutout 800 is tapered (not shown), with its smaller diameter toward the inside 808 of the bend. The wheel is also tapered (not shown). As shown in conjunction with FIGS. 60(*d*)-(*e*), a wheel 810 includes a central drive hole 816 in some embodiments (alternatively, at least two off-center drive holes may be used) and an eccentric circular pin 812 on its outer (larger diameter) surface 814. During fabrication of the strip, the wheel 810 is inserted into the circular cutout 800 from the outside before the upper 792 and lower 794 bands are joined. The overlap of the upper band 792 thus traps the wheel 810 within the cutout 800 as shown in the sectional views of FIGS. 60(*f*)-(*g*). In FIGS. 60(*h*)-(*i*), three sections of a continuous strip 790*a,b,c* have been joined together, one above the other, to form a portion of the cannula, by a suitable stylet. Starting with section 790*a*, as a new section (790*b*) is laid against section 790*a* from the inside to form a single winding (360 degrees) of the cannula, the pin of section 790*b* enters slot 796 in section 790*a*, and the bosses 804 enter the rectangular cutouts adjacent to the wheel. Prior to the pin 812 entering the slot, a rotational element on the stylet engages the wheel and rotates it to an orientation that places the eccentric pin at the des+ired height. Then, when the lower band of section 790*b* lies against the upper band of section 790*a*, the amount of overlap between the two bands is controlled by the position of the pin 812*a,b,c*, and the two bosses 804 resting against opposing flat sides of the wheel 810*a-c* prevent it from rotating. Moreover, since the strip 790*a-c* is bent and if only elastically deformed prefers to have a larger radius, there is a preload of the wheels 810a-c against the adjacent section of the strip which can help stabilize it.

As shown, the overlap between sections 790a and 790b is at its minimum, while that between sections 790b and 790c is at its maximum. Intermediate amounts of overlap are also possible, depending on polygon orientation. In some embodiment variations, rather than a polygonal wheel with bosses to lock its orientation, a smooth but high-friction wheel may be used, or a gear or sprocket may be used with one or more tabs which engage the teeth. If the wheel is smooth but tapered to match the circular cutout, then the natural tendency of the strip to straighten itself (if not fully plastically deformed) may force one section of the strip against the wheel and push it more tightly into the cutout, frictionally preventing it from rotating in the assembled cannula.

22$^{nd}$ Embodiment

Figure 61A:
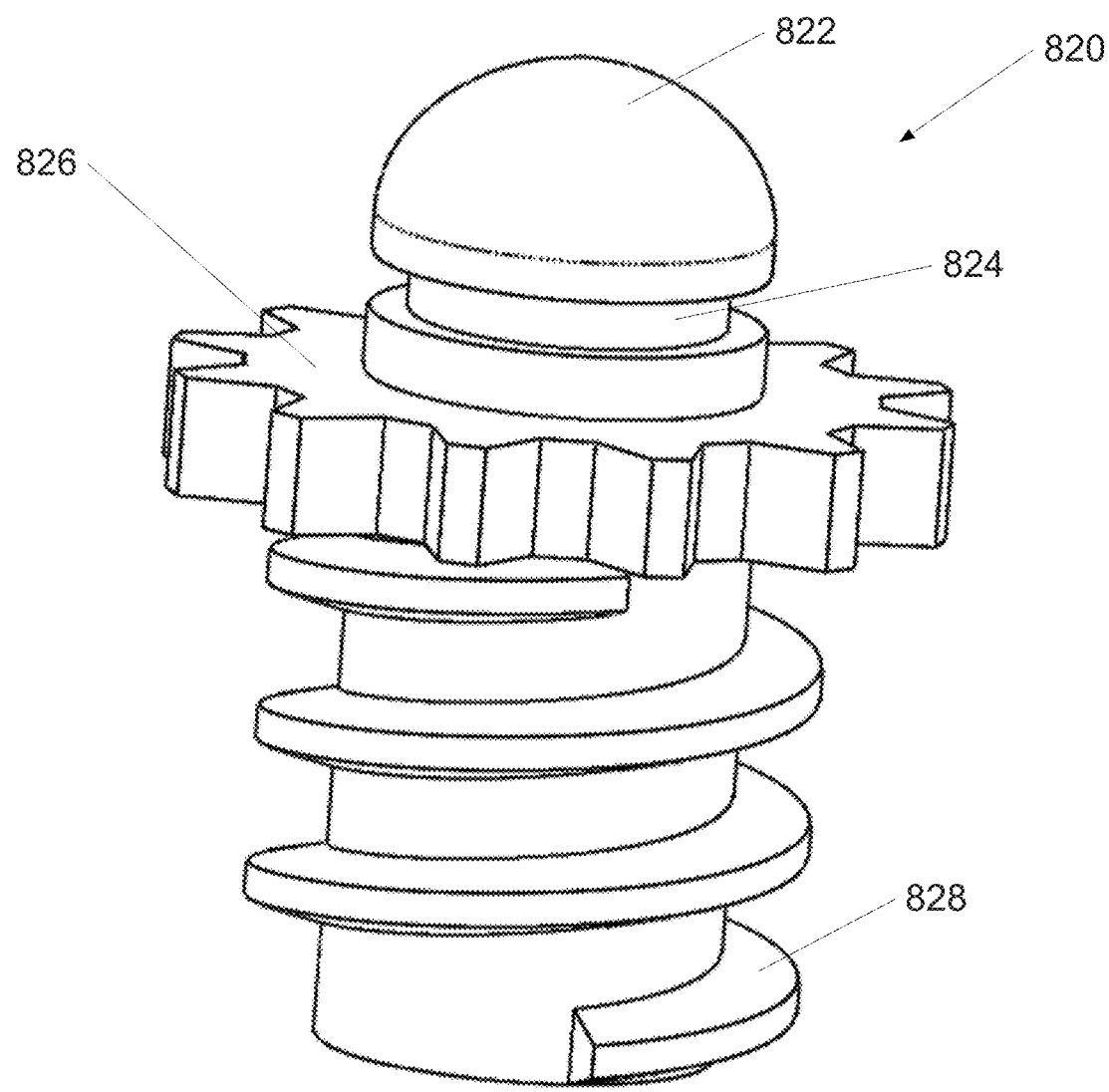
FIG. 61(a)-(p) depicts sections and components of a strip from a continuously distally assembled/disassembled curved cannula in which the strip width is locally adjustable, a gear to adjust it, and an assembled cannula.
Figure 61B:
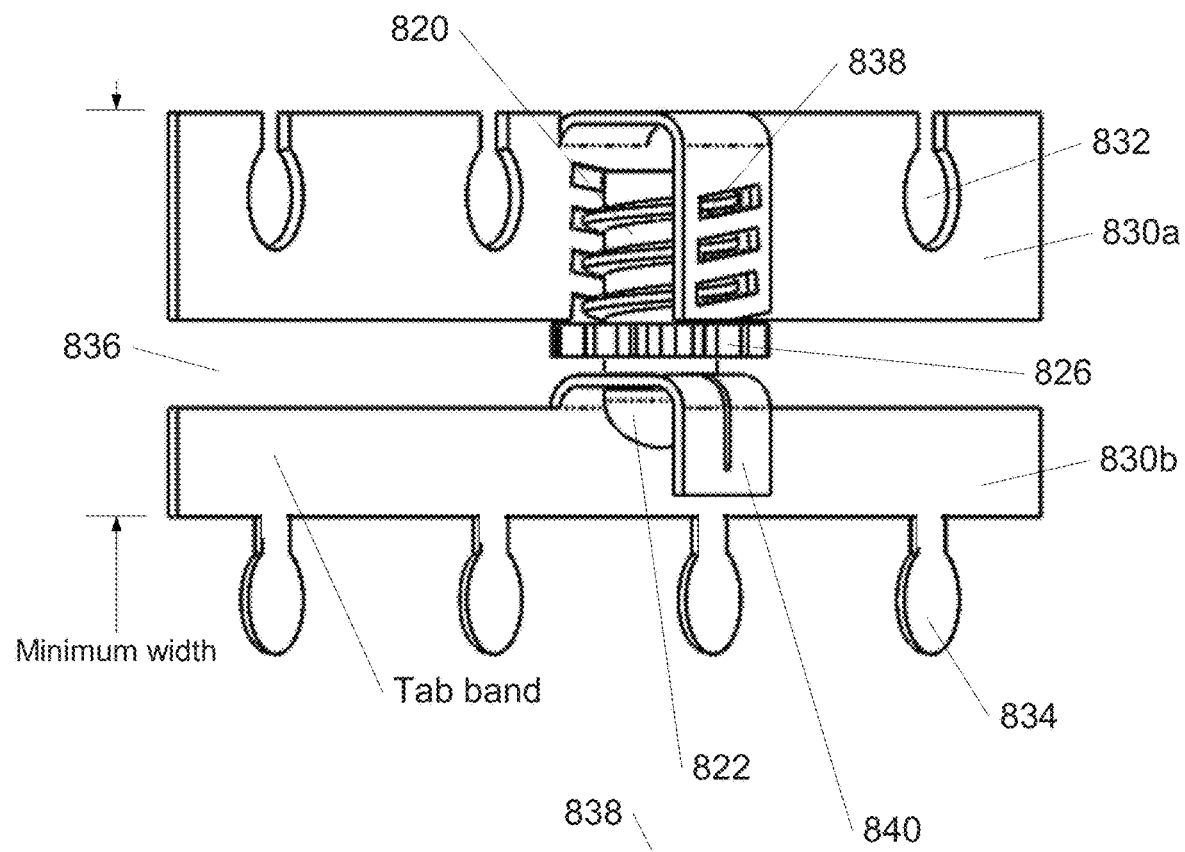
Figure 61C:
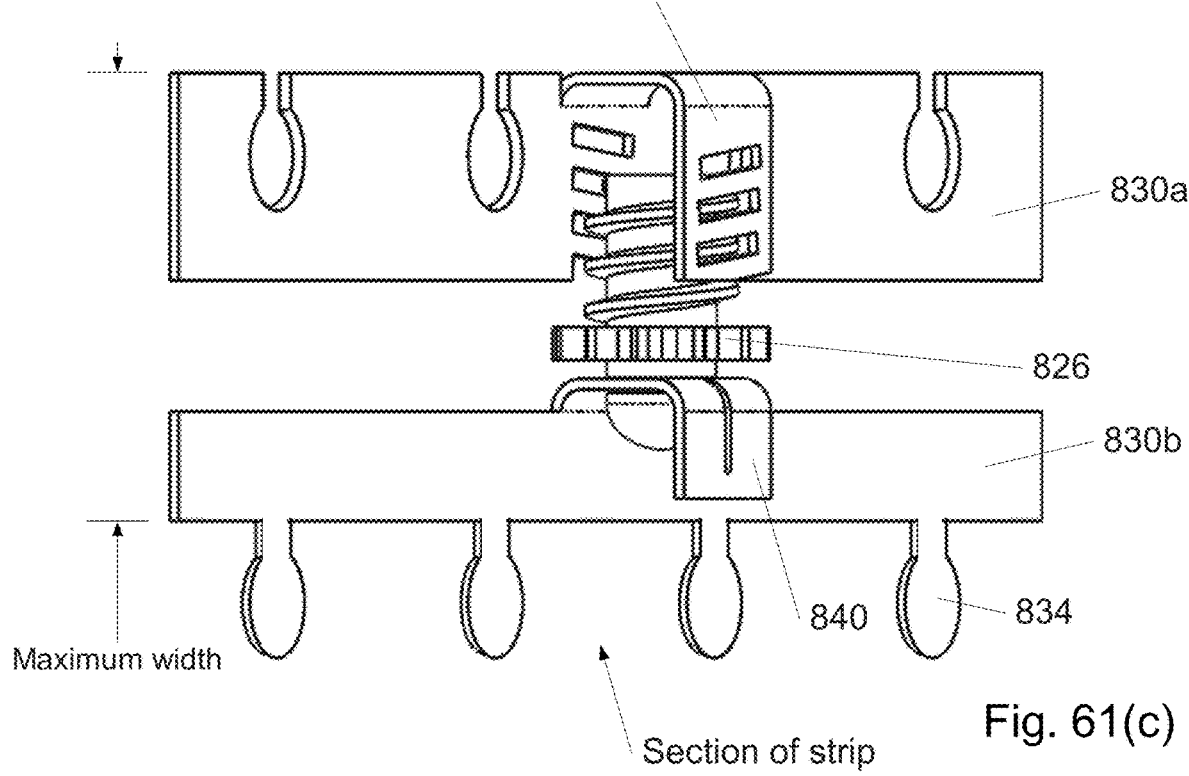

FIG. 61(a)-(c) depicts 3-D views of a section of a screw 820 and a variable-width strip used in some embodiments in a continuously distally assembled/disassembled curved cannula; the width can be locally adjusted using screws. One such screw 820, used in some embodiment variations, is shown in FIG. 61(a). The screw 820 comprises a tip 822, which is preferably tapered or rounded, a groove 824 beneath the tip 822, a thin gear 826, and a thread 828, which is positioned within threaded slot tab 838 (in FIG. 61(b)) and screw support tab 840. FIGS. 61(b)-(c) illustrate a section of the entire strip, comprising two bands 830a,b and a screw 820. One band 830a (the "hole band") incorporates holes 832 designed to accommodate tabs 834 from an adjacent strip section 830b. The other band 830b ("the tab band") incorporates tabs 834 designed for those holes 832; in some embodiment variations the tabs 834 are also tapered. The sizes of tabs and holes relative to other dimension of the band may vary from that shown in the figures; for example, they may be much smaller and more numerous than shown. The bands 830a,b (as well as elements of strips in other embodiments), may be laser cut, photochemically machined, electroformed, fineblanked, waterjet cut, plasma cut, abrasive jet cut, electrical discharge machined, or stamped, among other fabrication processes, some of which may be performed in a reel-to-reel manner, and some of which may form tapered holes 832 and tabs 834 (e.g., in laser cutting, adjusting focus, angle of incidence, power, assisting gas pressure, etc. can produce the desired taper. In some embodiments, taper can be introduced through post-processing of the parts, such as one-sided abrasive blasting or tumbling. In some embodiments, other methods of preventing tabs from passing entirely through holes may be used, such as incorporating material (e.g., through welding, deformation (e.g., stamping), electroplating) that forms a stop on one side of the hole, in some cases making a through hole into a blind hole. While in FIG. 61 tabs 834 and holes 832 are shown perpendicular to bands 830a,b in some embodiment variations they are at other angles (e.g., parallel to the cannula axis). Bands 830a,b can incorporate elements (e.g., produced by bending) which articulate with the screw 820 of FIG. 61(a). In some embodiment variations, to avoid the risk of catching tabs 838 and 840 on other elements, such as when bands 830a,b are passing through the cannula, they may include rounded/deflecting features (not shown). Referring to FIG. 61(b), the screw 820 connects the two bands 830a,b into a single, adjustable-width strip in which there is a variable gap 836 between the bands. In this figure and several others, the section of the strip shown is not "cut" parallel to the cannula axis, but rather, perpendicular to the strip long axis, and the strip is shown as horizontal, when in practice it would be tilted relative to the cannula long axis as it follows an approximately helical path around the cannula. An element on the hole band serves as a "nut" which retains the screw thread and into which the screw can be advanced or withdrawn by rotating it. If the band is formed from thin sheet, slots can be formed in it to accept the screw threads, a method commonly used in hose clamps, as shown. The nut is preferably rather tight on the screw, to prevent inadvertent rotation. An element in the tab band serves to support the tip of the screw. The element snaps into the groove on the screw and provides a bushing on which the screw can rotate freely. Taken together, the screw, the nut, and the support/bushing element comprise a variable adjuster. In some embodiment variations, the screw is double-ended with left and righthand threads, and both bands have nuts. In many of the figures shown, the adjusters are assumed to be on the inside surface of the strip (toward the cannula center axis), but in some embodiments they are on the outside. In some embodiment variations, holes are provided on the same band as the support/bushing, while tabs are provided on the same band as the nut.

In FIG. 61(b), the screw 820 is advanced fully into the nut, and the overall width of the strip in the region of the screw 820 is at minimized. In FIG. 61(c), however, the screw 820 is partially withdrawn from the nut (yet retaining engagement of enough thread) and the overall width of the strip is maximized. Thus by rotating the screw 820, the width of the strip can be varied. In practice, the screw 820 can be longer than that shown in the figures, allowing even greater variation.

As shown in FIG. 61(d), the support/bushing 840 may include a slot 842 which allows the hole for the screw tip 822 to stretch open slightly such that the tip of the screw 820 can snap into it during assembly, as shown in the sectional view of FIG. 61(e).

Figure 61F:
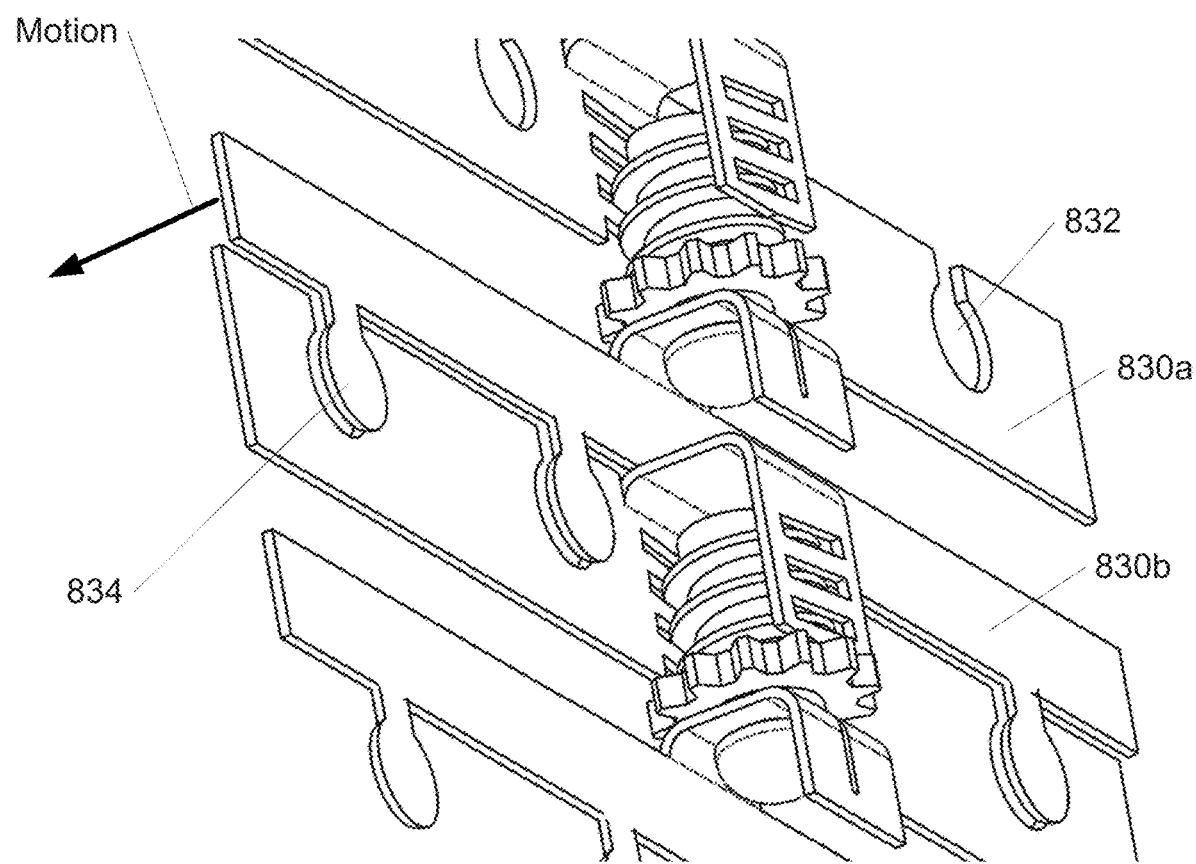
Figure 61G:
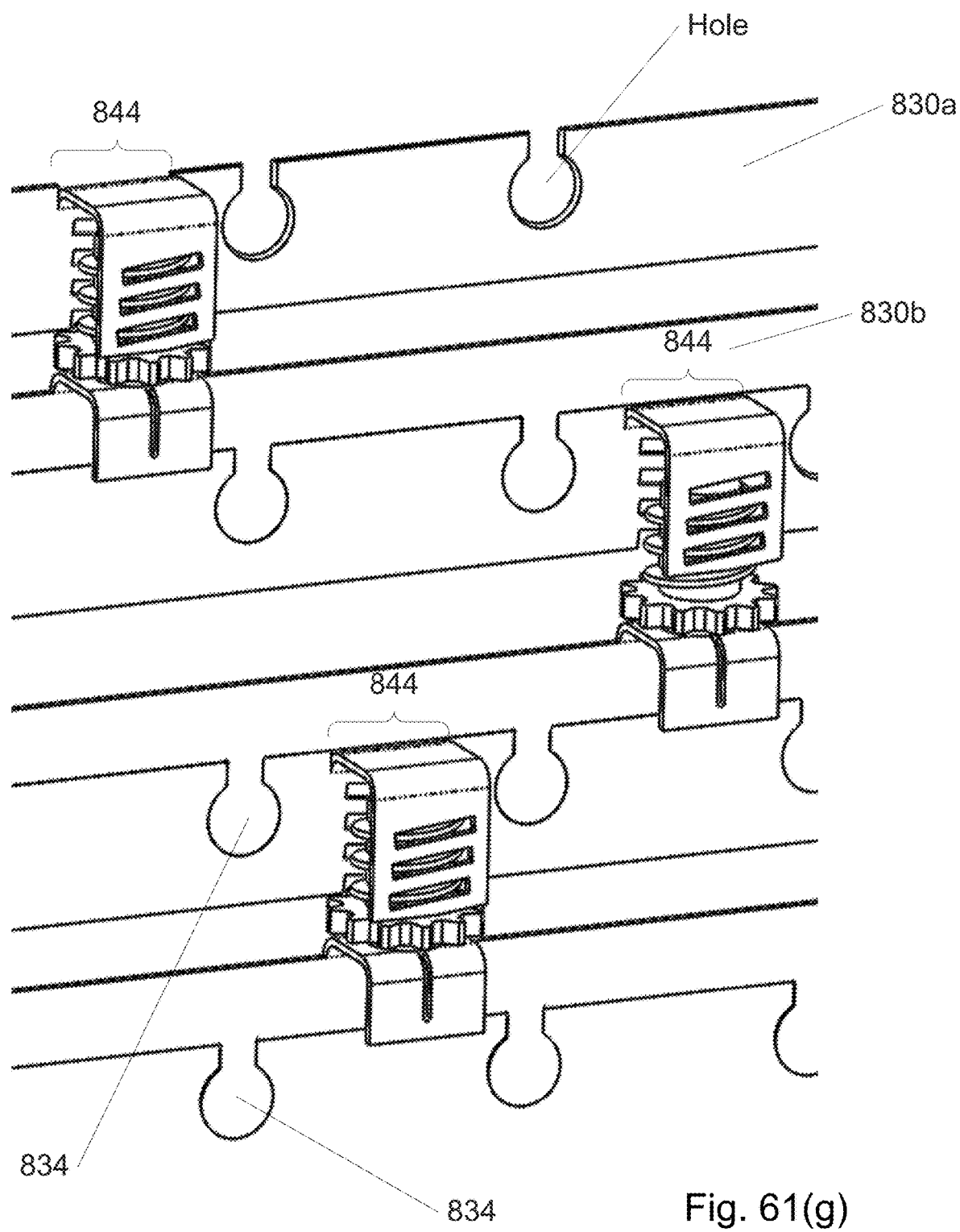
Figure 61H:
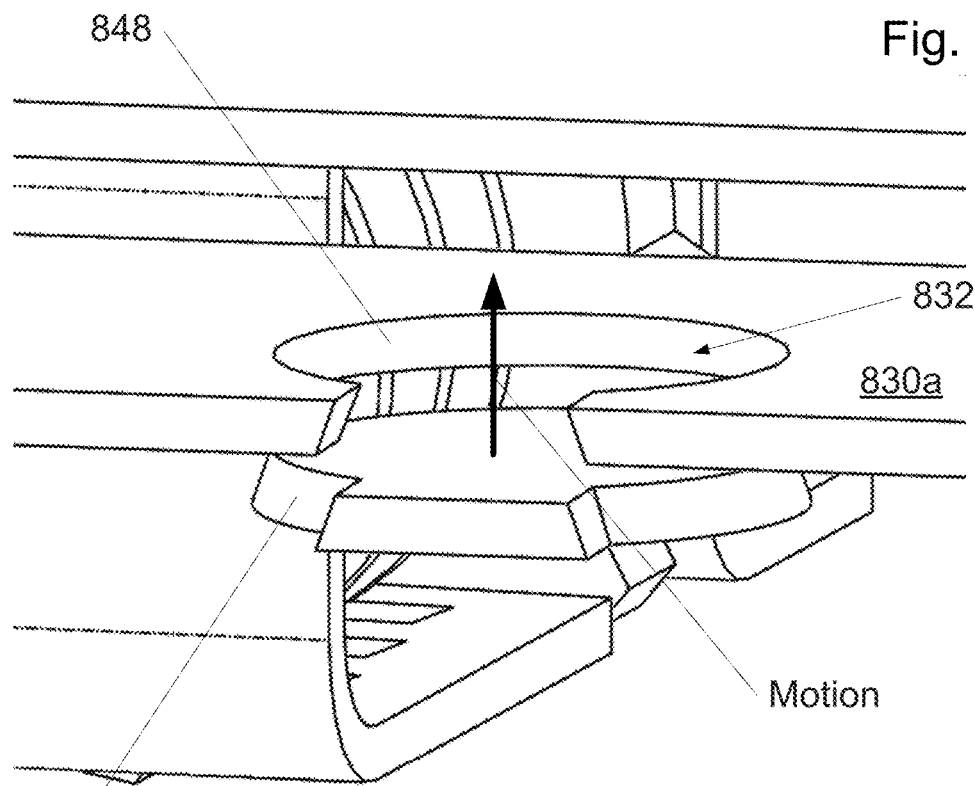
Figure 61I:
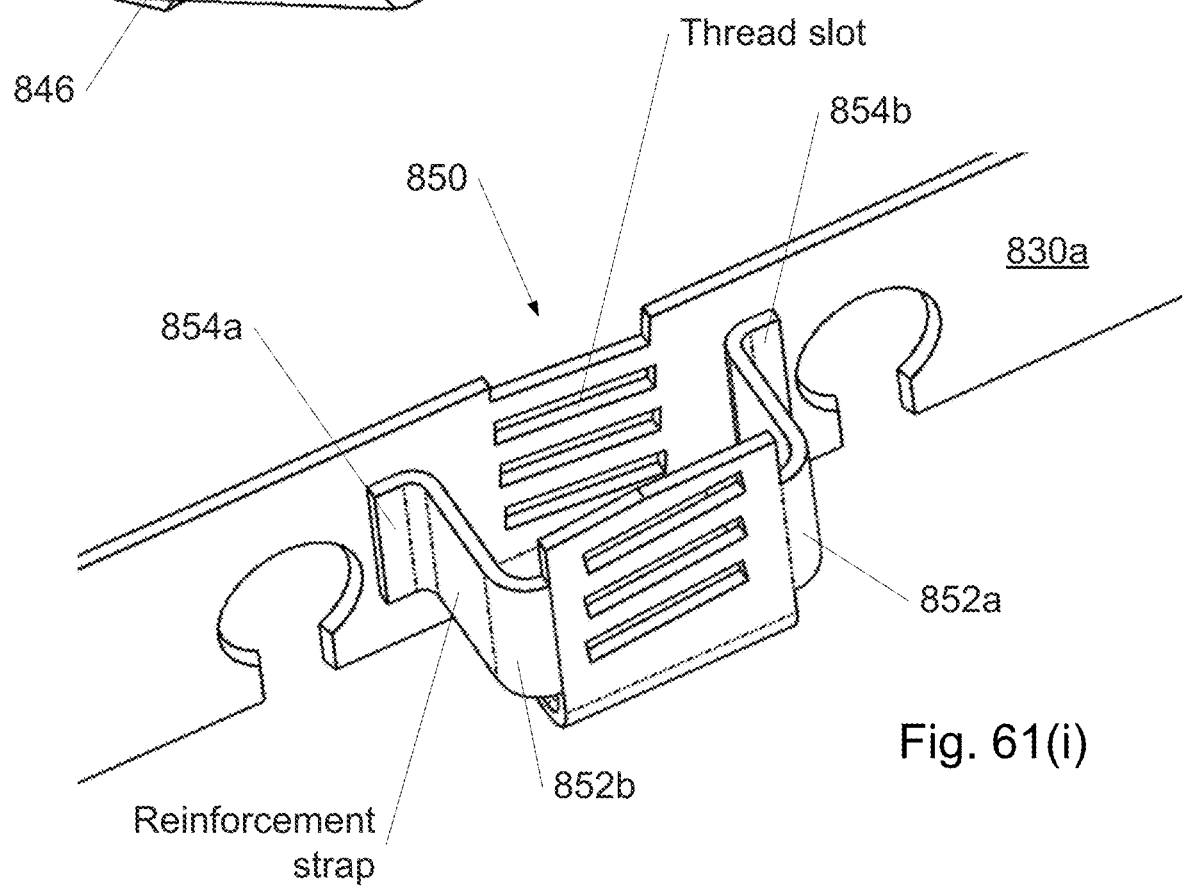
Figure 61J:
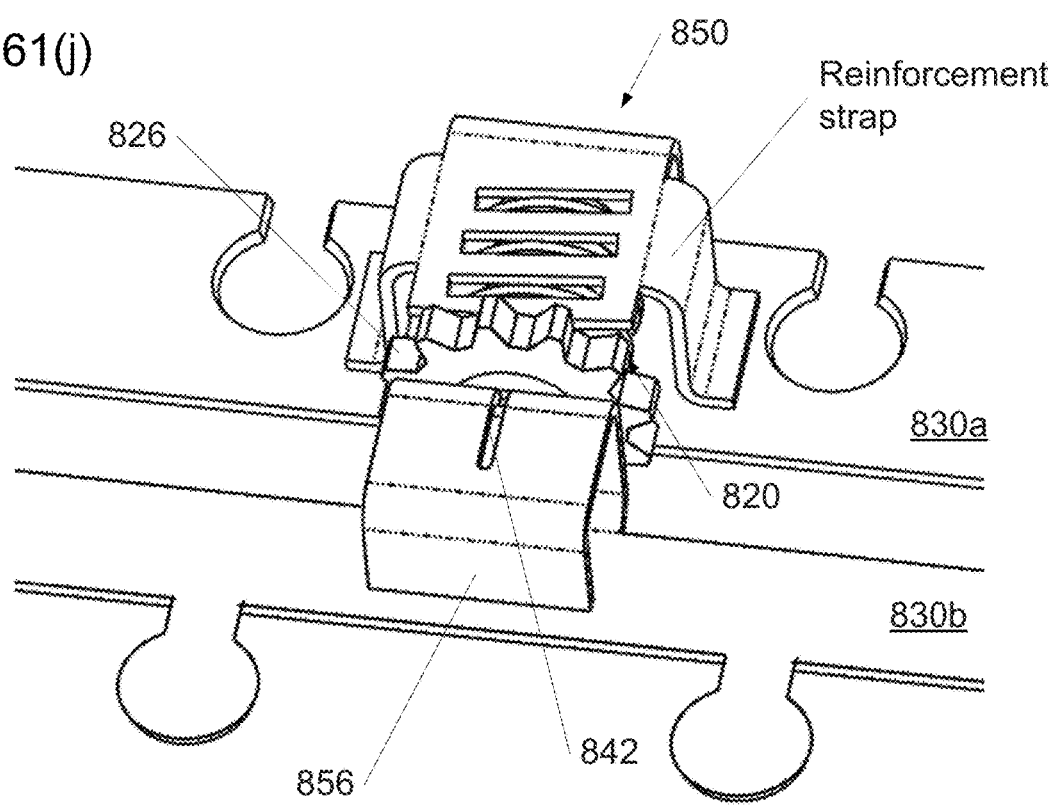
Figure 61K:
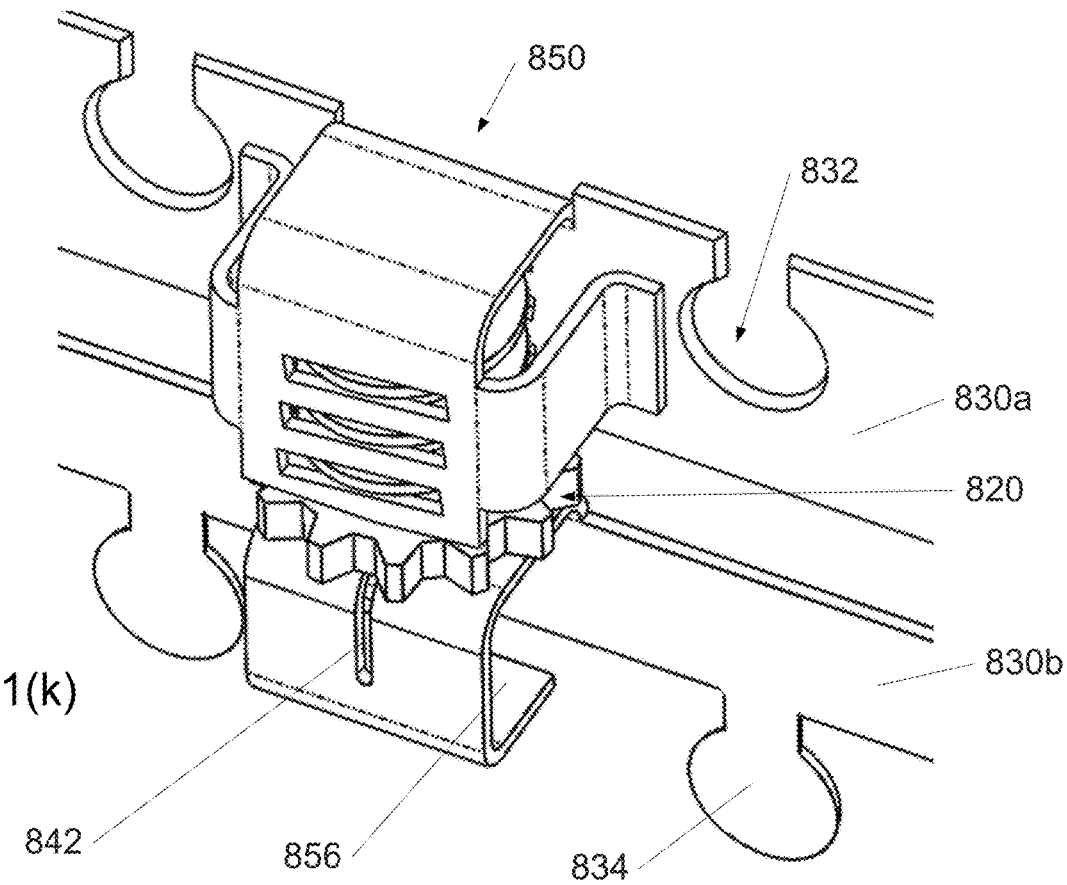
Figure 61L:
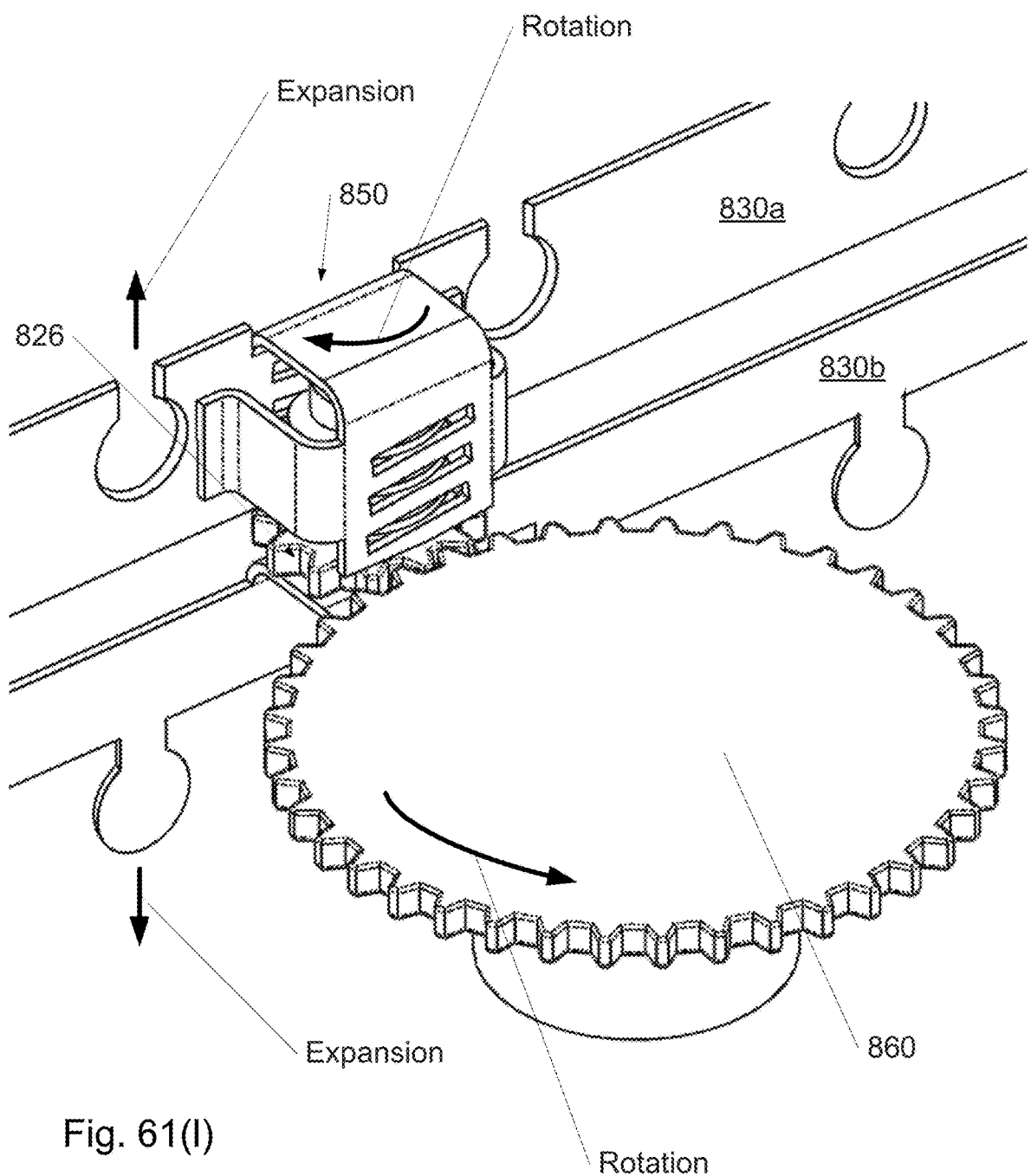
Figure 61M:
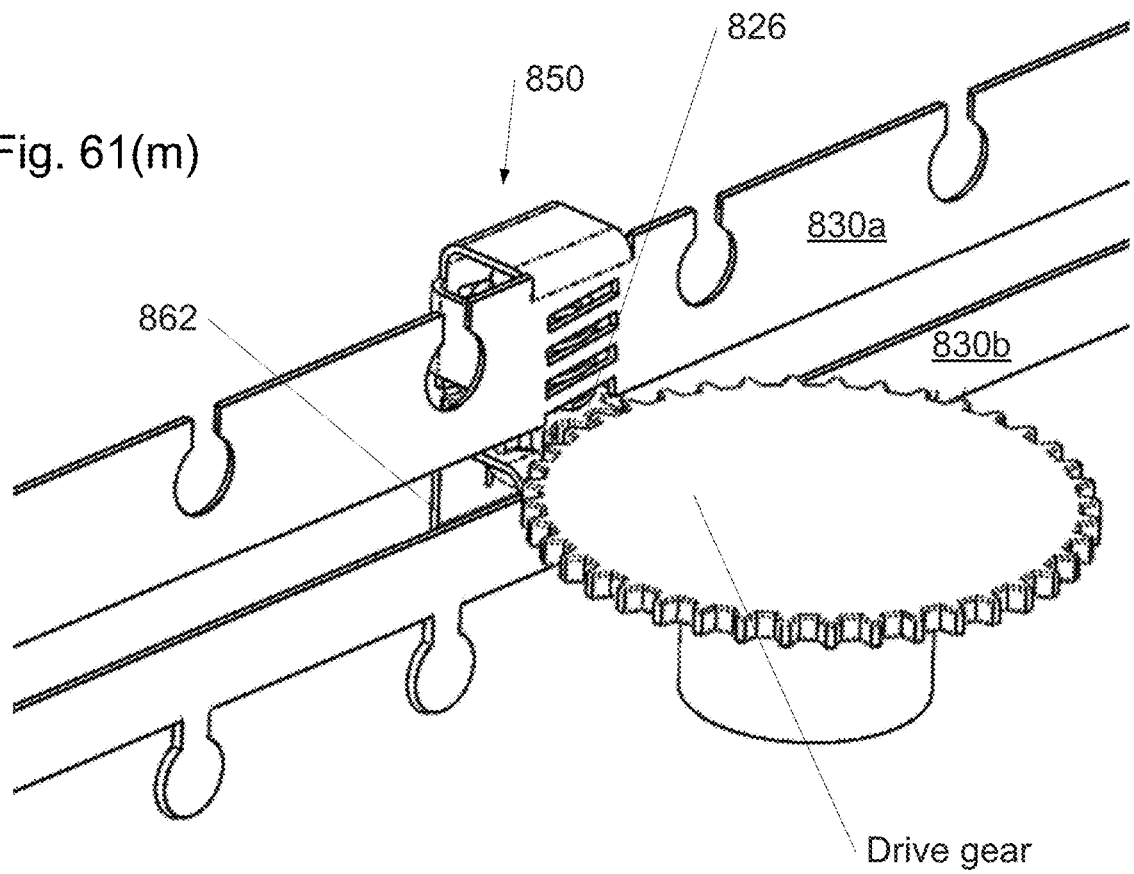
Figure 61N:
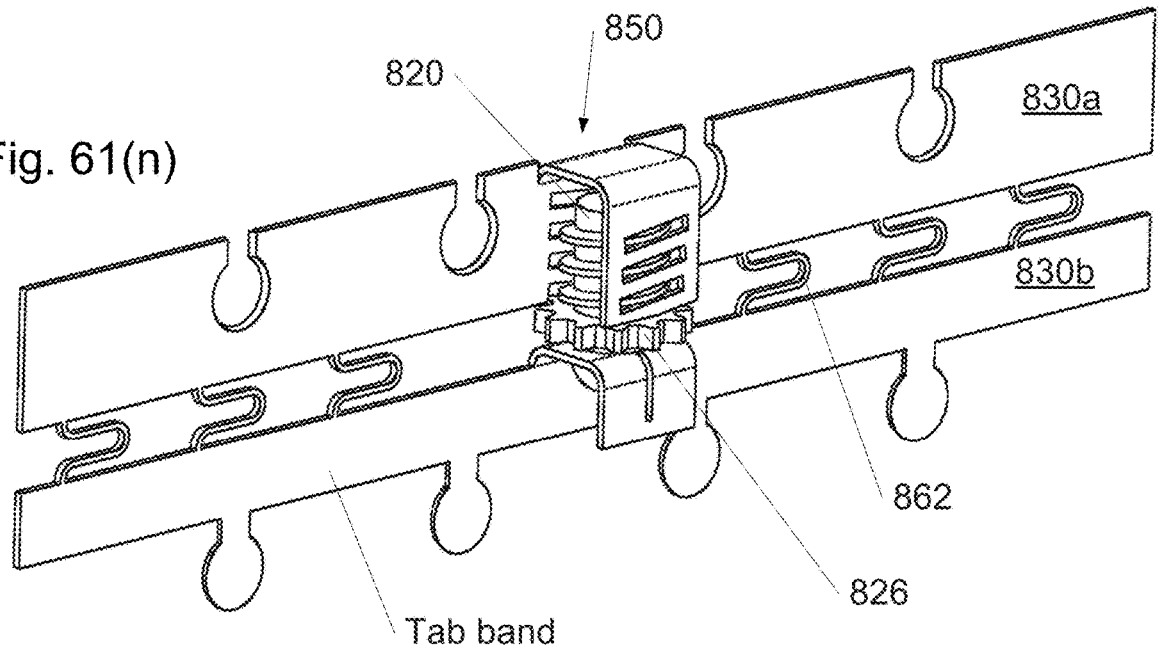

When two adjacent sections of strip are brought into proximity by the stylet, as they would be when growing the cannula, the tabs 834 in one section can fit into the holes 832 in the adjacent section as shown in FIG. 61(f). In this way, multiple windings of the cannula may be formed, each from a different section of the strip 830b. Flexural features (e.g., comprising transverse cuts in the bands) may be provided in this and other embodiments to facilitate mating of tabs 834 and holes 832 or other mating features, so that precise alignment is not required. FIG. 61(g) shows three such sections in which the adjacent sections of strip are brought into proximity by the stylet, as they would be when growing the cannula, the tabs 834 in one section can fit into the holes 832 in the adjacent section. Multiple (at least three) adjusters 844 are required along the circumference of a single, 360-degree winding of the strip to control the orientation of the winding, and thus the local curvature and direction (i.e., radius and plane of curvature) of the cannula. If three adjusters are used, the arrangement is somewhat analogous to a kinematic mount with three adjustable elements. The bottom and top adjusters have in the example shown been set to provide the minimum strip width in their vicinities, while the middle adjuster has been set to provide the maximum strip width. As long as there are an adequate number of adjusters per winding, it is possible in some embodiment variations (and in some other embodiments) to assemble cannulas with multiple diameters by allocating the desired number of tabs and holes to each winding; the choice of diameter may be made just before assembly. The diameter may also be varied in a single cannula from winding to winding in some embodiment variations.

FIG. 61(*h*) depicts in sectional view a tab 834 entering a hole 832. In some embodiment variations, the tabs 834 and holes 832 are tapered 846, 848, respectively as shown, such that the tab 834 cannot pass entirely through the hole 832. Such tapering can be achieved by single-sided photochemical machining, for example. This provides additional structural integrity, and due to the tendency of the strip to straighten itself if not fully plastically deformed, if the orientations of the tapered edges 846, 848 are correct, this tendency will help achieve a tight fit between tabs 834 and holes 832, reducing clearances that make the cannula less rigid. It should be noted, however, that as long as there are at least three tab/hole pairs for every winding of the cannula, then even with untapered tabs and holes, no tab can escape from its hole in an assembled cannula, since to do so would require lateral motion of other tabs in their holes. This is also true of the rings of the $17^{th}$ and $20^{th}$ Embodiments. In some embodiment variations, stops are provided to prevent tabs from passing through holes and out the other side; such stops can be made by bending a cut portion of band 830*a* so it obscures hole 832 on one side of the band, for example, or by bending a cut portion of tab 834; metal can be locally annealed to facilitate such bending if required.

FIG. 61(*i*) depicts a modified nut 850 which includes two reinforcement straps 852*a,b* that can be welded 854*a,b* or otherwise attached to the strip, preventing the two slotted portions of the nut from spreading apart. FIGS. 61(*j*)-(*k*) also depicts a modified support/bushing 850 which includes a deflector 856 section that minimizes the risk of the stylet or other object from catching on it.

The screw 820 of the adjuster 844 may be rotated by engaging its thin gear 826, for example with a drive gear as shown in FIG. 61(*l*). The drive gear 860 may be rotationally mounted to the stylet, and pressed against the screw gear 826 by the stylet. If the drive gear 860 is at the correct axial position along the cannula, it can engage the gear 826 of the screw 820 and adjust the height of the adjuster 850 and the width strips 830*a,b*. Since the strip cam follow, e.g., a roughly helical shape within the cannula, then if the gears are thin and there are a small number of adjusters 850 (e.g., three) per winding, it is possible to engage only one screw gear 826 at a time with a central, large diameter drive gear 860, since all screw gears 826 will be at different axial positions. The screw 820 and drive gears 860 should preferably be designed with teeth that allow meshing (e.g., radiused or chamfered edges) when the drive gear engages the screw gear 826, approaching it from one side or the other; either or both gears can rotate slightly to allow proper meshing. In some embodiments the adjusters 850 are located at the same azimuthal position around the cannula, unlike FIGS. 61(*o*)-(*p*), where the azimuth varies. This may allow faster post-assembly adjustment by the stylet of the cannula curvature amount and direction.

It is preferable in many applications that the lumen of the cannula be as unobstructed as possible. Thus in FIG. 61(*m*), in some embodiments the adjusters 850 are located on the external surface of the strip instead of the internal surface as in FIG. 61(*l*) and the drive gear 860 engages the screw gear 826 as it protrudes through the space between the bands of the strip. In some embodiment variations, the hole 830*a* and tab 830*b* strips or bands are joined together into a single strip having a variable width by means of flexures 862 (FIG. 61(*n*)). The flexures 862 may be designed to be plastically or elastically deformed as the strip changes its width. In some embodiment variations, the two bands 830*a,b* may be joined by a C-shaped band which completely surrounds the adjusters; this may be cut at intervals to allow flexing.

FIGS. 61(*o*)-(*p*) depict simplified views (FIG. 61(*p*) is a sectional view) of a section of a distally assembled cannula formed continuously by a strip of the kind shown in FIG. 61(*b*)-(*c*), with adjusters 850 located at intervals, and screw gears 826 protruding slightly into the lumen, where they can be engaged by a drive gear (not depicted) similar to that in FIG. 61(*m*). In the figure, the width of the strips, 830*a,b* is the same everywhere, and thus the cannula section is straight. However, by varying the relative heights of the adjusters 850 (and/or or the gap between strips, 830*a,b*), the cannula section can adopt a curved 3-D shape. Not shown are the tabs and holes that join adjacent strips, or the stylet which assembles and disassembles the cannula and in some embodiments also sets the heights of the adjusters. If only three adjusters are used per 360-degree winding (or more if there is some flexibility in the structure), it is possible in some embodiments to form an entire winding by joining the strip edges, and then set the "wedge angle" of the winding by setting the adjusters in the winding one at a time. This is an alternative to setting the adjusters as the winding is formed. Also, with preferably three adjusters, it is possible to adjust the shape of the cannula after it is assembled, by translating the drive gear to certain adjusters, engaging their screw gears, and varying their height.

In some embodiment variations, rather than using a screw with a tip that snaps into one band, a screw with both left and righthand threads (e.g., on either side of a central gear) can be used, with nuts provided for each thread of the screw. In some embodiments, rather than have a screw adjust the width of the strip and use means such as tabs and holes to interlock adjacent windings of the cannula, the screw may be used to adjust the relative overlap of one winding with another adjacent winding, and connect them together. In some embodiment variations, other than using tabs and holes to join adjacent strips, other means can be used, including all of those mentioned above. The same is true of all of the continuous distally assembled cannula embodiments.

$23^{rd}$ Embodiment

Figure 62A:
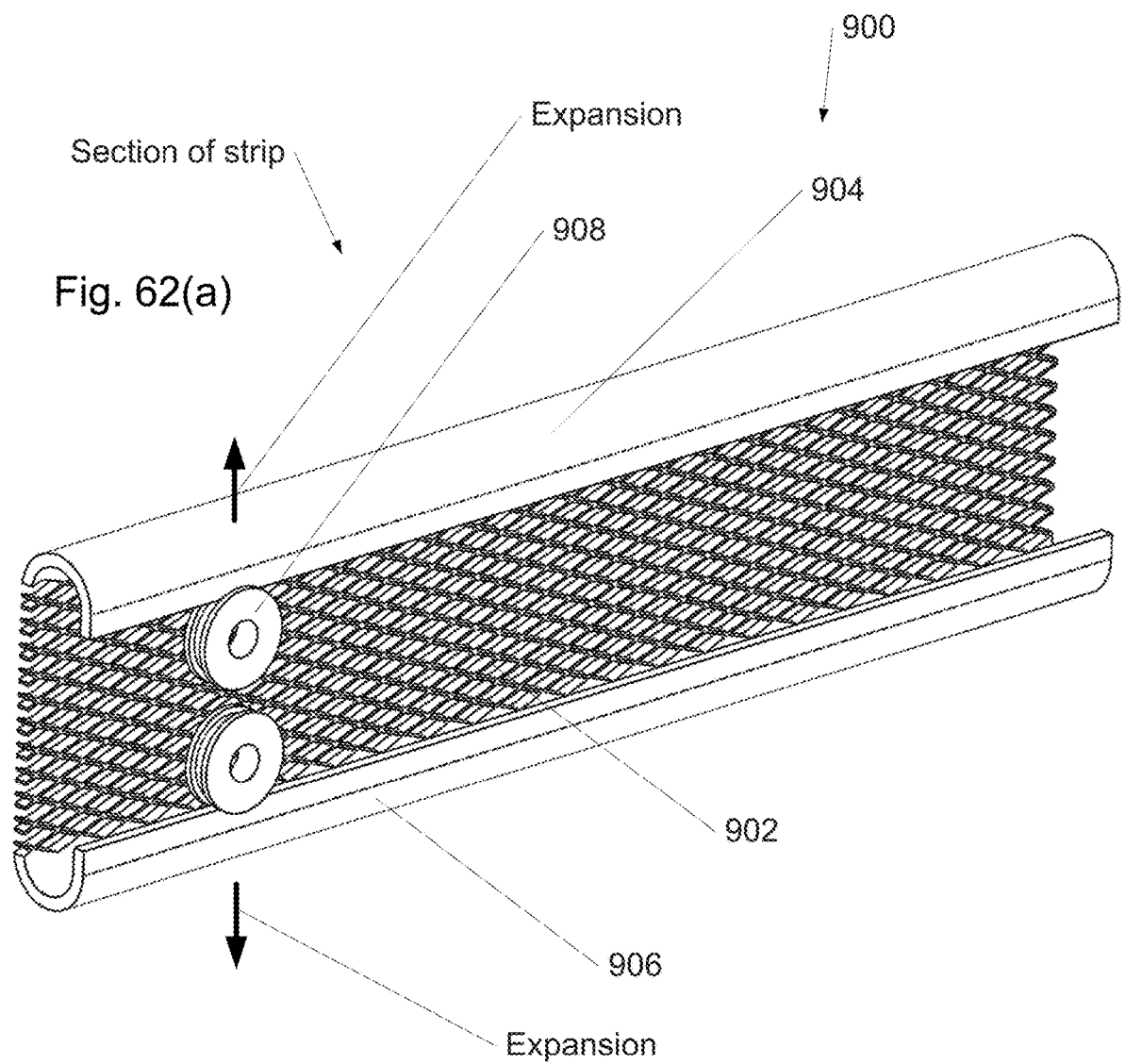
FIG. 62(a)-(b) shows a section of a strip from a continuously distally assembled/disassembled curved cannula in which the strip width is locally adjusted using an expandable region.
Figure 62B:
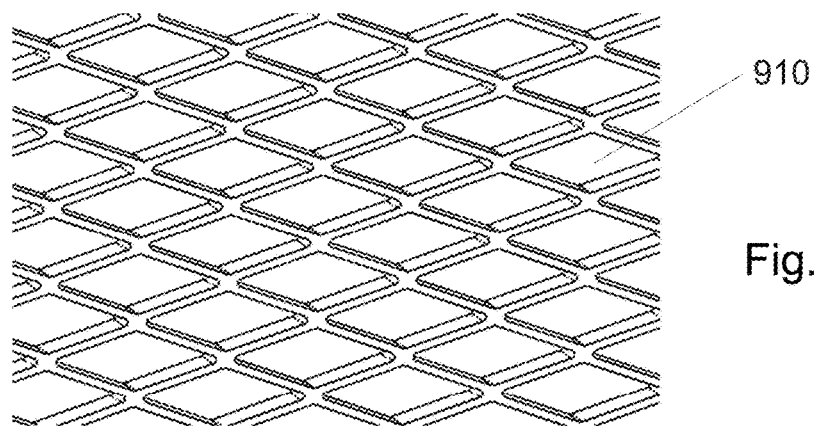

FIG. 62(*a*) depicts 3-D views of a section of a variable-width strip 900 used in some embodiments in a continuously distally assembled/disassembled curved cannula. The strip 900 comprises a central expandable region 902, shown enlarged in FIG. 62(*b*), sandwiched between an upper rail 904 and a lower rail 906, the entire structure forming a "C" shape. The structure can be produced by laser cutting or photochemical machining of a C-shaped extrusion, for example. Pulley-like wheels 908 are provided in some embodiments which ride along the upper rail 904 and/or lower rail 906. The wheels 908 roll on shafts (not shown) supported by a stylet, and the distance between the shaft axes can be changed continuously. For example, the stylet may comprise two coaxial tubes, which can be relatively translated along the tube axes so as to vary this distance. When the distance between the axes (and wheels) is increased, the expandable region—comprising material perforated (see perforation 910) with a diamond-like or other pattern as is known in the art of expanded metal and stent design—expands, plastically or elastically deforming the metal, and thereby increasing the width of the strip in the region. Not shown as gaps or cuts in the rails which allow the strip to contract longitudinally as it expands transversely. Such gaps, which in some embodiment variations may be oriented roughly parallel to the cannula axis or transversely, can also allow the strip to bend more easily, and may also be provided in the expandable region 902. Thus, as the wheels move along the strip, positioning each winding of the cannula adjacent to a more proximal winding and connecting the two together (e.g., using tabs and holes, not shown), the local strip width may be changed. In some embodiment variations, the expandable region is held in its final configuration by elements which are added to stabilize it against applied forces, such as a material which fills the perforations, and in such variations, the expandable region may be at least in part elastically deformed. In some embodiment variations, rather than push the two rails apart, the rails can be pushed together to reduce the width of the strip, or the width can be increased or decreased from an initial value.

24$^{th}$ Embodiment

Figure 63:
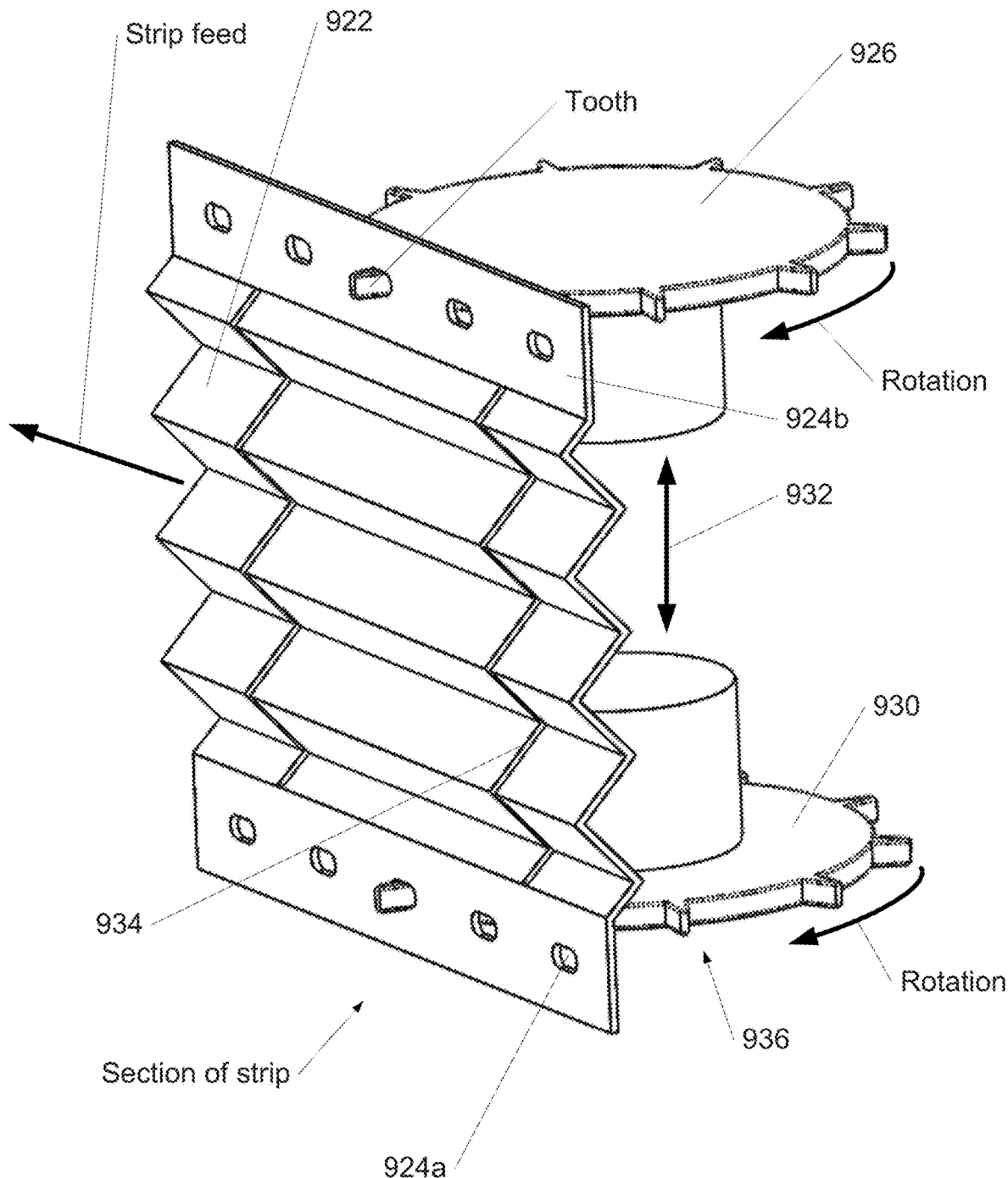
FIG. 63 shows a section of a strip from a continuously distally assembled/disassembled curved cannula in which the strip width is locally adjusted using a corrugated region.

FIG. 63 depicts a 3-D view of a section of a variable-width strip 920 used in some embodiments in a continuously distally assembled/disassembled curved cannula. The strip 920 has a corrugated region 922 between two sets of sprocket holes 924a,b. A rotating upper sprocket 926 is provided, supported by the stylet 936, with teeth 928 which engage the upper holes 924b, and a rotating lower sprocket 730 is similarly provided. As the stylet 936 rotates, the sprockets 926, 930 rotate, feeding the strip 920 into the growing cannula, forming a set of approximately helical windings. While this is occurring, the space 932 between the upper and lower sprockets 926, 930 can be varied continuously, e.g., by supporting the sprockets using two coaxial tubes which can be relatively translated along the tube axes, causing the corrugated region 922 to expand or compress (plastically or elastically) and thereby changing the width of the strip 920 and causing the cannula to curve. Cuts 934 can be provided in the corrugated section 922 such as those shown perpendicular to the strip long axis, parallel to the cannula axis, etc. to allow the strip 920 to bend more easily. In some embodiment variations, instead of a corrugated region, an expandable region like that in the 23$^{rd}$ Embodiment may be provided. In some embodiment variations, the shape of the corrugated region can be maintained against applied forces, e.g., by the addition of mechanical stabilizing elements.

25$^{th}$ Embodiment

FIG. 64 depicts an elevation view of a section of a variable-width strip 940 used in some embodiments in a continuously distally assembled/disassembled curved cannula. The strip 940 comprises an upper band 942 and lower band 944, two sets of fingers 946a,b—one moving and one fixed—and a flexure 948 which supports the moving fingers 946b. The moving fingers 946b and fixed fingers 946a can interdigitate/interleave with a varying amount of overlap, and in so doing, vary the distance between the upper and lower bands 942, 944, and thus the width of the strip 940. In some embodiments, to disengage the fingers 946a,b and change their position, the moving fingers 946b are pushed or pulled parallel to the strip long axis, causing the flexure to deform elastically. The separation of the upper and lower bands 942, 944 may then be adjusted. Next, the moving fingers 946b can be allowed to return to their original position as the flexure 948 relaxes, interleaving the fingers 946a,b again in a new position. In some embodiments, a boss on the rotating stylet (which as it turns is simultaneously joining one winding of the strip to an adjacent winding, not shown) can briefly engage the moving fingers 946a,b as the stylet rotates. In so doing, the moving fingers 946b can be pulled away from the fixed fingers 946a. Simultaneously, the distance between the upper and lower bands 942, 944 can be altered (e.g., the stylet may also include teeth which engage sprocket holes in the bands as in FIG. 63). In some embodiment variations, the flexures 948 are plastically deformed (or the fingers 946a,b are provided with a sliding capability) and the fingers 946a,b are not initially interleaved. The stylet then simply pushes (e.g., as its rotates) the moving fingers 946b into the fixed fingers 946a and they remain there, possibly retained in position by catch-like or ratcheting features.

In some embodiment variations, instead of interlaced fingers, a ratcheting mechanism may be provided such that when the two bands are pulled apart or pushed together locally, the new width is maintained by the mechanism.

26$^{th}$ Embodiment

FIG. 65(a) depicts a 3-D view of a (temporarily straight) section of C-shaped channel 950 forming a portion of a variable-width strip used in some embodiments of a continuously distally assembled/disassembled curved cannula. The channel 950 may be provided with a set of cuts 952 (e.g., across its width) to allow it to flex into a curved shape. FIG. 65(b) depicts a 3-D view of a cam 954 used with the channel. The cams 954 are elliptical as shown, but may have other shapes, and are provided with a drive hole 956 that allows them to be rotated. FIG. 65(c) shows a 3-D view of the strip section, comprising both channel 950 and one or more cams 954 which have been inserted into the channels so that their edges fit into the corners of the C shape. In the 3-D views of FIGS. 65(d)-(e), the cams 954a,b have been given two orientations. As shown, the orientations are the same for both cams 954a,b, but in practice they may be very different. In FIG. 65(d), the cams 954a,b are oriented so that their major axes are parallel to the longitudinal axis of strip 950. In this orientation, the cams 954a,b may only slightly stretch the channel 950—perhaps just enough to be retained in position by the reaction force of the channel clamping them—and the width of the strip is at its minimum. In FIG. 65(e), however, the cams 954a,b have been rotated (e.g., by inserting a driving element, which may be provided by the stylet, into their drive holes 956a,b) as shown such that the cam major axis is at a significant angle with respect to the long axis, and the strip 950 has deformed laterally to a substantially increased width. When the cam 954a,b major axes are perpendicular to the strip long axis, the width of the strip is maximized. Thus, the local width of the strip may be varied according to the cam 954a,b orientation.

The cams 954a,b may be initially located (e.g., by detents, a pivot, or clamping pressure) in between the cuts 952, so that they do not interfere with flexing of the channel. Once the channel is curved, the straight portion of the channel wall and the corner where that portion meets the curved portion, can press against the cams, helping to stabilize them in their desired orientations. Thus the orientations of the cams 954a,b may best be set before fully flexing the strip. In some embodiment variations, the cams 954a,b are retained in their orientations by teeth along their edges which fit into teeth within the C channel 950. In some embodiment variations, the cams 954a,b may be provided with flats along their edges to improve their rotational stability (e.g., they may be polygonal, but not with equal distances between opposite flats).

Figure 65F:
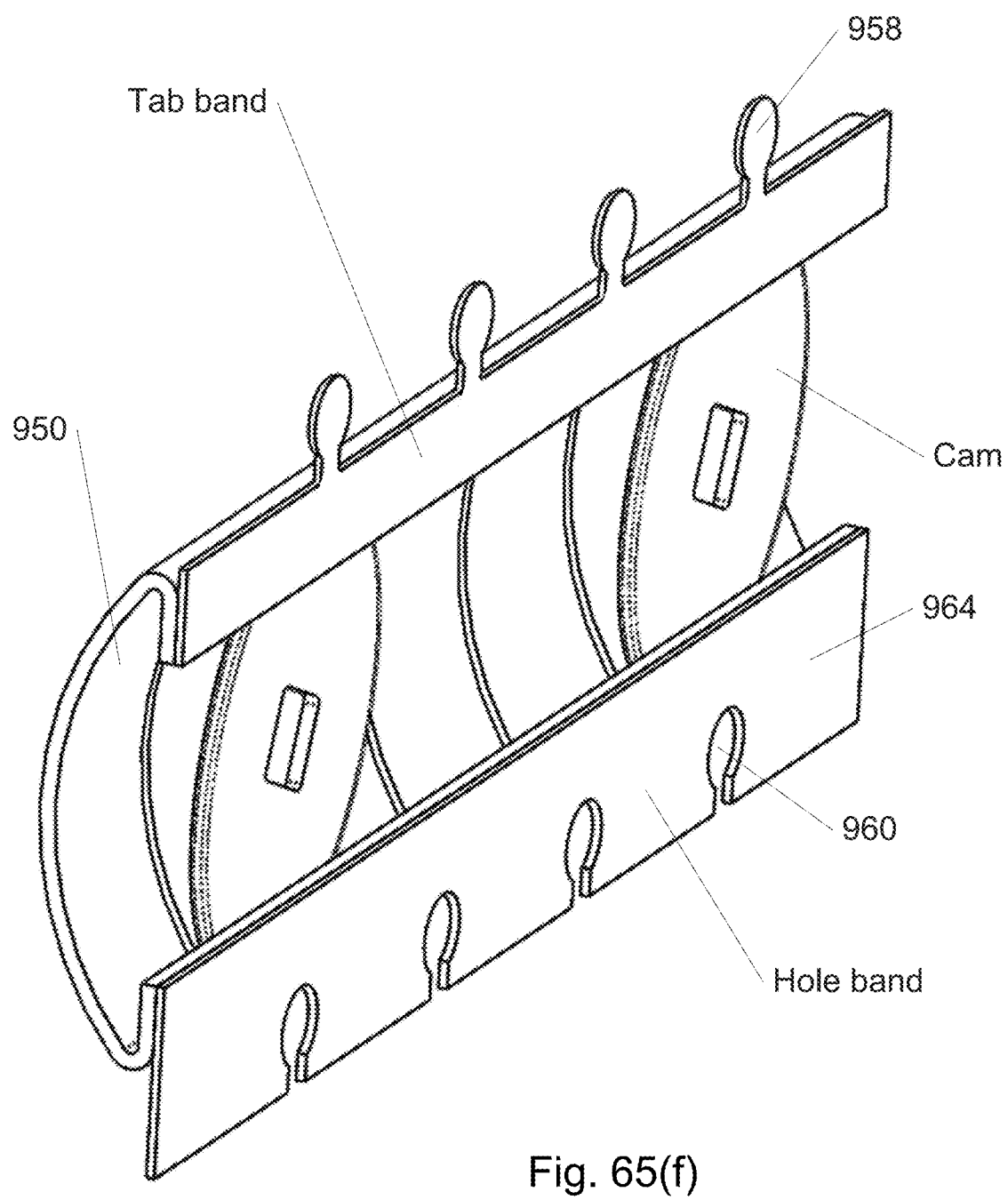

FIG. 65(f) depicts a strip similar to that in FIG. 65(d)-(e) but provided with structure for attaching the strip 950 to itself to form the windings of the cannula. As shown in one example, these structures include tabs 958 and holes 960 provided in attached (or integrated) bands 962, 964; however, other structures may also be used, as described elsewhere in this application.

In some embodiments, rather than using a C-shaped channel 950, a strip with an expandable region as in FIG. 62 may be used, as long as the expansion is elastic. In some embodiments, rather than these, a strip with a corrugated region such as in FIG. 63 may be used, again assuming elastic deformation of the corrugated region. In some embodiment variations, the location of the cams 954a,b may be varied (e.g., by the stylet sliding them within the channel) to better control the width of the strip. Indeed, in some embodiment variations, the cams 954a,b may have only be installed in a few orientations that are stable (e.g., major axis parallel or perpendicular to the strip long axis) and the wedge angle of the winding controlled by selecting among several cams with different axis dimensions, and locating them as needed along the strip (e.g., sliding them along the channel, if sufficiently loose; the cams can be kept from sliding too far by detents within the channel). In some embodiment variations, in lieu of cams 954a,b, pins of particular fixed lengths are used. If only the direction of curvature of the cannula is to be set, and each winding has a fixed wedge angle, then three or four cams of fixed width, or pins of fixed length, are all that is needed for each winding: the direction can be determined by where these are inserted in the channel. In some embodiment variations, the cams 954a,b can be fastened to the top and bottom flat sections of the channel in a way that allows rotation (e.g., via rivets), and when rotated using the drive hole, plastically deform the channel from a shape such as that in FIG. 65(e) to a shape such as that in FIG. 65(d). In some embodiment variations, cams (or pins) can be located inside the channel, while in some embodiment variations, if the minor axis is small enough to pass through the gap in the "C", they can be inserted into the channel where needed, then rotated.

27$^{th}$ Embodiment

Figure 66A:
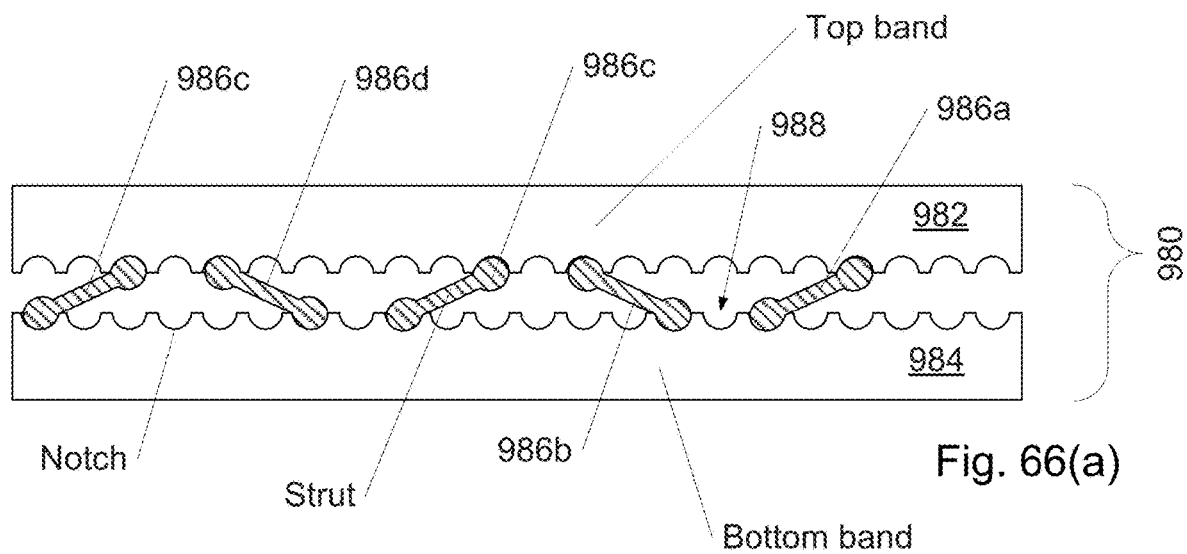
FIG. 66(a)-(g) shows a section and components of a strip from a continuously distally assembled/disassembled curved cannula in which the strip width is locally adjusted using struts or staples.
Figure 66B:
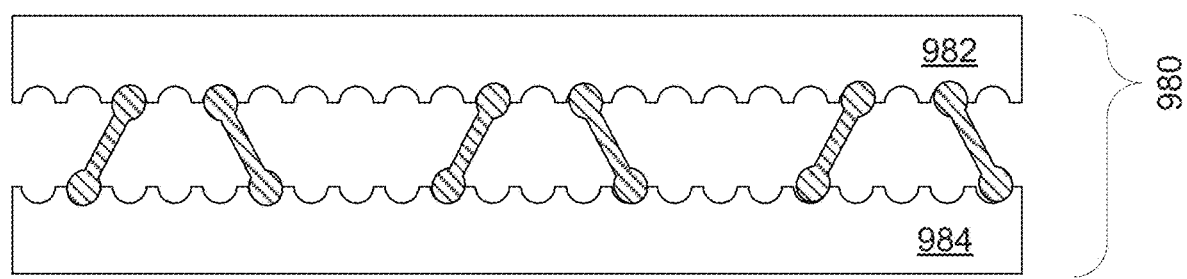
Figure 66C:
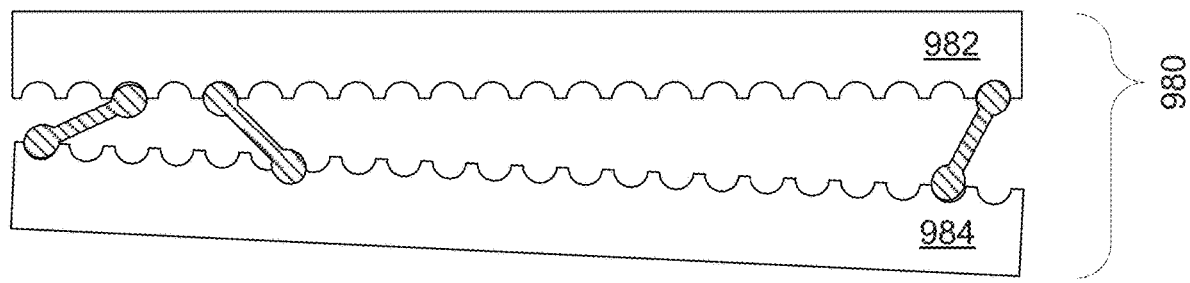

FIGS. 66(a)-(c) depict elevation views of a section of a variable-width strip 980 used in some embodiments of a continuously distally assembled/disassembled curved cannula. The strip 980 comprises at least two bands 982, 984 linked together by struts 986 a-e or similar elements. As shown in the figure, struts 986 a-e may fit into notches 988 in the bands 982, 984 such that they span across the two bands 982, 984 and keep them separate, either with a small separation (FIG. 66(a)), a large separation (FIG. 66(b)), or a varying separation (FIG. 66(c)), forming a wedge. Some struts are angled differently than others (e.g., some leaning to the left and some to the right as shown), preventing relative movement of the bands 982, 984 in shear which may make the structure collapse. The arrangement shown in FIGS. 66(a)-(c) is suitable when the cannula is loaded compressively along its long axis. If the cannula must handle tensile load, the struts 986a-e and notches 988 can be replaced by other elements such as U-shaped staples and holes, which will lock together the two bands 982, 984 in both compression and tension.

Figure 66D:
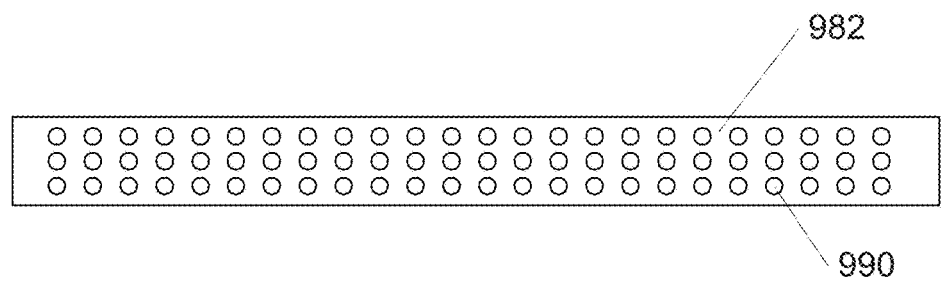
Figure 66E:
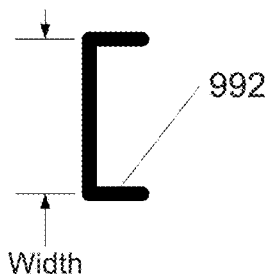
Figure 66F:
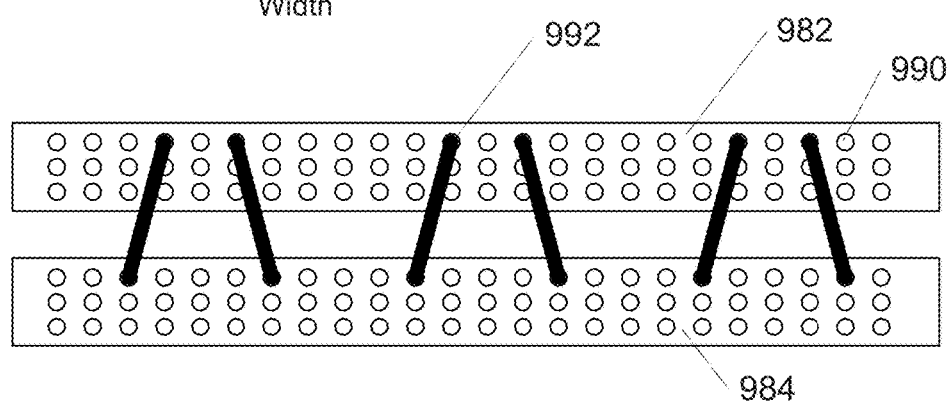
Figure 66G:
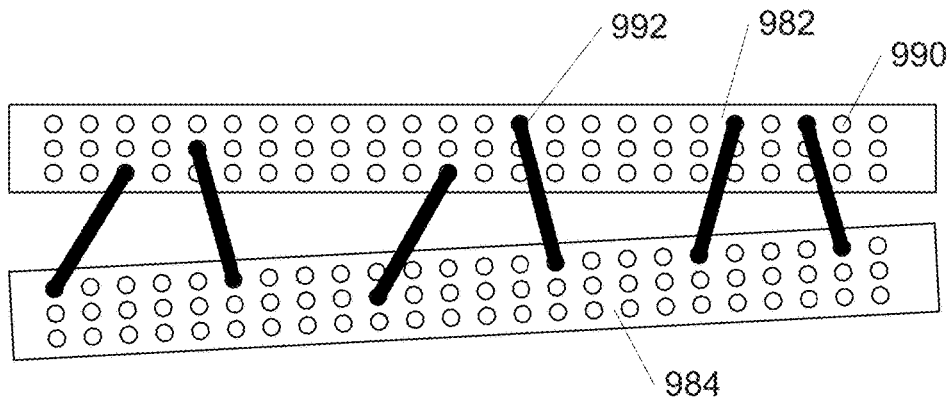

As previously described, a continuously distally assembled/disassembled curved cannula can use strips 982, 984 which overlap by variable amounts, or strips having variable widths (not depicted). FIG. 66(d) depicts in elevation view a strip 982 suitable for use in a curved cannula in which there is not necessarily any overlap between strips 982, 984 and the strips 982, 984 have constant width. The strips 982, 984 in general have a gap between them, and this gap can vary: sometimes being uniform and sometimes being non-uniform. The strips 982, 984 have an array of holes 990, which may be regularly spaced as shown, or irregular. FIG. 66(e) depicts a U-shaped staple (which can be removed for disassembly), which can be provided in various widths if required. In FIG. 66(f), the staples 992 have been inserted into holes 990 in the strips 982, 984 (e.g., by the stylet), linking them together in a stable configuration as long as the angles of the staples 992 are not the same and preferably, some staples 992 lean to the left and some to the right as shown in the figure. In some embodiment variations, the staples 992 are stretchable, not rigid.

In some embodiment variations, the staples 992 are not separate pieces, but are attached to the band or strip and are deformed (e.g., bent) so that their prongs enter suitable holes 990; this can be done by a mechanism on the stylet.

28$^{th}$ Embodiment

Figure 67A:
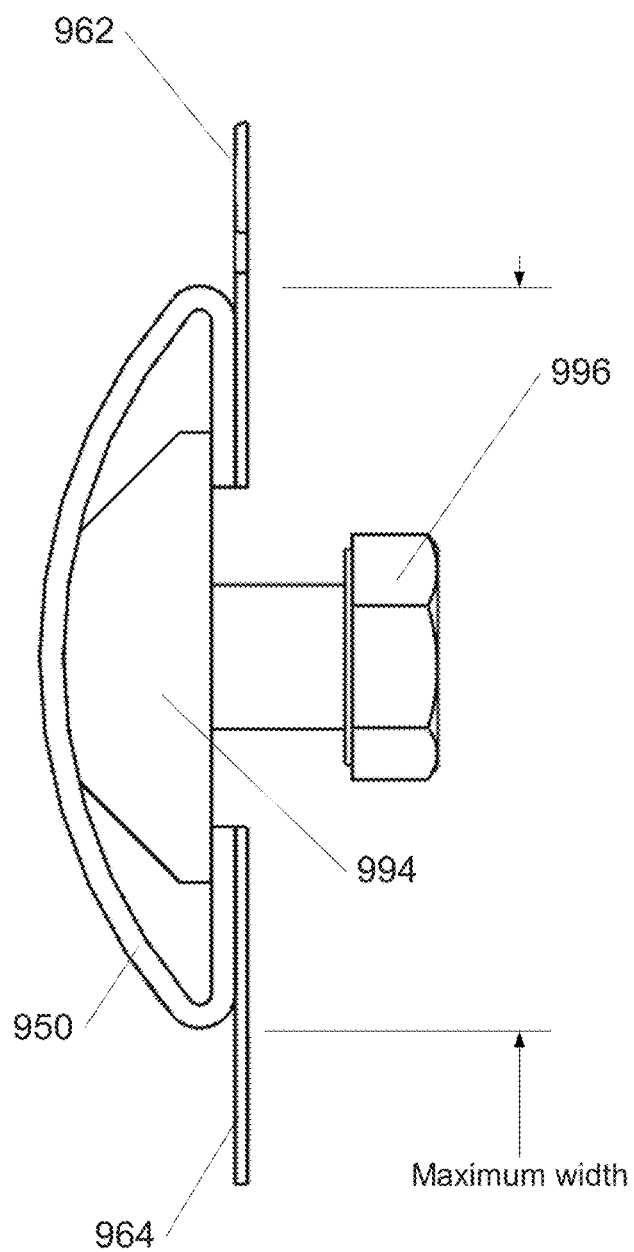
FIG. 67(a)-(d) shows sections and components of a strip from a continuously distally assembled/disassembled curved cannula in which the strip width is locally adjusted using a nut plate.
Figure 67B:
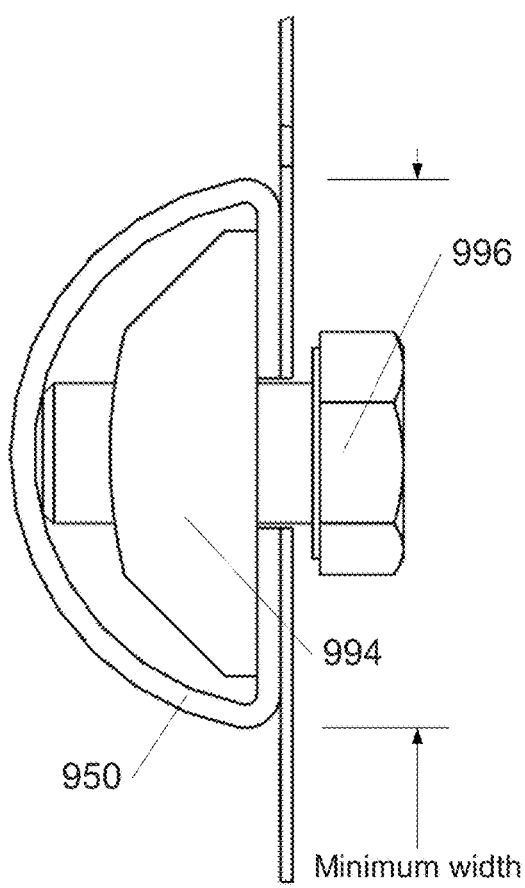
Figure 67C:
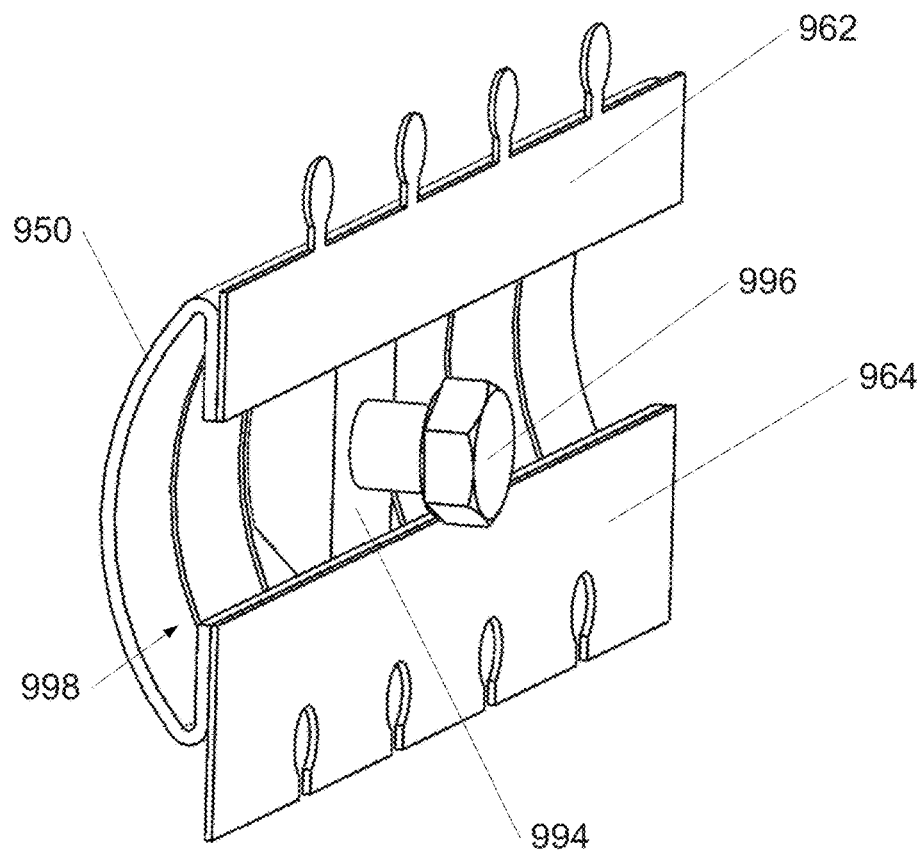
Figure 67D:
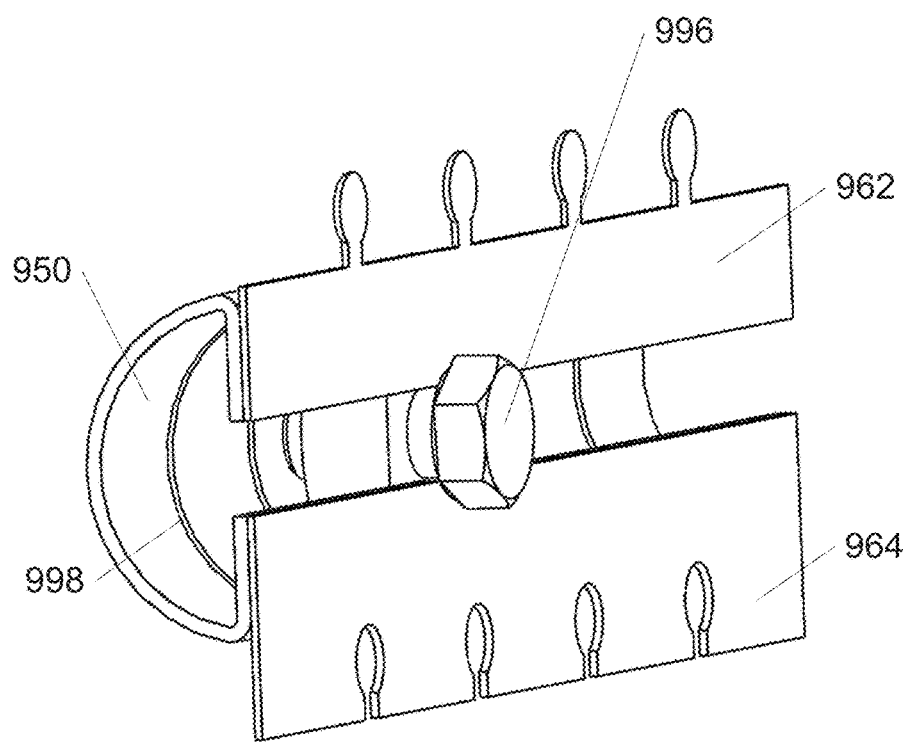
Figure 68A:
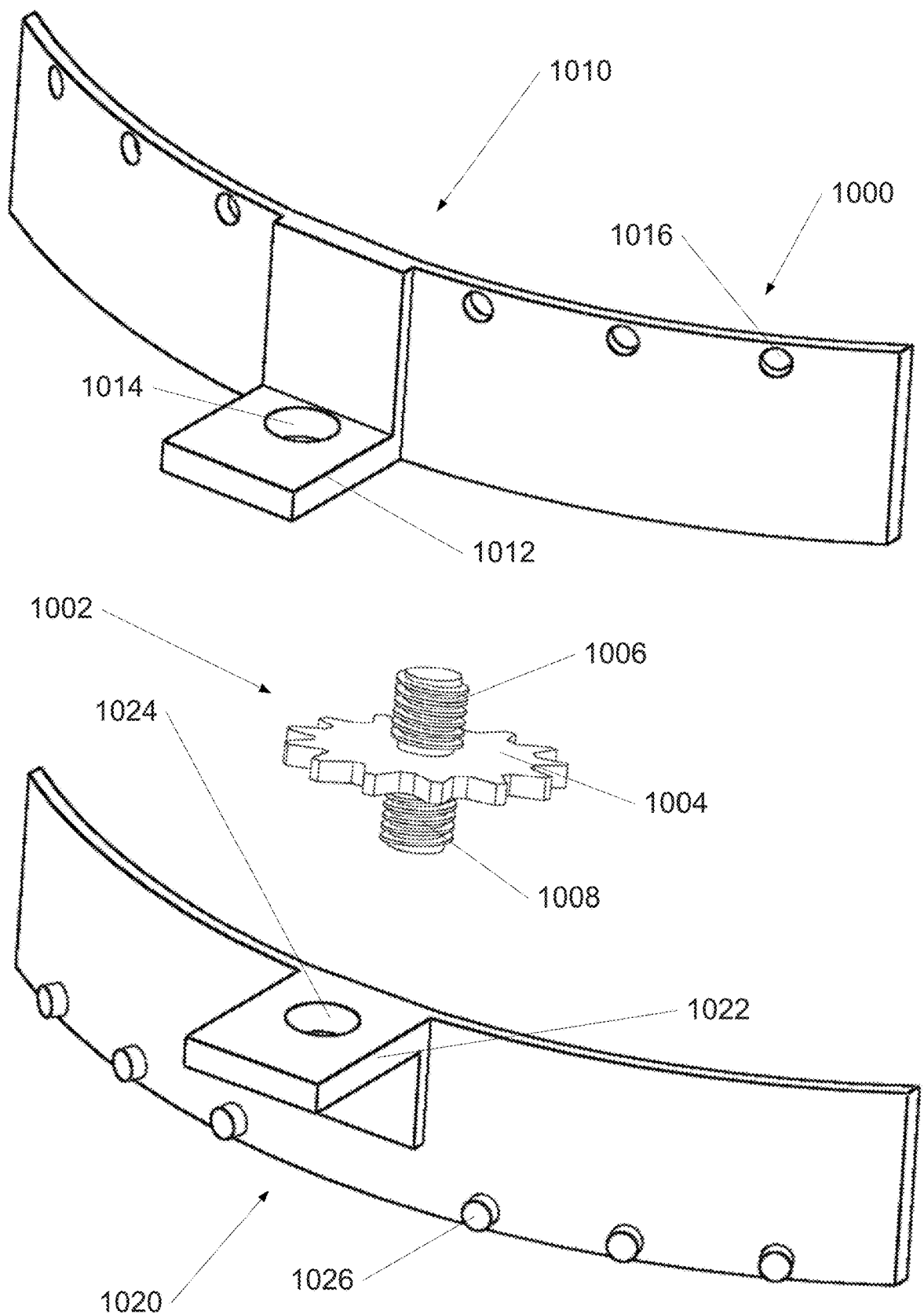
FIG. 68(a)-(e) shows sections and components of a strip from a continuously distally assembled/disassembled curved cannula in which the strip width is locally adjusted using a screw.
Figure 68B:
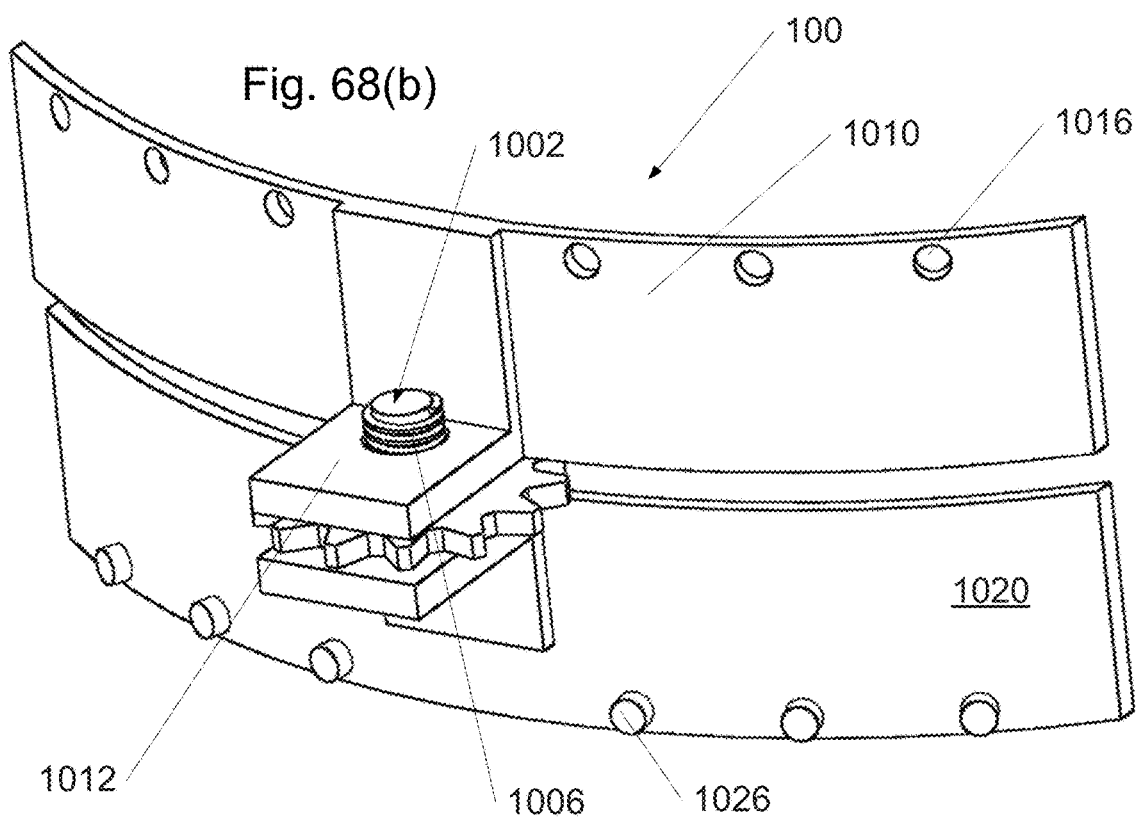
Figure 68C:
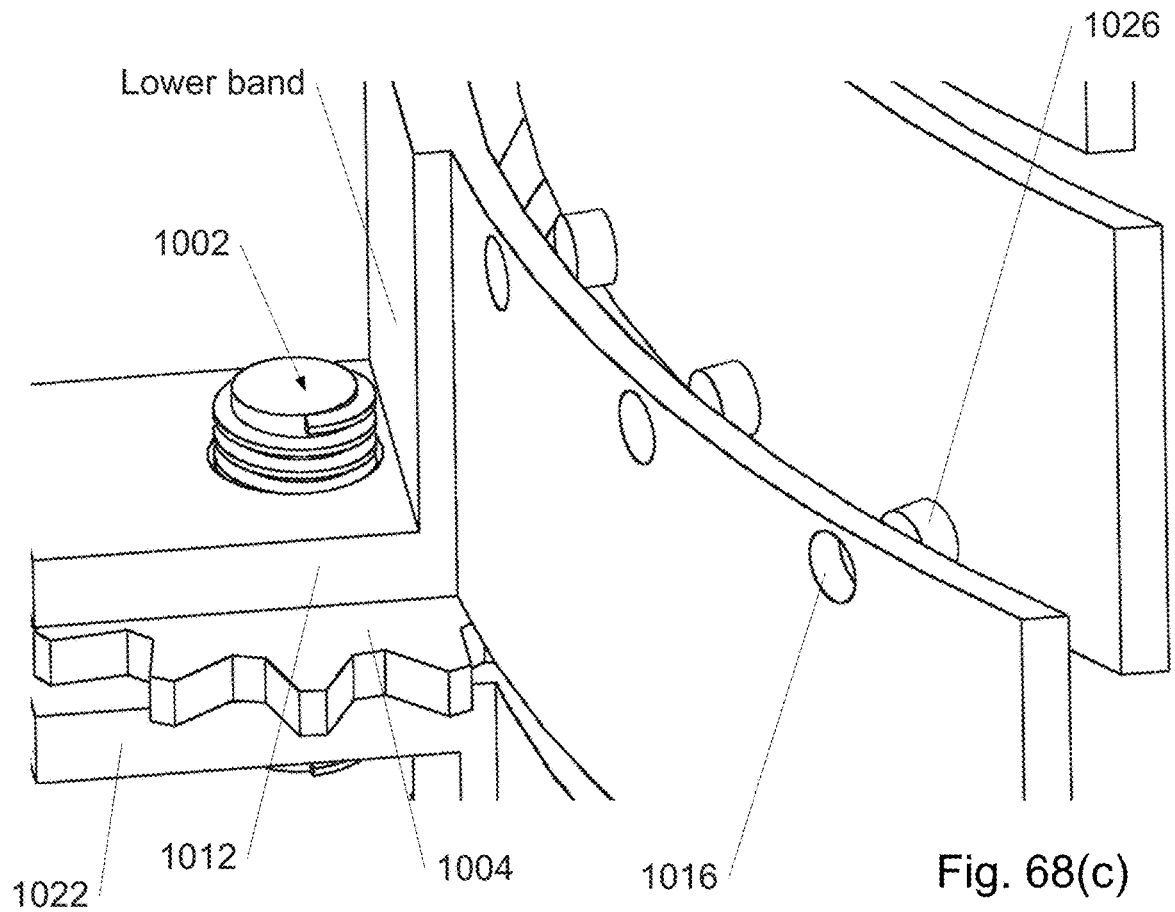
Figure 68D:
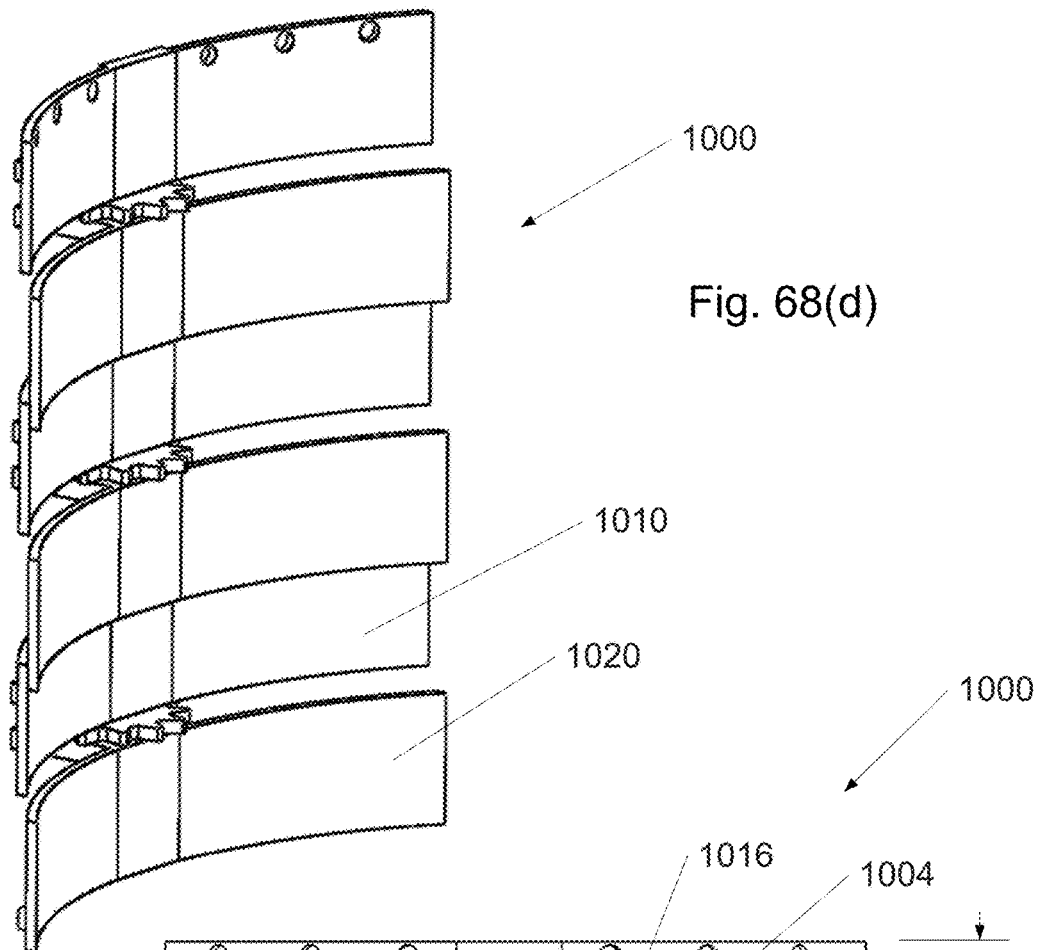
Figure 68E:
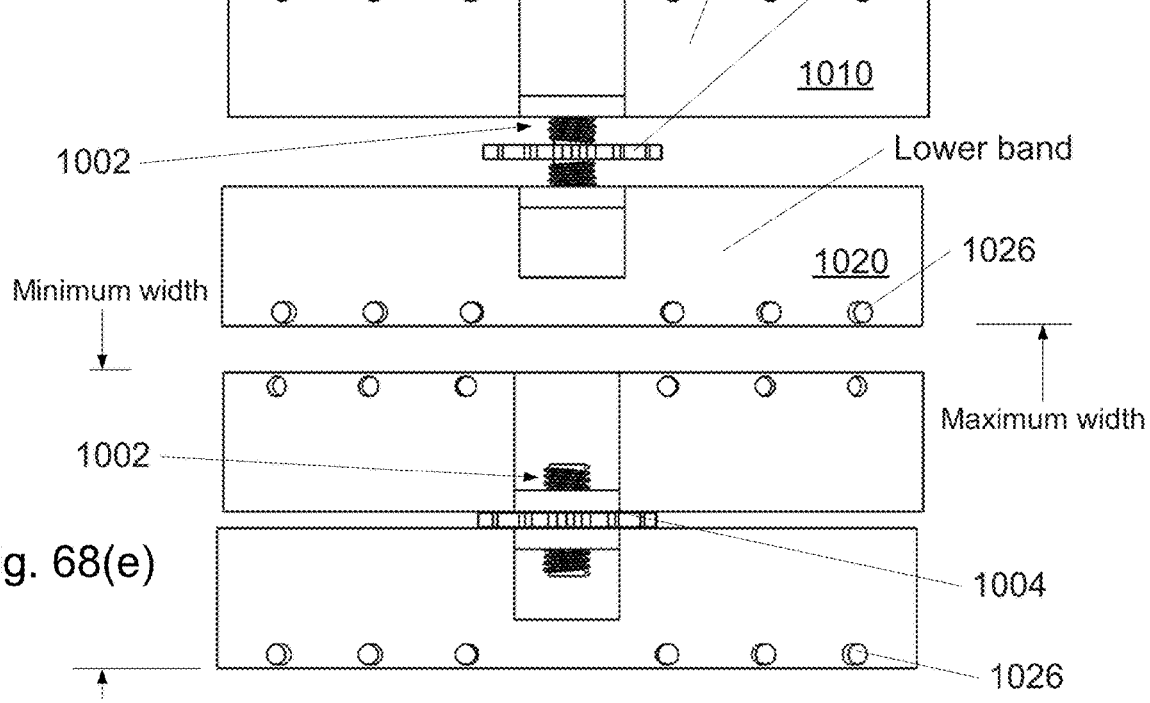

FIGS. 67(a)-(b) depict elevation sectional views of a C-shaped channel 950 similar to that of FIG. 65 which can be used in some embodiments of a continuously distally assembled/disassembled curved cannula. However, in lieu of a cam, the channel 950 is provided with a threaded "nut plate" 994 and a screw 996. A tab strip 962 and a hole strip 964 are also provided (shown in side view), to allow one strip section to be attached to another; however, other attachment structures can be used in some embodiments. The nut plate 994 is preferably shaped so that one surface conforms at least partially with the curved surface of the inner wall of the channel 950, such that the nut plate 994 is not able to move in the vertical (cross-channel) direction even before the screw 996 is tightened. In FIG. 67(a) and the 3-D view of FIG. 67(c), the screw 996 is loose and the local width of the strip is maximized. In FIG. 67(b) and the 3-D view of FIG. 57(d), the screw 996 has been tightened (e.g., by a mechanism on the stylet), forcing the screw 996 to push the inner wall of the channel 950 outwards. In so doing, the channel 950 adopts a deeper shape that is not as wide; thus when the screw 996 is fully tightened as shown, the local width is minimized. The channel preferably behaves elastically as the screw is tightened such that loosening the screw allows it to return to shallower shape that is wider. Cuts 998 may be provided in the channel to allow flexing. Initially the nut plates 994 may preferably be located away from the cuts 998, but once the channel 950 is curved, they may be slid to overlap the cuts 998. Tightening them in that position can tend to straighten the strip, and force the tabs into the holes, providing a preload if both are tapered. In FIGS. 67(c)-(d), additional bands have been added to the channel to provide for joining one winding to another, in the case shown, using tabs and holes.

By replacing the nut plate with a cam such as that in FIG. 65, it is possible to preload the cam against the channel such that it can positively lock in any desired orientation due to friction.

29$^{th}$ Embodiment

FIG. 68 depicts 3-D views of the components of variable-width strip 1000 used in some embodiments of a continuously distally assembled/disassembled curved cannula, with some similarities to the 22$^{nd}$ Embodiment. A screw 1002 with a thin central gear 1004 and left handed thread 1006 and righthand thread 1008 is provided. Also provided are an upper band 1010 having a narrow bracket 1012 with a threaded hole 1014 to accommodate the lefthand thread 1006 of the screw 1002, and with a set of holes 1016 which allow the band 1010 to be linked to a neighboring section of lower band 1020. Also provided is a lower band 1020 having a narrow bracket 1022 with a threaded hole 1024 to accommodate the righthand thread 1008 of the screw 1002, and with a set of pegs 1026 which fit into the holes 1016 on the upper band 1010, allowing the lower band 1020 to be linked to a neighboring section of upper band 1010. The bands 1010, 1020 are shown curved as they would be when incorporated into the cannula to form a portion of a winding. In some embodiment variations, brackets 1012 and 1022 may be produced by appropriately cutting and bending upper band 1010 and lower band 1020. In some embodiment variations, brackets 1012 and 1022 may be joined by a flexible element at a location which does not interfere with rotation of gear 1004, and thus brackets 1012 and 1022 and bands 1010 and 1020 may all be one piece. The flexible element may provide a preload that pulls together or pushes apart bands 1010 and 1020. In some embodiment variations, gear 1004 is attached to a single screw, serving as its head: the screw then passes through a clearance hole in bracket 1012 (or 1022) and screws into a thread (e.g., welded nut, microPEM® fastener (PennEngineering, Danboro, Pa.)) in bracket 1022 (or 1012); a slot in band 1010 or 1020 can be provided to allow the teeth of gear 1004 to be engaged from the inside of the cannula, and a flexure or spring between bands 1010 an 1020 can push the bands apart, acting against the screw, for example. In some embodiment variations, to avoid the risk of catching brackets 1012 and 1022 on other elements, such as when strip 1000 is passing through the cannula, they may include rounded/deflecting features (not shown).

In the 3-D view of FIG. 68(*b*), the strip 1000 is assembled. The gear 1004 protrudes through the gap between the bands 1010, 1020, allowing a drive gear on a stylet to engage it, as described already above. In some embodiments, the two brackets 1012, 1022 may be joined with a flexure at their outside edges, in which case the screw 1002 motion can be amplified since the flexure can act as a fulcrum. In FIG. 68(*c*), two adjacent sections of strip 1000 are shown being joined, such that the pegs 1026 of one enter the holes 1016 of another. Since the strip, if not fully plastically deformed, prefers to spring back to a larger radius, there is a natural preload of the lower band 1020 against the upper band 1010 when the strip is bent to form a portion of the cannula, which retains the pegs 1026 in the holes 1016. In some embodiment variations, the strips 1000 may be joined by other mechanically interlocking features such as arrays of bosses with appropriate shapes (e.g., circular, elliptical, hexagonal).

FIG. 68(*d*) shows a 3-D view of three sections of strip 1000 joined together. The bracket 1012 of the upper band 1010 is shorter than the bracket 1022 of the lower band 1020 such that when the strip 1000 is assembled, the inner radius of the upper band 1010 equals the outer radius of the lower band 1020. This allows for overlap of neighboring sections of the strip 1000 without changing the diameter. In the figure, the width of adjacent strip sections is the same. However, each portion of the strip 1000 can be individually adjusted. This is shown in the elevation views of FIG. 68(*e*), which illustrates two sections of strip, one with a maximum width, and one with a minimum width.

In some variations of this and the 22$^{nd}$ Embodiment, instead of a screw 1002 that changes the separation between the bands, the stylet can locally separate the bands by the required distance (e.g., using two coaxial graspers) and engage a locking mechanism such as a cam acting on a tab or rod fixed to one band and overlapping the other band) to set the distance between the bands. A less easily-reversible, variable-distance connection between bands can be made using welding, adhesives, and the like.

30$^{th}$ Embodiment

FIGS. 69(*a*)-(*b*) depict 3-D views (from outside and inside, respectively) of a band 830 serving as a component of a variable-width strip used in some embodiments of a continuously distally assembled/disassembled curved cannula. The band 1030 is shown curved as it would be when forming part of a cannula. The band 1030 comprises a fixed wedge 1032 connected to its body 1034 by a pedestal 1036 (which may be of a different width than shown, e.g., narrower), which allows for some flexing of the wedge relative to the body. Both the wedge 1032 and body 1034 are provided with elements such as female dovetail grooves 1038*a,b* (or T-slots, ZIPLOC®-type zipper connections, etc.), which allow interconnection of the band 1030 with one or more sliding wedges 1040 such as that in FIG. 69(*c*). The sliding wedge 1040 and the fixed wedge 1030 to which it is mated share a common ramp angle. The sliding wedge 1040 has two male dovetails 1042*a,b*, which can engage the female dovetails 1038*a,b* on the band 1030. It is also shown curved as it would be when part of the cannula. The dovetails (male or female) can be manufactured by single-sided photochemical machining, extrusion, etc., for example.

Pedestal 1036 may be of a different form than that shown in FIG. 69 in some embodiment variations. For example, it may comprise two flexural elements which support fixed wedge 1032. Such elements may have a serpentine shape that is in-plane with band 1030, and/or may be twisted in their midsections so that they are able to flex in the plane of band 1030. Rather than being formed from the same material as band 1030 and wedge 1032, pedestal 1036 may in some embodiment variations be produced, for example, by welding one or more wires (e.g., two symmetric wires) to band 1030 and wedge 1032.

FIGS. 69(*d*)-(*e*) are 3-D views (from outside and inside, respectively) of three sections of a strip 1050, each comprising a band 1030*a,b,c* and a sliding wedge 1040*a,b,c*, and each forming a portion of a winding of the cannula. Each band 1030*a,b,c* can be pre-assembled to a sliding wedge 1040*a,b,c* (e.g., with the two wedges pre-coupled), and during assembly of the cannula, the sliding wedges 1040*a,b,c* of one winding are joined to the body of the adjacent strip 1050 section. The circumferential position of a sliding wedge 1040*a,b,c* relative to its mating fixed wedge controls the local effective width of the strip 1050. Thus in FIG. 69(*d*), the middle sliding wedge 1040*b* is positioned so as to minimize the width, while the bottom sliding wedge 1040*c* is positioned to provide a relatively large width. The top sliding wedge 1040*a* is approximately in a middle position. In FIG. 69(*e*), depicting the strip 1050 sections from the inside of the cannula, the upper two sliding wedges 1040 *a,b* are roughly in a middle position, while the lower one 1040*c* is positioned to locally increase the width. Each sliding wedge 1040*a,b,c* can be provided with travel limit stops or frictional elements so that it is retained by the body and doesn't detach inadvertently move or detach. The ramp angle of the sliding and fixed wedges can be small enough that compressive or tensile axial loading on the cannula is not enough to cause motion of the sliding wedges 1040a,b,c, due to friction. Moreover, once the strip 1050 is bent to form windings of the cannula, the friction between the male 1042 (in FIG. 69(c)) and female dovetails 1038 (in FIG. 69(b)), or other junctions between elements of the strip 1050, will increase, in some embodiment variations preventing unwanted relative movement of the wedges. Other means of stabilizing the relative positions of the wedges may also be used, such as fasteners, adhesives, welding, and locking mechanisms.

Figure 69A:
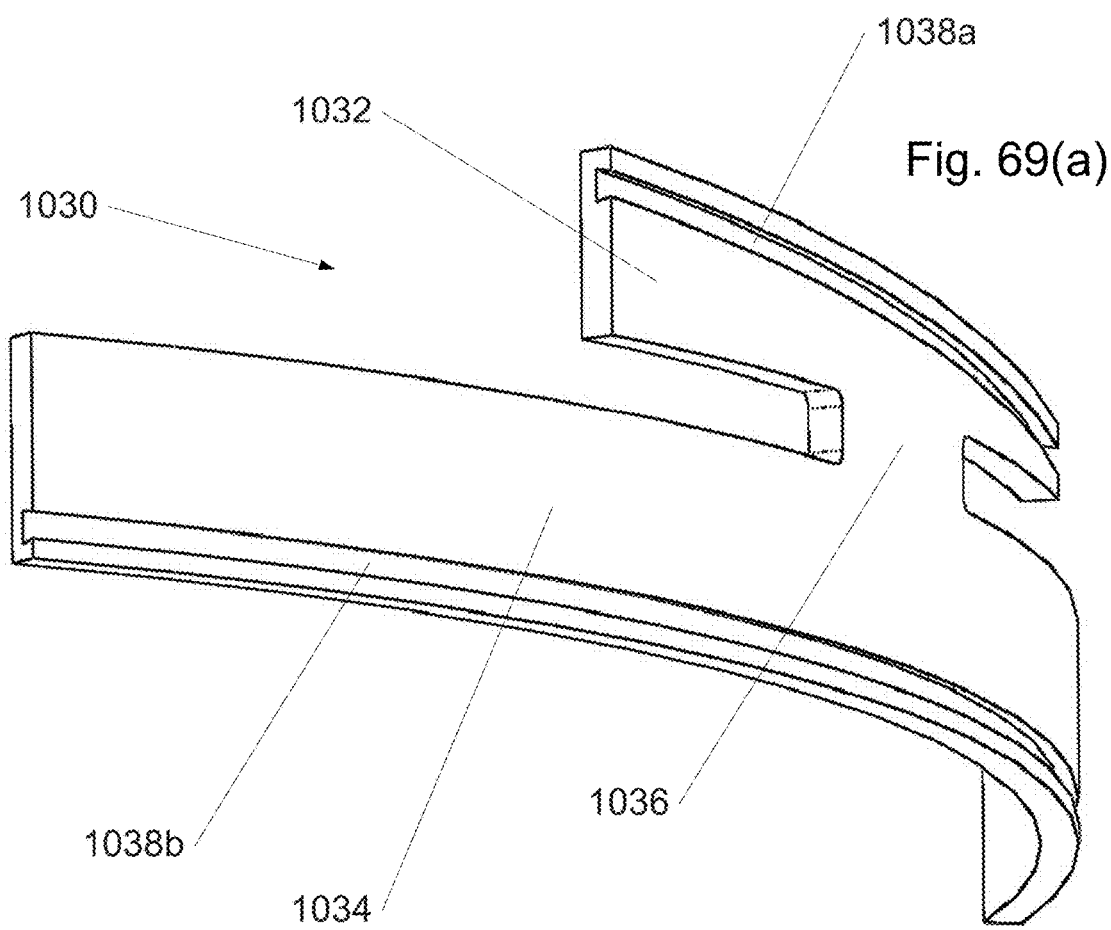
Figure 69B:
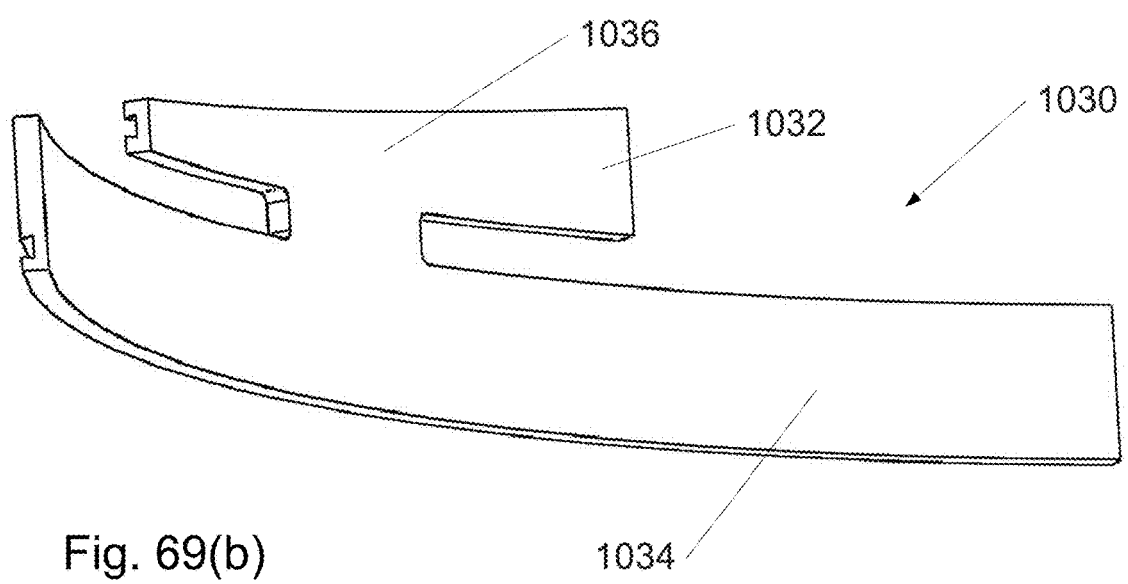
Figure 69C:
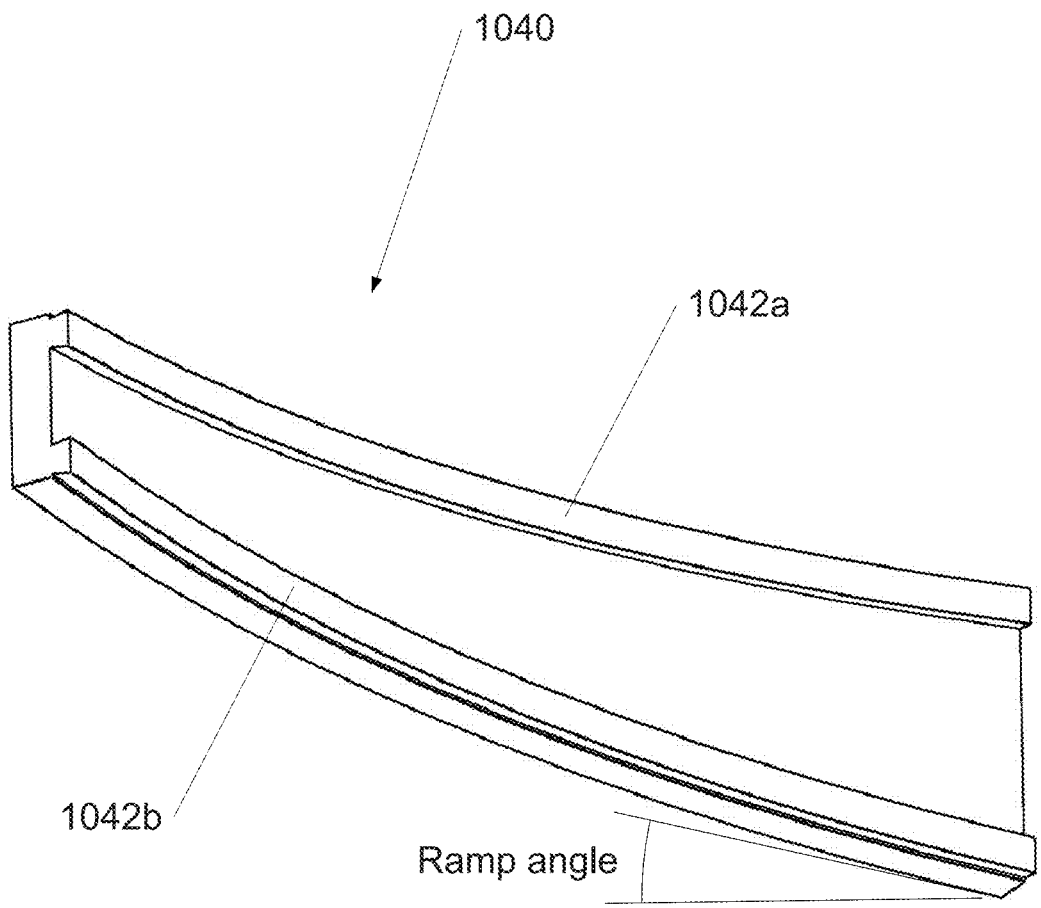
Figure 69D:
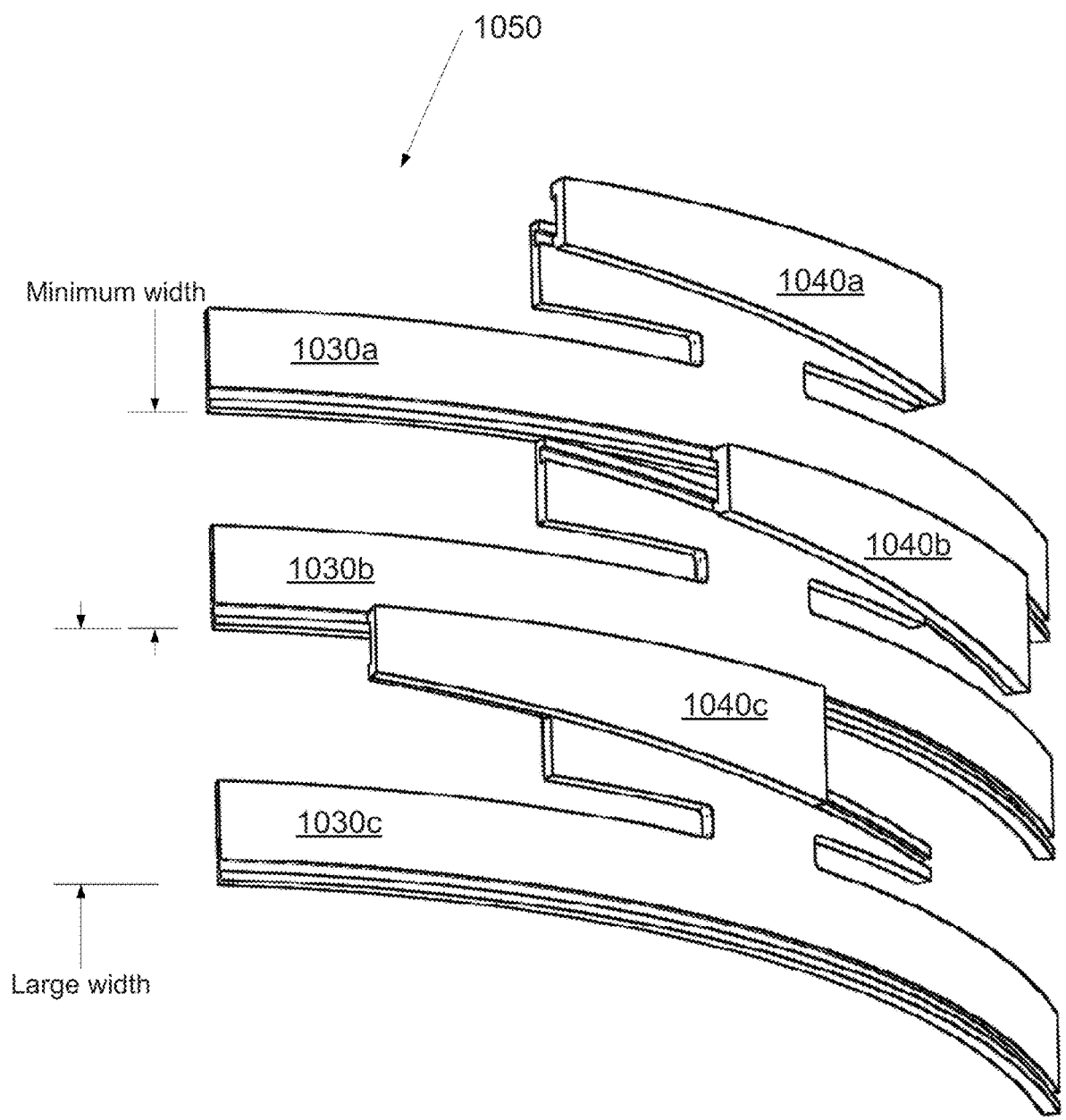
Figure 69E:
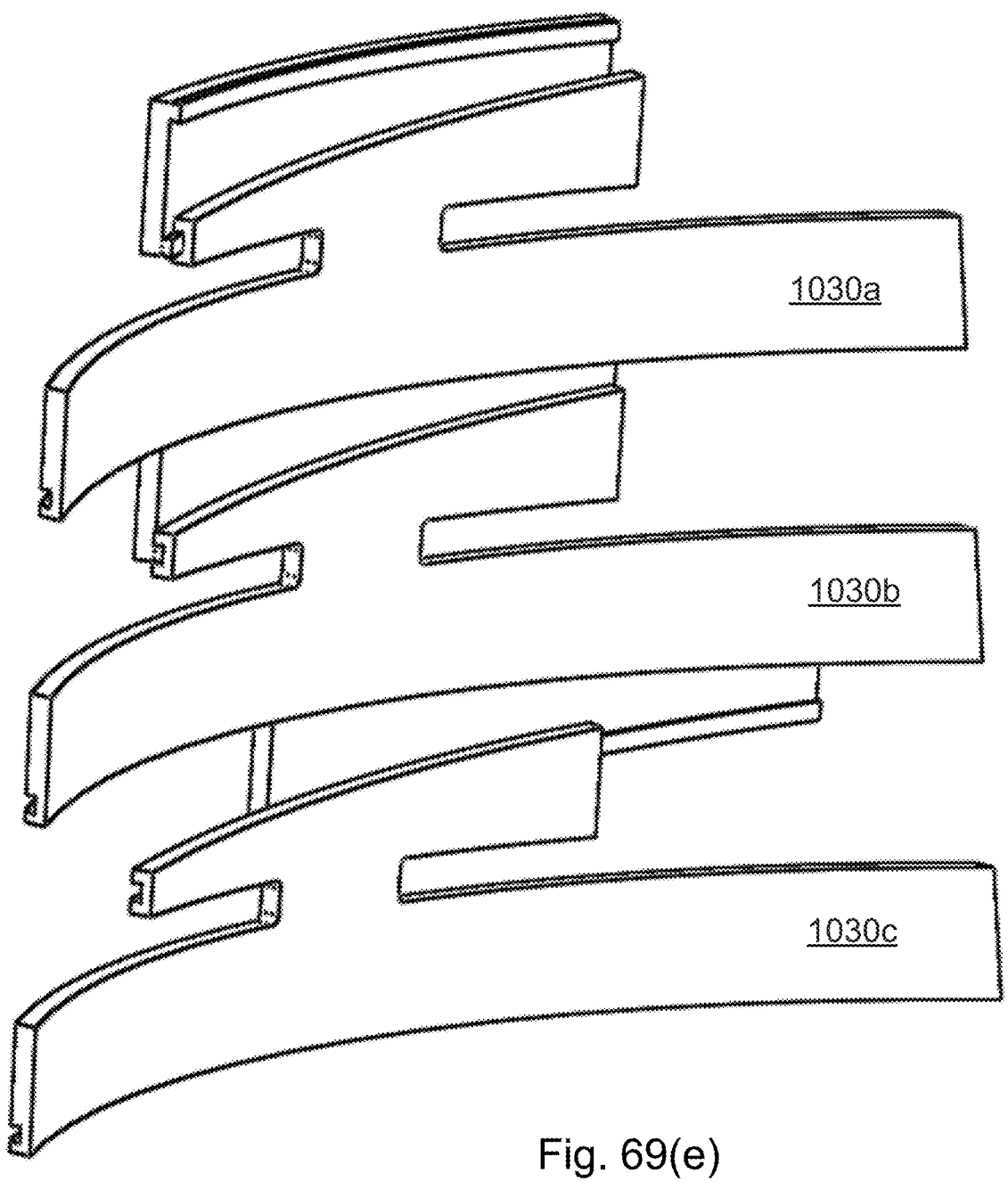
Figure 69I:
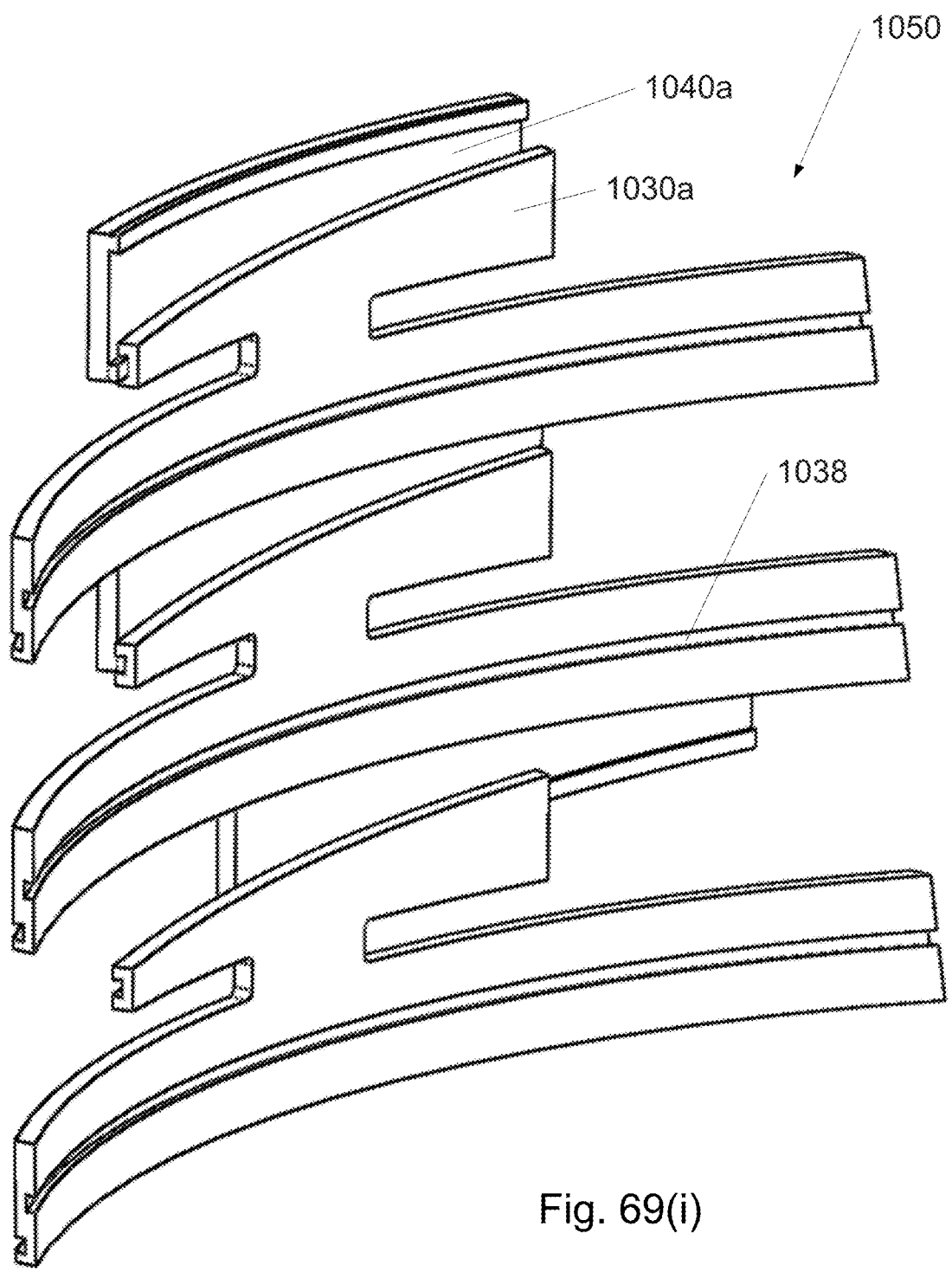

In the assemblies of FIGS. 69(d)-(e), the male and female dovetails 1042, 1038 are mated. However, while a male/female dovetail (1042/1038 in FIGS. 69(c) and (b)) is suitable for connecting the sliding and fixed wedges, it may not be suitable for connecting the sliding wedge to an adjacent body. Thus a different type of connection may be required, such as the compliant ZIPLOC®-type zipper connection shown in FIGS. 69(f)-(h). Such a connection allows for continuously-variable adjustment of the position of sliding wedges 1040 relative to fixed wedges 1032. However, many other attachment methods (e.g., those of FIG. 74) may be used, even if the adjustment is not continuously variable.

As shown in the 3-D sectional views of FIG. 69(f) and the 3-D view of FIG. 69(g), two sides of the connection can be joined together by virtue of the female feature 1062 deforming as it is pushed against the male feature 1064 (though in some embodiment variations the male feature may deform instead or as well). Side 1 1066 in the figure can represent the sliding wedge, while side 2 1068 can represent the body of the strip, or vice-versa. The male 1064 and female 1062 features can be manufactured through molding, or in the case of metal for example, also by welding 1070 a wire 1072 onto side 1 1066 for the male feature 1064, and welding 1070 a section of a tube 1074 onto side 2 1068 for the female feature 1062, as in FIG. 69(h). To increase flexibility, male 1064 and female 1062 features can incorporate cuts along their lengths in some embodiment variations. The stylet can be equipped to push together female feature 1062 and male feature 1064 during assembly, or during disassembly, pull them apart.

It is generally necessary to have a structure for the stylet to grasp and manipulate the strip during assembly and disassembly of the cannula. In the case of a strip of irregular shape such as that of the 30$^{th}$ Embodiment and in other embodiments, a track (e.g., a female dovetail 1038 as shown) may be provided on the inside surface of the strip as shown in the 3-D view of FIG. 69(i), which can be engaged by a suitable feature (e.g., a male dovetail) on the stylet. With the strip wound into an approximately helical shape, the female dovetail forms an approximately female track.

The positions of the sliding wedges 1040 may be set in advance, while the strip is being fed to the distal end of the cannula, or while the strip 1050 is being formed into windings of the cannula. For example, while the strip 1050 is being delivered, rollers, arms, or other elements (e.g., attached to the stylet) can separately drive the sliding wedges 1040, but at different relative speeds, thus causing sliding wedges 1040 to slide relative to the fixed wedges 1030, which are attached to the body of the strip 1080 (in FIG. 69(k)). Sliding wedges 1040 can be engaged, for example, by a U-shaped member which surrounds them and allows force to be applied to either their narrow or wide ends. The U-shaped member may be driven by a rotary actuator, for example, which itself rotates with the stylet.

Figure 69J:
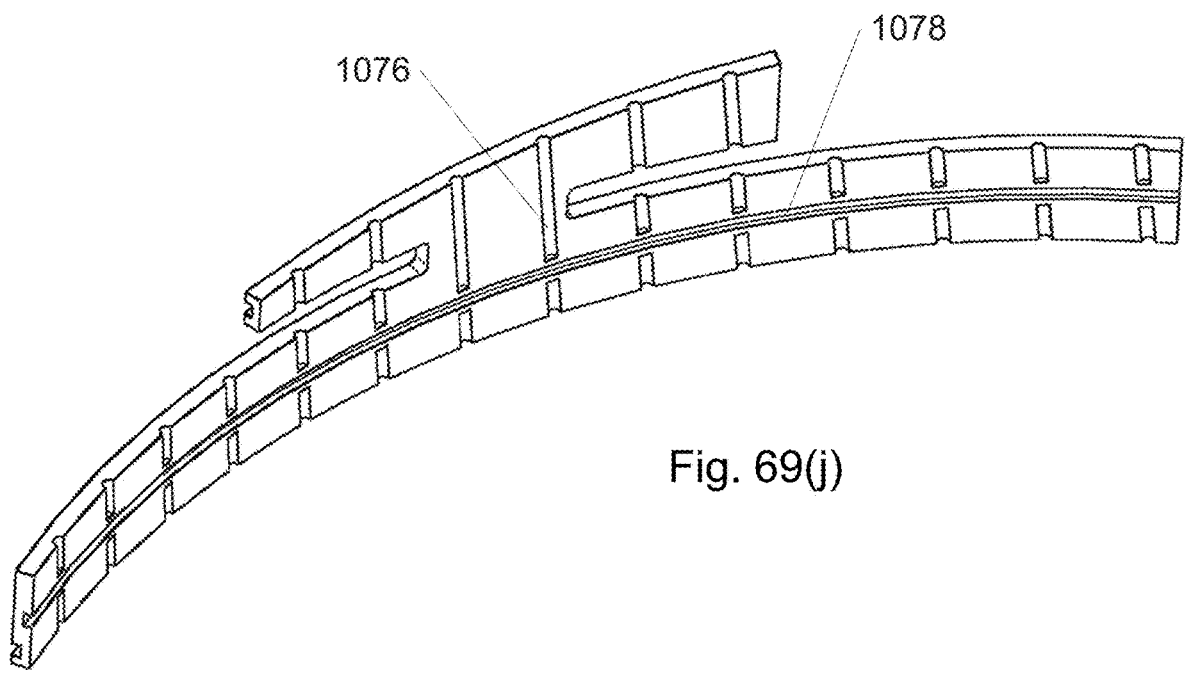
Figure 69K:
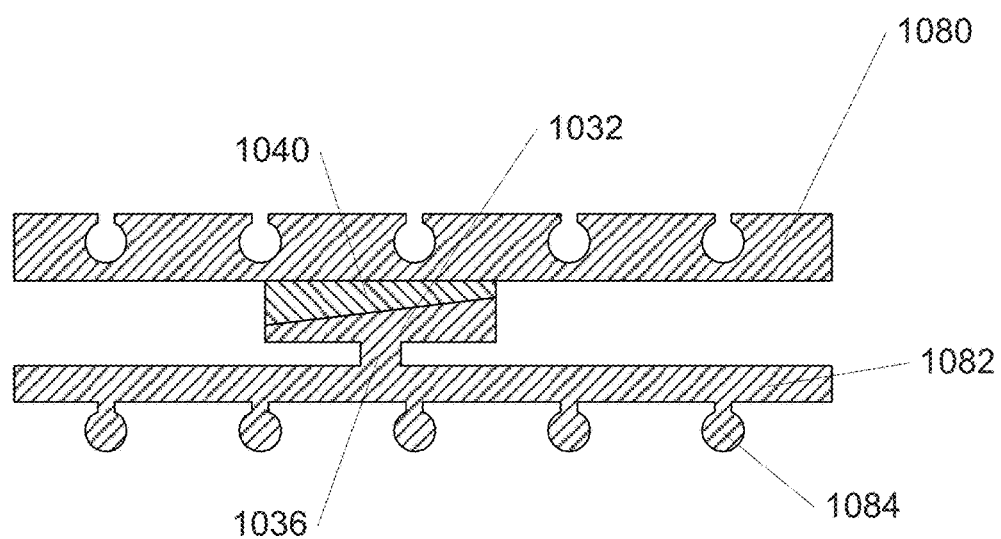
Figure 71A:
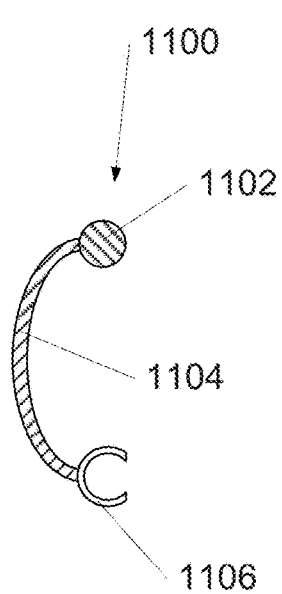
FIG. 71(a)-(d) shows a section and components of a strip from a continuously distally assembled/disassembled curved cannula in which the separation of wires is locally adjusted using stiffeners.
Figure 71B:
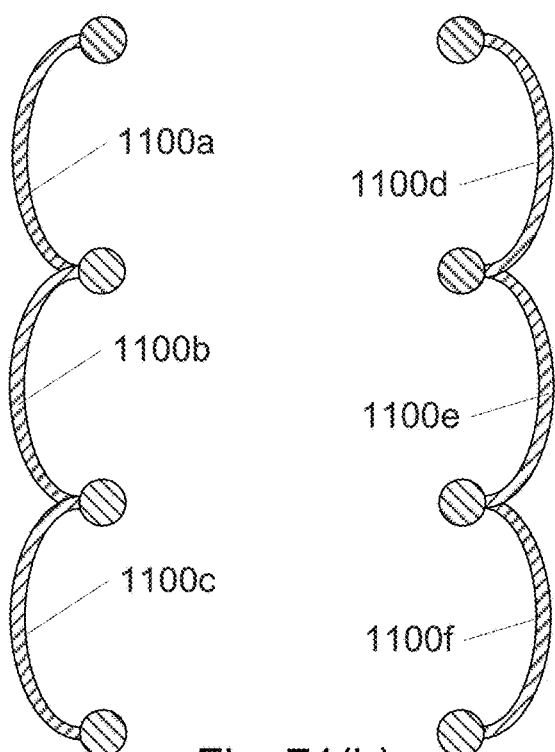
Figure 71C:
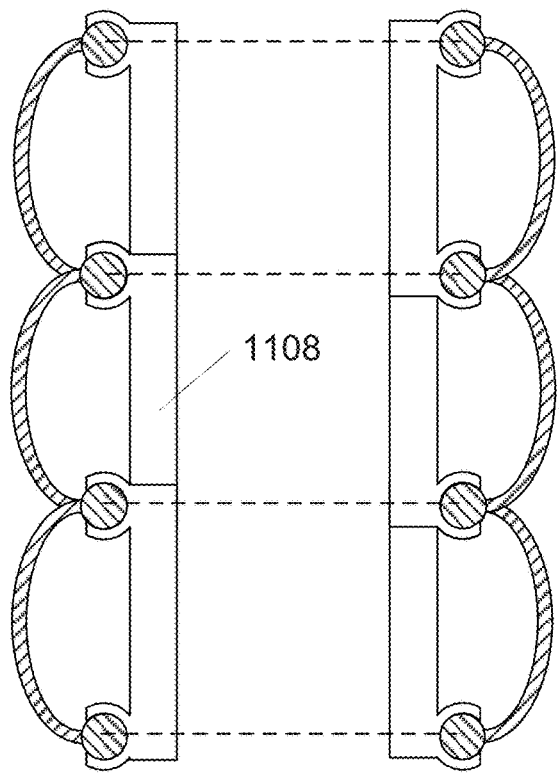
Figure 71D:
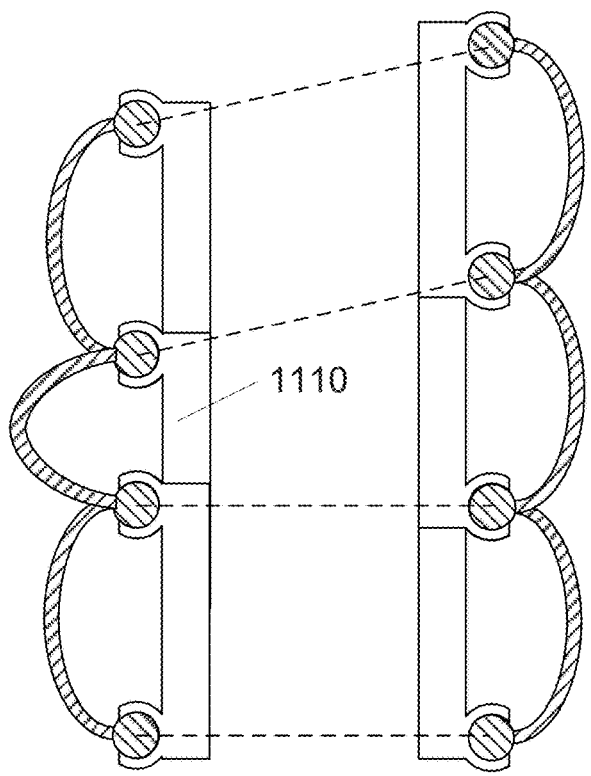

To reduce the bending stiffness of the strip of the 30$^{th}$ Embodiment, partial-depth cuts 1076 (or cuts which pass entirely through the strip) may be provided as shown in FIG. 69(j) (or if it is already flexible enough to bend in this direction, but too flexible in the width direction, ribs can be added to stiffen the strip). In some embodiment variations these do not intersect the female dovetail 1078 as shown, thus avoiding edges which may catch on the male dovetail of the stylet. Similar cuts 1076 may be provided on the sliding wedge 1040. FIG. 69(k) is an elevation view of a modified design similar to that of FIG. 69(d), but in which the strip 1050 comprises two bands 1080, 1082, a fixed wedge 1032 connected to one band by a pedestal 1036, and a sliding wedge 1040. The bands 1080, 1082 can be provided with inter-strip connection elements such as tabs 1084 on tab band 1082 and holes 1086 on hole band 1080, as shown. As before, positioning the sliding wedge relative to the fixed wedge changes the effective local width of the strip. Since mating features such as female dovetail 1038, male dovetail 1042, female feature 1062 (in FIG. 69(g)), and male feature 1064 (in FIG. 69(g)) are circumferentially continuous and can mate in a variety of positions, it is possible in some embodiment variations not only to assemble the cannula with a variety of constant diameters, but also to vary the diameter continuously (e.g., make it tapered).

In some embodiments, windings based on sliding wedges such as wedge 1040a of FIG. 69, as well as other joining/adjustment approaches, may be adjusted after the winding has been joined to its neighbor and become a part of the cannula. Indeed, adjustment may be done of windings which were formed much earlier. The stylet can move to the position of the winding to be adjusted. In the case of sliding wedges, the stylet can push or pull (which may be preferable to avoid buckling) on the sliding wedge such as wedge 1040a to adjust its position. However, since there can be considerable friction between fixed and sliding wedges when they are curved, and/or compressive or tensile stress on the coupling between them such as dovetails 1042a,b, the stylet can flatten a given wedge pair and unload the stress from the coupling if required, then adjust the sliding wedge position, then allow the wedges to re-curve and be reloaded.

31$^{st}$ Embodiment

FIG. 70 depicts cross-sectional elevation views of a tube 1090 which can serve as a component of a variable-width strip used in some embodiments of a continuously distally assembled/disassembled curved cannula. In FIG. 70(a), the tube 1090 is collapsed and at its maximum width. In FIG. 70(b), an expansion element 1092 (e.g., a ball, block, or powdered material) has been positioned within the tube 1090 to locally prop it open elastically, or deform it plastically (in which case the expansion element can be removed or relocated). In so doing, the tube 890 becomes narrower in width. While only depicting a single expansion element 1092, multiple expansion elements 1092 can be slid up or down the longitudinal axis of the tube 890 to the desired location as needed.

In some embodiment variations, the strip can comprise at pair of facing surfaces of which at least one is ramped. A ball, wheel, or other shape can roll or slide between these surfaces, pushing them apart, and thus altering the width of the strip. If the angle of the ramp is shallow, friction may retain the ball or other object in position, but detents can also be provided, or the object can be secured in place by other means (welding, adhesive, fastener, etc.).

32$^{nd}$ Embodiment

FIG. 71 depicts in sectional elevation views a portion of a continuously distally assembled/disassembled curved cannula, and the strip used to construct it. The cannula is similar in some respects to a flexible, wire-reinforced aluminum foil ducting used for clothes dryers and other applications, but is distally built-up from a strip, is more robust, and is provided with clips which rigidify it in the desired shape. In FIG. 71(a), a single strip 1100 is shown, comprising a wire 1102 and a band 1104 which may be appropriately scored, cut, or perforated as needed to be flexible in both directions. A structural element such as clip 1106 is depicted on one edge of the band 1104 to attach each winding of the strip to adjacent, more proximal winding. As the strip is wound (e.g., by a stylet within the cannula lumen), the clips 1106 are clipped onto the wire 1102 (in some embodiment variations, holes in the band adjacent to the wire are provided at intervals to allow the clip 1106 to surround the wire 1102). Without any stiffeners, the result of assembly of the strips 1100a-f is a flexible cannula such as that shown in FIG. 71(b). However, while the cannula is assembled, or in some embodiment variations afterwards, stiffeners can be added that clip onto the wire 1102 and set the distance between adjacent turns of the wire 1102. In FIG. 71(c), long stiffeners 1108 have been used exclusively, thus creating a constant distance between turns, which are parallel. In FIG. 71(d), short stiffeners 1110 have also been used, causing the turns to no longer all be parallel, thus introducing curvature into the cannula. In some embodiment variations, the stiffeners 1108, 1110 are provided in fixed lengths (of which long and short are examples) and in some embodiment variations the stiffeners 1108, 1110 are adjustable in length (e.g., using a screw, telescoping and locking elements, etc.) Stiffeners 1108, 1110 can be wide enough in the circumferential direction that they are stable against circumferential shear, or may be angled (e.g., some leaning to the left, some to the right) if not sufficiently wide to be stable. In some embodiment variations, the cannula can be comprised primarily of wire 1102 and stiffeners 1108, 1110, without the band 1104 and/or the clips 1106.

33$^{rd}$ Embodiment

Figure 72A:
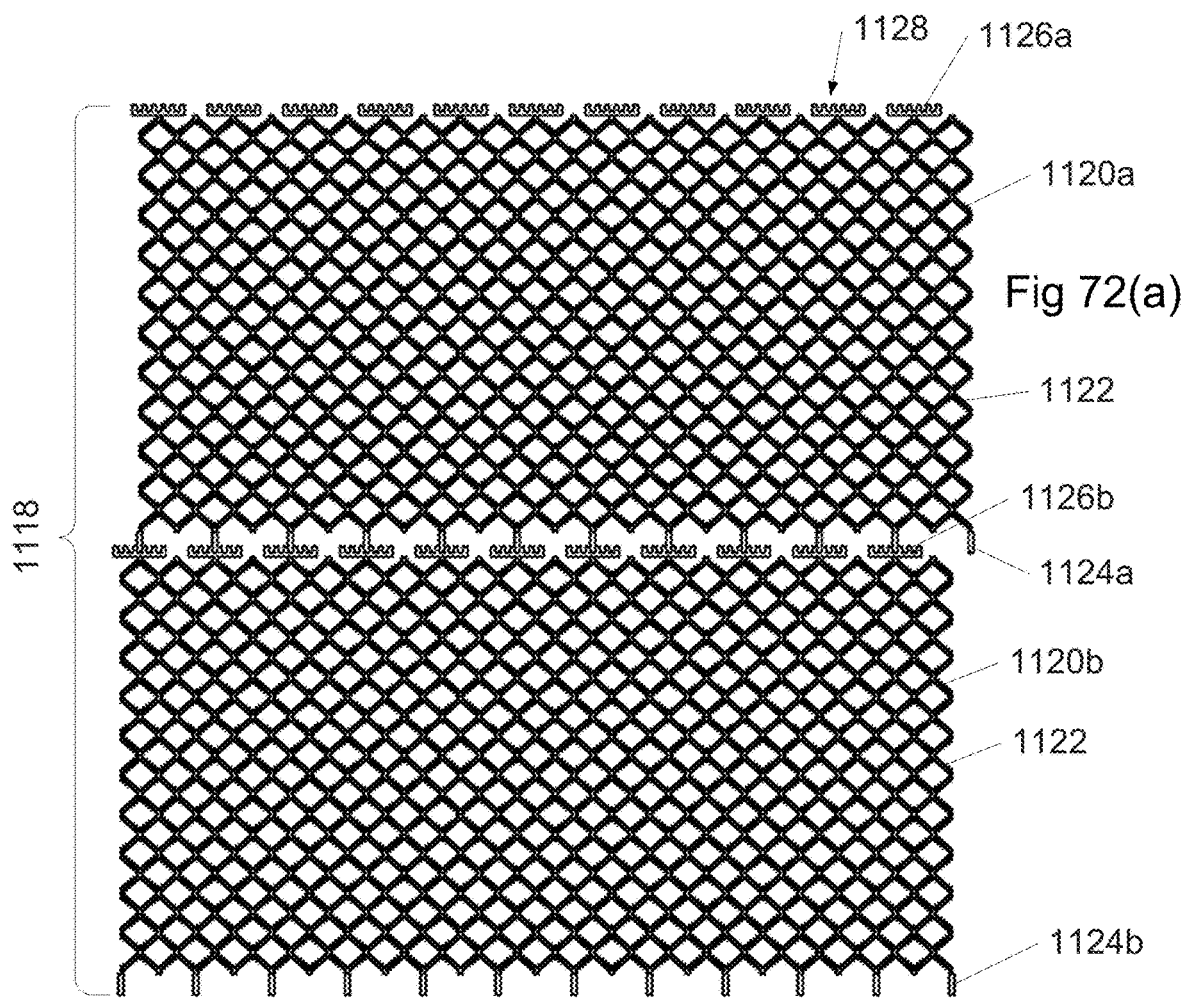
FIG. 72(a)-(b) shows a section of a strip from a continuously distally assembled/disassembled curved cannula in which the strip width is locally adjusted using an expandable region.
Figure 72B:
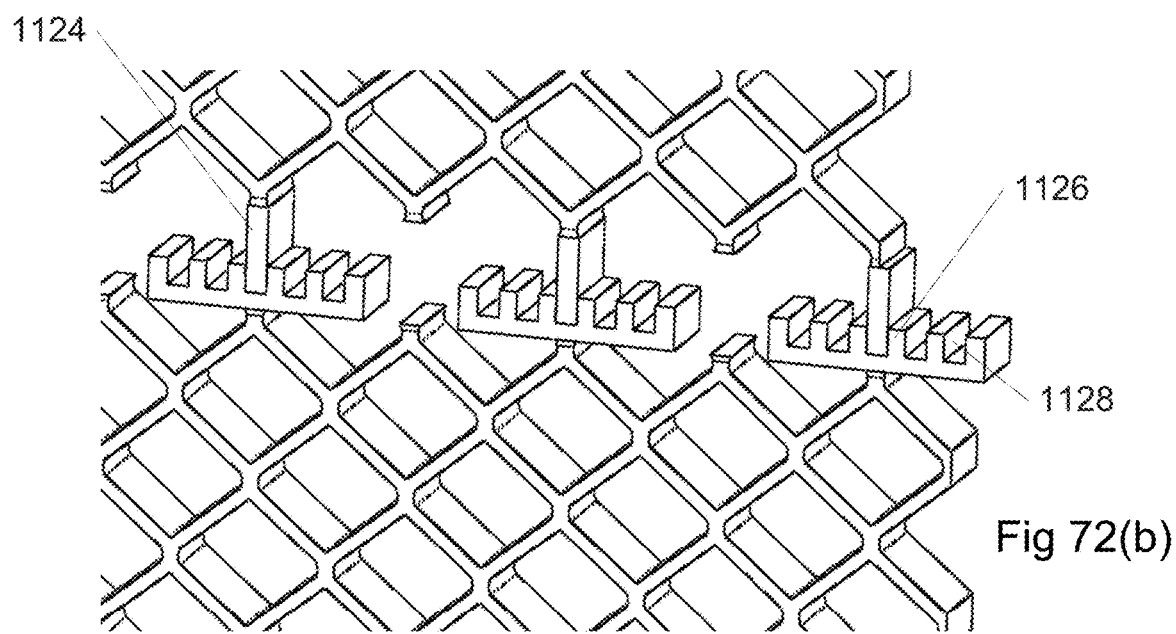

FIG. 72(a) depicts an elevation view of two adjacent sections 1120a,b of a variable-width strip 1118 used in some embodiments of a continuously distally assembled/disassembled curved cannula. A 3-D closeup view of the strip 1118 is shown in FIG. 72(b). The strip 1118 comprises an expandable region 1122 as with the strip of FIG. 62. At the bottom of sections 1120a,b are narrow tabs 1124a,b designed to fit into notches 1128 in notch plates 1126a,b fixed to the upper edge of the sections 1120a,b of the strip 1118. The stylet assembling the cannula can expand the strip 1118 width directly, or expand it by compressing it along its longitudinal axis, until the width is correct. Alternatively, the stylet can reduce the width by compressing it directly, or stretching it along its longitudinal axis. To maintain the strip 1118 at the desired width, the stylet can insert the tabs 1124a and/or 1124b into suitable notches 1128 in the notch plate 1126a and/or 1126b. To keep the tabs 1124a and/or 1124b from slipping out of the notches 1128 radially, the notch plate 1126a and/or 1126b can be provided with one or more sides (not depicted in FIG. 72(b), or the tabs and notches can be tapered radially, similar to the tabs and holes of FIG. 61(h). In this case, since the strip 1118 prefers to straighten itself when flexed if still elastically deformed, the wider end of the taper should be toward the inside of the cannula, and each new winding of the strip 1118, as the cannula is grown/assembled, will allow the tabs 1124 to slide into the notch plate 1126 from the inside. To keep the tabs 1124 from slipping out of the notches 1128 axially (approximately vertically in the figures), the tabs and notches can be shaped as male and female dovetails or similar (not depicted).

As shown in the Figures, all tabs are in the same notches on the plate (the center notch). However, the notch that is used can vary along the length of the strip, and thus the strip width can vary along its length. The angle of the diamonds (or other pattern) comprising the expandable region may be steeper than in FIG. 62 as shown, allowing the strip to easily expand or contract along its width if compressed or stretched along its long axis. However, the angle can also be shallow as in FIG. 62, amplifying small changes in the location of the tabs within the notch plate to create larger changes in strip width.

34$^{th}$ Embodiment

A continuously distally assembled/disassembled curved cannula having a shape that is known before it is deployed can be generated using a strip that is prefabricated with a variable width (e.g., by laser cutting or photochemical machining), according to a computerized design. Then, assembly is merely a matter of re-orienting the strip and attaching the edges of one winding to another.

Figure 73:
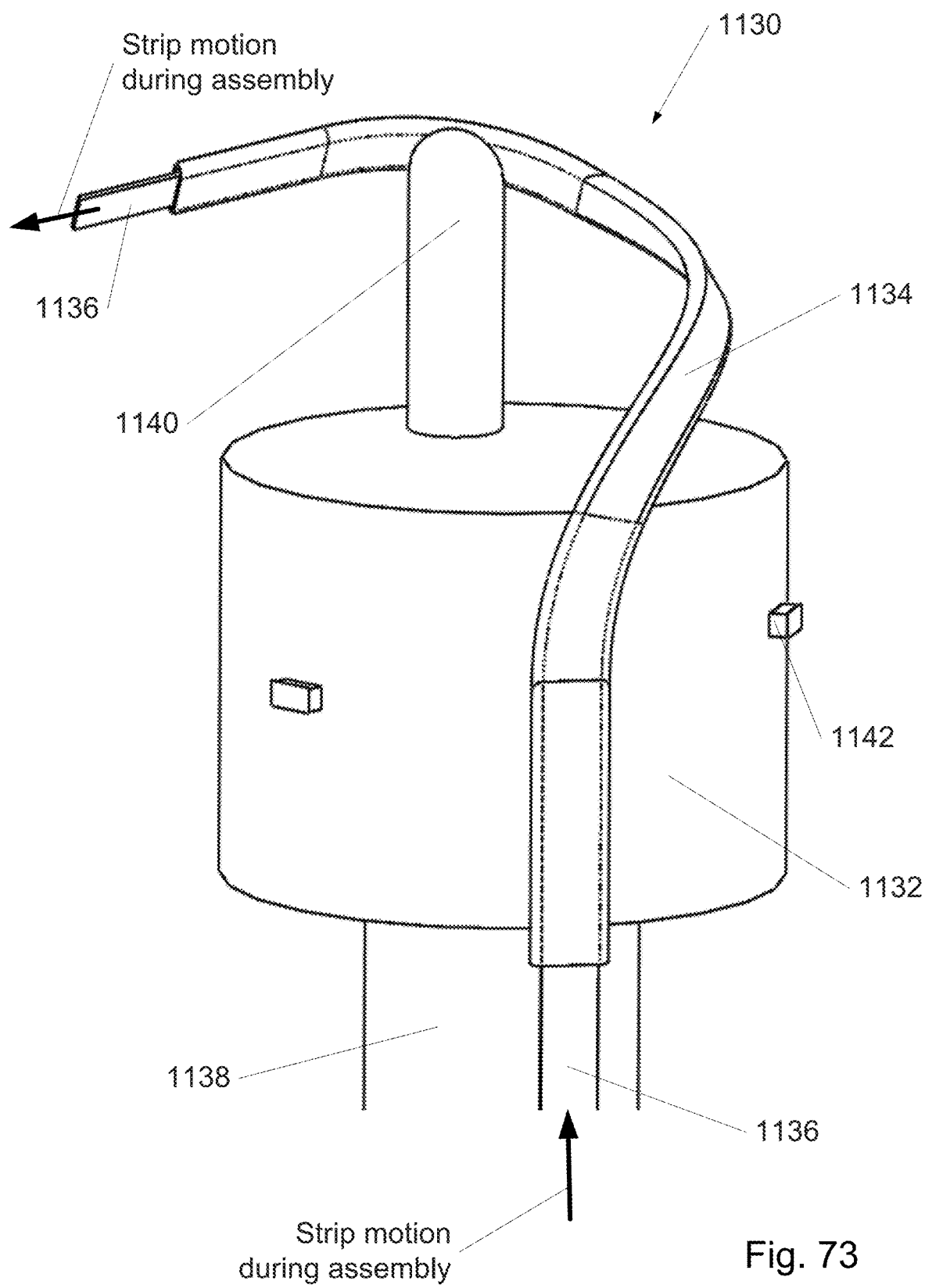
FIG. 73 shows a stylet head and strip for a continuously distally assembled/disassembled curved cannula.

Stylet for a Continuously Distally Assembled/Disassembled Curved Cannula:

FIG. 73 depicts a 3-D representation of the head 932 (in FIG. 63) of a stylet 1130 which can serve to assemble and disassemble a continuously distally assembled/disassembled curved cannula. The stylet 1130 may comprise a stylet shaft 1138 (e.g., a torque coil capable of bidirectional torquing) and a stylet "head" 1132 at its distal end opposite the stylet shaft 1138. The key function of the stylet 1130 is to join one winding of the one or more strips 1136 to its proximal neighbor, though the stylet 1130 also can adjust the overlap of one winding with respect to another, and/or the local width of the strip 1136, and/or the gap between windings. The stylet 1130 must also in many embodiments be able to disassemble the cannula by detaching windings (i.e., sections of one or more strips 1136) from one another (e.g., when rotating in the opposite direction than when joining windings to assemble the cannula), re-orienting the strip so it can return proximally down the cannula (e.g., where it can be spooled for storage and later use). In some embodiments, the stylet 1130 may also make the strip 1136 more uniform in width as it disassembles the cannula. To accomplish joining of the strip 1136, the stylet 1130 should re-orient the strip 1136 (e.g., twist and bend it) from its substantially axial orientation as shown in the lower portion of FIG. 73, to a more circumferential orientation along a roughly helical path as shown in the upper portion of the figure, and vice-versa (for disassembly). The re-orientation may involve twisting and/or bending of strip 1136 and may different (e.g., in a different direction) than that shown in FIG. 73. During cannula assembly, this can be done by pulling, pushing, or otherwise feeding or advancing the strip 1136 distally through a suitably shaped guide 1134, e.g., of flattened tubular shape as shown in FIG. 73, which can be located at or near the stylet head 1132. The strip may be stored on a spool or reel: during cannula assembly, it exits the spool and enters the proximal end of the growing cannula, and returns to the spool during disassembly. An actuator provided to rotate the spool may actively participate in disassembly, or simply provide light tension to take up the slack in the strip. In the figure—which should be understood only as an approximation—the guide 1134 does not necessarily twist and bend the strip 936 into the final orientation required. The guide 1134 can be supported on the head 1132 as needed by a guide support 1140. Not shown are rollers, sprockets, or the like which transport the strip 1136 within the guide 1134. For example, a pair of rollers located at the distal exit of the guide can press against the strip 1136 from two sides or edges and pull it through the guide 1134.

In some embodiments, instead of a guide, the strip 136 (in FIG. 11) can be re-oriented by a set of variously-oriented rollers or sprockets engaging the strip 1136 on its edges and/or surfaces (not depicted). In the case of the strips 830a,b of FIG. 61(b), rollers and sprockets may be provided for other purposes anyway. In some embodiments, the strip may be re-oriented by passing over a surface having an appropriate 3-D shape. To retain the strip against the surface, it may be placed under slight tension (e.g., by the action of a roller or sprocket distal to the surface and a friction source proximal to the surface), or attracted magnetically or by vacuum to the surface.

The strip must of course be flexible enough to allow re-orientation and deformation into the shape of a winding, and may incorporate full- or partial-depth cuts or be scored approximately parallel to its width or to the cannula axis at intervals to increase flexibility as described above. Or, in some embodiments, the strip may be generally flexible, but may include ribs or other thickened regions oriented similarly to the cuts and arranged at intervals to increase its stiffness in the width or cannula axis direction. Each winding of the cannula may be polygonal, with flat or curved faces, instead of smoothly circular, if the strip flexes primarily in cut regions, or between ribs. The strip may be designed to be elastically deformed or plastically deformed. If elastically deformed, the tendency of the strip to straighten itself can be helpful in some embodiments to provide a preload that interlocks the strip with itself. If plastically deformed, the strip can nonetheless be actively bent as needed to form the winding. Selective annealing (e.g., by laser) may be used in some embodiments to make certain regions of the strip more easily deformed than others. Especially if the strip is to remain only elastically deformed, then unless the strip is made from a superelastic material such as nickel-titanium, the deformation should be minimized.

In some embodiments, strip 1136 does not travel through the cannula the entire distance in a substantially flat shape as suggested by FIG. 73, but rather, is formed into a helical shape of smaller diameter (or if the strip is fed externally rather than through the lumen, than of larger diameter) than the cannula interior diameter. The windings of this inner helix can be loose or (if it is desired to push on the inner helix, for example) temporarily joined to one another. The inner helix can surround stylet shaft 1138, and be free to travel along and be guided by it. The pitch of the inner helix can be very different (e.g., greater) than the pitch of the cannula helix. If the strip is in the form of an inner helix, then the amount of twisting and/or bending required to re-orient it prior to attaching it to the cannula is greatly reduced. As a result, the strip does not need to be as flexible, and the complexity of the stylet can be reduced.

In FIG. 23, the strip 310 appears to bend with a small radius, as it seems to be positioned along the "front" side of the cannula (i.e., facing the viewer). In practice, to maximize this radius, is may be preferable that prior to being re-oriented, the strip 310 is located close to the cannula wall diametrically opposite the place where the strip 310 is joined to itself to form a winding of the cannula. In FIG. 23, joining occurs left of center near the front, so the initial strip 310 position might preferably be toward the rear right. The strip need not be always near the cannula wall, outside the stylet shaft. In some embodiments, the shaft is hollow and the strip is advanced through the shaft and exits from or near the stylet head. It may then bend toward the cannula wall before being re-oriented.

If the strip is at least partially plastically deformed when re-oriented and made to form a winding of the cannula, then during disassembly the stylet can assist in straightening it. The stylet can also serve to pre-bend the strip so that when formed into a winding, the forces tending to straighten it out are increased, which can help increase the preload that joins one winding stably to another.

As discussed in the various embodiments of a continuously distally assembled/disassembled cannula, the stylet can also be used to adjust the overlap of one winding with respect to another, and/or the local width of the strip, and can include various provisions for this that are not shown, such as translating and/or rotating elements which engage the strip. Joining the strip to itself and adjusting its curvature can be performed simultaneously in some embodiments, while in other embodiments it is sequential. During assembly of the cannula, as the strip is joined to itself, it is pulled distally along the cannula, either actively or passively.

If the stylet head is provided with features which engage the already-wound strip, the stylet can in some embodiments be pulled distally by simply rotating it from the proximal end. For example, if the strip contains a female dovetail 1038 like the strip 1050 of FIG. 69(i), and the stylet head 1132 has at least one male dovetail 1142 as shown in FIG. 73 (arranged to not interfere with the strip 1136), then rotation will cause the stylet 1130 to advance or retract, much like a screw does when turned within a nut. Having the head 932 of the stylet 1130 pulled instead of having to push it from the proximal end when assembling the cannula may be preferable, as it can minimize buckling of the stylet shaft 1138 and the need for centering devices like those of FIG. 56; however, stylet 1130 may be pushed in some embodiments. For example, stylet 1130 may comprise a flexible shaft that is wound on a spool which can rotate about an axis parallel with the proximal portion of the cannula; this rotation allows the head of the stylet to rotate as windings are established during cannula assembly, or broken down during disassembly. When the spool is both unwound and rotated, the shaft extends distally into the cannula while rotating (e.g., following a roughly helical path). In some embodiments, the spool on which the strip is wound (which may be the same spool in some embodiments) can be be rotated by the same actuator as that rotating the spool on which the stylet is wound. In some embodiments, at least one linear actuator may be used to provide linear motion of the stylet and/or strip.

A strip of constant width or constant overlap forming a straight cannula will follow a helical path with a constant pitch. A curved cannula, however, may have a variable pitch. Thus in some embodiments the ratio between the travel of the stylet along the cannula axis (which may be curved) and the number of stylet rotations may vary from location to location along the axis. In some embodiments, the location of the stylet along the cannula can be measured and used as feedback. For example, the stylet may include an optical sensor (e.g., a miniature camera such as those made by Medigus Ltd. (Omer, Israel) that detects features on the strip such as gaps and holes, regularly-spaced markings on its inside, etc. Mechanical sensing may also be used.

In some embodiments, the stylet may have centering rollers, wheels, or sprockets, or gears (e.g., 3-4 rollers which may have an elastomeric surface, sprockets which engage holes in the strip, or gears which engage corresponding teeth on the strip) which engage the inside diameter of the cannula and which rotate actively (i.e., driven) or passively to propel it up and down the cannula. The stylet head or portions thereof may rotate as needed to assemble or disassemble the cannula, or the entire stylet may rotate. If the rotation plane of the rollers is arranged to be approximately tangent to the roughly helical shape formed by the strip, the rollers may be driven to provide simultaneous axial and rotational motion of the stylet, or if the rollers turn passively as the head is moved, then they may turn with minimal friction. In some embodiments, the stylet may be centered within the cannula by balls, omnidirectional wheels, or low-friction material such as PTFE.

Overall, by rotating the stylet shaft, the stylet head can assemble the cannula by wrapping the strip and joining the strip to itself, adjusting the local overlap and/or width of the strip as needed, while the stylet moves distally through the growing cannula. At least one actuator can be provided to adjust the local strip overlap, width, etc. Especially for small diameter cannulas, the force supplied by this actuator can derive from pulling on the proximal end of a wire which is fed through the center of the stylet shaft and connects to an appropriate mechanism on the head.

In some embodiments, a winding may be connected to the adjacent winding just proximal to it while the winding is in a neutral (e.g., parallel top and bottom edges) state. After this, it can be plastically deformed into the desired wedge shape by the stylet and then released, or elastically deformed and locked into the wedge shape by the addition (or movement) of locking elements. In some embodiment variations, additional leverage may be gained when deforming the winding by arranging for the stylet to exert forces at a distance from the winding to be deformed, using the cannula as a lever arm to increase the moment.

In some embodiments, the stylet may incorporate sensors (e.g., at its distal end, or head) which allow assembly and/or disassembly to be monitored and controlled, and/or which allow the growth direction of the cannula to be determined based on images of the surrounding environment. Thus for example a small imaging device such as a side-looking or forward-looking camera may be incorporated into the stylet head, or a fiber optic imaging bundle. In some embodiments, the stylet may incorporate elements which allow a liner (e.g., to make the cannula fluid-tight) to be pushed or pulled through it, or otherwise deployed. In some embodiments, at least one cannula may be assembled within another, either sequentially or simultaneously, to create at least two lumens; in some embodiment variations, the apertures in one cannula can be substantially blocked by regions of an adjacent cannula, providing less porosity overall.

In some embodiments, rather than using the stylet to only assemble and disassemble the cannula, it can be left in place, working in concert with the cannula (i.e., the continuous, wound strip) and allowing more rapid changes in overall shape (further extending distally, retracting and extending in a new direction, etc.). Indeed, there are procedures that must be performed using the cannula while its shape is still expected to change. For example, the stylet may incorporate sensors such as a forward-looking camera so that the stylet/cannula combination can be used for inspection and surveillance. In some embodiments, the stylet may incorporate at least one lumen (e.g., fluid-tight), which allows various functions without having to withdraw the stylet from the cannula (which would provide a larger lumen, of course). For example, instruments, tools, and sensors may be passed through the stylet lumen. Or, fluids such as air or jetted water may run through the stylet lumen towards the distal end to dislodge dirt, soil, and debris in a search and rescue application, or to improve visibility if the stylet includes a camera at its distal end. Fluids (e.g., delivered through the stylet lumen, or through a hose, and directed radially) can also be used to keep the strip clean in areas containing features which are used to join windings to one another. For example, in a medical procedure saline may be transported toward the distal end in order to provide irrigation and maintain a clear field. A stylet lumen may also be used to aspirate material from the distal end (e.g., blood and loose tissue in a medical procedure, dirt, soil, and rocks in a search and rescue or underground/underwater tunnel boring operation).

35$^{th}$ Embodiment

Figure 75A:
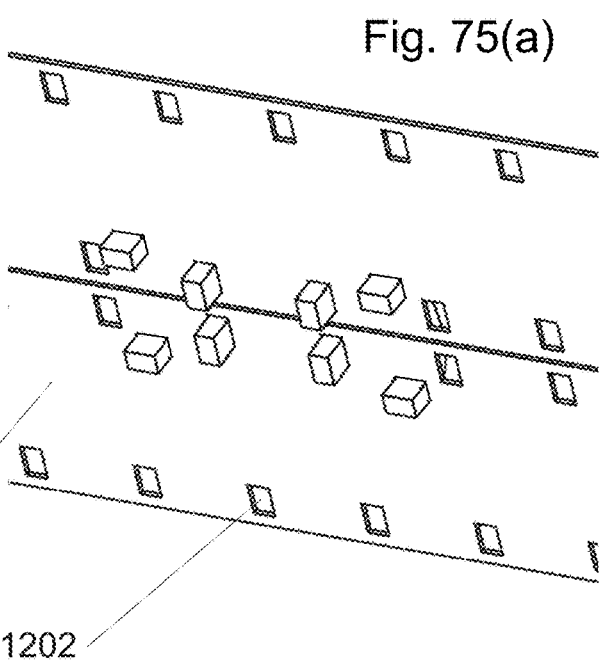
FIG. 75(a)-(c) shows a method of joining strips.
Figure 75B:
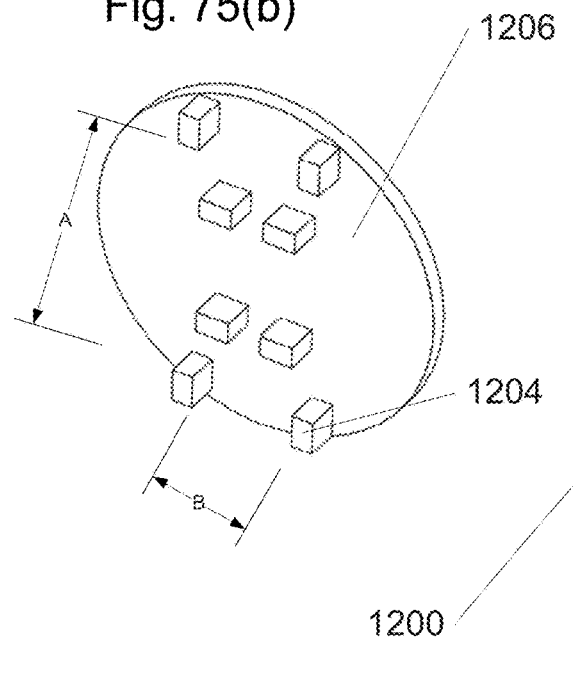
Figure 75C:
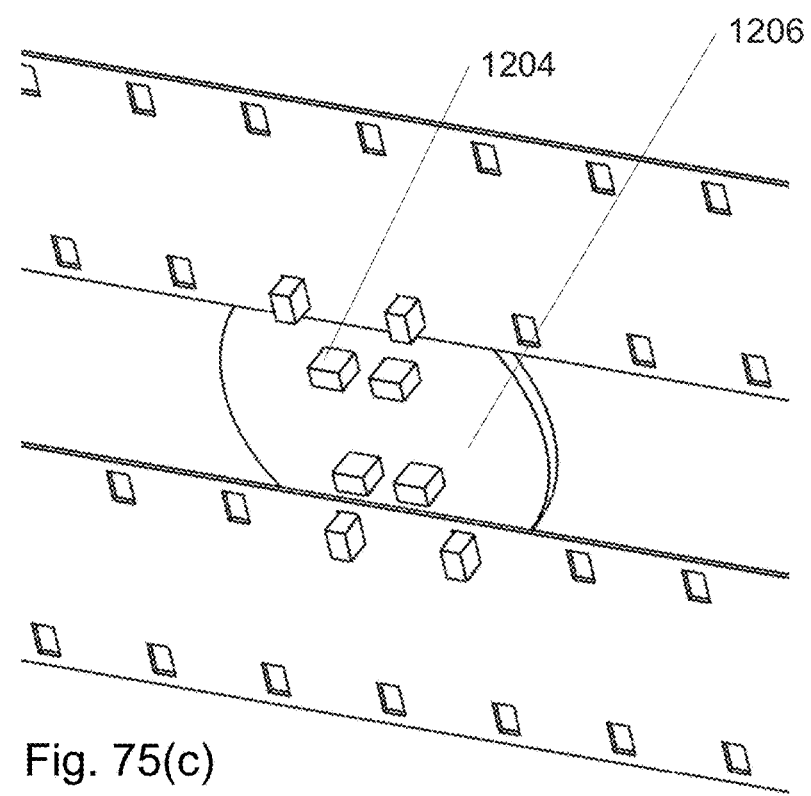

FIG. 75(a) depicts a 3-D view of strip 1200 perforated with holes 1202 (some of which are not shown) to accommodate the posts 1204 protruding from link 1206 shown in the 3-D view of FIG. 75(b). Holes are not necessarily rectangular; they can be square or circular, for example, and may be radiused at their edges. Posts 1204 are arranged on link 1206 in two groups with two different gaps A (wide) and B (narrow), and link 1206 can be rotated. In FIG. 75(a), link 1206 has been coupled to strips 100 with the posts separated by gap B entering holes 1202 near the edges of strips 100, while in In the 3-D view of FIG. 75(c), link 1206 has been coupled to strips 100 with the posts separated by gap A entering holes 1202 near the edges of strips 100. Since gap B is larger than gap A, strips 1200 are thus joined together by link 1206 with a greater separation in FIG. 75(c) than in FIG. 75(a). If strip 1200 is formed into the windings of a cannula and multiple (e.g., three) links are used to couple each winding, a curved cannula can be formed, in which windings are tapered (with non-parallel edges).

Figure 76:
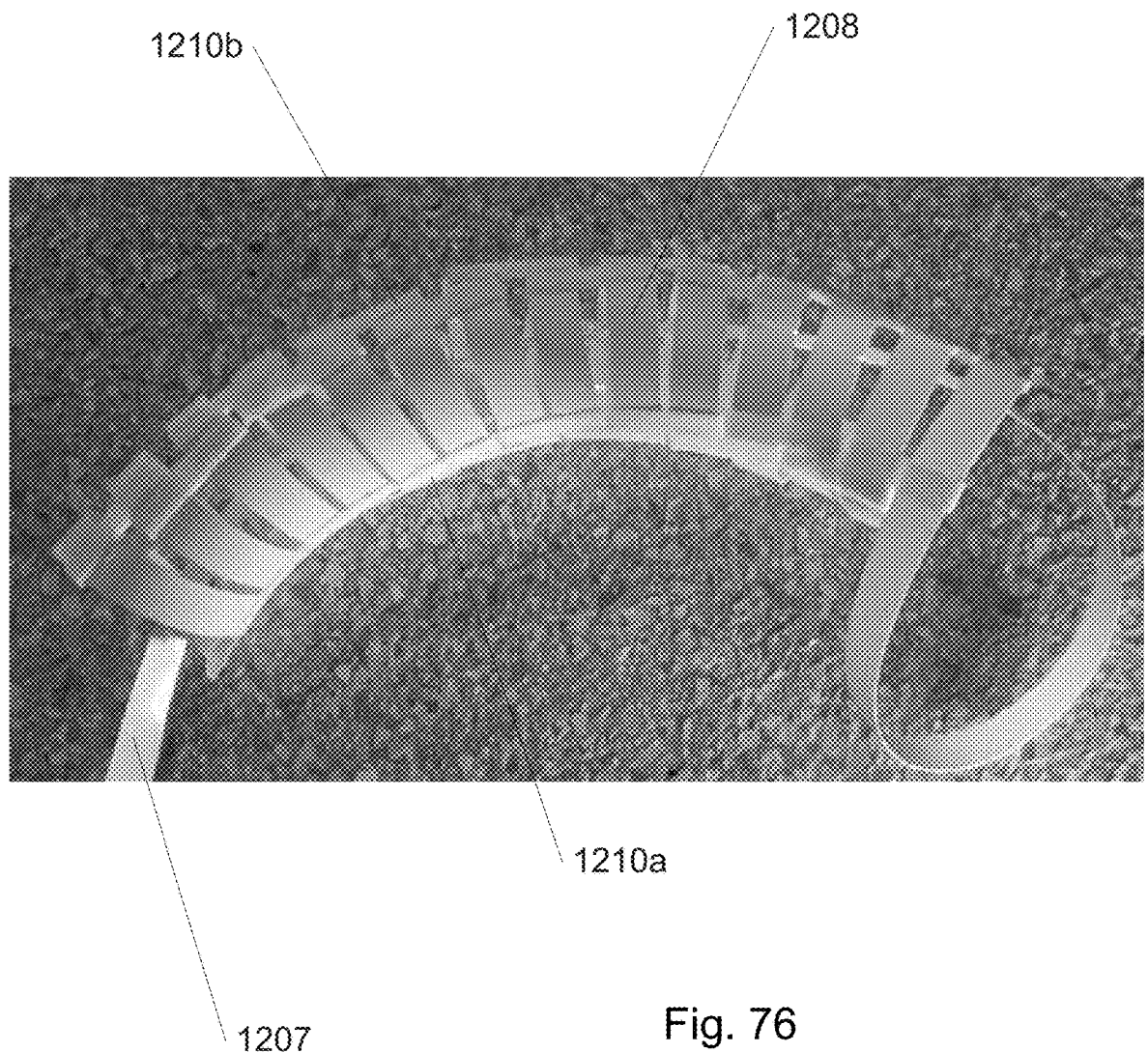
FIG. 76 shows a cannula produced by joining strips with clips.

This is further illustrated in the photograph of FIG. 76, in which a curved cannula results from coupling together strip 1207 into windings 1208 using short clips 1210a and long clips 1210b applied to the outside of each winding (in some embodiment variations, they can be applied to the inside or to both sides). Two long clips 1210b and one short clip 1210a are used per winding, approximately 120° apart. All clips are approximately aligned between windings, so that the tapers/incremental curvatures produced by adjacent windings are "in phase", much like the rings of FIG. 26b. The result is a cannula that curves with the minimum radius in the direction of the short clip (i.e., the curvature is in a plane that intersects the clip). Except for potential interference problems, two short clips 1210a and one long clip 1210b can be used instead in some embodiment variations. Similarly, a cannula wound from a strip such as strip 1200 held together by links 1206 with two different orientations— two creating a large separation as in FIG. 75(c), and one creating a small separation as in FIG. 75(a)—would be curved. The curvature is maximized (e.g., minimum radius) for a given winding, bending toward the link oriented to produce a smaller separation. An entire region of the cannula can thus curve as shown in FIG. 76 if the link orientations are in phase in that region.

It should be noted that the cannula of FIG. 76 (and a cannula produced using the strips of FIG. 75) constitutes a third method of creating a continuously distally assembled/disassembled curved cannula. Other embodiments involved a strip whose local width or overlap could be varied. In this cannula, however, the strip width is constant and the windings do not overlap. Rather, the spacing between windings varies, and there are features which connect the windings together and establish this spacing.

If all links 1206 (in FIG. 75) are oriented the same direction or orientation for a given winding, the winding will not be curved. Similarly, if only short clips 1210*a* or long clips 1210*b* (in FIG. 76) are used for a winding, the winding will not be curved. Thus for a single winding, there is a choice between maximally curved and uncurved, assuming links of two possible orientations and clips of two possible lengths. However, cannula curvatures with larger average radii can be produced using groups of adjacent windings. Assuming for the sake of illustration a cannula is formed using short and long clips such as clips 1210*a,b*. The circumferential (i.e., azimuthal around the long axis of the cannula) placement of the short clips, for example, establishes the plane of curvature. Assume a given winding M has its short clip at 0° (the "phase angle"). If adjacent winding N has a phase angle of 180°, the effect of both windings in combination will be similar to that of the "out of phase" rings of FIG. 26*a*: the section of the cannula will be approximately straight. If on the other hand, the phase angle for winding N is chosen to be other than 0° or 180°, a certain amount of curvature will be produced which will depend on the relative phase angle, and which will lie between minimum and maximum curvature. The plane of curvature will also be affected by the phase angle, and the angle can accumulate from winding to winding if always in the same direction. However, by alternating the direction of the phase angle difference from winding to winding (between clockwise and counterclockwise), the accumulation can be prevented, and curvature can be kept substantially planar and of the desired radius.

Links 1206 (in FIG. 75(*c*)) or clips 1210*a,b* (in FIG. 76) can be supplied to, and installed, by the stylet. In some embodiment variations, links 1206 or clips 1210*a,b* can be joined to one another in a continuous strip, e.g., with flexural elements between them. Indeed, in some embodiments, the cannula may be formed by two similar strips which interlock with one another to form a double-walled substantially helical, curved shape. In some embodiment variations, links 1206 can contain more than two groups of posts 1204 (in FIG. 75(*c*)) (e.g., three, allowing for three separations of strip 1200). In some embodiment variations, in lieu of a single link 1206 which can be installed with different orientations, several links with fixed lengths may be used.

36th Embodiment

Figure 77D:
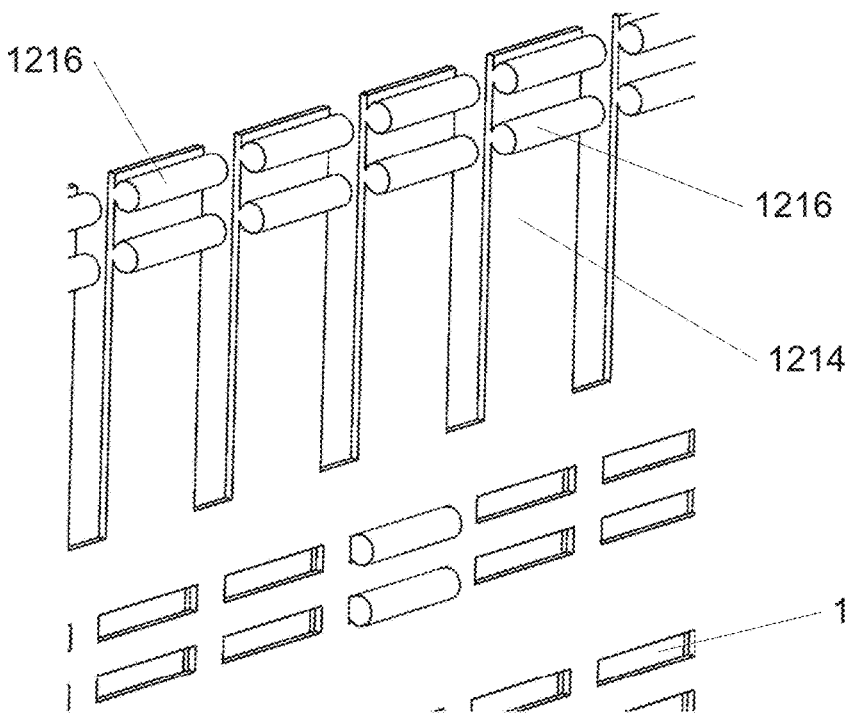
Figure 77E:
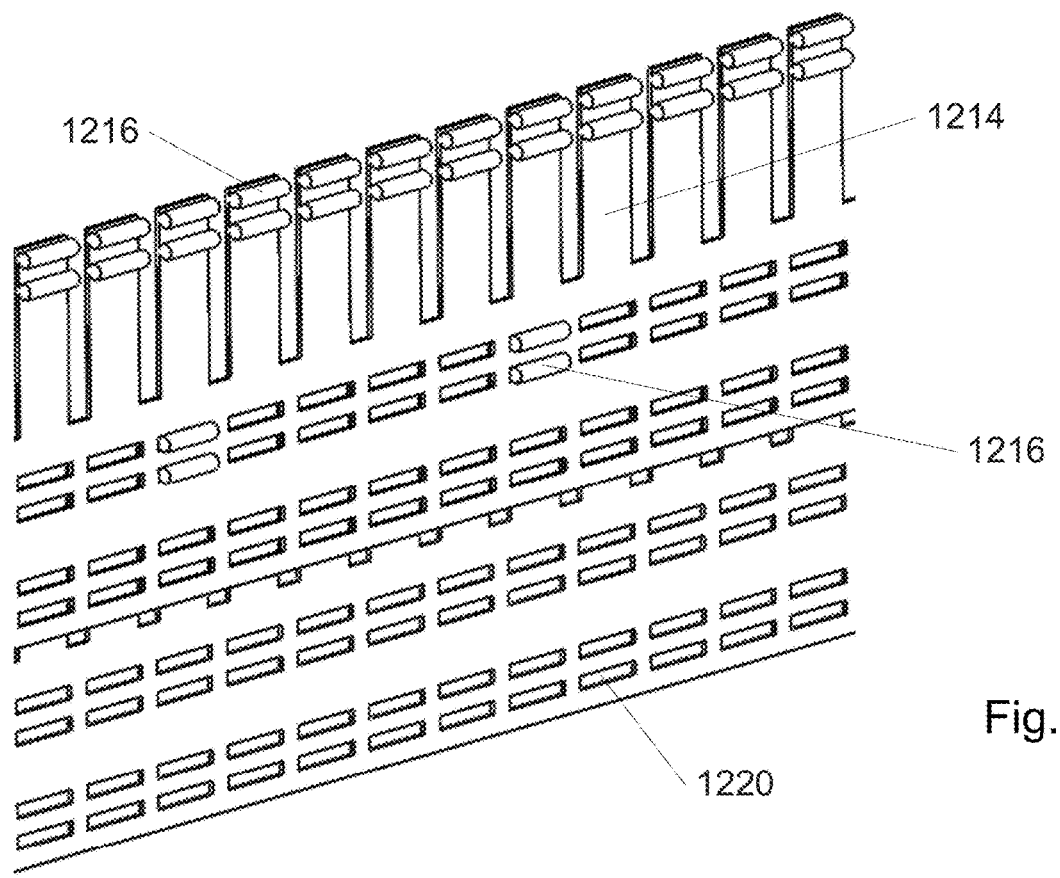

The 3-D views of FIG. 77 depicts an embodiment of a flexible strip capable of linking to itself to form windings of the cannula, without the need for links or clips as in the 35th Embodiment, and providing overlap between windings to reduce the number and size of gaps in the cannula. In FIG. 77(*a*), flexible strip 1212 is shown, comprising flexible fingers 1214 tipped with at least one wire 1216 (e.g., cylindrical) and at least two rows of slots 1218*a,b* (each row is shown with two slots, one for each wire, however, the skilled artisan would understand that more or less rows can be used, e.g., 1, 3, 4, 5, 6, 7, 8, 10, or more). Slots in row 1218*a* are higher than those in row 1218*b* as shown. Wires 1216 (two are shown) are fastened to fingers 1214 and have a reentrant surface. The shape of the wires 1216 is shown in this embodiment as generally cylindrical, however, the present invention also includes wires 1216 having other shapes, such as rectangular, square, oval, triangular, polyhedral, etc., with slots that match their overall shape. The wires 1216 are sized to fit tightly into slots such as slot 1220, with the material of strip 1212 able to elastically deform slightly when pushed against wires 1216 (and/or vice-versa), so as to allow wires 1216 to "snap" into slots 1220 (e.g., when pushed radially outward by the stylet) as shown by arrow in FIG. 77(*b*) and be retained as in FIG. 77(*c*). This couples fingers 1214 of one winding with slots of another winding as shown in FIGS. 77(*d*)-(*e*). Pushing can be done by a feature on the stylet, which presses on the rear of finger 1214 as shown in FIG. 77(*b*). In some embodiment variations, slots 1220 have a "keyhole" or other shape which is wider (not necessarily as wide as wires 1216) in one region, allowing wires 1216 to enter slots 1220 more easily. Strip 1212 can be bent slightly by the stylet to allow wires 1216 to enter slots 1220 in the wider region, e.g., if the wider region is toward the end of slots 1220 opposite the last wires 1216 to enter slots 1220. Then, once the winding is formed, wires 1216 cannot escape slots 1220, since strip 1212 is no longer sufficiently bent.

Since there are two rows 1218*a,b* wires 1216 (in FIG. 77(*a*)) can enter slots 1220 on either the top or bottom row when two windings are coupled together. If upper row 1218*a* is used as shown, windings overlap by the maximum amount, while if lower row 1218*b* is used, windings overlap by the minimum amount. In the specific design of FIG. 77, the minimum overlap provides over 30% more height than the maximum overlap. In FIGS. 75-76, the strips do not overlap but are separated by different amounts and are non-parallel in a curved region of the cannula. In the case of FIG. 77, the strips do overlap, but the effect is similar: if for example a winding is joined to another winding using top row slots 1218*a* in two locations around the circumference (e.g. 120° apart), and using bottom row slots 1218*b* in one location (i.e., a total of three fingers used per joint), then the windings will be non-parallel and induce a local curvature in the cannula, while using top 1218*a* or bottom 1218*b* slots for all three fingers will make the cannula locally straight. The plane of curvature can be established by selecting which wires 1216 are pressed into which slots 1220, and in some embodiment variations, not all fingers or not all slots are provided. If not all fingers are provided, however, gaps in the cannula are larger and more numerous. Unused fingers can remain adjacent to the neighboring winding, their tips deformed elastically slightly to allow room for wires 1216 between the two surfaces.

In some embodiment variations, only one wire 1216 (in FIG. 77(*a*)) is provided and each row 1218*a,b* only has one slot. However, such a variation may be mechanically weaker. In some embodiments, more than two wires per finger, with the corresponding number of slots, may be used. In some embodiment variations, more than two rows of slots are provided (e.g., a continuous sets of slots) allowing more than two possible ways to join the windings at each location, and/or more than three fingers to participate in making the joint.

A strip such as that of 1212, if made from metal (e.g., 301 stainless steel), can be manufactured, for example, using photochemical machining (e.g., reel-to-reel) or by stamping, with the wires fastened to it by welding (e.g., laser) or other methods. Since some windings must be non-parallel if the cannula includes curved regions, in some embodiment variations, welding is confined to a portion of wire 1216 (e.g., the center) to allow the wire to rotate slightly to accommodate the non-parallelism. Alternatively, wire 1216 may be replaced by one or more balls (e.g., distributed transversely (perpendicular to the length of the strip)) or compliance can be incorporated into the fingers (e.g., each may be twisted in its center region so as to be more flexible in the circumferential direction).

In some embodiment variations, slots 1220 are significantly longer than wires 1216 to allow for circumferential misalignment and easy of assembly. In some embodiment variations, slots 1220 are radiused to reduce stress concentrations. In some embodiment variations, fewer but wider fingers 1214 are used, with correspondingly fewer and wider slots 1220. In some embodiment variations, other approaches for coupling may be used in lieu of or in additional to these, such as magnets or a liner in combination with features which prevent relative shear between windings (e.g., bent tabs which fit into slots). In some embodiment variations, fingers 1214 can be provided with a lip, ridge, or tab (not shown) or similar features, or merely an extension of fingers 1214 beyond wires 1216, which enable the stylet to pull the wires free of the slots during disassembly of the cannula. In some embodiment variations, a tapered blade or similar can be inserted by the stylet between fingers 1214 and strip 1212 on the adjacent winding, or under the lip, ridge, or tab, to help separate the windings during disassembly.

If the strip is stamped, then reentrant features similar to those achieved by attaching a wire can be achieved. The 3-D views of FIGS. 78(*a*)-(*d*) depict such features including reentrant geometries 1222 which can be achieved by stamping alone. The designs of FIGS. 78 (*a*)-(*d*) may also serve as a sliding fastener such as is needed for a sliding wedge (FIG. 79). Other interlocking features which may be created by stamping or other methods and may be used in some embodiments include features such as those shaped like the greek letter omega which can be compressed by the stylet so as to fit through a slot or hole. When released, the "feet" of the omega shape expand on the other side of the slot to retain the feature in the slot until re-compressed. Features which require expansion rather than compression to enter or exit a slot or hole can also be used in some embodiments.

In some embodiments, strips can be interlocked for this and other embodiments by incorporating features that can only be interlocked with one another when one strip is bent and/or twisted with respect to another. Then, once the features are interlocked and the section of the strip in which they are located becomes unbent and/or untwisted to form a winding, the strips cannot be separated until the cannula is disassembled, at which time the strip is free to bend and/or twist again.

In general, features such as wires mated with slots, or stamped features such as those of FIG. 78 can be advantageous over the Ziploc-type fasteners as shown in FIG. 69, in that they allow the windings to be closer together.

Assuming that FIG. 77 shows the outside surface of two joined strips 1212 (i.e., facing toward the outside diameter of the cannula, it can be appreciated that the adjacent winding prevents outward buckling of fingers 1214. However, they may be subject to inward buckling due to compressive stress on the cannula, and so may be designed to be as short as possible. In some embodiments, inward buckling can be further prevented by inserting a liner inside the cannula after the windings have been joined since the outside surface of the liner can be adjacent to the inside surface of fingers 1214.

37*th* Embodiment

The 3-D view of FIG. 79 depict a embodiment with some similarities to the 30*th* Embodiment in that it comprises a strip whose effective width may be adjusted using a sliding wedge. In the current embodiment, sliding wedge 1224 is able to slide relative to the strip comprising band 1226 and boss 1232 by means of wire 1228, affixed to boss 1232 so as to expose a reentrant surface. Wire 1228 is angled so as to match the angle of slot 1230 in wedge 1224, and wedge 1224 may be pre-installed on the strip for example, by snapping wire 1228 into slot 1230. Thus the strip can comprise a continuous band with intermittent bosses to which sliding wedges are attached.

A second slot 1234 is provided on the wedge to engage ball 1236, itself having a reentrant surface during the process of assembling the cannula (i.e., forming windings from the strip and joining it to itself), by elastically snapping slot 1234 of wedge 1224 over ball 1236 (e.g., by action of the stylet, especially if wedge 1224 is facing the inside surface of the cannula). This may most easily be done when ball 1236 is not near the ends of slot 1234. Ball 1236 and wire 1228 may be fastened to band 1226 by laser welding, for example. In some embodiment variations, slot 1234 may be wider in one area to facilitate entry of ball 1236.

Several (e.g., three) bosses and wedges are provided per winding, with the bosses typically equally spaced. FIG. 79(*b*) shows three windings joined by balls as described. As shown in FIG. 79(*b*), by adjusting the wedge position relative to the boss (causing ball 1236 to side in slot 1234, and wire 1228 to slide in slot 1230), the distance between bands (in effect, the strip width), can be varied. For the sake of illustration, the wedge for the top winding has been adjusted to achieve the maximum width, while that for the bottom winding has been adjusted to achieve the minimum width. The wedge for the center winding has been adjusted for an intermediate height. FIG. 79(*c*), a view of a section of the three windings from the other sides (e.g., the side facing the outside of the cannula), makes this somewhat clearer.

Adjustment of wedges 1224 can be accomplished by pushing or pulling on wide edge 1236 or narrow edge 1238, or on other features. Adjustment can be done by the stylet (e.g., the stylet head) during assembly of the cannula, or can be done while the strip is en route to the distal end of the cannula, for example. Adjustment can create significant width changes: in the design shown, the strip width can be increased from a minimum value by over 30%. Since wedges in general will not be set to the same height (unless the cannula is to be straight in a region), the strips will not in general be parallel. However, each strip can rotate slightly at ball 1236 around its neighbor, allowing for non-parallelism.

In some embodiment variations, the mechanism for securing the position of wedge 1224 when the strip is not part of a winding (e.g., travelling through the lumen of the cannula) is provided. A detent produced by a small deformation of the wedge and/or strip can be used, for example for this purpose, and may be located at one end of travel for wedge 1224, centrally, or elsewhere. For single-use cannulas, a light adhesive, etc. may be used to secure the wedge. The force required to slide the wedge should of course not be so high that it interferes with sliding it when required.

Once the position of wedge 1224 is adjusted and the strip is curved into a winding, the increased friction between wedge 1224 and strip, in combination with the relatively shallow angle of slot 1230, will stabilize wedge 1224 against unwanted movement. Adjusting of wedge 1224 may be accomplished in some embodiment variations by a rotating or sliding finger or other element on the stylet which engages wedge 1224, e.g., at edge 1238 or 1236. If the tangential velocity of the finger is higher or lower than that of the stylet head, for example, wedge 1224 will move relative to boss 1232, either increasing or decreasing the effective width of the strip in the region of wedge 1238.

Figure 79A:
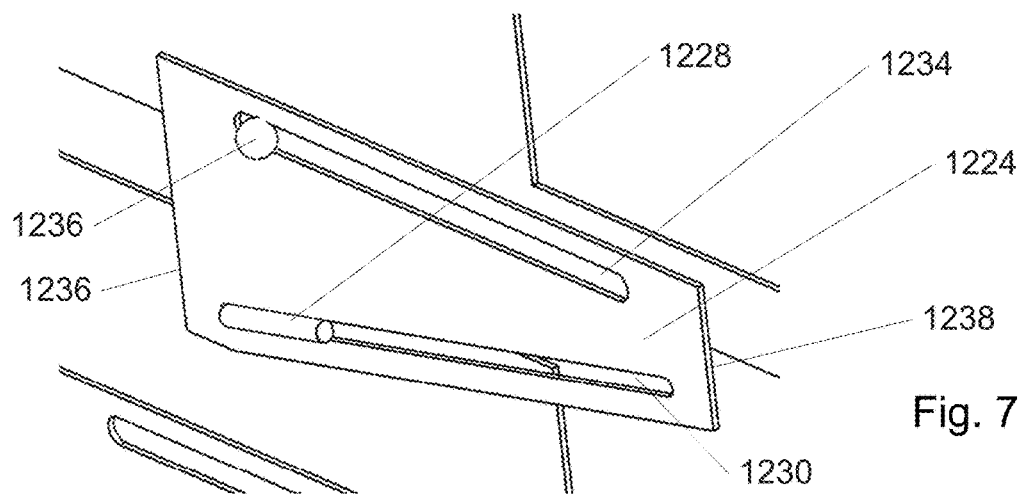
FIG. 79(a)-(d) depicts strips with sliding wedges.
Figure 79B:
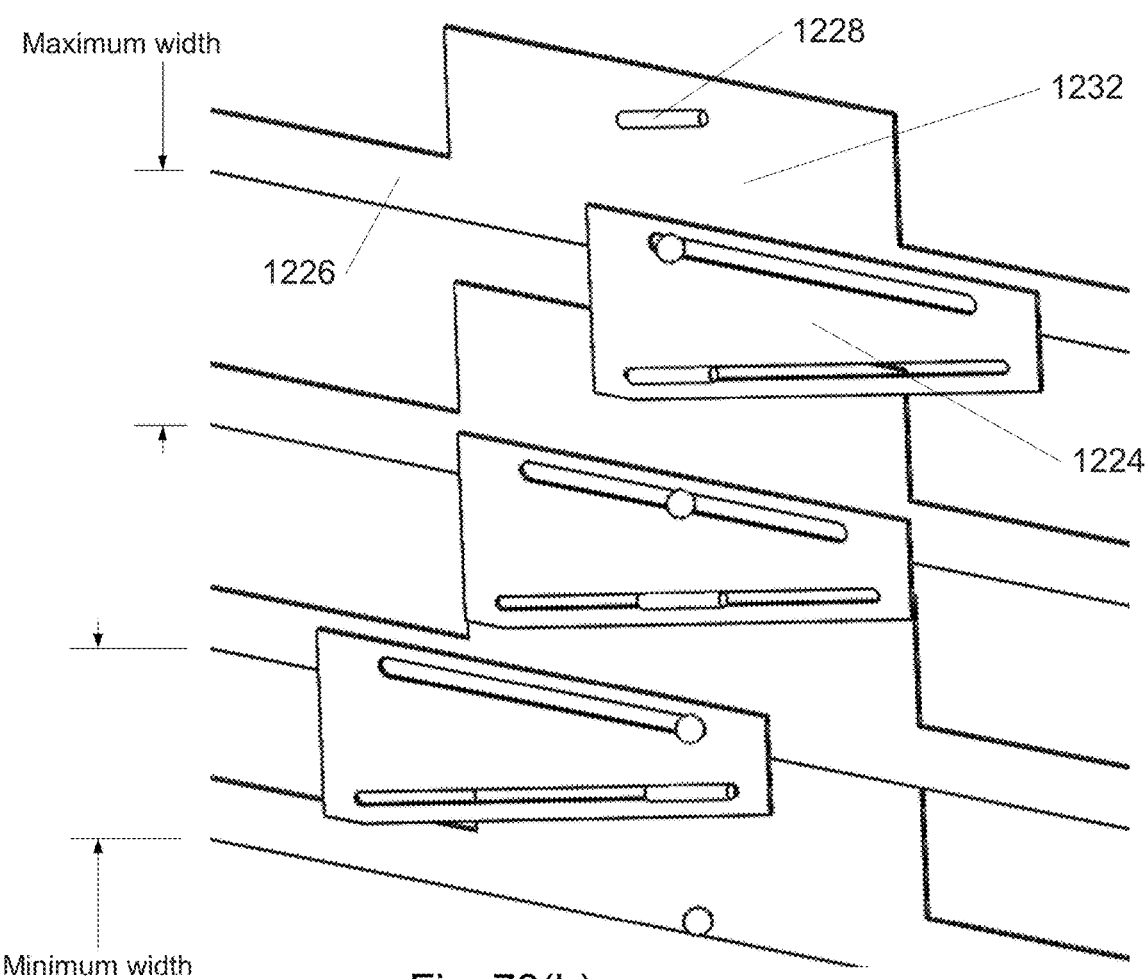
Figure 79C:
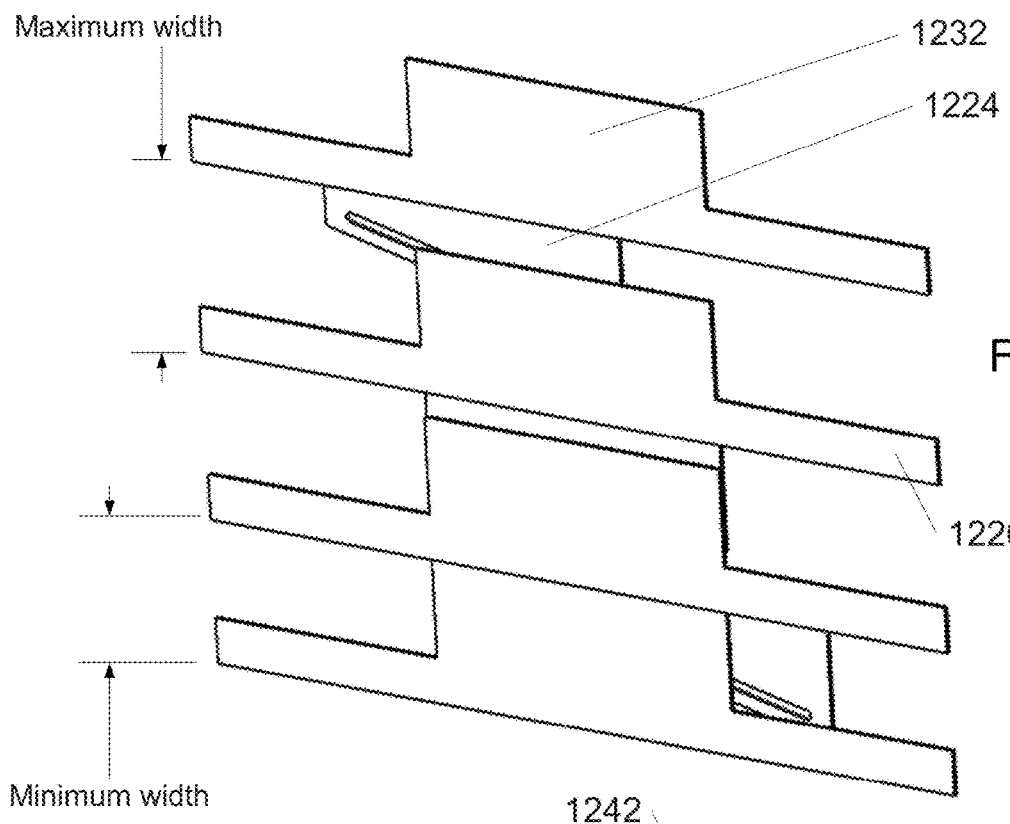
Figure 79D:
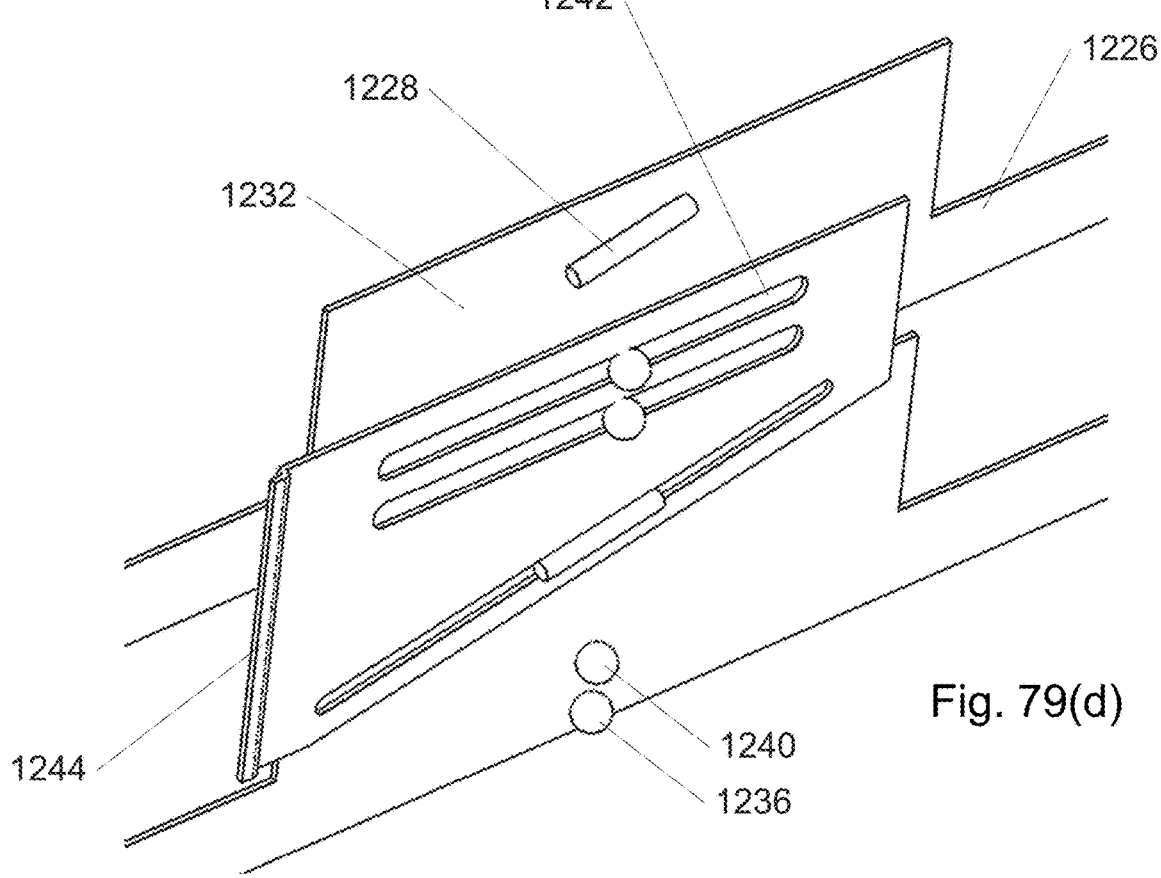

FIG. 79(d) shows a modified design used in some embodiment variations in which a second ball 1240 and corresponding slot 1242 are provided to distribute the load and minimize the risk of dislodging ball 1236. In some embodiment variations, a wire attached along at least a part of its length may be used in lieu of or in addition to a ball. Also shown in FIG. 79(d) is lip 1244 used in some embodiment variations which can be engaged by the stylet (e.g., as it rotates in the opposite direction than its direction when assembling the cannula) in order to pull wedge 1224 free of ball 1236 and (if applicable), ball 1240, so that the cannula can be disassembled. In some embodiment variations, a tapered blade or similar can be inserted by the stylet between boss 1232 and wedge 1224 during cannula disassembly to help separate "unsnap" it from ball 1236 and (if used) ball 1240. In some embodiment variations, slot 1234 may be spread apart by a tool on the stylet (e.g., a blade that twists within the slot) to facilitate release of ball 1236.

In some embodiment variations, in lieu of a single wedge 1224 associated with each boss 1232 a pair of wedges is provided which slide in opposite directions (toward or away from one another) to adjust strip width. In some embodiment variations (of this and other embodiments such as the 30$^{th}$ Embodiment), in lieu of slots and wires or balls, the edges of bands and wedges may be folded over to form a J-shaped "hem", with the hem on one part hooked that of another, thus providing a sliding coupling. One part may also be deformed after the two parts are joined, to prevent the coupling from separating. In some embodiment variations, ball 1236 may be located on wedge 1224 and slot 1234 may be located on boss 1232.

Figure 80:
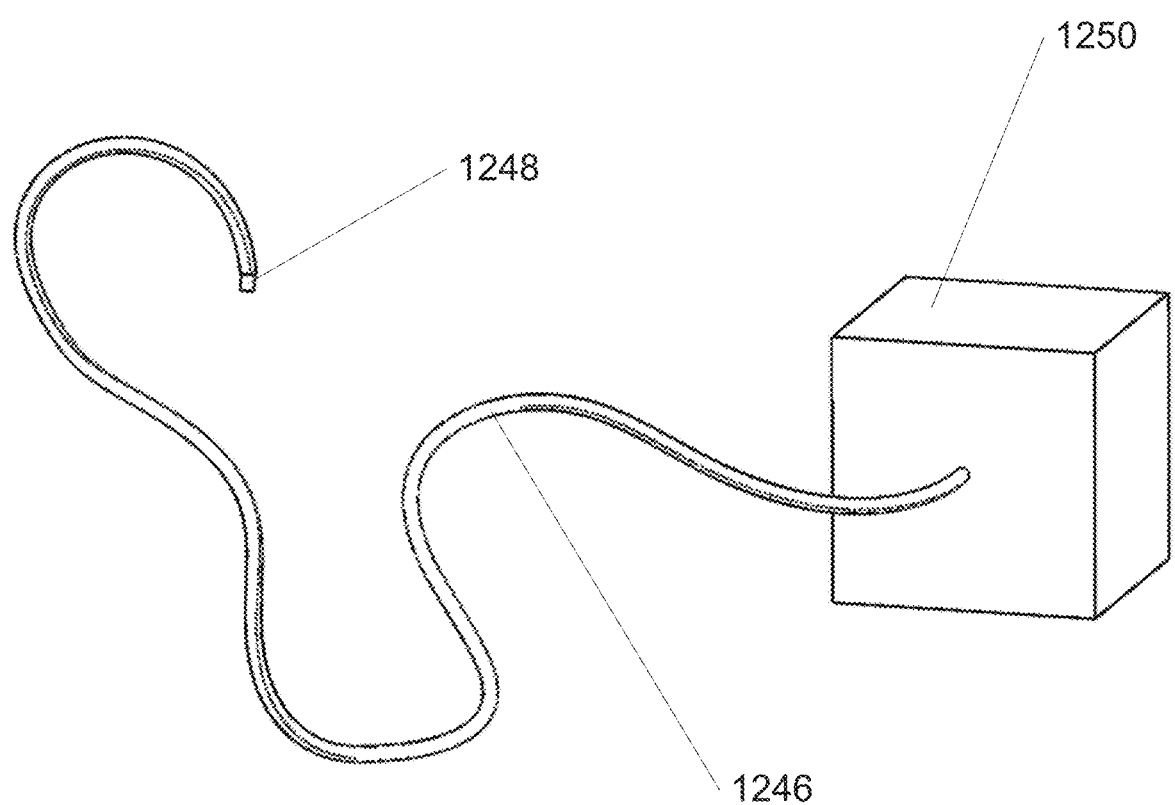
FIG. 80 depicts a cannula system.
Figure 81A:
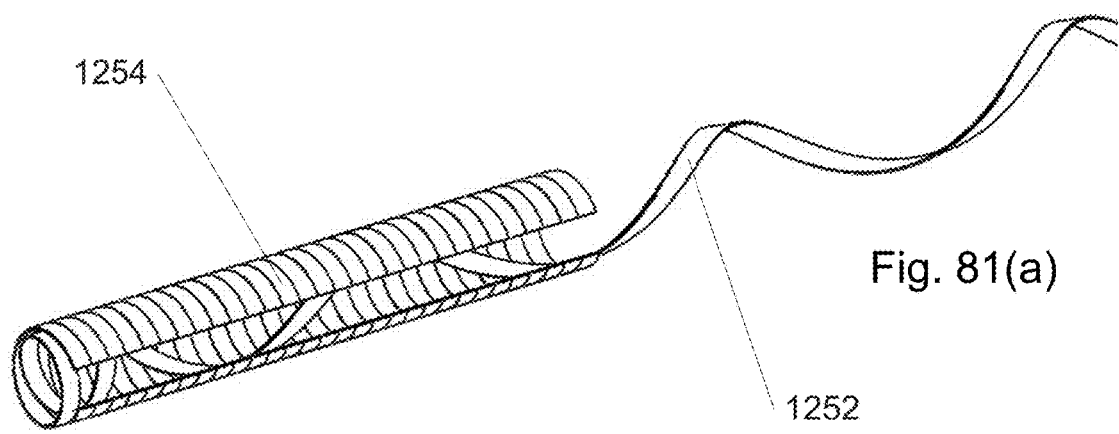
FIG. 81(a)-(b) depicts a cannula with an inner helix.
Figure 81B:
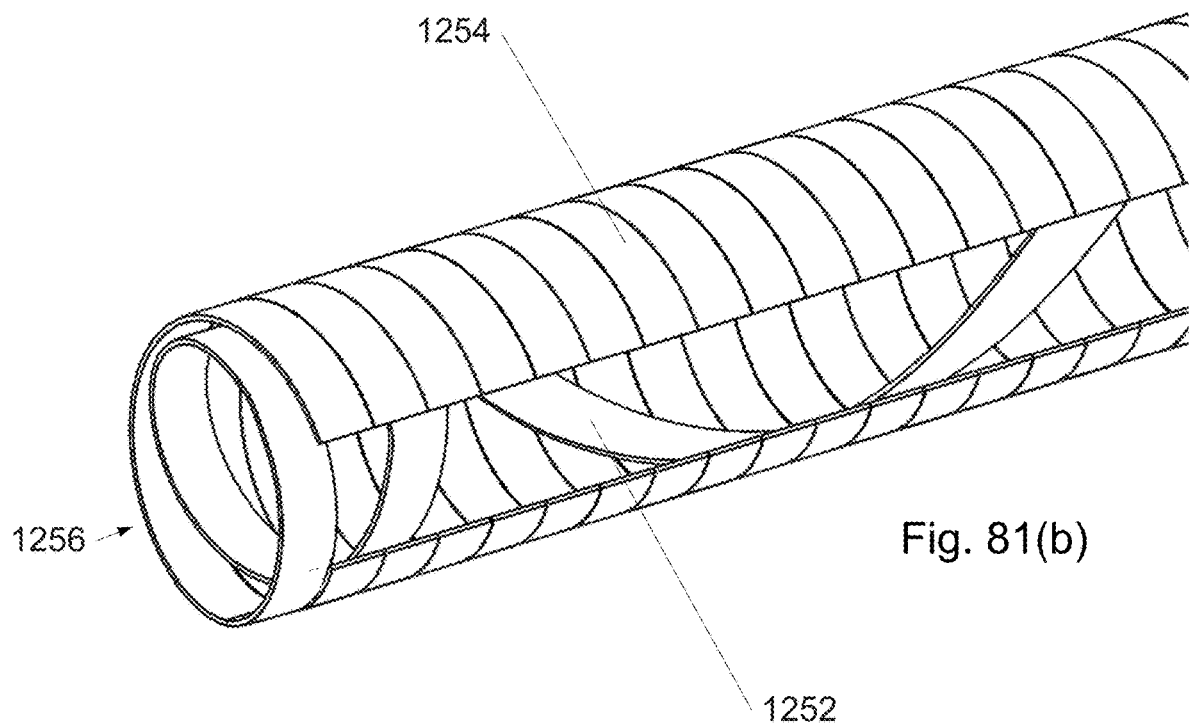

Continuously Distally Assembled/Disassembled Curved Cannula System:

As shown in the 3-D view of FIG. 80, a continuously distally assembled/disassembled curved cannula system may comprises three main hardware components: a cannula 1246 formed out of a strip of material, and which can distally elongate in a complex 3-D shape, a flexible stylet 1248 which fits within the lumen of the cannula (only the distal end of which is seen in the figure), and a console 1250 at the proximal end of the cannula. Cannula assembly and disassembly (the latter essentially a reversal of the assembly process, along the same path) may be accomplished by stylet 1248, driven by actuators housed in the console 1250, with sensor feedback as required. The actuator motions may be controlled via a computer or microcontroller by software that interprets the desired shape, specified by an operator at a high level (e.g., joystick, or pre-planned). Stylet 1248 must correctly orient the strip to form it into windings, join windings to one another, and adjust the local width, overlap, or spacing between the windings so as to curve cannula 1246 as needed. The strip is stored in the console 1250 and transported through the lumen of cannula toward the distal end. As the strip exits the console, the long axis of the strip is roughly parallel to the long axis of the cannula. However, it must end up with its long axis rotated through a large angle to form an approximately helical winding. Rather than attempt to re-orient the strip all at once when it reaches the distal end, in some embodiments the strip can begin its re-orientation more proximally, forming an inner helix 1252 as shown in the 3-D sectional view of FIG. 8(a) or its enlargement in FIG. 8(b). The inner helix has several turns (or more, in some embodiments) within cannula windings 1254. The inner helix may wrap loosely around the stylet shaft (not shown in FIG. 81), or may be guided around the shaft by angled rollers, etc. to minimize friction. In some embodiments, rotating the stylet shaft or a sleeve over it, or vibrating it, can also reduce friction. The pitch of the inner helix may be variable, decreasing as it approaches the distal end 1256. On reaching the distal end, the strip may be suitably oriented prior to joining by rollers, guides, or other means associated with the stylet head, as already described in conjunction with FIG. 73. It may be preferable in order to minimize friction to have the strip travel alongside the stylet shaft for most of the distance from console to distal end of the stylet, and the inner helix to therefore have a few small number of turns (only near the distal end of the stylet).

Figure 82:
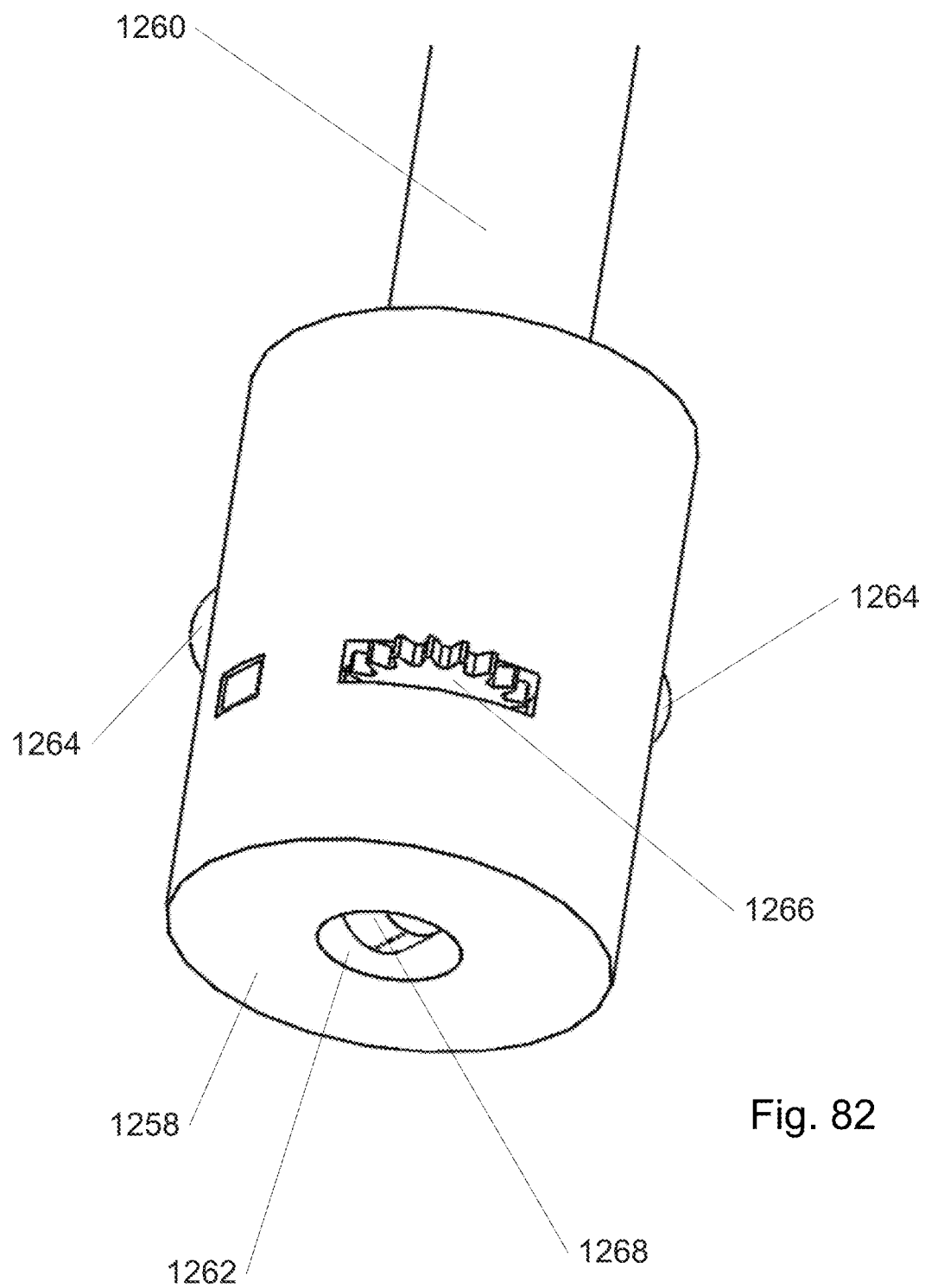
FIG. 82 shows the distal end of a stylet.

As shown in the 3-D view of FIG. 82, the stylet may comprise a head 1258 and a hollow, flexible shaft 1260 having a lumen 1262. Inside head 1258 may be included sockets for centering balls 1264 and a cavity for sprocket 1266. A flexure 1268 used to assemble a cannula made from a strip such as the designs of FIGS. 77 and 69 can be provided within head 1258. Sensors (e.g., a miniature forward-looking camera with LED lighting) associated with a specific application for the cannula may in some embodiments be incorporated in head 1258 and/or shaft 1260.

Figure 83:
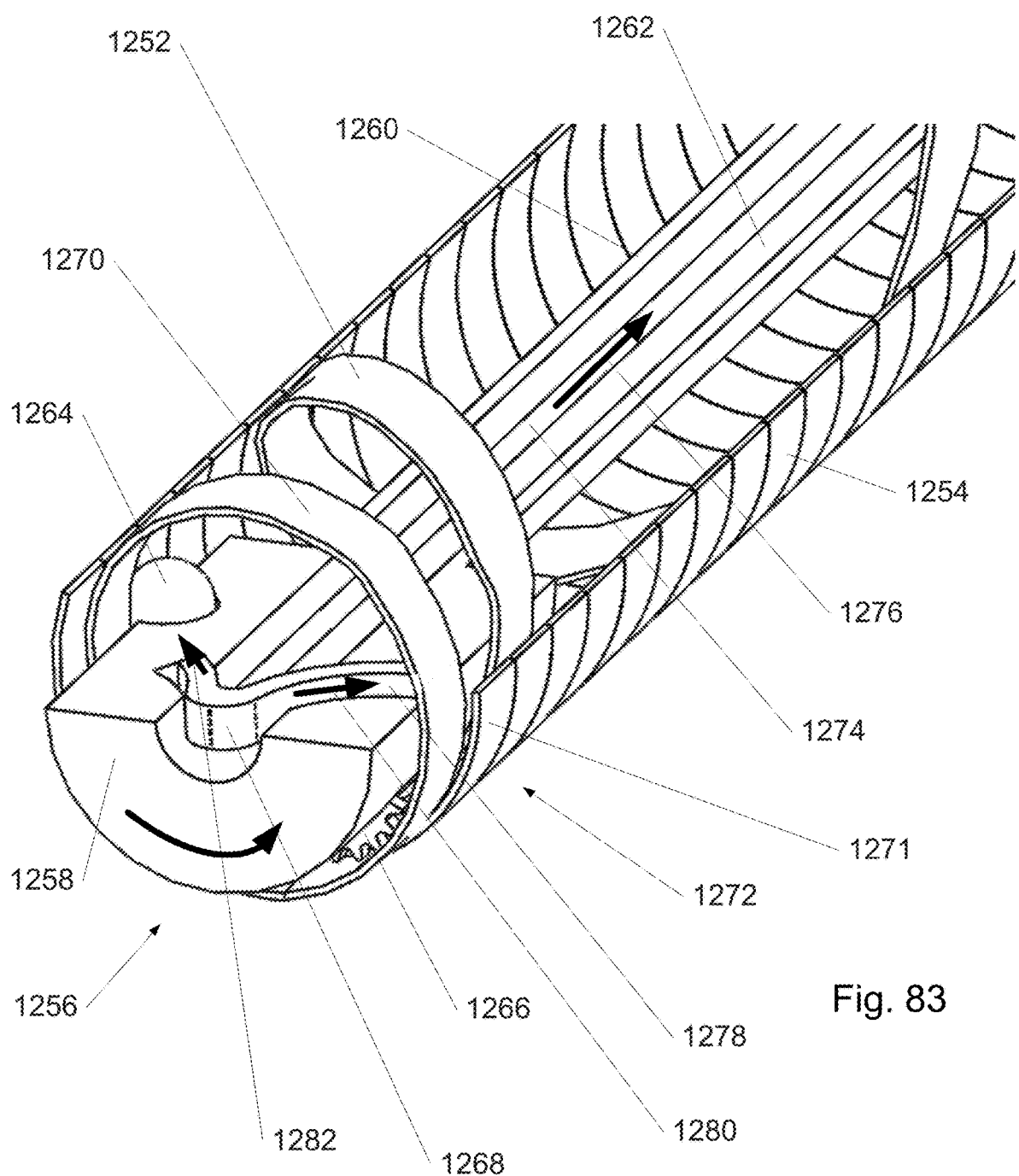
FIGS. 83-84(a)-(f) show views of the distal end of a cannula with stylet.

As shown in the 3-D partial sectional view of FIG. 83, windings such as winding 1270 are incrementally joined to one another (such as winding 1271) in region 1272 as stylet head 1258 rotates (e.g., counterclockwise as shown by the arrow, as seen from distal end 1256 of cannula), as inner helix 1252 enlarges in diameter near distal end 1256. Strips having designs similar to those of FIGS. 77 and 79 may be joined by pressing them together with a radial force that snaps wires 1216 into slots 1220 or snaps balls 1236 into slots 1234, for example. The radial force can be generated by the stylet head through various methods, including a bellcrank rotated by a pull wire (with the wire passing through or not passing through lumen 1262), a hydraulic or pneumatic element, a shape memory actuator, etc. In the example shown in FIG. 83, flexure 1268, actuated by pull wire 1274 passing, for example, through lumen 1262, can generate the radial force. Pulling on wire 1274 in the direction shown by arrow 1276 flexes flexure 1268, causing flexure tip 1278 to slide out of head 1258 in the direction shown by arrow 1280 and press on, for example, finger 1214 or wedge 1224, snapping finger 1214 or wedge 1224 into place and connecting windings 1270 and 1271. Depending on its design, flexure 1268 may also flex symmetrically and thus a portion may move within head 1258 as shown by arrow 1282, but this is of no significance. In summary, as stylet head 1258 rotates, the strip is gradually pulled from inner helix 1252 (thus causing the strip to advance distally along helix 1252), and allowed to expand (or actively expanded) and joined to form windings such as winding 1270 and winding 1271 (formed one rotation of head 1258 earlier than winding 1270).

As stylet head 1258 rotates, it also must translate according to the local pitch of the windings. In a curved section of the cannula, this varies around the circumference: being smaller on the inside than on the outside of the bend. Moreover, it can be difficult to push the stylet from its proximal end without it buckling (though in some embodiments centering devices such as those of FIG. 56 may be used). Therefore in some embodiments, the stylet may be designed to pull itself through the cannula at the appropriate speed. In FIG. 83, sprocket 1266 engages sprocket holes in the strip (not shown), which run in a continuous row along the long axis of the strip, somewhat similar to holes 1202 in FIG. 75 (e.g., in the design of FIG. 77, these may run between rows 1218a,b, or holes 1220 may serve also as sprocket holes). Sprocket 1266 can freely turn on its axis in some embodiments, its motion driven by the rotation of head 1258 and engagement in the sprocket holes. By remaining so engaged, sprocket 1266 thus pulls head 1258 forward as the latter rotates. The axis of rotation of sprocket 1266 is preferably substantially perpendicular to the axis of row of sprocket holes in its vicinity, although with adequate clearances such perpendicularity is less important. In some embodiments, more than one sprocket, engaging the cannula at more than one location (e.g., three sprockets 120° apart) may be used. In some embodiments, rollers, wheels, or other means may be used in lieu of or in addition to sprockets.

For sprocket 1266 to remain reliably engaged with sprocket holes, the shaft of sprocket 1266 may be spring-loaded in some embodiments, or head 1258 may be pressed in the direction of sprocket 1266, or at least kept at a substantially constant distance from windings such as winding 1270. In some embodiments, head 1258 is maintained concentric with the cannula. In some embodiments, distance may be maintained by providing other elements on head 1258 such as balls 1264. Balls 1264 may be rotating or non-rotating; in the latter case balls 1264 may rotate in sockets within head 1258 as head 1258 rotates and translates. If one sprocket 1266 is used as shown, two or more balls 1264 may be used to maintain the position of head 1258 within the cannula. In some embodiments, in lieu of balls, rollers, wheels, or other devices may be used.

In the case of a strip designed similarly to that of FIG. 77 (or similarly, if designed as in FIGS. 75-76) in addition to pressing finger 1214 to snap wires 1216 into slots 1220, the stylet can adjust the overlap between strips 1212 such that wires 1216 enter the correct rows of slots 1218a,b. For example, head 83 may be split into two sections, one distal and one proximal, each with a sprocket, and both rotating at the same speed but with at least one able to translate along the rotation axis so as to vary the distance between the sprockets. Given two windings such as windings 1270 and 1271, if each is engaged by one sprocket, then the overlap between the strips can be adjusted before wires 1216 are pressed into slot 1220.

Figure 84A:
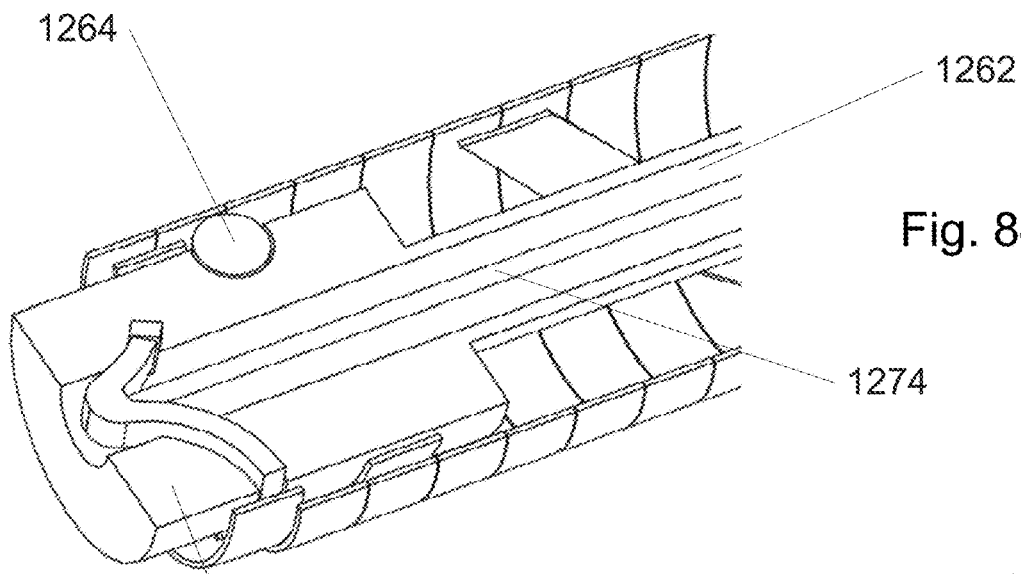
Figure 84B:
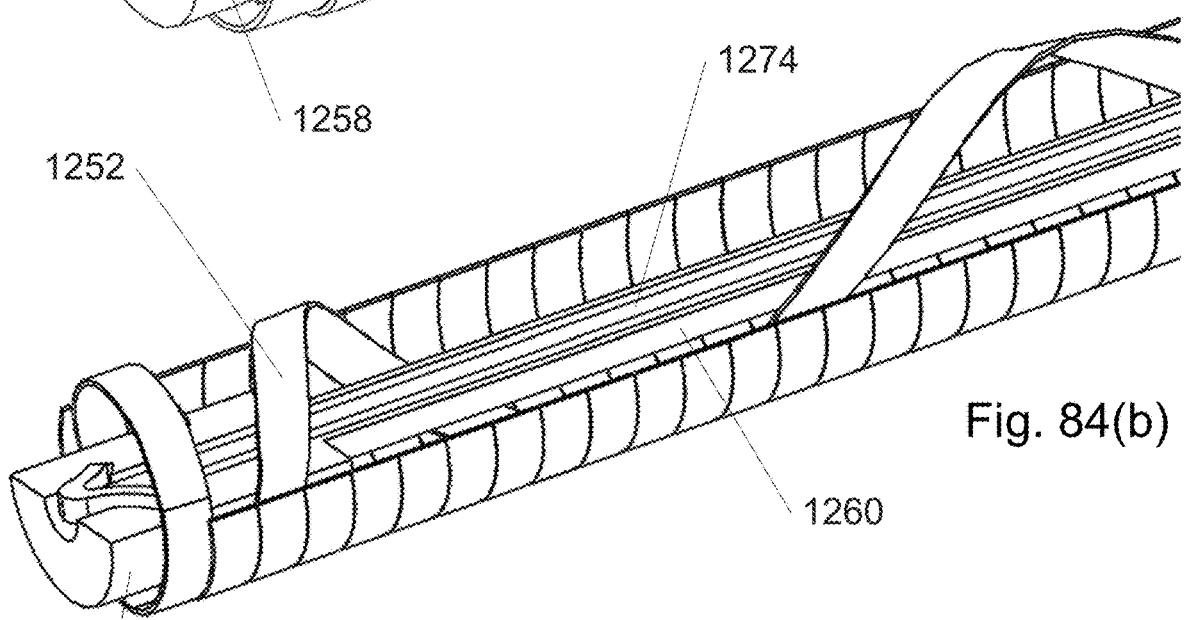
Figure 84C:
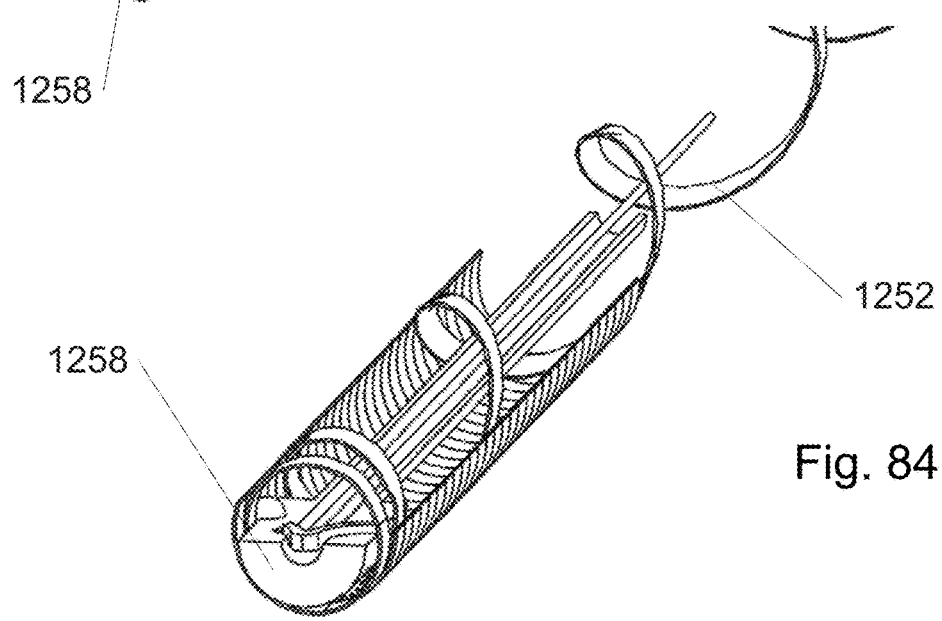

FIG. 84 shows various 3-D views, some sectional or partial sectional of the distal end of the cannula shown in FIG. 83(f), in particular, depicts a partial sectional view in which flexure 1268 and flexure tip 1278 may be seen clearly.

Figure 85:
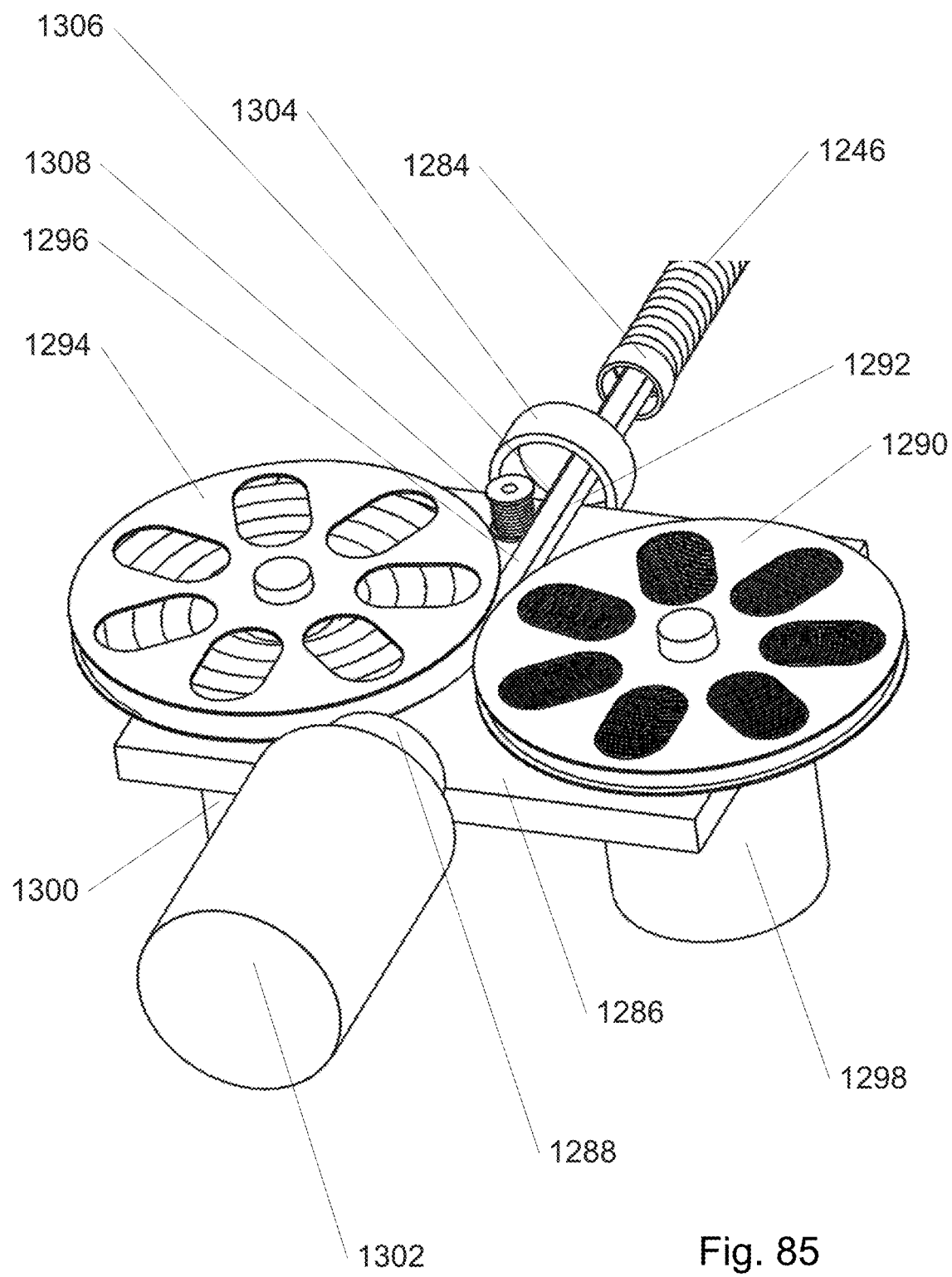
FIG. 85 show components of a proximal console for a cannula system.

FIG. 85 depicts a 3-D view of several of the internal components of console 1250 (in FIG. 80) that may be used in some embodiments, such as embodiments associated with a stylet of design similar to that of FIGS. 82-84. The cannula 1246 (in FIG. 80) is built upon a base tube 1284, which is attached to the console enclosure (not shown). Within the enclosure is a motorized rotating plate 1286 supported by bearings 1288. The plate supports a reel 1290 on which strip 1292 is wound, and a reel 1294 on which the stylet shaft 1296 is wound. A motor 1298 drives reel 1290, and a second motor 1300 drives reel 1294. A third motor 1302 rotates plate 1286, allowing both reels to rotate in the same direction around the longitudinal axis of shaft 1296 during assembly or disassembly of cannula 1246. Reels 1290 and 1294 serve to feed strip and stylet shaft, respectively, during assembly, and retract both during disassembly, applying the required tensions and removing slack. During disassembly, stylet motion is preferably the result of proximal tension applied by reel 1294, not distally compressing shaft 1296. Wiring for electrical devices such as cameras and LEDs, which may be mounted to the stylet, can run through the lumen of shaft 1296 and connect through slip rings, for example, associated with the rotation axis of reel 1294. If fluid (e.g., air to dislodge soil in a search and rescue application) must pass through shaft 1296, a rotating fluid coupling can be provided. Wiring and fluid tubing can run alongside the stylet shaft or wrap around it in a helical shape, in which case the wires and/or tubes can be wound up around their own reels or spools. Signals associated with sensors on stylet or cannula, as well as power for motors such as 1298 and 1300 may be communicated through slip ring/bearing 1304 on the rotation axis of plate 1286.

If used, pull wire 1306 (similar to pull wire 1274 of FIG. 83) may exit the stylet at or near its head and run alongside shaft 1296 as shown, wrapping around a motorized winch 1308 in some embodiments. Depending on the design of the strip (e.g., that of FIGS. 75-76, FIG. 77, or FIG. 79, for example), adjustment of strip width may require rotational or translational motion of a rotating or sliding finger, or axial motion of one section of the stylet head relative to another. To accommodate this adjustment, an additional actuator (not shown) can be mounted to plate 1286. If the stylet is provided with a grasper or other end effector, motors that manipulate a pull wire running through its lumen can be also mounted to plate 1286 so as to actuate it.

If required, components such as the stylet with pull wire 1306, etc. can be completely withdrawn from cannula 1246 without disassembling the latter, e.g., to provide a clear lumen for inserting devices and other payloads. An actuator to temporarily displace any console components that obstruct access may thus be needed. Also, to withdraw the stylet may require an additional actuator to decouple strip 1292 from the stylet (e.g., by retracting the sprocket and head-centering balls), allowing the stylet to be pulled out.

In some embodiments, payloads may be pushed or pulled by the stylet from one end of the cannula to another as the stylet advances or retracts (either during the assembly or disassembly of the cannula, or at other times). In some embodiments, payloads may be contained within capsules or otherwise provided with features such as sprockets which engage sprocket holes on the strip (e.g., the same ones used to translate the stylet). Such payloads can be transported through the cannula (with the stylet withdrawn) by causing them to spin (e.g., driving them with a rotating torque coil). In some embodiments, the stylet can leave sensors, actuators, or other devices at the distal end of the cannula and then itself withdraw. Wires can be then trailed back from the device, or the strip may provide electrical connections to the device by having wires embedded within it or insulated electrical traces on its surfaces. Of course, the device can also be wireless, including having its own power source, or the ability to harvest energy.

In some embodiments, multiple, separate cannulas can be assembled from a single strip, in which case, the console may include a cutter for strip 1292. In some embodiments, reel 1290 may be easily replaceable, and may be in the form of a replaceable cassette, allowing more strip to be added added to the cannula system. In some embodiments, a short working distance, side-looking camera (or simpler sensor) in the stylet head can be used to verify or facilitate the motions of the strip and stylet required to join one winding to another or to separate the windings. In some embodiments, it may be useful to know the precise shape of at least part of the cannula in real time, so that this data can be used for error correction: modifying the trajectory as the cannula is assembled. This may require proprioceptive sensors such as strain gauges or electromagnetic position/orientation sensors. In some embodiments, navigational sensors such as a camera may be required for a human operator to steer and navigate the cannula through obstacles in the environment, and may also be needed for the task at hand (e.g., inspection).

Low-level mechanical control of the cannula can be accomplished by software to interpret the growth path (e.g., specified by an operator in real time, or ahead of time) as low-level actuator commands (e.g., moving sliding wedges to specific positions, rotating the stylet at a particular speed). However, control of a distally-growing cannula, especially if very high aspect ratio, can be challenging. If not for tolerances, clearances, and material compliance, and if structural loads were non-existent, the evolving cannula shape should be fully deterministic. Thus reaching a known target with the distal end, for example, would be purely a matter of navigation or path planning, coupled with automated deployment. However, this is not the case, and the cannula shape and position of the distal end may deviate from what is desired unless compensated. With high length-to-diameter ratios and distal growth, loading of the cannula by body and contact forces can change dynamically as the cannula grows. While this is less of a problem in microgravity or in buoyant underwater applications, inertial and (if the cannula is immersed) viscous forces may still have significant effects.

The shape of the entire cannula may matter in some contexts (e.g., surgical, to minimize tissue trauma), as well as the position of the distal tip. The desired cannula shape may be achieved and maintained by model-based control, in which the effect of forces on the cannula are simulated (with input from test data) and the shape estimated.

With some designs of strip (e.g., those of FIGS. 61 and 79), the shape of a cannula in regions which have already been formed by distal growth can be modified. In some embodiments, one or more actively-tensioned cables running through the cannula lumen (or externally) may be used to adjust shape.

Convergence of the distal end of the cannula on a desired target can also be achieved in some embodiments by modifying the curvature settings of winding not yet deployed, ideally doing so in an iterative process of sensing cannula shape and/or distal end position, and re-calibrating.

In some embodiments, the feasibility of target attainment given current constraints (e.g., target position, undeployed cannula length), current distal position and orientation is important to determine. For example, an operator may need to decide whether to retract/disassemble the cannula partially and attempt to reach the target by extending it again along a new trajectory. This determination should include a safety factor that takes into account errors and expected additional proximal deformations as the cannula continues to extend.

Interlocking elements such as tabs 958 and holes 960 need not be flat as shown in FIG. 65 and other figures, or in the same plane as one another (e.g., a tab can be rotated with respect to the plane of a hole). In some embodiments, in order to maximize flexibility of the strip or its components such as bands, the strip thickness is minimized but features thicker than the strip (e.g., 3-D features) are provided. For example, in the 3-D view of FIG. 74(a), tab 1150 (here shown as rectangular in profile, though they may be curved as the tabs in other figures) has a curved shape in the lower portion which fits into hole 1152 of winding 1154, entering hole 1152 from the inside of the winding. In some embodiment variations, tab 1150 enters hole 1152 far enough that the curved sides of tab 1150 are deformed, and become preloaded against the edges of hole 1152, thus helping to retain tab 1150 through friction. In some embodiments, tab 1150 may comprise features which prevent deformation of its curved section beyond a certain point (e.g., at which tab 1150 could completely pass through hole 1152). Once tab 1150 is within hole 1152, it cannot be pulled out by motion in the directions shown by the arrows, and thus a tab 1150 near, for example, the proximal edge of one winding which engages a hole 1152 on the distal edge of another winding, can interlock the windings together. Tabs such as tab 1152 may be manufactured by stamping of thin metal, for example.

FIG. 74(b) depicts a 3-D view of a relatively flat tab 1156 and a hole 1158 in winding 1162. In the process of making hole 1158 (e.g., if stamped) or through a separate process (e.g., welding), stop 1160 can be provided. When tab 1156 enters hole 1158 in the direction shown by the arrow, tab motion beyond the outer surface of winding 1162 is prevented by stop 1160, thus allowing for examplel tab 1156 to be preloaded against stop 1160 (e.g., by the winding attempting to straighten itself) without any risk of tab 1156 exiting hole 1158.

FIG. 74(c) depicts a cross-sectional view of two adjacent cannula windings 1162 and 1172 in which winding 1162 is being connected to winding 1172 (both typically part of the same strip), involving substantially radial motion of winding 1162 as shown by the arrows. Winding 1162 in some embodiments has affixed to it in some embodiment variations a ball (e.g., a steel ball bearing) 1166 which may in some embodiment variations be inserted partially into a hole 1164 and attached by weld 1168 or other method. As winding 1162 approaches winding 1172, ball 1166 enters hole 1170 in winding 1172. Once windings 1162 and 1172 are in contact, motion of one winding relative to another as depicted by the arrows of FIG. 74(a) is restricted.

In some embodiment variations, ball 1166 may protrude further from winding 1162, providing an undercut which winding 1172 can hook onto. In some embodiment variations, e.g., ones in which winding 1162 is not adequately preloaded against winding 1172, hole 1170 in winding 1172 may have edges which are compliant and thus can allow winding 1172 to "snap" over ball 1166.

In some embodiments, rather than using a ball 1166 and a hole 1170 as in FIG. 74(c), windings 1162 and 1172 can be provided with interlocking features (e.g., by stamping) such as a concave feature on the inside surface of winding 1172 into which is inserted a convex feature (e.g., dome, bump) on the outside surface of winding 1162.

In some embodiments, magnets (e.g., NdFeB) attached to the strip may be used to join windings to one another, or to assist with alignment and engagement of windings which are joined by other methods. For example, the strip may be provided with magnets spaced regularly along or near their edges, with one pole (e.g., north) facing away from the strip and the other facing towards the strip. When two sections of the strip and then brought near one another to form windings, the magnets will attract one another.

In some embodiments of a continuously distally assembled/disassembled cannula, a cable or similar tension member, or a strut or similar compression member, can be used within or outside the cannula to stiffen it, e.g., by preloading windings against one another. In some embodiments, the stylet, if left within the lumen, can serve this function, while in some embodiments, a member can be inserted and connected to the windings (e.g., by the stylet after the assembly process) and removed (e.g., by the stylet prior to disassembly).

In some embodiments and applications, the stylet does not remain within the cannula after assembly, but is withdrawn (e.g., proximally) to allow full access to the lumen. In some embodiments and applications, the stylet does not significantly block the lumen, or access to the lumen is not required, and may remain inside the lumen. If the stylet has been removed or repositioned, it may be re-inserted or repositioned to allow disassembly of the cannula, or (if the design permits it) adjustment of the cannula.

Instead of a DASC instrument that is substantially constant in diameter as has been illustrated herein, in some embodiments DASC based on rings, continuous strip, or other approaches can have a tapered shape (e.g., smaller at the distal end). If the taper angle is relatively large, rings may be transported through the cannula without the need to compress and swivel them to fit, or require less compression and/or swiveling.

In some embodiments, multiple DASC devices may be used simultaneously in a procedure, either with the distal ends in different target regions or in the same target region but (e.g., with different approach angles). For example, two DASC devices in the same region with different approach angles can allow for triangulation useful in suturing, tissue, retraction, etc.

Instead of transporting material to the distal end of DASC through a lumen to extend it, in some embodiments material can be transported over (on the outside of) DASC, or alongside DASC, e.g., using DASC as a rail or guide for the material transport. In some embodiments, material necessary to extend DASC is obtained from the environment.

In some embodiments, the DASC lumen can be subdivided by inserting tubing after the desired shape has been assembled, or gradually as it is being assembled. For example, four tubes may be passed through the cannula: one for irrigation with saline, one providing a working channel for an instrument, and one providing a channel for an endoscope, and one providing a channel for a fiber optic illuminator. The remaining space in the lumen can then be used for aspiration.

In some embodiment variations, to minimize the time required for the stylet to connect a ring and/or make a long trip back to the ring stack to pick up another ring (or drop off another ring if disassembling the catheter), the rings can be stored more distally within the gradually-extending cannula. For example, rings can be held in a compressed state (e.g., within a tube, one behind the other) located inside the cannula. Such rings could be pushed out by a plunger. Or, rings could be held within a frame designed to allow the grippers to engage them and separate them from the frame: the rings may need to be oriented with the major axis of the compressed, substantially elliptical ring at an angle to the cannula axis to facilitate this.

In some embodiments, rather than storing rings proximally as in FIG. 30 and transporting them through the entire assembled length of the cannula (e.g., from the groin to the heart) as in FIG. 29 to reach the distal end where they are assembled, the rings may be stored within the cannula such that the most distal of such stored rings is stored far closer to the distal end. This can speed the assembly and disassembly processes, especially when it difficult to store rings in a stack such as stack 378 inside the body.

Figure 43A:
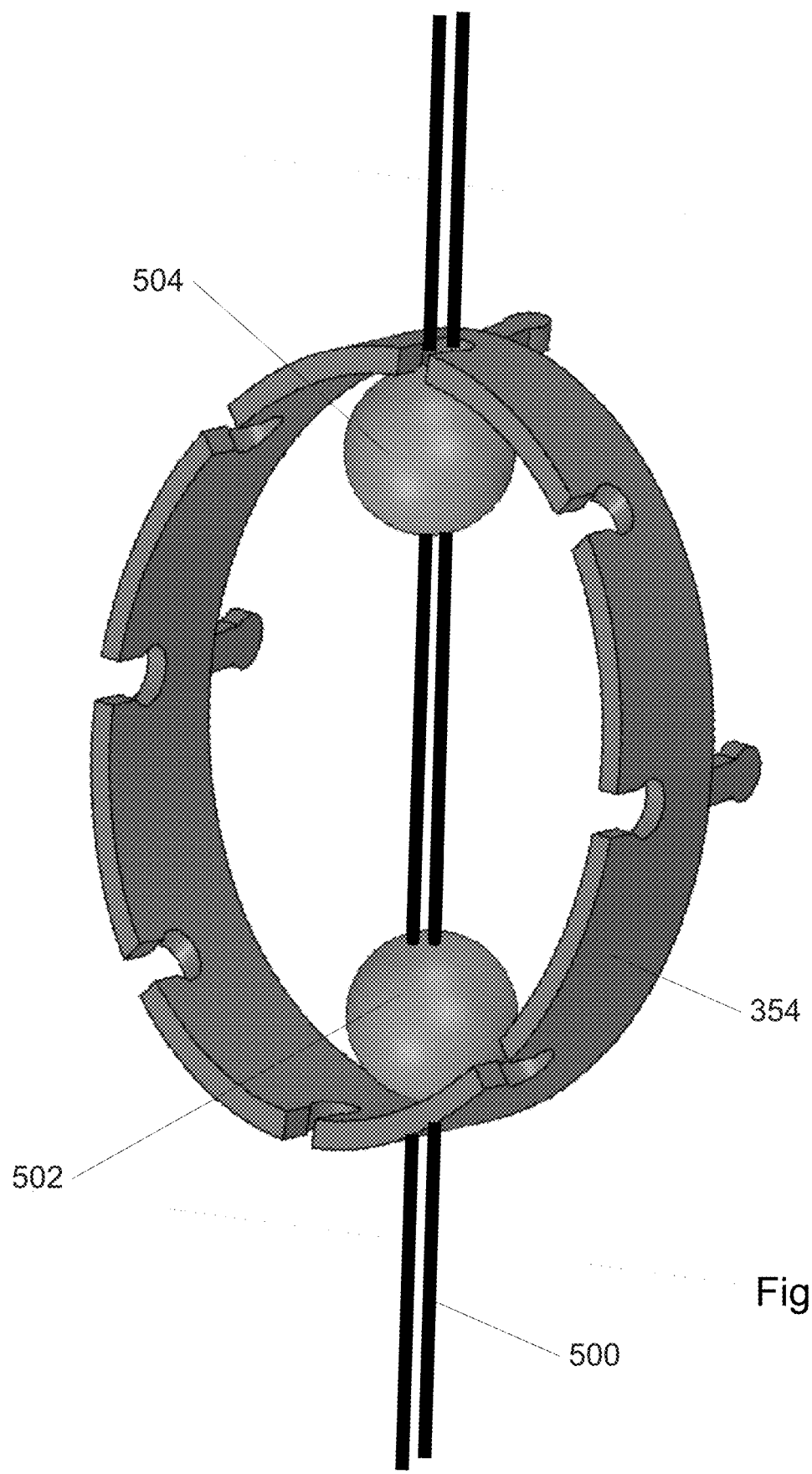
FIGS. 43(a)-(b) show a storage element for rings.
Figure 43B:
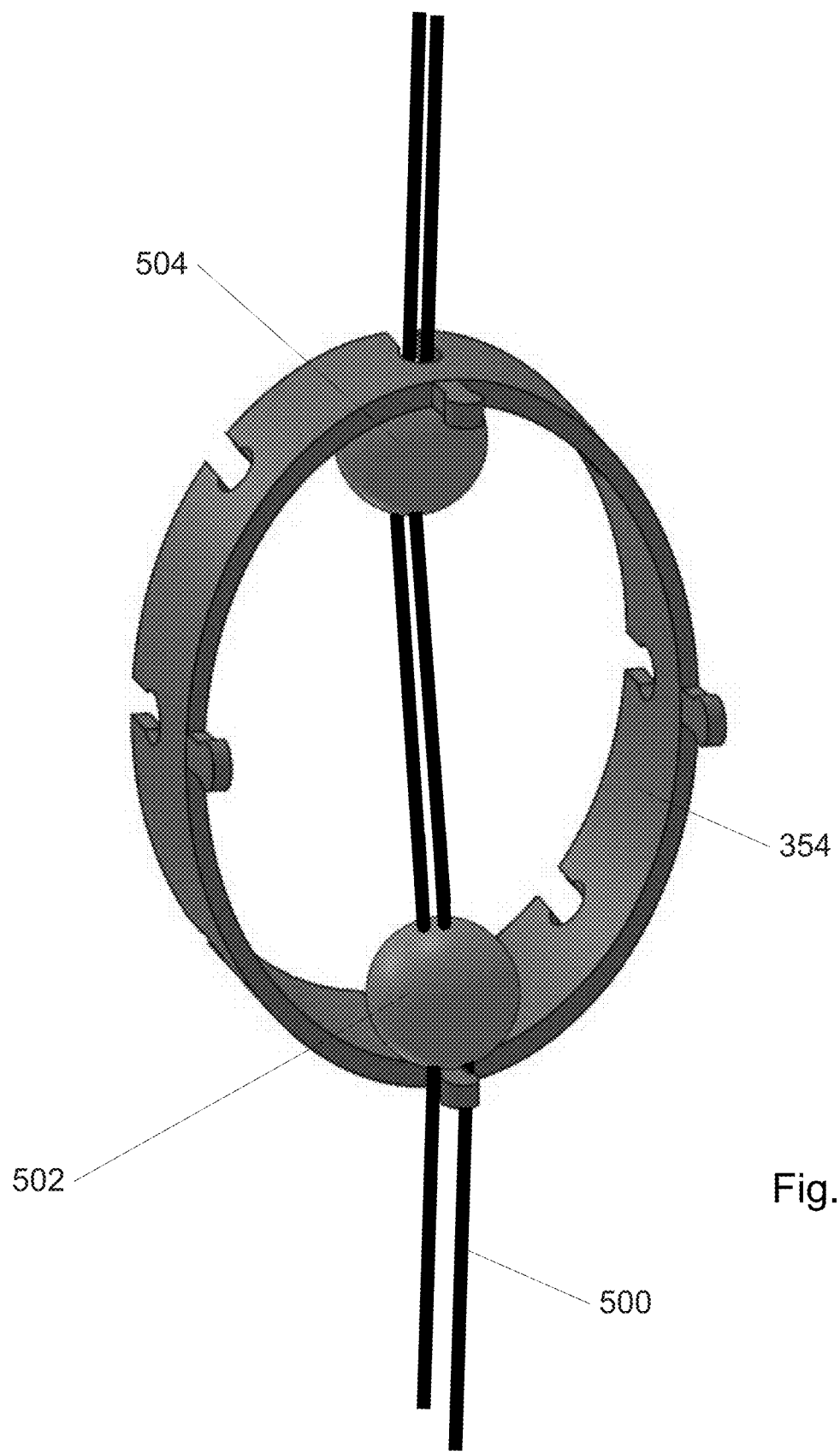
Figure 44:
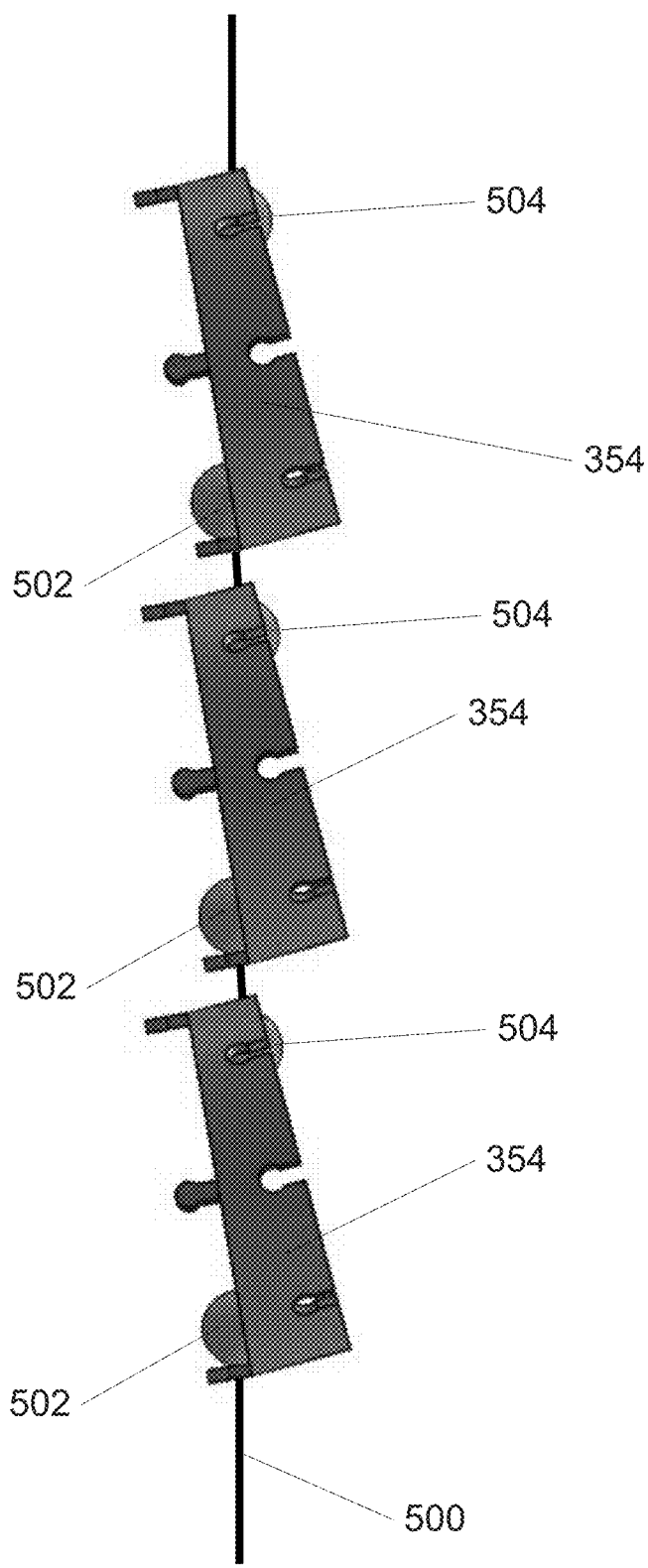
FIG. 44 shows a group of rings in a cannula.

In some embodiment variations, rings may be plastically deformed into a compressed form that allows them to be stored within the cannula adjacent to one another, or if their major axes are tilted with respect to the local cannula axis, with some overlap. In other embodiment variations, the rings are elastically deformed into an elliptical shape and retain that shape within the cannula without the aid of the stylet by means of a storage element. For example, as shown in FIGS. 43(*a*) and (*b*), the storage element may comprise a pair of cables with a set of suitably-spaced bumps, knots, or other projections (e.g., balls 502 and 504 as shown) along its length. If the cables pass through a ring, then by rotating and deforming the ring into an elliptical shape, it may be retained in that shape (if the cables are under tension) by fitting the cables into hole 360 at the distal end and around tab 358 at the proximal end, such that balls 502 and 504 press against the proximal and distal inner surfaces of the ring, respectively. Multiple deformed rings can be placed along the storage element as in FIG. 44, and the element and rings can be located within the cannula, such that a suitably designed stylet can grasp the most distal ring (e.g., compressing it slightly to make it more elliptical and loosen the pressure of the balls) and transport it distally to the distal end of the growing cannula, where it can be assembled. As the cannula lengthens, the storage element may be advanced so that the most distal stored ring is close to the distal end of the cannula. Disassembly from the distal end may also be performed, with the stylet returning the rings to the storage element, and if desired, the element can retract gradually as the cannula shortens. FIG. 44 depicts rings of the same kind; in practice rings of both types shown in FIG. 26 may alternate.

In some embodiment variations, the cables in the storage element are replaced by rigid segments terminating in balls such as balls 502 and 504, and a flexible element connects ball 504 of one segment with ball 502 of the next most distal segment. In such variations, the overall storage element need not be under tension, since the rigid segments and balls maintain the rings in the proper elliptical shape, and the storage element can bend in 3-D to follow the cannula shape.

In some embodiment variations, features such as notches may be added to the rings to engage the cable or rigid segments. For example, slots may be added to the proximal and distal edges of the rings adjacent to the holes and tabs used for interlocking, and the storage element can engage these. In some embodiment variations features may also be added to rings and/or balls (or other protrusions) to positively secure the rings (e.g., not releasing them until they are made even more elliptical). In some embodiment variations, a single cable may be used, with tab 358 slotted to allow the cable to enter it.

In some embodiments, the storage element may be in the form of a tube or guide within the lumen of the cannula, through which the rings are transported to the distal end of the cannula, and which keeps the rings in a deformed shape during transportation (e.g., preventing them from expanding, if elastically deformed, into an approximately circular shape). In some embodiments, the rings are at least partially plastically deformed into a shape which allows them to be transported through the cannula lumen without applying a substantial force, or any force, to them. Such rings can be fed continuously through the cannula (in some embodiments within a tube or guide), with one ring pushing the ring just distal to it along, for example. Once emerging from the distal end of the cannula, a mechanism can then deform the rings into the required circular shape and swivel and mate them as needed.

In some embodiments, the final circular shape may be maintained by a design that enables the tabs for the major axis of the ring (as-transported) to enter the holes of the ring just proximal to it from the inside rather than from the outside as in FIG. 32(*g*)-(*h*). This happens while the ring is forced to be slightly elliptical (under elastic conditions) with its major axis perpendicular to the major axis of the ring when transported.

In some embodiments, rings are segmented and hinged (e.g., four equal curved segments with hinges 90° apart). Such a ring can be folded into a flatter configuration for transportation through the cannula by pulling apart diametrically opposite hinges. In this state, rings can be continuously fed, end-to-end, through the cannula, either directly or through an internal tube or guide. Once a ring has reached the distal end of the cannula, it can be unfolded into a circular shape. To prevent it from folding/collapsing, tabs can be designed to enter holes in the ring just proximal to the ring in question such that the ring is held open. In some embodiment variations, the ring may be elastically deformed when mated with the adjacent ring to keep it from folding.

Figure 45A:
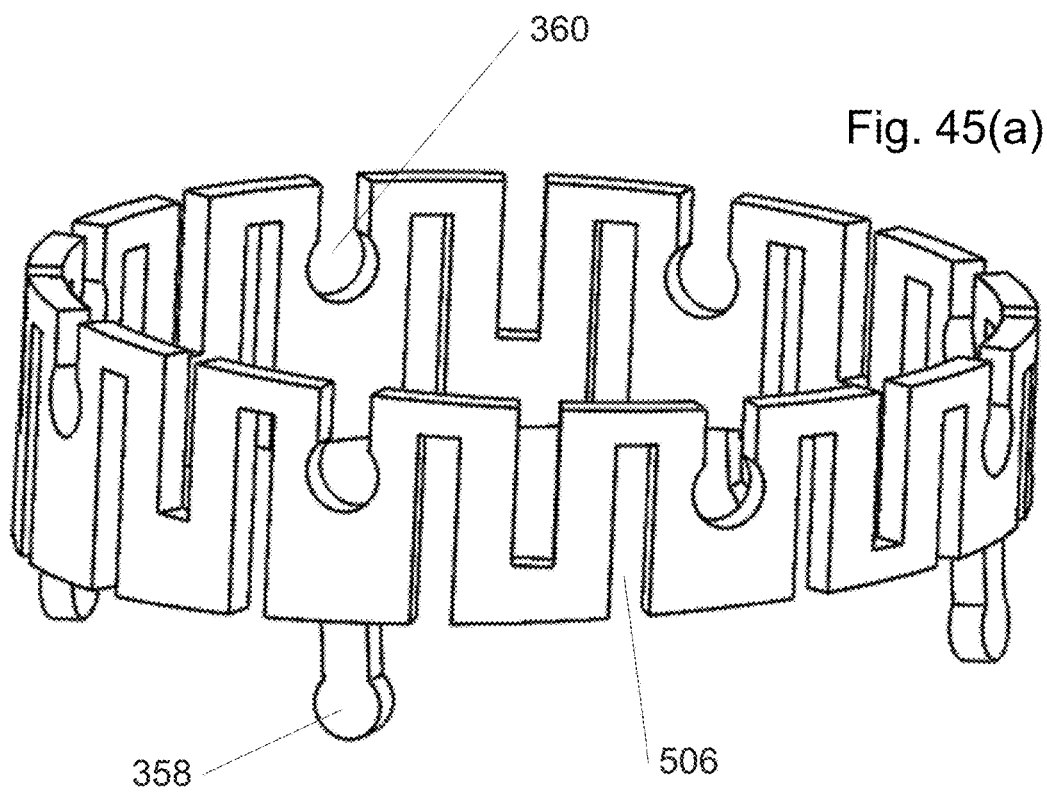
FIG. 45(a)-(b) shows expandable rings.
Figure 45B:
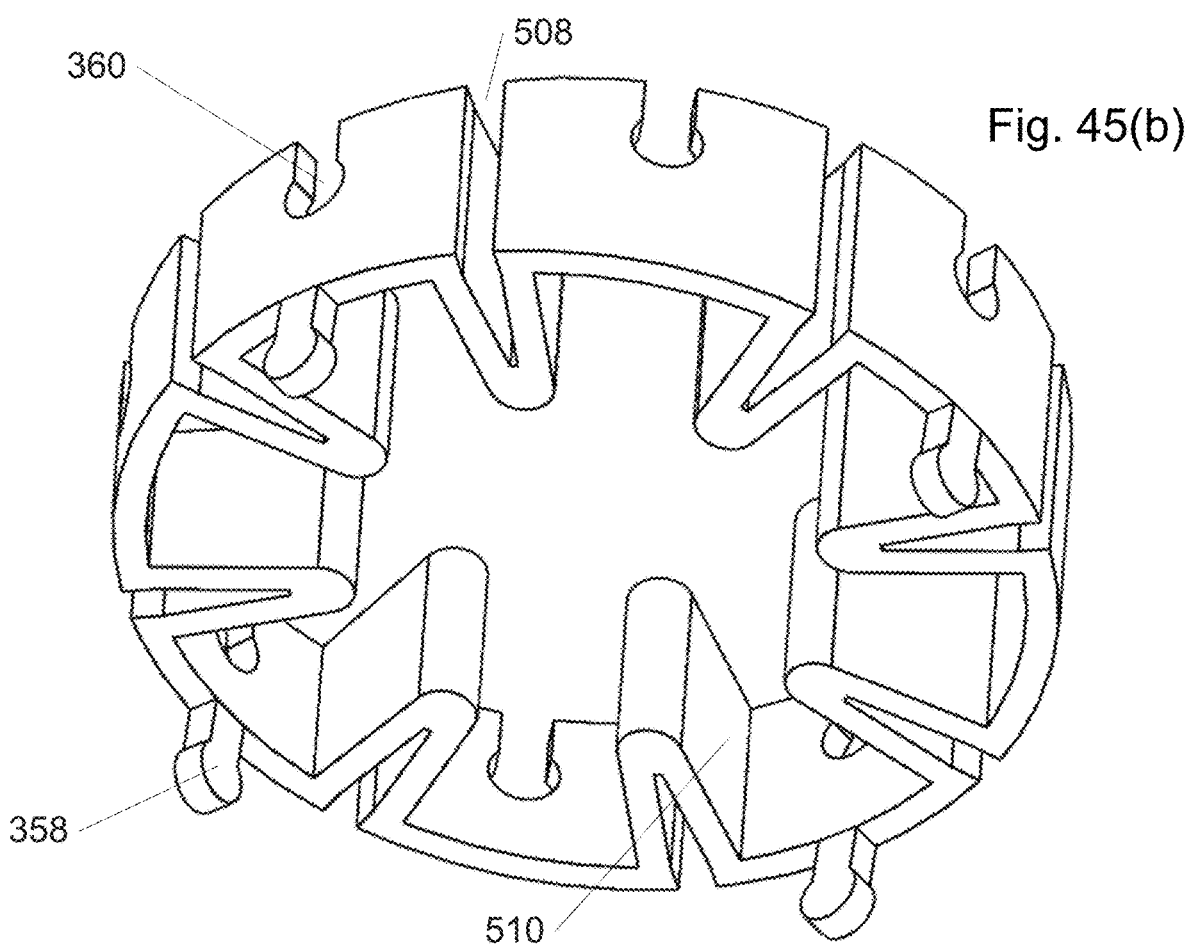

In some embodiments, rings are not themselves transported through the cannula. Rather, a continuous strip of material can be transported through it, having a shape which can be segmented and used to form rings at the distal end. For example, a segment of a strip having one or both edges that are sinusoidal in shape can be joined end-to-end to form a ring that is wedge-shaped/tapered on its proximal and/or distal surface. Segments may be cut off the strip as needed, or if pre-scored, perforated, or otherwise weakened, can be broken off. Joining can be accomplished with interlocking mechanical features, adhesives, welding, fasteners, and many other means known to the art. FIG. 45 depicts wedge-shaped rings having tabs and holes similar to ring 354 of FIG. 26, but which can be expanded from a smaller diameter, shown in the figure, to a larger diameter (not shown), thus allowing unexpanded rings to pass distally through the lumen of the cannula comprising already-assembled rings, and then, at the distal end of the cannula, be oriented at the desired angle, expanded, and interlocked to the cannula. The expansion of the ring(s) can involve plastic deformation, or if a locking mechanism is provided, can involve an elastic deformation. Over-expansion of the ring(s) to accommodate spring-back of the material can also be provided. FIG. 45(a) depicts a version of the expandable ring comprising four tabs and eight holes (however, the number of each can vary) wherein cuts 506 in the wall of the ring (which normally would have filleted corners for stress reduction) allow the ring to be stretched to a larger diameter, somewhat like a stent (e.g., through plastic deformation). FIG. 45(b) depicts a version (also comprising four tabs and eight holes, for example) wherein cuts 508 are provided and the cut edges of the ring are joined by internal hinges (e.g., plastically-deformable) 510 which also allow the ring to be stretched to a larger diameter. The stretching may be performed by a balloon or other expanding element, or by other means, and the assembly of the rings can be performed in a process similar to that of FIG. 14, but in which each rings is oriented such that the tabs enter holes in the next most proximal ring as the expansion occurs, locking the ring in place. Since, due to the wedge angle at which the ring mates with the next most proximal ring varies according to the ring orientation, the balloon or other element should accommodate the variable wedge angle, e.g., through compliance in the balloon or its attachment to a shaft or stylet such as tube 190. A cannula produced this way can be permanent (e.g., for use in an implant), or if the rings are plastically deformed as-stretched and means of re-compressing and withdrawing them through the cannula are provided, then the cannula can be disassembled after use.

Since the rings can change in diameter, there is no need to deform them into elliptical shapes and swivel them as in the 17$^{th}$ Embodiment. This can facilitate use of a cannula comprising such rings within solid tissue or within other environments in which there is little or no room beyond the circular confines of the distal cannula end as it evolves. If a balloon is used to expand the rings, it can serve a further purpose in displacing surrounding material (e.g., bluntly dissect tissue) to make room for the ring.

In some embodiments, rings such as those in the 17$^{th}$ Embodiment may be tethered to cables or wires to that they may be retrieved in case they are dropped inside a patient. The cables may be remain attached as long as the cannula is assembled (e.g., with the cables lying alongside the inner wall of the cannula, possibly sandwiched by a liner), or removed after assembly.

Instead of using tabs and holes such as those shown in FIG. 26 to interlock rings, in some embodiments rings may have features which lock together when the rings are mated are twisted through a small angle. Or, in some embodiments rings may be elliptical in shape when unstressed, and be joined together in pairs such that a smaller outside diameter on the face of one ring can fit inside a larger inside diameter of an adjacent ring. Initially the rings may be mated with their major axes substantially parallel, after which one may be rotated relative to the other through an angle (e.g., 90°) such that both rings are both forced into substantially circular shapes, and remain interlocked by virtue of friction or the inclusion of locking features. In lieu of the rings of FIG. 26 having solely holes or tabs on their opposite faces, in some embodiments they may have a mixture of tabs and holes.

In some embodiments rings have built-in curvatures (including rings of zero curvature in which the distal and proximal faces are parallel), much like groups of at least two rings of the kind shown in FIG. 26 have built-in curvatures. Appropriate selection and oriented assembly of such rings can produce a complexly-curved cannula.

In some embodiments, rings may be compressed and remain compressed when desired, or expanded and remain expanded when desired, by designing them to be bistable, with stable configurations of different diameters. For example, a ring may have an expanded shape similar to that of an open umbrella, and a compressed shape similar to that of an umbrella which has turned inside out. In lieu of rings with tabs and holes, rings having mating surfaces which interlock can be used. For example, a set of teeth similar to a crown gear may be provided on the mating surfaces, which may allow many more orientations than tabs and holes, since the teeth can be smaller and more numerous. However, the cannula should then be preloaded in compression to prevent teeth on the two mating rings from separating. This can be accomplished by one or more cables or wires running through the cannula, which can be anchored at every ring if necessary, or the anchor point transferred distally as more rings are added, or by other means, such as magnets.

Sensors may be provided in some embodiments to sense the bending radius of the cannula, detect the magnitude and direction of externally-applied forces, etc.

If the tabs of rings face proximally as in FIG. 32, they may catch on a liner that is pushed and/or twisted distally. Thus it may be preferable to reverse the ring orientation so that the tabs face distally.

In some embodiments, the rings may be sections of curved tubing, rather than sections of straight tubing. In such cases, the mating surfaces of the rings can be completely circular.

The strip used in continuously distally assembling/disassembly cannula, or elements of the strip or elements joining one winding of the strip to another, may be intentionally elastic, so as to impart deformability to the cannula when subject to external forces. This may be done for the entire cannula, or just for portions thereof.

A liner introduced into the cannula during or after assembly can be very flexible or stretchable with an outside diameter considerably smaller than the cannula inside diameter, allowing it to be pulled (or even pushed) easily through the cannula, and may be made from a lubricious material such as PTFE thin wall tubing. It may also have a pleated cross section (e.g, formed into a star shape). Once in place, in some embodiments fluid pressure may expand it, and the structure of the cannula (with good radial strength) prevents over-expansion.

In some embodiments, the cannula may be subject to forces which deform it, damage it, or limit the size and shapes it can attain. Such forces may include gravity, buoyancy, wind, viscous drag from fluid motion, friction, reaction forces from manipulated objects, etc. It can therefore be desirable to stabilize the cannula using various means. For example, helium balloons, magnets, or motorized propellers can support at least part of the cannula weight, and mechanisms such as deployable legs or arms—sometimes equipped with claws or other graspers—can support elevated portions of the cannula by making contact with the ground or surrounding features of the environment. For operation in water, the cannula may include ballast tanks, swim bladders, weights, and/or flotation devices (e.g., a double-walled, air-filled liner, a hollow stylet shaft, external floats), for example to achieve near-neutral buoyancy.

Shape memory alloys or polymers incorporated into the cannula may be used in some embodiments to rapidly change its shape once it has been assembled/extended.

In some situations such as certain medical procedures and search and rescue, the desired trajectory of the cannula cannot be predicted before the cannula is actually deployed, thus requiring real-time guidance and path planning. For example, in a search and rescue environment, the cannula may have penetrated through an aperture (e.g., in rubble) and is now in an empty "chamber" having another aperture somewhere else (as recognized by a camera/3-D scanner). To progress, it might be desirable for the cannula to advance though this second aperture. The process for a cannula based on rings can be as follows, and a similar process could be used for continuously distally assembled cannulas:

1. Identify the current position of the most distal ring (i.e., the current distal tip of the cannula. This might be done deterministically, if there is minimum clearance between rings and tight tolerances, or through sensing.

2. Measure the location of the aperture through which the cannula should grow. More specifically, identify a region within the area of the aperture through which the center of the cannula could move without colliding with the sides of the aperture. This needs to take into account the aperture geometry, the cannula diameter, the space needed to manipulate rings, and other factors.

3. Calculate potential trajectories (if more than one) and select the optimal trajectory (i.e., using time to enter the aperture, and select the optimal trajectory (e.g., that requiring the least time).

4. Calculate the sequence of ring orientations needed for the growing cannula to reach and penetrate the region and (simultaneously or subsequently) grow the cannula according to that sequence, thus penetrating through the aperture.

The various embodiments of the invention, set forth explicitly herein or otherwise ascertained from the teachings herein, may be used alone or in any combination.

Medical Applications:

A variety of medical procedures may benefit from the use of devices such as those described herein used as medical instruments to introduce and/or remove fluid, or provide a conduit for the delivery or retrieval of implants or instruments to or from a target region of the body. For example, cancer patients may have brachytherapy seeds implanted in or near tumors, have tissue biopsied or fluid aspirated for analysis, receive chemotherapy agents, or have tumors removed or ablated. Brachytherapy seeds are normally implanted at multiple sites. Biopsies or fluid aspiration may be performed in multiple locations. Chemotherapy is often delivered intravenously but can be more effective if delivered locally to the site of a tumor, minimizing systemic effects. Patients with atrial fibrillation may be treated by electrical ablation of selected regions of heart tissue. Patients in need of neuromodulation may be implanted with electrodes or other devices.

Continuously distally assembled/disassembled curved cannulas, since their stylets may remain inside as they grow, may be equipped to continuously dissect tissue (e.g., with a balloon, needle, or cutter) affixed to the end of the stylet, for example.

Devices such as those described herein may be made in different sizes, ranging from sub-millimeter in diameter to several centimeters or even larger.

As noted, devices such as those described herein may be used to deliver brachytherapy seeds. In some embodiments, multiple seeds may be loaded into the inner walls of a cannula at a desired axial spacing, and retained by the walls. As the instrument everts, it lengthens and delivers seed after seed into tissue. Such an instrument may extend for a distance, then retract, then extend in a different direction.

Devices such as those described herein may deliver other implants to tissue surfaces or sub-surface; delivery need not be through solid tissue.

Devices such as those described herein may be used to deliver devices which remove or ablate tissue—mechanically, or through laser, thermal, RF, microwave, or cryogenic means, for example.

Devices such as those described herein may deliver drugs such as chemotherapy drugs or pain medication, for example, or embolic particles, microspheres, and other materials. A device might tunnel through tissue and selected regions of organs such as the liver to form a complex 3-D shape that is "space filling" and dispense a drug or ablation agent through holes along the device, in a process akin to drip irrigation. Such a 3-D device might also be used to simultaneously ablate large volumes of unwanted tissue using chemical, radio frequency, ultrasonic, cryogenic, or other means.

Devices such as those described herein may be used for lung biopsy, avoiding delicate structures and minimizing the risk of pneumothorax.

Devices such as those described herein may be used for fine needle aspiration.

Devices such as those described herein may be used to deliver electrodes, or as implanted electrodes for neurostimulation, including deep brain stimulation. For example, a cochlear implant electrode that is atraumatically delivered within the cochlea and which has a large number of discrete electrodes can be distally assembled in a tapered or small diameter cylindrical shape matching that of the cochlea. Such a device may be based on an everting tube, a set of discrete tubes or rings, etc. If comprised of metal (e.g., Pt—Ir, stainless steel, nickel-titanium) rings as in FIG. 26 or FIG. 45, for example, the rings may be electrically insulated from one another by dielectric (e.g., elastomer) rings or gaskets/spacers, or at least one face (distal or proximal) of at least some rings can incorporate a dielectric material, to electrically isolate rings or groups of rings. Electrical connection to the metal rings can be achieved after the implant is delivered by atraumatically sliding into the lumen of the hollow electrode a multi-conductor cable with, for example, brushes that make contact to the rings from their interior surfaces. Separately, electrodes that grow into or around tissue, such as nerve cuff electrodes that wrap around a nerve as they distally assemble, may be used implemented using approaches discussed herein, so as to minimize the size of incision needed to deliver them, achieve more intimate contact with tissue, etc.

For some applications, devices such as those disclosed herein and their component parts may be perforated, textured, coated, or otherwise modified to improve the reaction or compatibility with tissue, such as minimizing the risk of thrombus, discouraging bacterial growth, encouraging tissue or bone growth, etc.

For some applications, devices such as those disclosed herein—or attached members such as catheters—may be stabilized, positioned (e.g., centered), and/or anchored inside a patient's body at one or more locations by an inflatable balloon, deployment of fixation devices, etc. For example, a balloon may be used on a device in its proximal region, while the distal region grows into the desired shape.

Devices such as those described herein may be used in minimally-invasive procedures such as sinus surgery and arthroscopic surgery.

Devices such as those described herein may be used within the ventricles of the brain to ablate/remove tumors, biopsy tissue, treat hydrocephalus, or provide injections. In addition, such devices may be used to cool the brain after stroke or other trauma: a cooling liquid compatible with cerebrospinal fluid can be introduced through a flexible catheter deployed within the device, with warm fluid withdrawn through the (e.g., annular) space surrounding the catheter. Fluids can pass through holes in the walls of the devices, or the device can be provided with a liner such that flow is directed through the end of the device and/or other locations. The device can be inserted through a small incision in the skull into the anterior horn of a lateral ventricle, and deployed toward the posterior horn and if desired, into the inferior horn. After deployment, or in some embodiment variations, during deployment, fluid exchange can occur, allowing the brain—and only the brain—to be efficiently cooled from within. Appropriate sealing may be used to prevent cerebrospinal fluid loss during deployment/assembly or retrieval/disassembly of the device and during operation.

Devices such as those described herein may be used in spinal surgery, for example, for microdiscectomy or foraminal stenosis, navigating around obstacles in small spaces. A distally assembled cannula might, for example, be used to provide percutaneous access to a laterally herniated cervical disc through a posterior approach while avoiding sensitive structures; this would avoid the need for the vertebral fusion of a frontal approach. Devices such as those described herein may also be used to "grow" an interbody fusion cage (e.g., with a helical shape) between two vertebral bodies. Since such a cage is distally assembled in-vivo, it can be delivered through a small incision.

Devices such as those described herein may be used in the treatment of atrial fibrillation by ablation (e.g., RF or cryoablation) of the wall of the heart. Such devices may be used to position an ablation electrode or other device against the heart wall during a procedure, or provide a stable platform for a steerable catheter, or may themselves act as an ablation device. For example, a device having a circular or other suitable shape can be deployed within the heart around the pulmonary vein and provided with RF energy or cryogenic cooling, and can be anchored to the heart wall during the procedure, so that it moves with the heart, or moved in synchrony with the heart. Force sensing can also be provided, e.g., by incorporating one or more rings with strain gauges into the device.

Devices such as those described herein may be used in the delivery of enteral feeding tubes through the pyloric sphincter of the stomach, to achieve transpyloric placement.

Devices such as those described herein may be used in urology for stone removal and to correct urinary drainage.

Devices such as those described herein may be used to deliver and affix tissue approximation and closure devices, e.g., in cardiology.

Devices such as those described herein may be used in injections of anesthetics, for example, for epidural spinal anesthesia.

Figure 42:
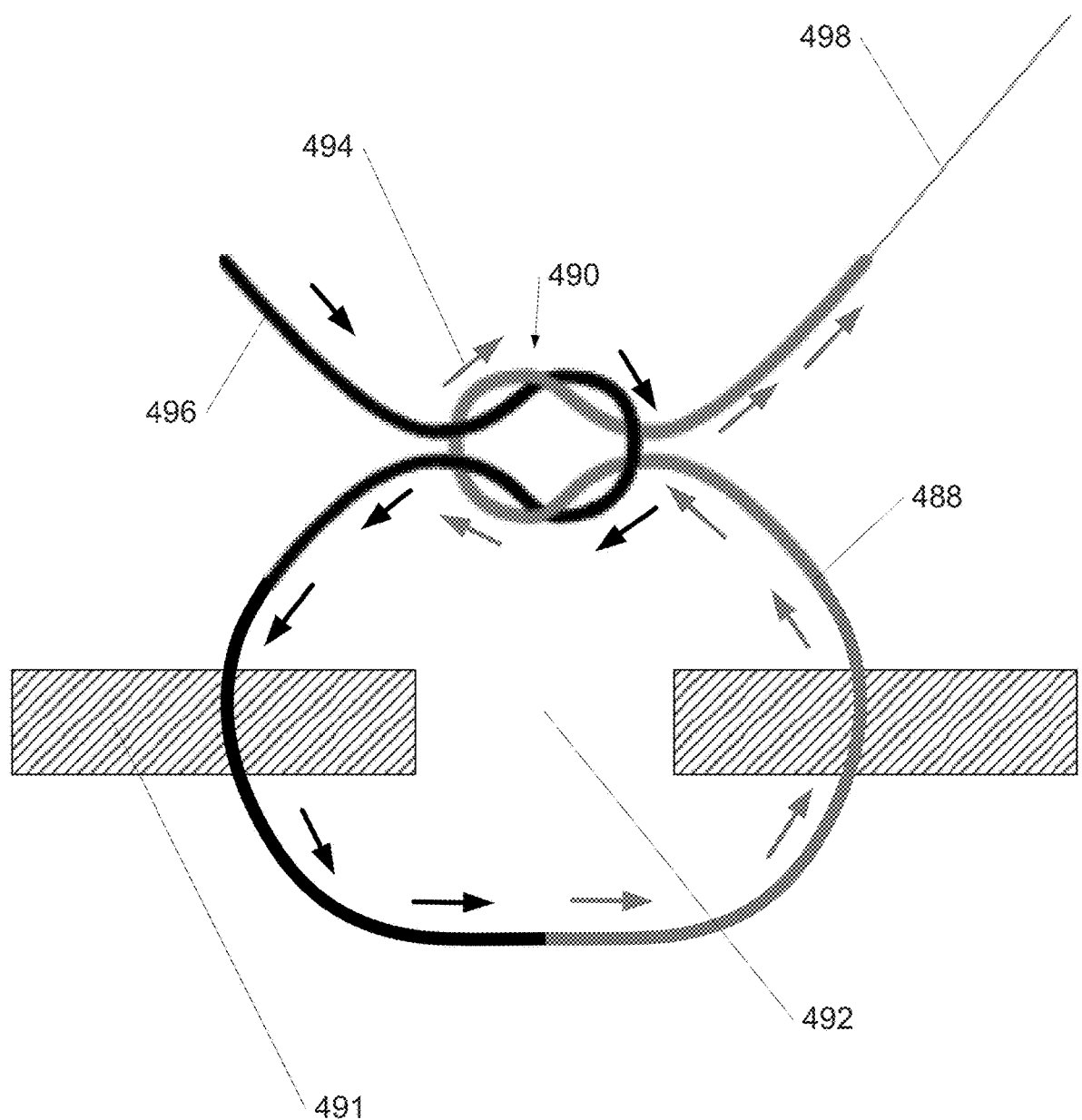
FIG. 42 shows a method of suturing and knotting.

Devices such as those described herein may be used to deliver sutures and similar materials, and form knots in suture. FIG. 42 depicts a cannula formed into a shape that includes a loop 488 and a square knot 490 (or another knot, such as a surgeon's knot). The proximal and distal sections of the cannula are shown differently shaded for clarity. Loop 488 passes through two walls of tissue 491 separated by gap 492, and the clinical objective is to approximate walls 491 to as to close gap 492. To accomplish this, as shown by cannula growth direction arrows 494, the cannula is assembled starting at proximal end 496, then forms a small loop that will later serve as one half of square knot 490, then continues to grow while penetrating through one wall of the tissue (in some embodiments a sharp stylet may be temporarily used to pierce the tissue), then through the other wall of tissue, then finishes the loop and grows to form the other half of square knot 490. Suture 498 is delivered through the cannula either gradually as it is assembled (similar to the way DASC can be assembled over a guidewire, described herein), or after the entire shape has been assembled (e.g., attached to the most distal ring, if DASC comprises rings). Once the distal end of suture 498 is anchored, the cannula can be disassembled over the suture, resulting in suture 498 having the shape of the cannula, i.e., manifesting a loop and tied into a square knot. The loop can then be tightened to approximate the tissue, and the knot tightened to keep the tissue approximated. Thus, the normally complex and difficult procedure of forming a loop and tying a knot when performed endoscopically can be achieved relatively automatically by DASC, and in spaces such as the upper airways where space is highly constrained.

Devices such as those described herein may be used to treat atrial fibrillation for example as follows: The device may be delivered into/extend into the left atrium of the heart and guide/support a steerable catheter, or itself adopt a shape (e.g., loop-like) in the distal region, with the distal region in contact with the atrium surrounding the ostia of the pulmonary veins (more than a single vein can be surrounded at a time). By applying energy (e.g., RF) through the device, tissue can be ablated such that electrical conduction paths contributing to fibrillation are interrupted.

Devices such as those described herein may be used to place epicardial leads on the heart, e.g., for biventricular pacing.

Devices such as those described herein may be used as annuloplasty rings, for example, to correct mitral valve regurgitation. The device can be inserted percutaneously through a small incision, enter the beating or stopped heart, and grow inside the heart into the complex 3-D shape required to reshape the valve annulus. The device would be anchored to tissue by one method of another. For example, if the device comprises rings such as those of FIG. 26, at least some rings can include barbs, clips, or other fixation features which grasp and/or penetrate the tissue. Attachment of tissue to the ring can occur after the ring is fully assembled, or gradually, as the ring grows. Barbs, clips, suture, and mechanisms for attaching the device to tissue can be passed through the lumen of the device, passed over it, or alongside it. In some embodiments, the distal end of the annuloplasty ring can interlock with its side to form a strong, closed loop.

Devices such as those described herein may be used to perform percutaneous bypass surgery, e.g., of peripheral arteries or coronary arteries. The device can create a proximal anastomosis to, for example, the aorta, e.g., by compressing the aorta wall between two rings such as those of FIG. 26, possibly specially adapted for this task. The device can then extend along a 3-D path to reach the target vessel and a distal anastomosis can be created with that vessel, e.g., using similar methods. Means of perforating the vessels can be provided, e.g., a stylet head of the kind shown in FIG. 37, or a separate sharp stylet passed through the device. Compression of vessel tissue between rings may be used to necrose tissue and create a hole. Modified (e.g., sharpened) versions of rings such as those of FIG. 26 can be used to cut holes in vessels, e.g., when rotated by the stylet.

Devices such as those described herein may be used as stents, stent grafts, shunts (e.g., aneurysm bypass shunts), conduits, and other implants through which bodily fluids pass, and which are intended to provide a patent lumen. For example, stents of adjustable length and curvature can be produced using multiple rings of the kind shown in FIG. 26, and stents for bifurcations can be assembled out of separate, coupled rings.

Devices such as those described herein may be used within the lumens of blood, lymph and other vessels to help navigate a guidewire or catheter through difficult bifurcations, tortuosity, calcification, or other complex anatomy, for example, in the brain.

Devices such as those described herein may be used in lieu of a guidewire, or in procedures that do not require a guidewire, in interventional radiology and other procedures within body lumens. Devices such as those described herein may be used in navigating tortuous vasculature such as in the brain, and for filling the sacs of neurovascular aneurysms in lieu of detachable coils.

Devices such as those described herein may be used for diagnostic and therapeutic procedures in the gastrointestinal system, such as the stomach, small intestine, and colon. In general, when deployed in narrow and/or curved lumens, devices such as those described herein can minimize potentially traumatic contact with nearly walls of tissue. In general, additional devices used in conjunction with instruments such as those described herein may be may be slid over the instrument. Or, other devices and materials may be passed through a lumen in the instrument. Or, the instrument may be used as a platform to support another instrument at its distal end which is desired for a procedure (e.g., a biopsy or ablation device). Distally extendable instruments may be used as type of steerable, fully or partially self-supporting, track along or inside of which devices and material can be transported.

Devices such as those described herein may be used as neural electrodes or other temporary or permanently-implanted structure which can be thin yet be inserted without buckling by growing from its distal end, yet be flexible so as to maximize compatibility with surrounding tissue.

Non-Medical Applications:

Devices such as those described herein may be used as robotic arms and manipulators.

Devices such as those described herein may be used for oil and gas exploration and production, for example, in lieu of standard casings normally placed within a well, or for drilling a well at any desired depth and angle (e.g., for horizontal drilling).

Devices such as those described herein may be used in civil engineering and architecture to create useful structures.

Devices such as those described herein may be used to navigate through irregular debris in search and rescue operations, (e.g., in collapsed mines, and collapsed buildings). A device (e.g., with an outside diameter in the range of 10-40 mm) can navigate autonomously or under operator control to grow in a complex 3-D shape through nooks and crannies (e.g., using a camera, laser-based instruments) to reach trapped disaster victims before heavy machinery can remove rubble to free them. It can deploy sensors along the way or upon reaching its destination, allowing its position and that of the victims to be identified. Through the lumen, air, water, food (e.g., in liquid form), and medical supplies can be furnished to the victims, and cameras and two-way communication devices can be delivered, allowing continuous communications. To facilitate its ability to extend through various materials at the disaster site, the device can be provided with a powerful vacuum system and if needed, an airproof liner, so that dust, dirt, and smaller rocks and debris can be extracted through it. When no alternative presents itself, a drill can be deployed through the device, driven hydraulically or using a rotating flexible shaft, allowing penetration of hard materials. In the case of a continuously distally assembled/disassembled curved cannula, the stylet can remain inside as the cannula grows, with its distal end near the cannula distal end, allowing the drill to function continuously. The device can also serve to deploy reinforcing cables that stabilize heavy debris at risk of shifting and collapsing on the victims, e.g., during rescue operations.

After an earthquake or other disaster leading to the collapse of a building, for example, rapidly locating and making contact with survivors is of paramount importance. This can be a very challenging task for first responders and for conventional robots since the environment is characterized by irregular debris forming multiple random, randomly-interconnected chambers, granular media, structures which may shift or collapse under additional weight, and other obstacles to mobility. The path from rescuer to victim, if one exists before lifting away the rubble, is often tortuous and accessible only through small chinks. A man-portable or vehicle-mounted cannula system could feature a cannula of, for example, 10-30 mm diameter that could be snaked through the chinks (even if filled with soil or other debris, which can be blown away), seeking out a passage to survivors whose locations may be pre-determined using canines, listening devices, radar, or by using the cannula system itself in an exploratory mode. While advancing, the cannula can avoid rubbing against and disturbing structures around it. Once it has reached its destination, two-way communications can be immediately established via microphone, loudspeaker, and camera. Perhaps more importantly, the cannula can continuously transport needed quantities of air, oxygen, water, and even food and medical supplies to victims through the lumen, maximizing the chances of survival before they can be reached. If the cannula is steered into what turns out to be a dead end, it can easily retract, in effect time-reversing the exact path it had taken, and then extend again in a new direction.

Devices such as those described herein (e.g., with a larger diameter than would be used for a medical application) may be used for disaster-related cleanup of hazardous environments, e.g., contaminated nuclear reactor and weapons sites, where they can be deployed through available openings, extend through stairwells without having to climb stairs or fly like a mobile robot (which consumes power), all the while being immune to hazards such as radiation (since there are no electronics required to grow and maneuver), and slippery or submerged surfaces. Through the lumen cleaning agents can be delivered, and debris can be vacuumed up, among other useful operations such as performing surveillance of the facility.

The decontamination and decommissioning of dangerous facilities such as nuclear power plants that have suffered accidents, such as the Fukushima Daiichi plant in Japan, of retired power plants worldwide, or of obsolete weapons facilities in the U.S., is a process needing years or decades to complete. It is also an extremely costly (e.g., $17B for Fukushima) and difficult process due to radioactive contamination, high temperatures and pressures, explosive materials, wet or submerged areas, rubble, and other factors which make the environment very inhospitable for human workers. Robots may therefore help complete the required activities including surveying and inspection, non-destructive evaluation, repair, and removal of contaminated debris and fluids. While wheeled, tracked, or legged robots can accomplish some tasks, their mobility is limited by the existence of surfaces which are difficult to traverse due to obstacles, liquids, granular materials, and gaps; by the three-dimensional nature of many structures (e.g., multiple floors, stairs, shafts); and by the need for power and communications. If tethered for power and communications, the tether limits maneuverability and can become tangled or snagged, yet untethered robots must rely on short-lived batteries. Flying drones can avoid surface hazards and move in any open direction; however, they too are limited by tethers or batteries, and can be too large to enter pipes, ducts, or narrow openings. Moreover, they must be well controlled to avoid collisions in cramped spaces. Finally, neither surface nor flying robots have much capability for material transport: the ability to deliver cleaning agents or remove contaminants.

A distally assembled cannula could be scaled to 10s of cm in diameter and 10s of meters long, as long as its weight can be supported by grappling surrounding objects, by deployable "stilts", or if immersed in liquid, by floats. Such a device could be extremely versatile and overcome some of the limitations of conventional robots. The cannula's console (FIG. 80) could be mounted at a fixed point, or attached to a mobile robot to extend its range. The cannula can extend within confined spaces and grow in 3-D to access target spaces within a facility, moving above debris and liquids on floors, up and down stairwells and shafts, through ducts, tunnels and doorways, and around dense groupings of pipes and cables. Once positioned, the cannula can act as a continuous, air/watertight conduit for material transport, allowing large volumes (e.g., of contaminated material) to be gradually transported (e.g., by suction).

A benefit of distally assembled cannula is that its operation can be highly tolerant of hazardous environments, such as those involving high temperatures and pressures, deep accumulations of liquids, and intense radiation. The cannula itself, made only from metal, is intrinsically radiation tolerant, though it may suffer embrittlement from intense radiation over time. The stylet can also be metal and designed so that all actuators are located at a distance within the console, which can be in a non-irradiated environment. Lighting and non-destructive testing (NDT) sensors (e.g., acoustic, optical, thermal) required at the distal end of the cannula can be radiation hardened. Metallic components can be coated if needed to suppress potential spark hazards near explosive materials. The cannula can operate for extended missions without maintenance and with constant communications from its distal to its proximal end; its shape should be largely deterministic, minimizing reliance on sensors and GPS to pinpoint the location of its distal end.

Devices such as those described herein may be used underwater to help clean and repair the hulls of large ships.

Devices such as those described herein may be used to travel through complex 3-D spaces such as piping networks.

Devices such as those described herein may be used to navigate around or through an object for purposes of inspection, delivery or retrieval of materials, etc.

Devices such as those described herein may be used to explore tunnels, trenches, crevices, fissures, and otherwise difficult-to-navigate areas. Such areas may be underwater or extraterrestrial, e.g., exploring deep ocean trenches or crevices on Mars. Devices such as those described herein may be used as a form of kinetic sculpture.

Devices such as those described herein may be used as toys, for example, in a construction set allowing complex 3-D tunnels to be quickly assembled (e.g., through which marbles may be released). In such uses, circular rings similar to those of FIG. 26 may be replaced by non-circular rings of different shapes (e.g., square, octagonal, triangular), and interlocking may involve manually compressing the rings and releasing them when their tabs (some or all) are within an adjacent ring. Moreover, if the toy is constructed from its distal end, to which the user has access, and there is therefore no reason to transport rings through its interior, then the rings can be pre-curved and/or much longer than would otherwise be possible. It is contemplated that any embodiment discussed in this specification can be implemented with respect to any method, kit, reagent, or composition of the invention, and vice versa. Furthermore, compositions of the invention can be used to achieve methods of the invention.

Devices such as those described herein may be used as molds or mandrels, in which a solidifiable material (e.g., concrete, thermoplastic, thermoset, UV-curable material, fiber-reinforced composite) is placed within or on the exterior surface of the device, and then solidified, maintaining the shape even if the device is thereafter removed (e.g., by disassembly). In some embodiments, a liner or a surrounding sleeve can be placed in or over the device before the solidifiable material is applied to provide a minimally-porous surface that retains the material. Material can be added gradually as the device is assembled, or added only once the entire device has been assembled.

Devices such as those described herein may be used in vacuum environments and under conditions of neutral buoyancy or low/zero gravity, for example, for inspection, manipulation, retrieval, transport of solid, liquid, or gas material. For example, such devices may allow inspection behind large objects that are difficult to move, within deep cavities within a structure, or inside deep and crevasses with complex shapes.

The International Space Station, among other current and future space platforms, has inspection requirements that are not easily met by existing robotic devices. For example, the ISS contains multiple, large racks of equipment. If there is a suspected leak or other potential issue behind such equipment, it normally would need to be removed in order to obtain access: a time-consuming process. A minimally invasive approach would be much preferred. If equipped with a miniature camera (e.g., on the stylet) and sufficiently small in diameter, a distally assembled cannula could be commanded to quickly weave its way through small openings and provide video of the environment behind the equipment. Being self-supporting especially in microgravity, the cannula could easily follow an arbitrary 3-D path, including for example growing out of a hole, extending across an open space, and entering another hole unaligned with the first hole.

The cannula console can be permanently mounted to a post or wall; with a 3 meter reach, for example, it would have access to a volume as large as 100 cubic meters. Multiple systems equipped with cameras and microphones could be so mounted, and be teleoperated by ground or mission crews to allow continuous monitoring of the ISS. Being compact with the cannula stowed, the cannula system could also be carried and delivered to the site of interest by a crew member, be attached to or carried by a larger robot, or even integrated into a free flying robot. Unlike free flying robots, cannulas can pass through very small openings, never needs to perch, and its actuators consume no power when the cannula is static. Since the cannula is tethered to the console, power can easily be supplied when extending or retracting or for operating a distal camera, etc.

In addition to inspection, other intravehicular space applications for cannulas include environmental surveys (e.g., sound level, air quality) with the appropriate sensor package, and inventory management (e.g., if equipped with an RFID reader). Extravehicular opportunities for cannulas include surveying internal damage to structures penetrated by micrometeoroids and orbital debris. Cannulas can be slender enough to fit under thermal blankets, leaving them intact while exploring what is hidden to the outside. It can be equipped with tactile and force sensors as required by the mission. Cannulas could assist in maintaining and repairing systems on board the ISS. It might have a role as a versatile, deployable structure able to transport tools and materials in support of space needs such as the Robotic Refueling Mission, docking assistance, and on-orbit assembly. Finally, planetary landers could use cannulas as a means for exploring deep and tortuous crevasses on the surface.

Cannulas can be built to contain no electronics or actuators and thus be tolerant to radiation and to temperature extremes. While the stylet may include actuators and sensors, it can be withdrawn when not needed, minimizing its exposure. The cannula or stylet can be equipped with grippers and other tools, and being hollow, many devices can be passed through it such as a borescope with steerable tip. While the cannula by itself is not fluid-tight, it can be made so by delivering a flexible liner, allowing transport of liquids and gasses.

Devices such as those described herein may be used for underwater exploration (e.g., of trenches), surveillance (e.g., naval intelligence gathering in environments obscured by underwater vegetation such as reeds in swampy areas), economically laying conduit for underground power and fiber optic cables, and even to plant seeds underground (e.g., as the cannula retracts, seeds could be pushed out).

Devices such as those described herein may be used by bomb squads to inspect, safely de-activate, or remotely detonate a bomb; or in urban police, military, and anti-terror actions in which surveillance, delivery of a non-lethal weapon, etc. within a building or other structure is needed, and access is limited to circuitous paths and/or small openings.

Devices such as those described herein may be used to supply buildings and vehicles from another building or vehicle, for example, for in-air refueling of one aircraft by another, or for recharging or refueling of an unmanned aerial vehicle from the ground.

Devices such as those described herein may be used to transport objects using fluid forces, such as using gas or liquid pressure, or the force of rapidly-expanding gas after an explosion (i.e., devices such as those described herein may be used as steerable gun barrels).

Devices such as those described herein may be used in firefighting to carry water (or other flowable extinguishing agent), delivering the water within a building on any required floor through a small opening (e.g., a hole in a window produced by the distal end of the device through cutting or breaking). Fumes and smoke may also be extracted by devices such as those described herein.

Devices such as those described herein may be used to support light fixtures, cameras, and the like for photography and cinematography.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. DiMaio, S and Salcudean, S. Needle insertion modeling and simulation, IEEE Trans. Robot. Autom., vol. 19, pp. 864-875, 2003.
2. Glozman, D. and Shoham, M., Image-guided robotic flexible needle steering, IEEE Trans. Robot., vol. 23, pp. 459-467, 2007.
3. Okazawa, S., Ebrahimi, R., Chuang, J., Salcudean, S., Rohling, R., Hand-held steerable needle device, IEEE/ASME Trans. Mechatron., vol. 10, pp. 285-296, 2005.
4. Webster, R. Kim, J., Cowan, N., Chirikjian, G., Okamura, A., Nonholonomic modeling of needle steering, Int. J. Robot. Res., vol. 25, pp. 509-525, 2006.
5. Majewicz, A., Marra, S., van Vledder, M., Lin, M., Choti, M., Song, D., Okamura, A. Behavior of Tip-Steerable Needles in ex vivo and in vivo Tissue, IEEE Trans Biomed Eng. 2012 October; 59(10):2705-2715. PMID: 22711767.
6. Goksel, O., Dehghan, E., Salcudean, S. Modeling and simulation of flexible needles.
   Medical Engineering & Physics, 2009, 7:1153-1162. PMID: 19674926.
7. Sears, P. and Dupont, P. A steerable needle technology using curved concentric tubes, Proceedings of the 2006 IEEE/RSJ International Conference on Intelligent Robots and Systems (IROS), Beijing, China, Oct. 9-15, 2006: 2850-2856. PMID: 23685532.
8. Dupont, P., Lock, J., Itkowitz, B., Butler, E. Design and control of concentric tube robots, IEEE Transactions Robotics, vol. 26(2): 209-225, 2010. PMID: 21258648. http://www.ncbi.nlm.nih.gov/pmc/articles/PMC3022350/pdf/nihms-251097.pdf.
9. Dupont, P., Gosline, A., Vasilyev, N., Lock, J., Butler, E., Folk, C., Cohen, A., Veeramani, A., Wu, M., Schmitz, G., Chen, R., del Nido, P. Concentric tube robots for minimally invasive surgery. Hamlyn Symposium on Medical robotics: 3-4, 2012. http://www.bioeng.nus.edu.sg/biomm/pdfs/dupont2012concentricHamlyn.pdf.
10. Webster, R., Romano, J., Cowan, N. Mechanics of precurved-tube continuum robots. IEEE Transactions Robotics, vol. 25(1): 67-78, 2009.
11. Gosline A., Vasilyev N. V., Butler, E., Folk, C., Cohen, A., Chen, R., Lang, N., del Nido, P. J., Dupont, P. E. Percutaneous intracardiac beating-heart surgery using metal MEMS tissue approximation tools. Int J Robotics Research 2012; 31:1081-1093. PMID: 23750066, PMCID: PMC3671619 (available Aug. 1, 2013).
12. Mahvash M. and Zenati, M. Toward a hybrid snake robot for single-port surgery, 33rd Annual International Conference of the IEEE EMBS, Boston, Mass., Aug. 30-Sep. 3, 2011:5372-5375. PMID: 22255552.
13. Lee, W., Chamorro III, Andres, Weitzner, B., Robotically controlled medical instrument, U.S. Pat. No. 7,854,738 (2010).
14. Saadat, V., Ewers, R., Chen, C. Shape lockable apparatus and method for advancing an instrument through unsupported anatomy, U.S. Pat. No. 7,128,708 (2006).
15. Degani, A., Choset, H., Wolf, A., Ota, T., Zenati, M. Percutaneous intrapericardial interventions using a highly articulated robotic probe, Proceedings of the 2006 IEEE/RAS-EMBS International Conference on Biomedical Robotics and Biomechatronics, February, 2006, pp. 7-12.
16. Chapman, M., Tokota, T., Ota, T., Tully, S., Schwartzman, D., Zubiate, B., Wright, C., Choset, H., Zenati, M. A highly articulated robotic system (CardioARM) is safer than a rigid system for intrapericardial intervention in a porcine model, in: IEEE ICRA Full Day Workshop. IEEE, Anchorage (2010).
17. Ohline, R., Tartaglia, J., Belson, A., Roth, A., Keller, W., Anderson, S., Julian, C. Tendon-driven endoscope and methods of insertion, U.S. Pat. No. 6,858,005 (2005).
18. Konstantin, B., Pauker, F., Viebach, T. Everting tube comprising two-component lubricant, U.S. Patent Application #US2008/0058596 (2007).

What is claimed is:

1. A method of forming a self-supporting elongatable and retractable tube comprising:
   obtaining a flexible strip of material having a length that is large in comparison to a width of the flexible strip;
   forming a section of the strip into a distal winding of a tube by curving the section and joining the distal winding to an adjacent section;
   advancing the strip through a lumen of the tube from a proximal to a distal location;
   wherein the tube elongates through an addition of one or more windings that are added at a distal end of the flexible strip to form the self-supporting elongatable and retractable tube, wherein the self-supporting and retractable tube is a tube that needs no support after forming the tube, wherein self-supporting is a tube that does not collapse from its weight after its formed; and
   reversing the step of forming the self-supporting and retractable tube to retract the tube with the strip.

2. The method of claim 1, wherein at least one of: (1) the forming comprises joining a proximal edge of a section of the strip to a distal edge of an adjacent section of the strip; (2) the width of the portion of the strip is varied; (3) the forming comprises overlapping the proximal edge of a section of the strip with a distal edge of an adjacent section of the strip; (4) an amount of overlap of the section of the strip is varied; or (5) the strip comprises at least two wedges and a variation in the width comprises adjusting the relative position of the at least two windings.

3. A method of forming a self-supporting elongatable and retractable tube comprising:
   obtaining a flexible strip of material having a length and a width, the width of the flexible strip having a first and a second edge;
   winding the flexible strip into a tube, wherein the first edge of the flexible material contacts or overlaps the second edge to form the tube;
   advancing the flexible strip distally through a lumen of the tube, wherein the tube elongates through an addition of windings at a distal end of the flexible strip to form the self-supporting elongatable and retractable tube, wherein the self-supporting and retractable tube is a tube that needs no support after forming the tube; and
   reversing the step of forming the self-supporting and retractable tube to retract the tube with the flexible strip.

4. The method of claim 3, further comprising the step of mechanically joining the first edge of the flexible strip to the second edge of the flexible strip as the tube elongates.

5. The method of claim 3, further comprising the step of overlapping the first and the second edges of the flexible strip to mechanically strengthen the tube and/or allow for a variable amount of overlap between the first and second edge.

6. The method of claim 5, wherein the amount of overlap of a first and a second edge of the flexible strip is varied along a portion of the length of the flexible strip to produce a change in an elongation direction of the tube.

7. The method of claim 3, wherein the width of the winding of the strip is varied along the length of the flexible strip to produce a change in an elongation direction of the tube.

8. The method of claim 7, wherein a variation in the width of the flexible strip comprises adjusting a relative position of one or more windings that comprise the flexible strip.

\* \* \* \* \*